US012807714B2

(12) United States Patent
Tsurushita et al.

(10) Patent No.: US 12,807,714 B2
(45) Date of Patent: Nov. 24, 2026

(54) ANTIBODIES AGAINST OX40

(71) Applicant: JN BIOSCIENCES LLC, Mountain View, CA (US)

(72) Inventors: Naoya Tsurushita, Palo Alto, CA (US); J. Yun Tso, Menlo Park, CA (US)

(73) Assignee: JN Biosciences LLC, Mountain View, CA (US)

( * ) Notice: Subject to any disclaimer, the term of this patent is extended or adjusted under 35 U.S.C. 154(b) by 1071 days.

(21) Appl. No.: 17/723,084

(22) Filed: Apr. 18, 2022

(65) Prior Publication Data

US 2022/0251214 A1 Aug. 11, 2022

Related U.S. Application Data

(62) Division of application No. 16/683,073, filed on Nov. 13, 2019, now Pat. No. 11,332,532.

(60) Provisional application No. 62/838,579, filed on Apr. 25, 2019, provisional application No. 62/760,328, filed on Nov. 13, 2018.

(51) Int. Cl.
*C07K 16/28* (2006.01)

(52) U.S. Cl.
CPC ...... *C07K 16/2827* (2013.01); *C07K 16/2878* (2013.01); *C07K 2317/21* (2013.01); *C07K 2317/24* (2013.01); *C07K 2317/31* (2013.01); *C07K 2317/52* (2013.01); *C07K 2317/565* (2013.01); *C07K 2317/624* (2013.01); *C07K 2317/75* (2013.01)

(58) Field of Classification Search
CPC ............ C07K 16/2827; C07K 16/2878; C07K 2317/21; C07K 2317/24; C07K 2317/31; C07K 2317/52; C07K 2317/565; C07K 2317/624; C07K 2317/75; C07K 2317/76; C07K 16/2803; C07K 16/2863; C07K 16/2818; C07K 2317/622; C07K 2317/64; C07K 2317/71
See application file for complete search history.

(56) References Cited

U.S. PATENT DOCUMENTS

| | | | | |
|---|---|---|---|---|
| 9,789,183 | B1 | 10/2017 | Wang et al. | |
| 11,332,532 | B2 * | 5/2022 | Tsurushita | C07K 16/2863 |
| 2016/0376357 | A1 | 12/2016 | Rother et al. | |
| 2018/0002437 | A1 | 1/2018 | Guerra et al. | |
| 2018/0207266 | A1 | 7/2018 | Danling et al. | |
| 2020/0165341 | A1 | 5/2020 | Tsurushita et al. | |
| 2021/0024640 | A1 * | 1/2021 | Calzone et al. | C07K 16/28 |

FOREIGN PATENT DOCUMENTS

| | | | |
|---|---|---|---|
| JP | 2015-502373 | A | 1/2015 |
| JP | 2016-528287 | A | 9/2016 |
| JP | 2018-209175 | A | 4/2018 |
| WO | WO 2015/026684 | A1 | 2/2015 |
| WO | WO 2017/019846 | A1 | 2/2017 |
| WO | WO 2017/019846 | A8 | 2/2017 |
| WO | WO 2017/123673 | A2 | 7/2017 |
| WO | WO 2018/002339 | A1 | 1/2018 |
| WO | WO 2018/071913 | A2 | 4/2018 |
| WO | WO 2018/202549 | A1 | 11/2018 |
| WO | WO 2020/102233 | A1 | 5/2020 |

OTHER PUBLICATIONS

Briney et al. (Nature. Feb. 2019;566(7744):393-397. PMID: 30664748) (Year: 2019).*
Herold et al. (Nature Scientific Reports, 7:12276, Sep. 25, 2017; PMID: 28947772) (Year: 2017).*
Koenig et al. (PNAS. Jan. 24, 2017;114(4):E486-E495; PMID: 28057863) (Year: 2017).*
Labrijn et al. (Nat Rev Drug Discov. Aug. 2019;18(8):585-608. PMID: 31175342) (Year: 2019).*
Sela-Culang et al. (Fron. Immuno., vol. 4, Article 302, Oct. 2013; PMID: 24115948) (Year: 2013).*
Nakakido et al. (Sci Rep. Aug. 22, 2024;14(1):19533. PMID: 39174623) (Year: 2024).*
Van Regenmortel. Mapping Epitope Structure and Activity: From One-Dimensional Prediction to Four-Dimensional Description of Antigenic Specificity. Methods. Jun. 1996;9(3):465-72. doi: 10.1006/meth.1996.0054. PMID: 8812702. (Year: 1996).*
Alsaab, et al., "PD-1 and PD-L1 Checkpoint Signaling Inhibition for Cancer Immunotherapy: Mechanism, Combinations, and Clinical Outcome," Frontiers in Pharmacology, vol. 8, Article 561, (Aug. 2017).
Dahlen, et al., "Bispecific antibodies in cancer immunotherapy," Therapeutic Advances in Vaccines and Immunotherapy, vol. 6(1), 3-17, (2018).
Weidle, et al., "The Intriguing Options of Multispecific Antibody Formats for Treatment of Cancer," Cancer Genomics & Proteomics, 10: 1-17, (2013).
Canadian Application No. 3,115,545, Office Action mailed Dec. 28, 2023.
EP 19885284.0 Extended European Search Report mailed Sep. 27, 2022.
U.S. Appl. No. 16/683,073, Notice of Allowance and Interview Summary mailed Jan. 14, 2022.
U.S. Appl. No. 16/683,073, Requirement for Restriction/Election mailed Jul. 30, 2021.

(Continued)

*Primary Examiner* — Misook Yu
*Assistant Examiner* — Alec Jon Peters
(74) *Attorney, Agent, or Firm* — Alston Bird LLP

(57) ABSTRACT

The invention provides bispecific antibodies having one arm binding to a cancer associated antigen on a cancer cell, such as CD33, EGFR or PD-L1, and a second arm binding to a costimulatory molecule, such as OX40, CD40, GITR, ICOS or 4-1BB. Bridging by the bispecific antibody between cancer cells expressing the cancer associated antigen and immune cells expressing the costimulatory molecule results in clustering of the costimulatory molecules and selective activation of the immune cells at a location proximate to the cancer cells. Thus, the immune cells can exert an immunotherapeutic effect against the cancer cells with reduced toxicity to healthy tissue.

20 Claims, 13 Drawing Sheets

Specification includes a Sequence Listing.

(56) References Cited

OTHER PUBLICATIONS

WIPO Application No. PCT/US2019/060982, PCT International Preliminary Report on Patentability mailed May 18, 2021.
WIPO Application No. PCT/US2019/060982, PCT International Search Report and Written Opinion of the International Searching Authority mailed Mar. 24, 2020.
Japanese Application No. 2024-177387, Office Action mailed Oct. 27, 2025.

* cited by examiner

Figs. 1A-D

SEQUENCE LISTING

<160> NUMBER OF SEQ ID NOS: 143

<210> SEQ ID NO 1
<211> LENGTH: 364
<212> TYPE: PRT
<213> ORGANISM: Homo sapiens

<400> SEQUENCE: 1

```
Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255
```

Val Val His Gly Ala Ile Gly Gly Ala Gly Val Thr Ala Leu Leu Ala
260 265 270

Leu Cys Leu Cys Leu Ile Phe Phe Ile Val Lys Thr His Arg Arg Lys
275 280 285

Ala Ala Arg Thr Ala Val Gly Arg Asn Asp Thr His Pro Thr Thr Gly
290 295 300

Ser Ala Ser Pro Lys His Gln Lys Lys Ser Lys Leu His Gly Pro Thr
305 310 315 320

Glu Thr Ser Ser Cys Ser Gly Ala Ala Pro Thr Val Glu Met Asp Glu
325 330 335

Glu Leu His Tyr Ala Ser Leu Asn Phe His Gly Met Asn Pro Ser Lys
340 345 350

Asp Thr Ser Thr Glu Tyr Ser Glu Val Arg Thr Gln
355 360

<210> SEQ ID NO 2
<211> LENGTH: 135
<212> TYPE: PRT
<213> ORGANISM: Artificial sequence
<220> FEATURE:
<223> OTHER INFORMATION: Synthesized

<400> SEQUENCE: 2

Met Gly Trp Ser Trp Ile Phe Phe Phe Leu Leu Ser Gly Thr Ala Ser
1 5 10 15

Val Leu Ser Gln Val Gln Leu Val Gln Ser Gly Ala Glu Val Lys Lys
20 25 30

Pro Gly Ser Ser Val Lys Val Ser Cys Lys Ala Ser Gly Tyr Thr Phe
35 40 45

Thr Asp Tyr Asn Met His Trp Val Arg Gln Ala Pro Gly Gln Gly Leu
50 55 60

Glu Trp Ile Gly Tyr Ile Tyr Pro Tyr Asn Gly Gly Thr Gly Tyr Asn
65 70 75 80

Gln Lys Phe Lys Ser Lys Ala Thr Ile Thr Ala Asp Glu Ser Thr Asn
85 90 95

Thr Ala Tyr Met Glu Leu Ser Ser Leu Arg Ser Glu Asp Thr Ala Val
100 105 110

Tyr Tyr Cys Ala Arg Gly Arg Pro Ala Met Asp Tyr Trp Gly Gln Gly
115 120 125

Thr Leu Val Thr Val Ser Ser
130 135

<210> SEQ ID NO 3
<211> LENGTH: 98
<212> TYPE: PRT
<213> ORGANISM: Artificial sequence
<220> FEATURE:
<223> OTHER INFORMATION: Synthesized

<400> SEQUENCE: 3

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val


<210> SEQ ID NO 4
<211> LENGTH: 15
<212> TYPE: PRT
<213> ORGANISM: Artificial sequence
<220> FEATURE:
<223> OTHER INFORMATION: Synthesized

<400> SEQUENCE: 4

Glu Pro Lys Ser Cys Asp Lys Thr His Thr Cys Pro Pro Cys Pro
1               5                   10                  15


<210> SEQ ID NO 5
<211> LENGTH: 110
<212> TYPE: PRT
<213> ORGANISM: Artificial sequence
<220> FEATURE:
<223> OTHER INFORMATION: Synthesized

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 6
<211> LENGTH: 107
<212> TYPE: PRT
<213> ORGANISM: Artificial sequence
<220> FEATURE:
<223> OTHER INFORMATION: Synthesized

<400> SEQUENCE: 6

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60
```

```
Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 7
<211> LENGTH: 131
<212> TYPE: PRT
<213> ORGANISM: Artificial sequence
<220> FEATURE:
<223> OTHER INFORMATION: Synthesized

<400> SEQUENCE: 7

Met Glu Lys Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Glu Ser
        35                  40                  45

Val Asp Asn Tyr Gly Ile Ser Phe Met Asn Trp Phe Gln Gln Lys Pro
    50                  55                  60

Gly Gly Ala Pro Lys Leu Leu Ile Tyr Ala Ala Ser Asn Gln Gly Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Asp Asp Phe Ala Thr Tyr Tyr Cys
            100                 105                 110

Gln Gln Ser Lys Glu Val Pro Trp Thr Phe Gly Gln Gly Thr Lys Val
        115                 120                 125

Glu Ile Lys
    130


<210> SEQ ID NO 8
<211> LENGTH: 107
<212> TYPE: PRT
<213> ORGANISM: Artificial sequence
<220> FEATURE:
<223> OTHER INFORMATION: Synthesized

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 9
<211> LENGTH: 8
<212> TYPE: PRT
<213> ORGANISM: Artificial sequence
<220> FEATURE:
<223> OTHER INFORMATION: Synthesized

<400> SEQUENCE: 9

Asp Tyr Lys Asp Asp Asp Asp Lys
1               5


<210> SEQ ID NO 10
<211> LENGTH: 37
<212> TYPE: PRT
<213> ORGANISM: Artificial sequence
<220> FEATURE:
<223> OTHER INFORMATION: Synthesized

<400> SEQUENCE: 10

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35


<210> SEQ ID NO 11
<211> LENGTH: 238
<212> TYPE: PRT
<213> ORGANISM: Artificial sequence
<220> FEATURE:
<223> OTHER INFORMATION: Synthesized

<400> SEQUENCE: 11

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Thr Gly Gly Gly Asp Tyr
            180                 185                 190

Lys Asp Asp Asp Asp Lys Gly Gly Gly Pro Asn Lys Gly Ser Gly Thr
        195                 200                 205
```

```
Thr Ser Gly Thr Thr Arg Leu Leu Ser Gly His Thr Cys Phe Thr Leu
    210                 215                 220

Thr Gly Leu Leu Gly Thr Leu Val Thr Met Gly Leu Leu Thr
225                 230                 235


<210> SEQ ID NO 12
<211> LENGTH: 138
<212> TYPE: PRT
<213> ORGANISM: Artificial sequence
<220> FEATURE:
<223> OTHER INFORMATION: Synthesized

<400> SEQUENCE: 12

Met Gly Arg Leu Thr Ser Ser Phe Leu Leu Leu Ile Val Pro Ala Tyr
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Ile Met His Trp Val Arg Gln Ala Pro Gly Gln Gly Leu
    50                  55                  60

Glu Trp Ile Gly Tyr Ile Asn Pro Tyr Asn Ser Gly Thr Lys Tyr Asn
65                  70                  75                  80

Glu Lys Phe Lys Gly Arg Val Thr Ile Thr Ser Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala His Tyr Tyr Gly Ser Thr Phe Thr Met Asp Tyr Trp
        115                 120                 125

Gly Gln Gly Thr Thr Val Thr Val Ser Ser
    130                 135


<210> SEQ ID NO 13
<211> LENGTH: 5
<212> TYPE: PRT
<213> ORGANISM: Artificial sequence
<220> FEATURE:
<223> OTHER INFORMATION: Synthesized

<400> SEQUENCE: 13

Ser Tyr Ile Met His
1               5


<210> SEQ ID NO 14
<211> LENGTH: 17
<212> TYPE: PRT
<213> ORGANISM: Artificial sequence
<220> FEATURE:
<223> OTHER INFORMATION: Synthesized

<400> SEQUENCE: 14

Tyr Ile Asn Pro Tyr Asn Ser Gly Thr Lys Tyr Asn Glu Lys Phe Lys
1               5                   10                  15

Gly


<210> SEQ ID NO 15
<211> LENGTH: 10
<212> TYPE: PRT
<213> ORGANISM: Artificial sequence
<220> FEATURE:
<223> OTHER INFORMATION: Synthesized
```

<400> SEQUENCE: 15

```
Tyr Tyr Gly Ser Thr Phe Thr Met Asp Tyr
1               5                   10
```

<210> SEQ ID NO 16
<211> LENGTH: 127
<212> TYPE: PRT
<213> ORGANISM: Artificial sequence
<220> FEATURE:
<223> OTHER INFORMATION: Synthesized

<400> SEQUENCE: 16

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Arg Thr Tyr Leu Asn Trp Tyr Gln Gln Lys Pro Gly Lys Val Pro
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Val Ala Thr Tyr Tyr Cys Gln Gln Gly Asn
            100                 105                 110

Thr Leu Pro Trp Thr Phe Gly Gly Gly Thr Lys Val Glu Ile Lys
        115                 120                 125
```

<210> SEQ ID NO 17
<211> LENGTH: 11
<212> TYPE: PRT
<213> ORGANISM: Artificial sequence
<220> FEATURE:
<223> OTHER INFORMATION: Synthesized

<400> SEQUENCE: 17

```
Arg Ala Ser Gln Asp Ile Arg Thr Tyr Leu Asn
1               5                   10
```

<210> SEQ ID NO 18
<211> LENGTH: 7
<212> TYPE: PRT
<213> ORGANISM: Artificial sequence
<220> FEATURE:
<223> OTHER INFORMATION: Synthesized

<400> SEQUENCE: 18

```
Tyr Thr Ser Arg Leu His Ser
1               5
```

<210> SEQ ID NO 19
<211> LENGTH: 9
<212> TYPE: PRT
<213> ORGANISM: Artificial sequence
<220> FEATURE:
<223> OTHER INFORMATION: Synthesized

<400> SEQUENCE: 19

```
Gln Gln Gly Asn Thr Leu Pro Trp Thr
1               5
```

<210> SEQ ID NO 20
<211> LENGTH: 110
<212> TYPE: PRT
<213> ORGANISM: Artificial sequence
<220> FEATURE:
<223> OTHER INFORMATION: Synthesized

<400> SEQUENCE: 20

Ala Pro Glu Ala Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys
100 105 110

<210> SEQ ID NO 21
<211> LENGTH: 277
<212> TYPE: PRT
<213> ORGANISM: Homo sapiens

<400> SEQUENCE: 21

Met Cys Val Gly Ala Arg Arg Leu Gly Arg Gly Pro Cys Ala Ala Leu
1 5 10 15

Leu Leu Leu Gly Leu Gly Leu Ser Thr Val Thr Gly Leu His Cys Val
20 25 30

Gly Asp Thr Tyr Pro Ser Asn Asp Arg Cys Cys His Glu Cys Arg Pro
35 40 45

Gly Asn Gly Met Val Ser Arg Cys Ser Arg Ser Gln Asn Thr Val Cys
50 55 60

Arg Pro Cys Gly Pro Gly Phe Tyr Asn Asp Val Val Ser Ser Lys Pro
65 70 75 80

Cys Lys Pro Cys Thr Trp Cys Asn Leu Arg Ser Gly Ser Glu Arg Lys
85 90 95

Gln Leu Cys Thr Ala Thr Gln Asp Thr Val Cys Arg Cys Arg Ala Gly
100 105 110

Thr Gln Pro Leu Asp Ser Tyr Lys Pro Gly Val Asp Cys Ala Pro Cys
115 120 125

Pro Pro Gly His Phe Ser Pro Gly Asp Asn Gln Ala Cys Lys Pro Trp
130 135 140

Thr Asn Cys Thr Leu Ala Gly Lys His Thr Leu Gln Pro Ala Ser Asn
145 150 155 160

Ser Ser Asp Ala Ile Cys Glu Asp Arg Asp Pro Pro Ala Thr Gln Pro
165 170 175

Gln Glu Thr Gln Gly Pro Pro Ala Arg Pro Ile Thr Val Gln Pro Thr
180 185 190

Glu Ala Trp Pro Arg Thr Ser Gln Gly Pro Ser Thr Arg Pro Val Glu
195 200 205

```
Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275


<210> SEQ ID NO 22
<211> LENGTH: 241
<212> TYPE: PRT
<213> ORGANISM: Artificial sequence
<220> FEATURE:
<223> OTHER INFORMATION: Synthesized

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Thr Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Gly Asn Thr Leu Pro Trp
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Val Gln
        115                 120                 125

Ser Gly Ala Glu Val Lys Lys Pro Gly Ser Ser Val Lys Val Ser Cys
    130                 135                 140

Lys Ala Ser Gly Tyr Thr Phe Thr Ser Tyr Ile Met His Trp Val Arg
145                 150                 155                 160

Gln Ala Pro Gly Gln Gly Leu Glu Trp Ile Gly Tyr Ile Asn Pro Tyr
                165                 170                 175

Asn Ser Gly Thr Lys Tyr Asn Glu Lys Phe Lys Gly Arg Val Thr Ile
            180                 185                 190

Thr Ser Asp Lys Ser Thr Ser Thr Ala Tyr Met Glu Leu Ser Ser Leu
        195                 200                 205

Arg Ser Glu Asp Thr Ala Val Tyr Tyr Cys Ala His Tyr Tyr Gly Ser
    210                 215                 220

Thr Phe Thr Met Asp Tyr Trp Gly Gln Gly Thr Thr Val Thr Val Ser
225                 230                 235                 240

Ser


<210> SEQ ID NO 23
<211> LENGTH: 358
<212> TYPE: PRT
<213> ORGANISM: Artificial sequence
<220> FEATURE:
```

<223> OTHER INFORMATION: Synthesized

<400> SEQUENCE: 23

Gly Gln Pro Arg Glu Pro Gln Val Tyr Thr Leu Pro Pro Ser Arg Asp
1 5 10 15

Glu Leu Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Lys Leu Thr Val Asp Lys Ser Arg Trp Gln Gln Gly
65 70 75 80

Asn Val Phe Ser Cys Ser Val Met His Glu Ala Leu His Asn His Tyr
85 90 95

Thr Gln Lys Ser Leu Ser Leu Ser Pro Gly Ser Gly Gly Gly Gly Ser
100 105 110

Gly Gly Gly Gly Ser Asp Ile Gln Met Thr Gln Ser Pro Ser Ser Leu
115 120 125

Ser Ala Ser Val Gly Asp Arg Val Thr Ile Thr Cys Arg Ala Ser Gln
130 135 140

Asp Ile Arg Thr Tyr Leu Asn Trp Tyr Gln Gln Lys Pro Gly Lys Val
145 150 155 160

Pro Lys Leu Leu Ile Tyr Tyr Thr Ser Arg Leu His Ser Gly Val Pro
165 170 175

Ser Arg Phe Ser Gly Ser Gly Ser Gly Thr Asp Tyr Thr Leu Thr Ile
180 185 190

Ser Ser Leu Gln Pro Glu Asp Val Ala Thr Tyr Tyr Cys Gln Gln Gly
195 200 205

Asn Thr Leu Pro Trp Thr Phe Gly Gly Gly Thr Lys Val Glu Ile Lys
210 215 220

Gly Gly Gly Gly Ser Gly Gly Gly Gly Ser Gly Gly Gly Gly Ser Gln
225 230 235 240

Val Gln Leu Val Gln Ser Gly Ala Glu Val Lys Lys Pro Gly Ser Ser
245 250 255

Val Lys Val Ser Cys Lys Ala Ser Gly Tyr Thr Phe Thr Ser Tyr Ile
260 265 270

Met His Trp Val Arg Gln Ala Pro Gly Gln Gly Leu Glu Trp Ile Gly
275 280 285

Tyr Ile Asn Pro Tyr Asn Ser Gly Thr Lys Tyr Asn Glu Lys Phe Lys
290 295 300

Gly Arg Val Thr Ile Thr Ser Asp Lys Ser Thr Ser Thr Ala Tyr Met
305 310 315 320

Glu Leu Ser Ser Leu Arg Ser Glu Asp Thr Ala Val Tyr Tyr Cys Ala
325 330 335

His Tyr Tyr Gly Ser Thr Phe Thr Met Asp Tyr Trp Gly Gln Gly Thr
340 345 350

Thr Val Thr Val Ser Ser
355

<210> SEQ ID NO 24
<211> LENGTH: 697
<212> TYPE: PRT
<213> ORGANISM: Artificial sequence
<220> FEATURE:

<223> OTHER INFORMATION: Synthesized

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Ser Gly Gly
        435                 440                 445

Gly Gly Ser Gly Gly Gly Gly Ser Asp Ile Gln Met Thr Gln Ser Pro
    450                 455                 460

Ser Ser Leu Ser Ala Ser Val Gly Asp Arg Val Thr Ile Thr Cys Arg
465                 470                 475                 480

Ala Ser Gln Asp Ile Arg Thr Tyr Leu Asn Trp Tyr Gln Gln Lys Pro
                485                 490                 495

Gly Lys Val Pro Lys Leu Leu Ile Tyr Tyr Thr Ser Arg Leu His Ser
            500                 505                 510

Gly Val Pro Ser Arg Phe Ser Gly Ser Gly Ser Gly Thr Asp Tyr Thr
        515                 520                 525

Leu Thr Ile Ser Ser Leu Gln Pro Glu Asp Val Ala Thr Tyr Tyr Cys
    530                 535                 540

Gln Gln Gly Asn Thr Leu Pro Trp Thr Phe Gly Gly Gly Thr Lys Val
545                 550                 555                 560

Glu Ile Lys Gly Gly Gly Gly Ser Gly Gly Gly Gly Ser Gly Gly Gly
                565                 570                 575

Gly Ser Gln Val Gln Leu Val Gln Ser Gly Ala Glu Val Lys Lys Pro
            580                 585                 590

Gly Ser Ser Val Lys Val Ser Cys Lys Ala Ser Gly Tyr Thr Phe Thr
        595                 600                 605

Ser Tyr Ile Met His Trp Val Arg Gln Ala Pro Gly Gln Gly Leu Glu
    610                 615                 620

Trp Ile Gly Tyr Ile Asn Pro Tyr Asn Ser Gly Thr Lys Tyr Asn Glu
625                 630                 635                 640

Lys Phe Lys Gly Arg Val Thr Ile Thr Ser Asp Lys Ser Thr Ser Thr
                645                 650                 655

Ala Tyr Met Glu Leu Ser Ser Leu Arg Ser Glu Asp Thr Ala Val Tyr
            660                 665                 670

Tyr Cys Ala His Tyr Tyr Gly Ser Thr Phe Thr Met Asp Tyr Trp Gly
        675                 680                 685

Gln Gly Thr Thr Val Thr Val Ser Ser
    690                 695


<210> SEQ ID NO 25
<211> LENGTH: 218
<212> TYPE: PRT
<213> ORGANISM: Artificial sequence
<220> FEATURE:
<223> OTHER INFORMATION: Synthesized

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Gly Ala Pro
        35                  40                  45

Lys Leu Leu Ile Tyr Ala Ala Ser Asn Gln Gly Ser Gly Val Pro Ser
    50                  55                  60
```

Arg Phe Ser Gly Ser Gly Ser Gly Thr Asp Phe Thr Leu Thr Ile Ser
65 70 75 80

Ser Leu Gln Pro Asp Asp Phe Ala Thr Tyr Tyr Cys Gln Gln Ser Lys
85 90 95

Glu Val Pro Trp Thr Phe Gly Gln Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 26
<211> LENGTH: 19
<212> TYPE: PRT
<213> ORGANISM: Artificial sequence
<220> FEATURE:
<223> OTHER INFORMATION: Synthesized

<400> SEQUENCE: 26

Met Gly Trp Ser Trp Ile Phe Phe Phe Leu Leu Ser Gly Thr Ala Ser
1 5 10 15

Val Leu Ser

<210> SEQ ID NO 27
<211> LENGTH: 243
<212> TYPE: PRT
<213> ORGANISM: Artificial sequence
<220> FEATURE:
<223> OTHER INFORMATION: Synthesized

<400> SEQUENCE: 27

Met Asp Pro Asn Phe Trp Leu Gln Val Gln Glu Ser Val Thr Val Gln
1 5 10 15

Glu Gly Leu Cys Val Leu Val Pro Cys Thr Phe Phe His Pro Ile Pro
20 25 30

Tyr Tyr Asp Lys Asn Ser Pro Val His Gly Tyr Trp Phe Arg Glu Gly
35 40 45

Ala Ile Ile Ser Arg Asp Ser Pro Val Ala Thr Asn Lys Leu Asp Gln
50 55 60

Glu Val Gln Glu Glu Thr Gln Gly Arg Phe Arg Leu Leu Gly Asp Pro
65 70 75 80

Ser Arg Asn Asn Cys Ser Leu Ser Ile Val Asp Ala Arg Arg Arg Asp
85 90 95

Asn Gly Ser Tyr Phe Phe Arg Met Glu Arg Gly Ser Thr Lys Tyr Ser
100 105 110

Tyr Lys Ser Pro Gln Leu Ser Val His Val Thr Asp Leu Thr His Arg
115 120 125

```
Pro Lys Ile Leu Ile Pro Gly Thr Leu Glu Pro Gly His Ser Lys Asn
    130                 135                 140

Leu Thr Cys Ser Val Ser Trp Ala Cys Glu Gln Gly Thr Pro Pro Ile
145                 150                 155                 160

Phe Ser Trp Leu Ser Ala Ala Pro Thr Ser Leu Gly Pro Arg Thr Thr
                165                 170                 175

His Ser Ser Val Leu Ile Ile Thr Pro Arg Pro Gln Asp His Gly Thr
            180                 185                 190

Asn Leu Thr Cys Gln Val Lys Phe Ala Gly Ala Gly Val Thr Thr Glu
        195                 200                 205

Arg Thr Ile Gln Leu Asn Val Thr Tyr Val Pro Gln Asn Pro Thr Thr
    210                 215                 220

Gly Ile Phe Pro Gly Asp Gly Ser Gly Lys Gln Glu Thr Arg Ala Gly
225                 230                 235                 240

Val Val His


<210> SEQ ID NO 28
<211> LENGTH: 1210
<212> TYPE: PRT
<213> ORGANISM: Homo sapiens

<400> SEQUENCE: 28

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255
```

```
Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670
```

```
Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080
```

```
Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200

Ser Ser  Glu Phe Ile Gly Ala
    1205                 1210
```

<210> SEQ ID NO 29
<211> LENGTH: 138
<212> TYPE: PRT
<213> ORGANISM: Artificial sequence
<220> FEATURE:
<223> OTHER INFORMATION: Synthesized

<400> SEQUENCE: 29

```
Met Ala Val Leu Ala Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala
    130                 135
```

<210> SEQ ID NO 30
<211> LENGTH: 127
<212> TYPE: PRT
<213> ORGANISM: Artificial sequence
<220> FEATURE:
<223> OTHER INFORMATION: Synthesized

<400> SEQUENCE: 30

```
Met Arg Ala Pro Ala Gln Phe Leu Gly Phe Leu Leu Phe Trp Ile Pro
1               5                   10                  15

Ala Ser Arg Ser Asp Ile Leu Leu Thr Gln Ser Pro Val Ile Leu Ser
            20                  25                  30
```

```
Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Asn Asn
            100                 105                 110

Asn Trp Pro Thr Thr Phe Gly Ala Gly Thr Lys Leu Glu Leu Lys
        115                 120                 125


<210> SEQ ID NO 31
<211> LENGTH: 375
<212> TYPE: PRT
<213> ORGANISM: Artificial sequence
<220> FEATURE:
<223> OTHER INFORMATION: Synthesized

<400> SEQUENCE: 31

Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
        35                  40                  45

Cys Val Gln Pro Glu Phe His Cys Gly Asp Pro Cys Cys Thr Thr Cys
    50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
        115                 120                 125

Val Pro Gly Ser Pro Pro Ala Glu Pro Leu Gly Thr Gly Gly Gly Glu
    130                 135                 140

Pro Lys Ser Cys Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270
```

Glu Pro Gln Val Tyr Thr Leu Pro Pro Ser Arg Asp Glu Leu Thr Lys
275 280 285

Asn Gln Val Ser Leu Thr Cys Leu Val Lys Gly Phe Tyr Pro Ser Asp
290 295 300

Ile Ala Val Glu Trp Glu Ser Asn Gly Gln Pro Glu Asn Asn Tyr Lys
305 310 315 320

Thr Thr Pro Pro Val Leu Asp Ser Asp Gly Ser Phe Phe Leu Tyr Ser
325 330 335

Lys Leu Thr Val Asp Lys Ser Arg Trp Gln Gln Gly Asn Val Phe Ser
340 345 350

Cys Ser Val Met His Glu Ala Leu His Asn His Tyr Thr Gln Lys Ser
355 360 365

Leu Ser Leu Ser Pro Gly Lys
370 375

<210> SEQ ID NO 32
<211> LENGTH: 137
<212> TYPE: PRT
<213> ORGANISM: Artificial sequence
<220> FEATURE:
<223> OTHER INFORMATION: Synthesized

<400> SEQUENCE: 32

Met Ala Val Leu Gly Leu Leu Leu Cys Leu Val Thr Phe Pro Ser Cys
1 5 10 15

Val Leu Ser Gln Val Thr Leu Lys Glu Ser Gly Pro Val Leu Val Lys
20 25 30

Pro Thr Glu Thr Leu Thr Leu Thr Cys Thr Val Ser Gly Phe Ser Leu
35 40 45

Thr Asp Tyr Gly Val Ser Trp Ile Arg Gln Pro Pro Gly Lys Ala Leu
50 55 60

Glu Trp Leu Gly Val Ile Trp Gly Gly Gly Gly Thr Tyr Tyr Asn Ser
65 70 75 80

Ala Leu Lys Ser Arg Leu Thr Ile Ser Lys Asp Thr Ser Lys Ser Gln
85 90 95

Val Val Leu Thr Met Thr Asn Met Asp Pro Val Asp Thr Ala Thr Tyr
100 105 110

Tyr Cys Ala Lys His Pro Tyr Gly His Phe Gly Met Asp Tyr Trp Gly
115 120 125

Gln Gly Thr Thr Val Thr Val Ser Ser
130 135

<210> SEQ ID NO 33
<211> LENGTH: 5
<212> TYPE: PRT
<213> ORGANISM: Artificial sequence
<220> FEATURE:
<223> OTHER INFORMATION: Synthesized

<400> SEQUENCE: 33

Asp Tyr Gly Val Ser
1 5

<210> SEQ ID NO 34
<211> LENGTH: 16
<212> TYPE: PRT
<213> ORGANISM: Artificial sequence
<220> FEATURE:
<223> OTHER INFORMATION: Synthesized

<400> SEQUENCE: 34

Val Ile Trp Gly Gly Gly Gly Thr Tyr Tyr Asn Ser Ala Leu Lys Ser
1 5 10 15

<210> SEQ ID NO 35
<211> LENGTH: 10
<212> TYPE: PRT
<213> ORGANISM: Artificial sequence
<220> FEATURE:
<223> OTHER INFORMATION: Synthesized

<400> SEQUENCE: 35

His Pro Tyr Gly His Phe Gly Met Asp Tyr
1 5 10

<210> SEQ ID NO 36
<211> LENGTH: 127
<212> TYPE: PRT
<213> ORGANISM: Artificial sequence
<220> FEATURE:
<223> OTHER INFORMATION: Synthesized

<400> SEQUENCE: 36

Met Arg Val Leu Ala Glu Leu Leu Gly Leu Leu Leu Phe Cys Phe Leu
1 5 10 15

Gly Val Arg Cys Asp Ile Gln Met Thr Gln Ser Pro Ser Ser Leu Ser
20 25 30

Ala Ser Val Gly Asp Arg Val Thr Ile Thr Cys His Ala Ser Gln Asn
35 40 45

Ile Asn Val Trp Leu Ser Trp Tyr Gln Gln Lys Pro Gly Lys Val Pro
50 55 60

Lys Leu Leu Ile Tyr Lys Ala Ser Asn Leu His Thr Gly Val Pro Ser
65 70 75 80

Arg Phe Ser Gly Ser Gly Ser Gly Thr Asp Phe Thr Leu Thr Ile Ser
85 90 95

Ser Leu Gln Pro Glu Asp Val Ala Thr Tyr Tyr Cys Gln Gln Gly Gln
100 105 110

Ser Tyr Pro Leu Thr Phe Gly Gly Gly Thr Lys Val Glu Ile Lys
115 120 125

<210> SEQ ID NO 37
<211> LENGTH: 11
<212> TYPE: PRT
<213> ORGANISM: Artificial sequence
<220> FEATURE:
<223> OTHER INFORMATION: Synthesized

<400> SEQUENCE: 37

His Ala Ser Gln Asn Ile Asn Val Trp Leu Ser
1 5 10

<210> SEQ ID NO 38
<211> LENGTH: 7
<212> TYPE: PRT
<213> ORGANISM: Artificial sequence
<220> FEATURE:
<223> OTHER INFORMATION: Synthesized

<400> SEQUENCE: 38

Lys Ala Ser Asn Leu His Thr
1 5

<210> SEQ ID NO 39
<211> LENGTH: 9
<212> TYPE: PRT
<213> ORGANISM: Artificial sequence
<220> FEATURE:
<223> OTHER INFORMATION: Synthesized

<400> SEQUENCE: 39

Gln Gln Gly Gln Ser Tyr Pro Leu Thr
1 5

<210> SEQ ID NO 40
<211> LENGTH: 241
<212> TYPE: PRT
<213> ORGANISM: Homo sapiens

<400> SEQUENCE: 40

Met Ala Gln His Gly Ala Met Gly Ala Phe Arg Ala Leu Cys Gly Leu
1 5 10 15

Ala Leu Leu Cys Ala Leu Ser Leu Gly Gln Arg Pro Thr Gly Gly Pro
20 25 30

Gly Cys Gly Pro Gly Arg Leu Leu Leu Gly Thr Gly Thr Asp Ala Arg
35 40 45

Cys Cys Arg Val His Thr Thr Arg Cys Cys Arg Asp Tyr Pro Gly Glu
50 55 60

Glu Cys Cys Ser Glu Trp Asp Cys Met Cys Val Gln Pro Glu Phe His
65 70 75 80

Cys Gly Asp Pro Cys Cys Thr Thr Cys Arg His His Pro Cys Pro Pro
85 90 95

Gly Gln Gly Val Gln Ser Gln Gly Lys Phe Ser Phe Gly Phe Gln Cys
100 105 110

Ile Asp Cys Ala Ser Gly Thr Phe Ser Gly Gly His Glu Gly His Cys
115 120 125

Lys Pro Trp Thr Asp Cys Thr Gln Phe Gly Phe Leu Thr Val Phe Pro
130 135 140

Gly Asn Lys Thr His Asn Ala Val Cys Val Pro Gly Ser Pro Pro Ala
145 150 155 160

Glu Pro Leu Gly Trp Leu Thr Val Val Leu Leu Ala Val Ala Ala Cys
165 170 175

Val Leu Leu Leu Thr Ser Ala Gln Leu Gly Leu His Ile Trp Gln Leu
180 185 190

Arg Ser Gln Cys Met Trp Pro Arg Glu Thr Gln Leu Leu Leu Glu Val
195 200 205

Pro Pro Ser Thr Glu Asp Ala Arg Ser Cys Gln Phe Pro Glu Glu Glu
210 215 220

Arg Gly Glu Arg Ser Ala Glu Glu Lys Gly Arg Leu Gly Asp Leu Trp
225 230 235 240

Val

<210> SEQ ID NO 41
<211> LENGTH: 240
<212> TYPE: PRT
<213> ORGANISM: Artificial sequence
<220> FEATURE:
<223> OTHER INFORMATION: Synthesized

<400> SEQUENCE: 41

Asp Ile Gln Met Thr Gln Ser Pro Ser Ser Leu Ser Ala Ser Val Gly
1 5 10 15

Asp Arg Val Thr Ile Thr Cys His Ala Ser Gln Asn Ile Asn Val Trp
20 25 30

Leu Ser Trp Tyr Gln Gln Lys Pro Gly Lys Val Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Gln Gly Gln Ser Tyr Pro Leu
85 90 95

Thr Phe Gly Gly Gly Thr Lys Val Glu Ile Lys Gly Gly Gly Gly Ser
100 105 110

Gly Gly Gly Gly Ser Gly Gly Gly Gly Ser Gln Val Thr Leu Lys Glu
115 120 125

Ser Gly Pro Val Leu Val Lys Pro Thr Glu Thr Leu Thr Leu Thr Cys
130 135 140

Thr Val Ser Gly Phe Ser Leu Thr Asp Tyr Gly Val Ser Trp Ile Arg
145 150 155 160

Gln Pro Pro Gly Lys Ala Leu Glu Trp Leu Gly Val Ile Trp Gly Gly
165 170 175

Gly Gly Thr Tyr Tyr Asn Ser Ala Leu Lys Ser Arg Leu Thr Ile Ser
180 185 190

Lys Asp Thr Ser Lys Ser Gln Val Val Leu Thr Met Thr Asn Met Asp
195 200 205

Pro Val Asp Thr Ala Thr Tyr Tyr Cys Ala Lys His Pro Tyr Gly His
210 215 220

Phe Gly Met Asp Tyr Trp Gly Gln Gly Thr Thr Val Thr Val Ser Ser
225 230 235 240

<210> SEQ ID NO 42
<211> LENGTH: 357
<212> TYPE: PRT
<213> ORGANISM: Artificial sequence
<220> FEATURE:
<223> OTHER INFORMATION: Synthesized

<400> SEQUENCE: 42

Gly Gln Pro Arg Glu Pro Gln Val Tyr Thr Leu Pro Pro Ser Arg Asp
1 5 10 15

Glu Leu Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Lys Leu Thr Val Asp Lys Ser Arg Trp Gln Gln Gly
65 70 75 80

Asn Val Phe Ser Cys Ser Val Met His Glu Ala Leu His Asn His Tyr
85 90 95

Thr Gln Lys Ser Leu Ser Leu Ser Pro Gly Ser Gly Gly Gly Gly Ser
100 105 110

```
Gly Gly Gly Gly Ser Asp Ile Gln Met Thr Gln Ser Pro Ser Ser Leu
        115                 120                 125

Ser Ala Ser Val Gly Asp Arg Val Thr Ile Thr Cys His Ala Ser Gln
    130                 135                 140

Asn Ile Asn Val Trp Leu Ser Trp Tyr Gln Gln Lys Pro Gly Lys Val
145                 150                 155                 160

Pro Lys Leu Leu Ile Tyr Lys Ala Ser Asn Leu His Thr Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Val Ala Thr Tyr Tyr Cys Gln Gln Gly
        195                 200                 205

Gln Ser Tyr Pro Leu Thr Phe Gly Gly Gly Thr Lys Val Glu Ile Lys
    210                 215                 220

Gly Gly Gly Gly Ser Gly Gly Gly Gly Ser Gly Gly Gly Gly Ser Gln
225                 230                 235                 240

Val Thr Leu Lys Glu Ser Gly Pro Val Leu Val Lys Pro Thr Glu Thr
                245                 250                 255

Leu Thr Leu Thr Cys Thr Val Ser Gly Phe Ser Leu Thr Asp Tyr Gly
            260                 265                 270

Val Ser Trp Ile Arg Gln Pro Pro Gly Lys Ala Leu Glu Trp Leu Gly
        275                 280                 285

Val Ile Trp Gly Gly Gly Gly Thr Tyr Tyr Asn Ser Ala Leu Lys Ser
    290                 295                 300

Arg Leu Thr Ile Ser Lys Asp Thr Ser Lys Ser Gln Val Val Leu Thr
305                 310                 315                 320

Met Thr Asn Met Asp Pro Val Asp Thr Ala Thr Tyr Tyr Cys Ala Lys
                325                 330                 335

His Pro Tyr Gly His Phe Gly Met Asp Tyr Trp Gly Gln Gly Thr Thr
            340                 345                 350

Val Thr Val Ser Ser
        355
```

<210> SEQ ID NO 43
<211> LENGTH: 699
<212> TYPE: PRT
<213> ORGANISM: Artificial sequence
<220> FEATURE:
<223> OTHER INFORMATION: Synthesized

<400> SEQUENCE: 43

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110
```

```
Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Asp Ile Gln Met Thr
    450                 455                 460

Gln Ser Pro Ser Ser Leu Ser Ala Ser Val Gly Asp Arg Val Thr Ile
465                 470                 475                 480

Thr Cys His Ala Ser Gln Asn Ile Asn Val Trp Leu Ser Trp Tyr Gln
                485                 490                 495

Gln Lys Pro Gly Lys Val Pro Lys Leu Leu Ile Tyr Lys Ala Ser Asn
            500                 505                 510

Leu His Thr Gly Val Pro Ser Arg Phe Ser Gly Ser Gly Ser Gly Thr
        515                 520                 525
```

Asp Phe Thr Leu Thr Ile Ser Ser Leu Gln Pro Glu Asp Val Ala Thr
530 535 540

Tyr Tyr Cys Gln Gln Gly Gln Ser Tyr Pro Leu Thr Phe Gly Gly Gly
545 550 555 560

Thr Lys Val Glu Ile Lys Gly Gly Gly Gly Ser Gly Gly Gly Gly Ser
565 570 575

Gly Gly Gly Gly Ser Gln Val Thr Leu Lys Glu Ser Gly Pro Val Leu
580 585 590

Val Lys Pro Thr Glu Thr Leu Thr Leu Thr Cys Thr Val Ser Gly Phe
595 600 605

Ser Leu Thr Asp Tyr Gly Val Ser Trp Ile Arg Gln Pro Pro Gly Lys
610 615 620

Ala Leu Glu Trp Leu Gly Val Ile Trp Gly Gly Gly Gly Thr Tyr Tyr
625 630 635 640

Asn Ser Ala Leu Lys Ser Arg Leu Thr Ile Ser Lys Asp Thr Ser Lys
645 650 655

Ser Gln Val Val Leu Thr Met Thr Asn Met Asp Pro Val Asp Thr Ala
660 665 670

Thr Tyr Tyr Cys Ala Lys His Pro Tyr Gly His Phe Gly Met Asp Tyr
675 680 685

Trp Gly Gln Gly Thr Thr Val Thr Val Ser Ser
690 695

<210> SEQ ID NO 44
<211> LENGTH: 214
<212> TYPE: PRT
<213> ORGANISM: Artificial sequence
<220> FEATURE:
<223> OTHER INFORMATION: Synthesized

<400> SEQUENCE: 44

Asp Ile Leu Leu Thr Gln Ser Pro Val Ile Leu Ser Val Ser Pro Gly
1 5 10 15

Glu Arg Val Ser Phe Ser Cys Arg Ala Ser Gln Ser Ile Gly Thr Asn
20 25 30

Ile His Trp Tyr Gln Gln Arg Thr Asn Gly Ser Pro Arg Leu Leu Ile
35 40 45

Lys Tyr Ala Ser Glu Ser Ile Ser Gly Ile Pro Ser Arg Phe Ser Gly
50 55 60

Ser Gly Ser Gly Thr Asp Phe Thr Leu Ser Ile Asn Ser Val Glu Ser
65 70 75 80

Glu Asp Ile Ala Asp Tyr Tyr Cys Gln Gln Asn Asn Asn Trp Pro Thr
85 90 95

Thr Phe Gly Ala Gly Thr Lys Leu Glu Leu Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 45
<211> LENGTH: 216
<212> TYPE: PRT
<213> ORGANISM: Homo sapiens

<400> SEQUENCE: 45

Gln Arg Pro Thr Gly Gly Pro Gly Cys Gly Pro Gly Arg Leu Leu Leu
1 5 10 15

Gly Thr Gly Thr Asp Ala Arg Cys Cys Arg Val His Thr Thr Arg Cys
20 25 30

Cys Arg Asp Tyr Pro Gly Glu Glu Cys Cys Ser Glu Trp Asp Cys Met
35 40 45

Cys Val Gln Pro Glu Phe His Cys Gly Asp Pro Cys Cys Thr Thr Cys
50 55 60

Arg His His Pro Cys Pro Pro Gly Gln Gly Val Gln Ser Gln Gly Lys
65 70 75 80

Phe Ser Phe Gly Phe Gln Cys Ile Asp Cys Ala Ser Gly Thr Phe Ser
85 90 95

Gly Gly His Glu Gly His Cys Lys Pro Trp Thr Asp Cys Thr Gln Phe
100 105 110

Gly Phe Leu Thr Val Phe Pro Gly Asn Lys Thr His Asn Ala Val Cys
115 120 125

Val Pro Gly Ser Pro Pro Ala Glu Pro Leu Gly Trp Leu Thr Val Val
130 135 140

Leu Leu Ala Val Ala Ala Cys Val Leu Leu Leu Thr Ser Ala Gln Leu
145 150 155 160

Gly Leu His Ile Trp Gln Leu Arg Ser Gln Cys Met Trp Pro Arg Glu
165 170 175

Thr Gln Leu Leu Leu Glu Val Pro Pro Ser Thr Glu Asp Ala Arg Ser
180 185 190

Cys Gln Phe Pro Glu Glu Glu Arg Gly Glu Arg Ser Ala Glu Glu Lys
195 200 205

Gly Arg Leu Gly Asp Leu Trp Val
210 215

<210> SEQ ID NO 46
<211> LENGTH: 621
<212> TYPE: PRT
<213> ORGANISM: Artificial sequence
<220> FEATURE:
<223> OTHER INFORMATION: Synthesized

<400> SEQUENCE: 46

Leu Glu Glu Lys Lys Val Cys Gln Gly Thr Ser Asn Lys Leu Thr Gln
1 5 10 15

Leu Gly Thr Phe Glu Asp His Phe Leu Ser Leu Gln Arg Met Phe Asn
20 25 30

Asn Cys Glu Val Val Leu Gly Asn Leu Glu Ile Thr Tyr Val Gln Arg
35 40 45

Asn Tyr Asp Leu Ser Phe Leu Lys Thr Ile Gln Glu Val Ala Gly Tyr
50 55 60

-continued

```
Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480
```

Val Cys His Ala Leu Cys Ser Pro Glu Gly Cys Trp Gly Pro Glu Pro
485 490 495

Arg Asp Cys Val Ser Cys Arg Asn Val Ser Arg Gly Arg Glu Cys Val
500 505 510

Asp Lys Cys Asn Leu Leu Glu Gly Glu Pro Arg Glu Phe Val Glu Asn
515 520 525

Ser Glu Cys Ile Gln Cys His Pro Glu Cys Leu Pro Gln Ala Met Asn
530 535 540

Ile Thr Cys Thr Gly Arg Gly Pro Asp Asn Cys Ile Gln Cys Ala His
545 550 555 560

Tyr Ile Asp Gly Pro His Cys Val Lys Thr Cys Pro Ala Gly Val Met
565 570 575

Gly Glu Asn Asn Thr Leu Val Trp Lys Tyr Ala Asp Ala Gly His Val
580 585 590

Cys His Leu Cys His Pro Asn Cys Thr Tyr Gly Cys Thr Gly Pro Gly
595 600 605

Leu Glu Gly Cys Pro Thr Asn Gly Pro Lys Ile Pro Ser
610 615 620

<210> SEQ ID NO 47
<211> LENGTH: 409
<212> TYPE: PRT
<213> ORGANISM: Artificial sequence
<220> FEATURE:
<223> OTHER INFORMATION: Synthesized

<400> SEQUENCE: 47

Glu Pro Pro Thr Ala Cys Arg Glu Lys Gln Tyr Leu Ile Asn Ser Gln
1 5 10 15

Cys Cys Ser Leu Cys Gln Pro Gly Gln Lys Leu Val Ser Asp Cys Thr
20 25 30

Glu Phe Thr Glu Thr Glu Cys Leu Pro Cys Gly Glu Ser Glu Phe Leu
35 40 45

Asp Thr Trp Asn Arg Glu Thr His Cys His Gln His Lys Tyr Cys Asp
50 55 60

Pro Asn Leu Gly Leu Arg Val Gln Gln Lys Gly Thr Ser Glu Thr Asp
65 70 75 80

Thr Ile Cys Thr Cys Glu Glu Gly Trp His Cys Thr Ser Glu Ala Cys
85 90 95

Glu Ser Cys Val Leu His Arg Ser Cys Ser Pro Gly Phe Gly Val Lys
100 105 110

Gln Ile Ala Thr Gly Val Ser Asp Thr Ile Cys Glu Pro Cys Pro Val
115 120 125

Gly Phe Phe Ser Asn Val Ser Ser Ala Phe Glu Lys Cys His Pro Trp
130 135 140

Thr Ser Cys Glu Thr Lys Asp Leu Val Val Gln Gln Ala Gly Thr Asn
145 150 155 160

Lys Thr Asp Val Val Cys Gly Pro Gln Asp Arg Leu Arg Thr Gly Gly
165 170 175

Gly Glu Pro Lys Ser Cys Asp Lys Thr His Thr Cys Pro Pro Cys Pro
180 185 190

Ala Pro Glu Leu Leu Gly Gly Pro Ser Val Phe Leu Phe Pro Pro Lys
195 200 205

Pro Lys Asp Thr Leu Met Ile Ser Arg Thr Pro Glu Val Thr Cys Val
210 215 220

Val Val Asp Val Ser His Glu Asp Pro Glu Val Lys Phe Asn Trp Tyr
225 230 235 240

Val Asp Gly Val Glu Val His Asn Ala Lys Thr Lys Pro Arg Glu Glu
245 250 255

Gln Tyr Asn Ser Thr Tyr Arg Val Val Ser Val Leu Thr Val Leu His
260 265 270

Gln Asp Trp Leu Asn Gly Lys Glu Tyr Lys Cys Lys Val Ser Asn Lys
275 280 285

Ala Leu Pro Ala Pro Ile Glu Lys Thr Ile Ser Lys Ala Lys Gly Gln
290 295 300

Pro Arg Glu Pro Gln Val Tyr Thr Leu Pro Pro Ser Arg Asp Glu Leu
305 310 315 320

Thr Lys Asn Gln Val Ser Leu Thr Cys Leu Val Lys Gly Phe Tyr Pro
325 330 335

Ser Asp Ile Ala Val Glu Trp Glu Ser Asn Gly Gln Pro Glu Asn Asn
340 345 350

Tyr Lys Thr Thr Pro Pro Val Leu Asp Ser Asp Gly Ser Phe Phe Leu
355 360 365

Tyr Ser Lys Leu Thr Val Asp Lys Ser Arg Trp Gln Gln Gly Asn Val
370 375 380

Phe Ser Cys Ser Val Met His Glu Ala Leu His Asn His Tyr Thr Gln
385 390 395 400

Lys Ser Leu Ser Leu Ser Pro Gly Lys
405

<210> SEQ ID NO 48
<211> LENGTH: 138
<212> TYPE: PRT
<213> ORGANISM: Artificial sequence
<220> FEATURE:
<223> OTHER INFORMATION: Synthesized

<400> SEQUENCE: 48

Met Lys Leu Trp Leu Asn Trp Val Phe Leu Leu Thr Leu Leu His Gly
1 5 10 15

Ile Gln Cys Gln Val Gln Leu Val Gln Ser Gly Ala Glu Val Lys Lys
20 25 30

Pro Gly Ser Ser Val Lys Val Ser Cys Lys Ala Ser Gly Tyr Thr Phe
35 40 45

Thr Ser Tyr Trp Leu His Trp Val Arg Gln Ala Pro Gly Gln Gly Leu
50 55 60

Glu Trp Ile Gly Arg Ile Asp Pro Asn Ser Gly Asp Thr Lys Tyr Asn
65 70 75 80

Glu Lys Phe Lys Ser Arg Ala Thr Ile Thr Val Asp Lys Ser Thr Ser
85 90 95

Thr Ala Tyr Met Glu Leu Ser Ser Leu Arg Ser Glu Asp Thr Ala Val
100 105 110

Tyr Tyr Cys Ala Arg Tyr Tyr Tyr Gly Arg Ser Tyr Phe Asp Tyr Trp
115 120 125

Gly Gln Gly Thr Thr Val Thr Val Ser Ser
130 135

<210> SEQ ID NO 49
<211> LENGTH: 5
<212> TYPE: PRT
<213> ORGANISM: Artificial sequence
<220> FEATURE:
<223> OTHER INFORMATION: Synthesized

<400> SEQUENCE: 49

Ser Tyr Trp Leu His
1               5

<210> SEQ ID NO 50
<211> LENGTH: 17
<212> TYPE: PRT
<213> ORGANISM: Artificial sequence
<220> FEATURE:
<223> OTHER INFORMATION: Synthesized

<400> SEQUENCE: 50

Arg Ile Asp Pro Asn Ser Gly Asp Thr Lys Tyr Asn Glu Lys Phe Lys
1               5                   10                  15

Ser

<210> SEQ ID NO 51
<211> LENGTH: 10
<212> TYPE: PRT
<213> ORGANISM: Artificial sequence
<220> FEATURE:
<223> OTHER INFORMATION: Synthesized

<400> SEQUENCE: 51

Tyr Tyr Tyr Gly Arg Ser Tyr Phe Asp Tyr
1               5                   10

<210> SEQ ID NO 52
<211> LENGTH: 127
<212> TYPE: PRT
<213> ORGANISM: Artificial sequence
<220> FEATURE:
<223> OTHER INFORMATION: Synthesized

<400> SEQUENCE: 52

Met Asp Phe Gln Val Gln Ile Phe Ser Phe Leu Leu Ile Ser Ala Val
1               5                   10                  15

Ile Ile Ser Arg Gly Glu Ile Val Leu Thr Gln Ser Pro Ala Thr Leu
            20                  25                  30

Ser Leu Ser Pro Gly Glu Arg Ala Thr Leu Ser Cys Ser Ala Ser Ser
        35                  40                  45

Ser Val Ser Tyr Met His Trp Tyr Gln Gln Lys Pro Gly Gln Ala Pro
    50                  55                  60

Arg Arg Trp Ile Tyr Asp Thr Ser Lys Leu Ala Ser Gly Val Pro Ala
65                  70                  75                  80

Arg Phe Ser Gly Ser Gly Ser Gly Thr Asp Tyr Thr Leu Thr Ile Ser
                85                  90                  95

Ser Leu Glu Pro Glu Asp Phe Ala Val Tyr Tyr Cys Gln Gln Trp Ser
            100                 105                 110

Ser Asn Pro Leu Thr Phe Gly Gly Gly Thr Lys Val Glu Ile Lys
        115                 120                 125

<210> SEQ ID NO 53
<211> LENGTH: 10
<212> TYPE: PRT
<213> ORGANISM: Artificial sequence
<220> FEATURE:
<223> OTHER INFORMATION: Synthesized

<400> SEQUENCE: 53

Ser Ala Ser Ser Ser Val Ser Tyr Met His
1 5 10

<210> SEQ ID NO 54
<211> LENGTH: 7
<212> TYPE: PRT
<213> ORGANISM: Artificial sequence
<220> FEATURE:
<223> OTHER INFORMATION: Synthesized

<400> SEQUENCE: 54

Asp Thr Ser Lys Leu Ala Ser
1 5

<210> SEQ ID NO 55
<211> LENGTH: 9
<212> TYPE: PRT
<213> ORGANISM: Artificial sequence
<220> FEATURE:
<223> OTHER INFORMATION: Synthesized

<400> SEQUENCE: 55

Gln Gln Trp Ser Ser Asn Pro Leu Thr
1 5

<210> SEQ ID NO 56
<211> LENGTH: 277
<212> TYPE: PRT
<213> ORGANISM: Homo sapiens

<400> SEQUENCE: 56

Met Val Arg Leu Pro Leu Gln Cys Val Leu Trp Gly Cys Leu Leu Thr
1 5 10 15

Ala Val His Pro Glu Pro Pro Thr Ala Cys Arg Glu Lys Gln Tyr Leu
20 25 30

Ile Asn Ser Gln Cys Cys Ser Leu Cys Gln Pro Gly Gln Lys Leu Val
35 40 45

Ser Asp Cys Thr Glu Phe Thr Glu Thr Glu Cys Leu Pro Cys Gly Glu
50 55 60

Ser Glu Phe Leu Asp Thr Trp Asn Arg Glu Thr His Cys His Gln His
65 70 75 80

Lys Tyr Cys Asp Pro Asn Leu Gly Leu Arg Val Gln Gln Lys Gly Thr
85 90 95

Ser Glu Thr Asp Thr Ile Cys Thr Cys Glu Glu Gly Trp His Cys Thr
100 105 110

Ser Glu Ala Cys Glu Ser Cys Val Leu His Arg Ser Cys Ser Pro Gly
115 120 125

Phe Gly Val Lys Gln Ile Ala Thr Gly Val Ser Asp Thr Ile Cys Glu
130 135 140

Pro Cys Pro Val Gly Phe Phe Ser Asn Val Ser Ser Ala Phe Glu Lys
145 150 155 160

Cys His Pro Trp Thr Ser Cys Glu Thr Lys Asp Leu Val Val Gln Gln
165 170 175

Ala Gly Thr Asn Lys Thr Asp Val Val Cys Gly Pro Gln Asp Arg Leu
180 185 190

Arg Ala Leu Val Val Ile Pro Ile Ile Phe Gly Ile Leu Phe Ala Ile
195 200 205

```
Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275
```

<210> SEQ ID NO 57
<211> LENGTH: 240
<212> TYPE: PRT
<213> ORGANISM: Artificial sequence
<220> FEATURE:
<223> OTHER INFORMATION: Synthesized

<400> SEQUENCE: 57

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys Gly Gly Gly Gly Ser Gly
            100                 105                 110

Gly Gly Gly Ser Gly Gly Gly Gly Ser Gln Val Gln Leu Val Gln Ser
        115                 120                 125

Gly Ala Glu Val Lys Lys Pro Gly Ser Ser Val Lys Val Ser Cys Lys
    130                 135                 140

Ala Ser Gly Tyr Thr Phe Thr Ser Tyr Trp Leu His Trp Val Arg Gln
145                 150                 155                 160

Ala Pro Gly Gln Gly Leu Glu Trp Ile Gly Arg Ile Asp Pro Asn Ser
                165                 170                 175

Gly Asp Thr Lys Tyr Asn Glu Lys Phe Lys Ser Arg Ala Thr Ile Thr
            180                 185                 190

Val Asp Lys Ser Thr Ser Thr Ala Tyr Met Glu Leu Ser Ser Leu Arg
        195                 200                 205

Ser Glu Asp Thr Ala Val Tyr Tyr Cys Ala Arg Tyr Tyr Tyr Gly Arg
    210                 215                 220

Ser Tyr Phe Asp Tyr Trp Gly Gln Gly Thr Thr Val Thr Val Ser Ser
225                 230                 235                 240
```

<210> SEQ ID NO 58
<211> LENGTH: 357
<212> TYPE: PRT
<213> ORGANISM: Artificial sequence
<220> FEATURE:
<223> OTHER INFORMATION: Synthesized

<400> SEQUENCE: 58

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Ser Gly Gly Gly Gly Ser
            100                 105                 110

Gly Gly Gly Gly Ser Glu Ile Val Leu Thr Gln Ser Pro Ala Thr Leu
        115                 120                 125

Ser Leu Ser Pro Gly Glu Arg Ala Thr Leu Ser Cys Ser Ala Ser Ser
    130                 135                 140

Ser Val Ser Tyr Met His Trp Tyr Gln Gln Lys Pro Gly Gln Ala Pro
145                 150                 155                 160

Arg Arg Trp Ile Tyr Asp Thr Ser Lys Leu Ala Ser Gly Val Pro Ala
                165                 170                 175

Arg Phe Ser Gly Ser Gly Ser Gly Thr Asp Tyr Thr Leu Thr Ile Ser
            180                 185                 190

Ser Leu Glu Pro Glu Asp Phe Ala Val Tyr Tyr Cys Gln Gln Trp Ser
        195                 200                 205

Ser Asn Pro Leu Thr Phe Gly Gly Gly Thr Lys Val Glu Ile Lys Gly
    210                 215                 220

Gly Gly Gly Ser Gly Gly Gly Gly Ser Gly Gly Gly Gly Ser Gln Val
225                 230                 235                 240

Gln Leu Val Gln Ser Gly Ala Glu Val Lys Lys Pro Gly Ser Ser Val
                245                 250                 255

Lys Val Ser Cys Lys Ala Ser Gly Tyr Thr Phe Thr Ser Tyr Trp Leu
            260                 265                 270

His Trp Val Arg Gln Ala Pro Gly Gln Gly Leu Glu Trp Ile Gly Arg
        275                 280                 285

Ile Asp Pro Asn Ser Gly Asp Thr Lys Tyr Asn Glu Lys Phe Lys Ser
    290                 295                 300

Arg Ala Thr Ile Thr Val Asp Lys Ser Thr Ser Thr Ala Tyr Met Glu
305                 310                 315                 320

Leu Ser Ser Leu Arg Ser Glu Asp Thr Ala Val Tyr Tyr Cys Ala Arg
                325                 330                 335

Tyr Tyr Tyr Gly Arg Ser Tyr Phe Asp Tyr Trp Gly Gln Gly Thr Thr
            340                 345                 350

Val Thr Val Ser Ser
        355

<210> SEQ ID NO 59
<211> LENGTH: 696
<212> TYPE: PRT
<213> ORGANISM: Artificial sequence
<220> FEATURE:
<223> OTHER INFORMATION: Synthesized

<400> SEQUENCE: 59

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asp Tyr
20 25 30

Asn Met His Trp Val Arg Gln Ala Pro Gly Gln Gly Leu Glu Trp Ile
35 40 45

Gly Tyr Ile Tyr Pro Tyr Asn Gly Gly Thr Gly Tyr Asn Gln Lys Phe
50 55 60

Lys Ser Lys Ala Thr Ile Thr Ala Asp Glu Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Gly Arg Pro Ala Met Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Ala Ala Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Ser Gly Gly
        435                 440                 445

Gly Gly Ser Gly Gly Gly Gly Ser Glu Ile Val Leu Thr Gln Ser Pro
    450                 455                 460

Ala Thr Leu Ser Leu Ser Pro Gly Glu Arg Ala Thr Leu Ser Cys Ser
465                 470                 475                 480

Ala Ser Ser Ser Val Ser Tyr Met His Trp Tyr Gln Gln Lys Pro Gly
                485                 490                 495

Gln Ala Pro Arg Arg Trp Ile Tyr Asp Thr Ser Lys Leu Ala Ser Gly
            500                 505                 510

Val Pro Ala Arg Phe Ser Gly Ser Gly Ser Gly Thr Asp Tyr Thr Leu
        515                 520                 525

Thr Ile Ser Ser Leu Glu Pro Glu Asp Phe Ala Val Tyr Tyr Cys Gln
    530                 535                 540

Gln Trp Ser Ser Asn Pro Leu Thr Phe Gly Gly Gly Thr Lys Val Glu
545                 550                 555                 560

Ile Lys Gly Gly Gly Gly Ser Gly Gly Gly Gly Ser Gly Gly Gly Gly
                565                 570                 575

Ser Gln Val Gln Leu Val Gln Ser Gly Ala Glu Val Lys Lys Pro Gly
            580                 585                 590

Ser Ser Val Lys Val Ser Cys Lys Ala Ser Gly Tyr Thr Phe Thr Ser
        595                 600                 605

Tyr Trp Leu His Trp Val Arg Gln Ala Pro Gly Gln Gly Leu Glu Trp
    610                 615                 620

Ile Gly Arg Ile Asp Pro Asn Ser Gly Asp Thr Lys Tyr Asn Glu Lys
625                 630                 635                 640

Phe Lys Ser Arg Ala Thr Ile Thr Val Asp Lys Ser Thr Ser Thr Ala
                645                 650                 655

Tyr Met Glu Leu Ser Ser Leu Arg Ser Glu Asp Thr Ala Val Tyr Tyr
            660                 665                 670

Cys Ala Arg Tyr Tyr Tyr Gly Arg Ser Tyr Phe Asp Tyr Trp Gly Gln
        675                 680                 685

Gly Thr Thr Val Thr Val Ser Ser
    690                 695
```

<210> SEQ ID NO 60
<211> LENGTH: 458
<212> TYPE: PRT
<213> ORGANISM: Artificial sequence
<220> FEATURE:
<223> OTHER INFORMATION: Synthesized

<400> SEQUENCE: 60

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60
```

```
Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His Thr Gly
    210                 215                 220

Gly Gly Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 61
<211> LENGTH: 138

<212> TYPE: PRT
<213> ORGANISM: Artificial sequence
<220> FEATURE:
<223> OTHER INFORMATION: Synthesized

<400> SEQUENCE: 61

Met Glu Trp Asn Trp Val Val Leu Phe Leu Leu Ser Leu Thr Ala Gly
1 5 10 15

Val Tyr Ala Gln Val Gln Leu Val Gln Ser Gly Ala Glu Val Lys Lys
20 25 30

Pro Gly Ser Ser Val Lys Val Ser Cys Lys Ala Ser Gly Phe Thr Phe
35 40 45

Ser Ser Ser Tyr Ile Ser Trp Val Arg Gln Ala Pro Gly Gln Gly Leu
50 55 60

Glu Trp Ile Ala Trp Ile Tyr Ala Gly Thr Gly Gly Thr Ser Tyr Asn
65 70 75 80

Gln Lys Phe Thr Gly Arg Ala Thr Ile Thr Val Asp Glu Ser Thr Ser
85 90 95

Thr Ala Tyr Met Glu Leu Ser Ser Leu Arg Ser Glu Asp Thr Ala Val
100 105 110

Tyr Tyr Cys Ala Arg His Glu Gly Val Tyr Trp Tyr Phe Asp Val Trp
115 120 125

Gly Gln Gly Thr Thr Val Thr Val Ser Ser
130 135

<210> SEQ ID NO 62
<211> LENGTH: 5
<212> TYPE: PRT
<213> ORGANISM: Artificial sequence
<220> FEATURE:
<223> OTHER INFORMATION: Synthesized

<400> SEQUENCE: 62

Ser Ser Tyr Ile Ser
1 5

<210> SEQ ID NO 63
<211> LENGTH: 17
<212> TYPE: PRT
<213> ORGANISM: Artificial sequence
<220> FEATURE:
<223> OTHER INFORMATION: Synthesized

<400> SEQUENCE: 63

Trp Ile Tyr Ala Gly Thr Gly Gly Thr Ser Tyr Asn Gln Lys Phe Thr
1 5 10 15

Gly

<210> SEQ ID NO 64
<211> LENGTH: 10
<212> TYPE: PRT
<213> ORGANISM: Artificial sequence
<220> FEATURE:
<223> OTHER INFORMATION: Synthesized

<400> SEQUENCE: 64

His Glu Gly Val Tyr Trp Tyr Phe Asp Val
1 5 10

<210> SEQ ID NO 65
<211> LENGTH: 127
<212> TYPE: PRT

<213> ORGANISM: Artificial sequence
<220> FEATURE:
<223> OTHER INFORMATION: Synthesized

<400> SEQUENCE: 65

Met Asp Phe Gln Val Gln Ile Phe Ser Phe Leu Leu Ile Ser Ala Val
1 5 10 15

Ile Met Ser Arg Gly Glu Ile Val Leu Thr Gln Ser Pro Ala Thr Leu
20 25 30

Ser Leu Ser Pro Gly Glu Arg Ala Thr Leu Ser Cys Ser Ala Ser Ser
35 40 45

Ser Val Ser Tyr Met His Trp Tyr Gln Gln Lys Pro Gly Gln Ala Pro
50 55 60

Arg Pro Trp Ile Tyr Asp Thr Ser Asn Leu Ala Ser Gly Phe Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys His Gln Arg Ser
100 105 110

Ser Tyr Pro Trp Thr Phe Gly Gly Gly Thr Lys Val Glu Ile Lys
115 120 125

<210> SEQ ID NO 66
<211> LENGTH: 10
<212> TYPE: PRT
<213> ORGANISM: Artificial sequence
<220> FEATURE:
<223> OTHER INFORMATION: Synthesized

<400> SEQUENCE: 66

Ser Ala Ser Ser Ser Val Ser Tyr Met His
1 5 10

<210> SEQ ID NO 67
<211> LENGTH: 7
<212> TYPE: PRT
<213> ORGANISM: Artificial sequence
<220> FEATURE:
<223> OTHER INFORMATION: Synthesized

<400> SEQUENCE: 67

Asp Thr Ser Asn Leu Ala Ser
1 5

<210> SEQ ID NO 68
<211> LENGTH: 9
<212> TYPE: PRT
<213> ORGANISM: Artificial sequence
<220> FEATURE:
<223> OTHER INFORMATION: Synthesized

<400> SEQUENCE: 68

His Gln Arg Ser Ser Tyr Pro Trp Thr
1 5

<210> SEQ ID NO 69
<211> LENGTH: 290
<212> TYPE: PRT
<213> ORGANISM: Homo sapiens

<400> SEQUENCE: 69

Met Arg Ile Phe Ala Val Phe Ile Phe Met Thr Tyr Trp His Leu Leu
1 5 10 15

```
Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 70
<211> LENGTH: 699
<212> TYPE: PRT
<213> ORGANISM: Artificial sequence
<220> FEATURE:
<223> OTHER INFORMATION: Synthesized

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Ser Ser
            20                  25                  30

Tyr Ile Ser Trp Val Arg Gln Ala Pro Gly Gln Gly Leu Glu Trp Ile
        35                  40                  45

Ala Trp Ile Tyr Ala Gly Thr Gly Gly Thr Ser Tyr Asn Gln Lys Phe
    50                  55                  60

Thr Gly Arg Ala Thr Ile Thr Val Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg His Glu Gly Val Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Asp Ile Gln Met Thr
    450                 455                 460

Gln Ser Pro Ser Ser Leu Ser Ala Ser Val Gly Asp Arg Val Thr Ile
465                 470                 475                 480

Thr Cys His Ala Ser Gln Asn Ile Asn Val Trp Leu Ser Trp Tyr Gln
                485                 490                 495
```

```
Gln Lys Pro Gly Lys Val Pro Lys Leu Leu Ile Tyr Lys Ala Ser Asn
            500                 505                 510

Leu His Thr Gly Val Pro Ser Arg Phe Ser Gly Ser Gly Ser Gly Thr
        515                 520                 525

Asp Phe Thr Leu Thr Ile Ser Ser Leu Gln Pro Glu Asp Val Ala Thr
    530                 535                 540

Tyr Tyr Cys Gln Gln Gly Gln Ser Tyr Pro Leu Thr Phe Gly Gly Gly
545                 550                 555                 560

Thr Lys Val Glu Ile Lys Gly Gly Gly Gly Ser Gly Gly Gly Gly Ser
                565                 570                 575

Gly Gly Gly Gly Ser Gln Val Thr Leu Lys Glu Ser Gly Pro Val Leu
            580                 585                 590

Val Lys Pro Thr Glu Thr Leu Thr Leu Thr Cys Thr Val Ser Gly Phe
        595                 600                 605

Ser Leu Thr Asp Tyr Gly Val Ser Trp Ile Arg Gln Pro Pro Gly Lys
    610                 615                 620

Ala Leu Glu Trp Leu Gly Val Ile Trp Gly Gly Gly Gly Thr Tyr Tyr
625                 630                 635                 640

Asn Ser Ala Leu Lys Ser Arg Leu Thr Ile Ser Lys Asp Thr Ser Lys
                645                 650                 655

Ser Gln Val Val Leu Thr Met Thr Asn Met Asp Pro Val Asp Thr Ala
            660                 665                 670

Thr Tyr Tyr Cys Ala Lys His Pro Tyr Gly His Phe Gly Met Asp Tyr
        675                 680                 685

Trp Gly Gln Gly Thr Thr Val Thr Val Ser Ser
    690                 695


<210> SEQ ID NO 71
<211> LENGTH: 213
<212> TYPE: PRT
<213> ORGANISM: Artificial sequence
<220> FEATURE:
<223> OTHER INFORMATION: Synthesized

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Pro Trp Ile Tyr
        35                  40                  45

Asp Thr Ser Asn Leu Ala Ser Gly Phe Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Arg Ser Ser Tyr Pro Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 72
<211> LENGTH: 700
<212> TYPE: PRT
<213> ORGANISM: Artificial sequence
<220> FEATURE:
<223> OTHER INFORMATION: Synthesized

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Ser Ser
            20                  25                  30

Tyr Ile Ser Trp Val Arg Gln Ala Pro Gly Gln Gly Leu Glu Trp Ile
        35                  40                  45

Ala Trp Ile Tyr Ala Gly Thr Gly Gly Thr Ser Tyr Asn Gln Lys Phe
    50                  55                  60

Thr Gly Arg Ala Thr Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Gly Val Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Asp Ile Gln Met Thr
    450                 455                 460

Gln Ser Pro Ser Ser Leu Ser Ala Ser Val Gly Asp Arg Val Thr Ile
465                 470                 475                 480

Thr Cys Arg Ala Ser Gln Asp Ile Arg Thr Tyr Leu Asn Trp Tyr Gln
                485                 490                 495

Gln Lys Pro Gly Lys Val Pro Lys Leu Leu Ile Tyr Tyr Thr Ser Arg
            500                 505                 510

Leu His Ser Gly Val Pro Ser Arg Phe Ser Gly Ser Gly Ser Gly Thr
        515                 520                 525

Asp Tyr Thr Leu Thr Ile Ser Ser Leu Gln Pro Glu Asp Val Ala Thr
    530                 535                 540

Tyr Tyr Cys Gln Gln Gly Asn Thr Leu Pro Trp Thr Phe Gly Gly Gly
545                 550                 555                 560

Thr Lys Val Glu Ile Lys Gly Gly Gly Gly Ser Gly Gly Gly Gly Ser
                565                 570                 575

Gly Gly Gly Gly Ser Gln Val Gln Leu Val Gln Ser Gly Ala Glu Val
            580                 585                 590

Lys Lys Pro Gly Ser Ser Val Lys Val Ser Cys Lys Ala Ser Gly Tyr
        595                 600                 605

Thr Phe Thr Ser Tyr Ile Met His Trp Val Arg Gln Ala Pro Gly Gln
    610                 615                 620

Gly Leu Glu Trp Ile Gly Tyr Ile Asn Pro Tyr Asn Ser Gly Thr Lys
625                 630                 635                 640

Tyr Asn Glu Lys Phe Lys Gly Arg Val Thr Ile Thr Ser Asp Lys Ser
                645                 650                 655

Thr Ser Thr Ala Tyr Met Glu Leu Ser Ser Leu Arg Ser Glu Asp Thr
            660                 665                 670

Ala Val Tyr Tyr Cys Ala His Tyr Tyr Gly Ser Thr Phe Thr Met Asp
        675                 680                 685

Tyr Trp Gly Gln Gly Thr Thr Val Thr Val Ser Ser
    690                 695                 700
```

<210> SEQ ID NO 73
<211> LENGTH: 222
<212> TYPE: PRT

<213> ORGANISM: Homo sapiens

<400> SEQUENCE: 73

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr His
    210                 215                 220

<210> SEQ ID NO 74
<211> LENGTH: 137
<212> TYPE: PRT
<213> ORGANISM: Artificial sequence
<220> FEATURE:
<223> OTHER INFORMATION: Synthesized

<400> SEQUENCE: 74

Met Gly Trp Asn Trp Ile Phe Leu Phe Leu Ser Gly Thr Ala Gly Val
1               5                   10                  15

His Cys Gln Val Gln Leu Val Gln Ser Gly Ala Glu Val Lys Lys Pro
            20                  25                  30

Gly Ser Ser Val Lys Val Ser Cys Lys Ala Ser Gly Tyr Thr Phe Thr
        35                  40                  45

Ser Tyr Gly Ile Asn Trp Val Arg Gln Ala Pro Gly Gln Gly Leu Glu
    50                  55                  60

Trp Ile Gly Tyr Ile Tyr Pro Gly Ser Gly Gly Pro Val Tyr Asn Gln
65                  70                  75                  80

Lys Phe Lys Gly Arg Val Thr Leu Thr Ala Asp Lys Ser Thr Ser Thr
                85                  90                  95

Ala Tyr Met Glu Leu Ser Ser Leu Arg Ser Glu Asp Thr Ala Val Tyr
            100                 105                 110

Tyr Cys Ala Arg Glu Asn Tyr Arg Tyr Trp Tyr Phe Asp Val Trp Gly
        115                 120                 125

Gln Gly Thr Thr Val Thr Val Ser Ser
130 135

<210> SEQ ID NO 75
<211> LENGTH: 5
<212> TYPE: PRT
<213> ORGANISM: Artificial sequence
<220> FEATURE:
<223> OTHER INFORMATION: Synthesized

<400> SEQUENCE: 75

Ser Tyr Gly Ile Asn
1 5

<210> SEQ ID NO 76
<211> LENGTH: 17
<212> TYPE: PRT
<213> ORGANISM: Artificial sequence
<220> FEATURE:
<223> OTHER INFORMATION: Synthesized

<400> SEQUENCE: 76

Tyr Ile Tyr Pro Gly Ser Gly Gly Pro Val Tyr Asn Gln Lys Phe Lys
1 5 10 15

Gly

<210> SEQ ID NO 77
<211> LENGTH: 10
<212> TYPE: PRT
<213> ORGANISM: Artificial sequence
<220> FEATURE:
<223> OTHER INFORMATION: Synthesized

<400> SEQUENCE: 77

Glu Asn Tyr Arg Tyr Trp Tyr Phe Asp Val
1 5 10

<210> SEQ ID NO 78
<211> LENGTH: 128
<212> TYPE: PRT
<213> ORGANISM: Artificial sequence
<220> FEATURE:
<223> OTHER INFORMATION: Synthesized

<400> SEQUENCE: 78

Met His Phe Gln Val Gln Ile Phe Ser Phe Leu Leu Ile Ser Ala Ser
1 5 10 15

Val Ile Met Ser Arg Gly Asp Ile Gln Leu Thr Gln Ser Pro Ser Phe
20 25 30

Leu Ser Ala Ser Val Gly Asp Arg Val Thr Ile Thr Cys Ser Ala Ser
35 40 45

Ser Ser Val Asn Tyr Met His Trp Phe Gln Gln Lys Pro Gly Lys Ala
50 55 60

Pro Lys Leu Trp Ile Tyr Ser Thr Ser Asn Leu Ala Ser Gly Val Pro
65 70 75 80

Ser Arg Phe Ser Gly Ser Gly Ser Gly Thr Glu Phe Thr Leu Thr Ile
85 90 95

Ser Ser Leu Gln Pro Glu Asp Phe Ala Thr Tyr Tyr Cys Gln Gln Arg
100 105 110

Ser Ser Tyr Pro Leu Thr Phe Gly Gly Gly Thr Lys Val Glu Ile Lys
115 120 125

<210> SEQ ID NO 79
<211> LENGTH: 10
<212> TYPE: PRT
<213> ORGANISM: Artificial sequence
<220> FEATURE:
<223> OTHER INFORMATION: Synthesized

<400> SEQUENCE: 79

Ser Ala Ser Ser Ser Val Asn Tyr Met His
1               5                   10

<210> SEQ ID NO 80
<211> LENGTH: 7
<212> TYPE: PRT
<213> ORGANISM: Artificial sequence
<220> FEATURE:
<223> OTHER INFORMATION: Synthesized

<400> SEQUENCE: 80

Ser Thr Ser Asn Leu Ala Ser
1               5

<210> SEQ ID NO 81
<211> LENGTH: 9
<212> TYPE: PRT
<213> ORGANISM: Artificial sequence
<220> FEATURE:
<223> OTHER INFORMATION: Synthesized

<400> SEQUENCE: 81

Gln Gln Arg Ser Ser Tyr Pro Leu Thr
1               5

<210> SEQ ID NO 82
<211> LENGTH: 700
<212> TYPE: PRT
<213> ORGANISM: Artificial sequence
<220> FEATURE:
<223> OTHER INFORMATION: Synthesized

<400> SEQUENCE: 82

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Gly Leu Glu Trp Ile
        35                  40                  45

Gly Tyr Ile Tyr Pro Gly Ser Gly Gly Pro Val Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asn Tyr Arg Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

-continued

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Asp Ile Gln Met Thr
    450                 455                 460

Gln Ser Pro Ser Ser Leu Ser Ala Ser Val Gly Asp Arg Val Thr Ile
465                 470                 475                 480

Thr Cys Arg Ala Ser Gln Asp Ile Arg Thr Tyr Leu Asn Trp Tyr Gln
                485                 490                 495

Gln Lys Pro Gly Lys Val Pro Lys Leu Leu Ile Tyr Tyr Thr Ser Arg
            500                 505                 510

Leu His Ser Gly Val Pro Ser Arg Phe Ser Gly Ser Gly Ser Gly Thr
        515                 520                 525

Asp Tyr Thr Leu Thr Ile Ser Ser Leu Gln Pro Glu Asp Val Ala Thr
    530                 535                 540

Tyr Tyr Cys Gln Gln Gly Asn Thr Leu Pro Trp Thr Phe Gly Gly Gly
545                 550                 555                 560

Thr Lys Val Glu Ile Lys Gly Gly Gly Gly Ser Gly Gly Gly Gly Ser
                565                 570                 575
```

Gly Gly Gly Gly Ser Gln Val Gln Leu Val Gln Ser Gly Ala Glu Val
580 585 590

Lys Lys Pro Gly Ser Ser Val Lys Val Ser Cys Lys Ala Ser Gly Tyr
595 600 605

Thr Phe Thr Ser Tyr Ile Met His Trp Val Arg Gln Ala Pro Gly Gln
610 615 620

Gly Leu Glu Trp Ile Gly Tyr Ile Asn Pro Tyr Asn Ser Gly Thr Lys
625 630 635 640

Tyr Asn Glu Lys Phe Lys Gly Arg Val Thr Ile Thr Ser Asp Lys Ser
645 650 655

Thr Ser Thr Ala Tyr Met Glu Leu Ser Ser Leu Arg Ser Glu Asp Thr
660 665 670

Ala Val Tyr Tyr Cys Ala His Tyr Tyr Gly Ser Thr Phe Thr Met Asp
675 680 685

Tyr Trp Gly Gln Gly Thr Thr Val Thr Val Ser Ser
690 695 700

<210> SEQ ID NO 83
<211> LENGTH: 213
<212> TYPE: PRT
<213> ORGANISM: Artificial sequence
<220> FEATURE:
<223> OTHER INFORMATION: Synthesized

<400> SEQUENCE: 83

Asp Ile Gln Leu Thr Gln Ser Pro Ser Phe Leu Ser Ala Ser Val Gly
1 5 10 15

Asp Arg Val Thr Ile Thr Cys Ser Ala Ser Ser Ser Val Asn Tyr Met
20 25 30

His Trp Phe Gln Gln Lys Pro Gly Lys Ala Pro Lys Leu Trp Ile Tyr
35 40 45

Ser Thr Ser Asn Leu Ala Ser Gly Val Pro Ser Arg Phe Ser Gly Ser
50 55 60

Gly Ser Gly Thr Glu Phe Thr Leu Thr Ile Ser Ser Leu Gln Pro Glu
65 70 75 80

Asp Phe Ala Thr Tyr Tyr Cys Gln Gln Arg Ser Ser Tyr Pro Leu Thr
85 90 95

Phe Gly Gly Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 84

<211> LENGTH: 137
<212> TYPE: PRT
<213> ORGANISM: Artificial sequence
<220> FEATURE:
<223> OTHER INFORMATION: Synthesized

<400> SEQUENCE: 84

```
Met Met Val Leu Ser Leu Leu Tyr Leu Leu Thr Ala Leu Pro Gly Ile
1               5                   10                  15

Leu Ser Gln Val Gln Leu Gln Glu Ser Gly Pro Gly Leu Val Lys Pro
            20                  25                  30

Ser Gln Thr Leu Ser Leu Thr Cys Thr Val Ser Gly Asp Ser Ile Ser
        35                  40                  45

Ser Gly Tyr Trp Asn Trp Ile Arg Gln Pro Pro Gly Lys Gly Leu Glu
    50                  55                  60

Tyr Met Gly Tyr Ile Ser Tyr Thr Gly Ser Thr Tyr Ser Asn Pro Ser
65                  70                  75                  80

Leu Lys Ser Arg Val Thr Ile Ser Arg Asp Thr Ser Lys Asn Gln Phe
                85                  90                  95

Ser Leu Lys Leu Ser Ser Val Thr Ala Ala Asp Thr Ala Val Tyr Tyr
            100                 105                 110

Cys Ala Arg Ser Gln Asn Trp Glu Arg Ala Trp Phe Ala Tyr Trp Gly
        115                 120                 125

Gln Gly Thr Leu Val Thr Val Ser Ser
    130                 135
```

<210> SEQ ID NO 85
<211> LENGTH: 5
<212> TYPE: PRT
<213> ORGANISM: Artificial sequence
<220> FEATURE:
<223> OTHER INFORMATION: Synthesized

<400> SEQUENCE: 85

```
Ser Gly Tyr Trp Asn
1               5
```

<210> SEQ ID NO 86
<211> LENGTH: 16
<212> TYPE: PRT
<213> ORGANISM: Artificial sequence
<220> FEATURE:
<223> OTHER INFORMATION: Synthesized

<400> SEQUENCE: 86

```
Tyr Ile Ser Tyr Thr Gly Ser Thr Tyr Ser Asn Pro Ser Leu Lys Ser
1               5                   10                  15
```

<210> SEQ ID NO 87
<211> LENGTH: 11
<212> TYPE: PRT
<213> ORGANISM: Artificial sequence
<220> FEATURE:
<223> OTHER INFORMATION: Synthesized

<400> SEQUENCE: 87

```
Ser Gln Asn Trp Glu Arg Ala Trp Phe Ala Tyr
1               5                   10
```

<210> SEQ ID NO 88
<211> LENGTH: 128
<212> TYPE: PRT
<213> ORGANISM: Artificial sequence
<220> FEATURE:
<223> OTHER INFORMATION: Synthesized

<400> SEQUENCE: 88

```
Met Asp Phe Gln Val Gln Ile Phe Ser Phe Leu Leu Ile Ser Ala Ser
1               5                   10                  15

Val Ile Met Ser Arg Gly Asp Ile Gln Met Thr Gln Ser Pro Ser Ser
            20                  25                  30

Leu Ser Ala Ser Val Gly Asp Arg Val Thr Ile Thr Cys Ser Ala Ser
        35                  40                  45

Ser Ser Val Ser Tyr Met His Trp Tyr Gln Gln Lys Pro Gly Lys Ala
    50                  55                  60

Pro Lys Leu Trp Ile Tyr Asp Thr Ser Lys Leu Ala Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Phe Gln Gly
            100                 105                 110

Ser Gly Tyr Pro Phe Thr Phe Gly Gly Gly Thr Lys Val Glu Ile Lys
        115                 120                 125
```

<210> SEQ ID NO 89
<211> LENGTH: 10
<212> TYPE: PRT
<213> ORGANISM: Artificial sequence
<220> FEATURE:
<223> OTHER INFORMATION: Synthesized

<400> SEQUENCE: 89

```
Ser Ala Ser Ser Ser Val Ser Tyr Met His
1               5                   10
```

<210> SEQ ID NO 90
<211> LENGTH: 7
<212> TYPE: PRT
<213> ORGANISM: Artificial sequence
<220> FEATURE:
<223> OTHER INFORMATION: Synthesized

<400> SEQUENCE: 90

```
Asp Thr Ser Lys Leu Ala Ser
1               5
```

<210> SEQ ID NO 91
<211> LENGTH: 9
<212> TYPE: PRT
<213> ORGANISM: Artificial sequence
<220> FEATURE:
<223> OTHER INFORMATION: Synthesized

<400> SEQUENCE: 91

```
Phe Gln Gly Ser Gly Tyr Pro Phe Thr
1               5
```

<210> SEQ ID NO 92
<211> LENGTH: 700
<212> TYPE: PRT
<213> ORGANISM: Artificial sequence
<220> FEATURE:
<223> OTHER INFORMATION: Synthesized

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Asp Ser Ile Ser Ser Gly
            20                  25                  30

Tyr Trp Asn Trp Ile Arg Gln Pro Pro Gly Lys Gly Leu Glu Tyr Met
        35                  40                  45

Gly Tyr Ile Ser Tyr Thr Gly Ser Thr Tyr Ser Asn Pro Ser Leu Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Gln Asn Trp Glu Arg Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Ser Gly Gly Gly Gly Ser Gly Gly Gly Gly Ser Asp Ile Gln Met Thr
450 455 460

Gln Ser Pro Ser Ser Leu Ser Ala Ser Val Gly Asp Arg Val Thr Ile
465 470 475 480

Thr Cys Arg Ala Ser Gln Asp Ile Arg Thr Tyr Leu Asn Trp Tyr Gln
485 490 495

Gln Lys Pro Gly Lys Val Pro Lys Leu Leu Ile Tyr Tyr Thr Ser Arg
500 505 510

Leu His Ser Gly Val Pro Ser Arg Phe Ser Gly Ser Gly Ser Gly Thr
515 520 525

Asp Tyr Thr Leu Thr Ile Ser Ser Leu Gln Pro Glu Asp Val Ala Thr
530 535 540

Tyr Tyr Cys Gln Gln Gly Asn Thr Leu Pro Trp Thr Phe Gly Gly Gly
545 550 555 560

Thr Lys Val Glu Ile Lys Gly Gly Gly Gly Ser Gly Gly Gly Gly Ser
565 570 575

Gly Gly Gly Gly Ser Gln Val Gln Leu Val Gln Ser Gly Ala Glu Val
580 585 590

Lys Lys Pro Gly Ser Ser Val Lys Val Ser Cys Lys Ala Ser Gly Tyr
595 600 605

Thr Phe Thr Ser Tyr Ile Met His Trp Val Arg Gln Ala Pro Gly Gln
610 615 620

Gly Leu Glu Trp Ile Gly Tyr Ile Asn Pro Tyr Asn Ser Gly Thr Lys
625 630 635 640

Tyr Asn Glu Lys Phe Lys Gly Arg Val Thr Ile Thr Ser Asp Lys Ser
645 650 655

Thr Ser Thr Ala Tyr Met Glu Leu Ser Ser Leu Arg Ser Glu Asp Thr
660 665 670

Ala Val Tyr Tyr Cys Ala His Tyr Tyr Gly Ser Thr Phe Thr Met Asp
675 680 685

Tyr Trp Gly Gln Gly Thr Thr Val Thr Val Ser Ser
690 695 700

<210> SEQ ID NO 93
<211> LENGTH: 213
<212> TYPE: PRT
<213> ORGANISM: Artificial sequence
<220> FEATURE:
<223> OTHER INFORMATION: Synthesized

<400> SEQUENCE: 93

Asp Ile Gln Met Thr Gln Ser Pro Ser Ser Leu Ser Ala Ser Val Gly
1 5 10 15

Asp Arg Val Thr Ile Thr Cys Ser Ala Ser Ser Ser Val Ser Tyr Met
20 25 30

His Trp Tyr Gln Gln Lys Pro Gly Lys Ala Pro Lys Leu Trp Ile Tyr
35 40 45

Asp Thr Ser Lys Leu Ala Ser Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

Asp Phe Ala Thr Tyr Tyr Cys Phe Gln Gly Ser Gly Tyr Pro Phe Thr
85 90 95

Phe Gly Gly Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 94
<211> LENGTH: 5
<212> TYPE: PRT
<213> ORGANISM: Artificial sequence
<220> FEATURE:
<223> OTHER INFORMATION: Synthesized

<400> SEQUENCE: 94

Asp Tyr Asn Met His
1 5

<210> SEQ ID NO 95
<211> LENGTH: 17
<212> TYPE: PRT
<213> ORGANISM: Artificial sequence
<220> FEATURE:
<223> OTHER INFORMATION: Synthesized

<400> SEQUENCE: 95

Tyr Ile Tyr Pro Tyr Asn Gly Gly Thr Gly Tyr Asn Gln Lys Phe Lys
1 5 10 15

Ser

<210> SEQ ID NO 96
<211> LENGTH: 7
<212> TYPE: PRT
<213> ORGANISM: Artificial sequence
<220> FEATURE:
<223> OTHER INFORMATION: Synthesized

<400> SEQUENCE: 96

Gly Arg Pro Ala Met Asp Tyr
1 5

<210> SEQ ID NO 97
<211> LENGTH: 15
<212> TYPE: PRT
<213> ORGANISM: Artificial sequence
<220> FEATURE:
<223> OTHER INFORMATION: Synthesized

<400> SEQUENCE: 97

Arg Ala Ser Glu Ser Val Asp Asn Tyr Gly Ile Ser Phe Met Asn
1               5                   10                  15

<210> SEQ ID NO 98
<211> LENGTH: 7
<212> TYPE: PRT
<213> ORGANISM: Artificial sequence
<220> FEATURE:
<223> OTHER INFORMATION: Synthesized

<400> SEQUENCE: 98

Ala Ala Ser Asn Gln Gly Ser
1               5

<210> SEQ ID NO 99
<211> LENGTH: 9
<212> TYPE: PRT
<213> ORGANISM: Artificial sequence
<220> FEATURE:
<223> OTHER INFORMATION: Synthesized

<400> SEQUENCE: 99

Gln Gln Ser Lys Glu Val Pro Trp Thr
1               5

<210> SEQ ID NO 100
<211> LENGTH: 5
<212> TYPE: PRT
<213> ORGANISM: Artificial sequence
<220> FEATURE:
<223> OTHER INFORMATION: Synthesized

<400> SEQUENCE: 100

Asn Tyr Gly Val His
1               5

<210> SEQ ID NO 101
<211> LENGTH: 16
<212> TYPE: PRT
<213> ORGANISM: Artificial sequence
<220> FEATURE:
<223> OTHER INFORMATION: Synthesized

<400> SEQUENCE: 101

Val Ile Trp Ser Gly Gly Asn Thr Asp Tyr Asn Thr Pro Phe Thr Ser
1               5                   10                  15

<210> SEQ ID NO 102
<211> LENGTH: 11
<212> TYPE: PRT
<213> ORGANISM: Artificial sequence
<220> FEATURE:
<223> OTHER INFORMATION: Synthesized

<400> SEQUENCE: 102

Ala Leu Thr Tyr Tyr Asp Tyr Glu Phe Ala Tyr
1               5                   10

<210> SEQ ID NO 103
<211> LENGTH: 11
<212> TYPE: PRT
<213> ORGANISM: Artificial sequence
<220> FEATURE:
<223> OTHER INFORMATION: Synthesized

<400> SEQUENCE: 103

Arg Ala Ser Gln Ser Ile Gly Thr Asn Ile His
1 5 10

<210> SEQ ID NO 104
<211> LENGTH: 7
<212> TYPE: PRT
<213> ORGANISM: Artificial sequence
<220> FEATURE:
<223> OTHER INFORMATION: Synthesized

<400> SEQUENCE: 104

Tyr Ala Ser Glu Ser Ile Ser
1 5

<210> SEQ ID NO 105
<211> LENGTH: 9
<212> TYPE: PRT
<213> ORGANISM: Artificial sequence
<220> FEATURE:
<223> OTHER INFORMATION: Synthesized

<400> SEQUENCE: 105

Gln Gln Asn Asn Asn Trp Pro Thr Thr
1 5

<210> SEQ ID NO 106
<211> LENGTH: 699
<212> TYPE: PRT
<213> ORGANISM: Artificial sequence
<220> FEATURE:
<223> OTHER INFORMATION: Synthesized

<400> SEQUENCE: 106

Gln Val Gln Leu Val Gln Ser Gly Ala Glu Val Lys Lys Pro Gly Ser
1 5 10 15

Ser Val Lys Val Ser Cys Lys Ala Ser Gly Phe Thr Phe Ser Ser Ser
20 25 30

Tyr Ile Ser Trp Val Arg Gln Ala Pro Gly Gln Gly Leu Glu Trp Ile
35 40 45

Ala Trp Ile Tyr Ala Gly Thr Gly Gly Thr Ser Tyr Asn Gln Lys Phe
50 55 60

Thr Gly Arg Ala Thr Ile Thr Val Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg His Glu Gly Val Tyr Trp Tyr Phe Asp Val Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

-continued

Ser Asn Thr Lys Val Asp Lys Lys Val Glu Pro Lys Ser Cys Asp Lys
210 215 220

Thr His Thr Cys Pro Pro Cys Pro Ala Pro Glu Ala Ala Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Ser Gly Gly Gly Gly Ser Gly Gly Gly Gly Ser Asp Ile Gln Met Thr
450 455 460

Gln Ser Pro Ser Ser Leu Ser Ala Ser Val Gly Asp Arg Val Thr Ile
465 470 475 480

Thr Cys His Ala Ser Gln Asn Ile Asn Val Trp Leu Ser Trp Tyr Gln
485 490 495

Gln Lys Pro Gly Lys Val Pro Lys Leu Leu Ile Tyr Lys Ala Ser Asn
500 505 510

Leu His Thr Gly Val Pro Ser Arg Phe Ser Gly Ser Gly Ser Gly Thr
515 520 525

Asp Phe Thr Leu Thr Ile Ser Ser Leu Gln Pro Glu Asp Val Ala Thr
530 535 540

Tyr Tyr Cys Gln Gln Gly Gln Ser Tyr Pro Leu Thr Phe Gly Cys Gly
545 550 555 560

Thr Lys Val Glu Ile Lys Gly Gly Gly Gly Ser Gly Gly Gly Gly Ser
565 570 575

Gly Gly Gly Gly Ser Gln Val Thr Leu Lys Glu Ser Gly Pro Val Leu
580 585 590

Val Lys Pro Thr Glu Thr Leu Thr Leu Thr Cys Thr Val Ser Gly Phe
595 600 605

Ser Leu Thr Asp Tyr Gly Val Ser Trp Ile Arg Gln Pro Pro Gly Lys
610 615 620

```
Cys Leu Glu Trp Leu Gly Val Ile Trp Gly Gly Gly Gly Thr Tyr Tyr
625                 630                 635                 640

Asn Ser Ala Leu Lys Ser Arg Leu Thr Ile Ser Lys Asp Thr Ser Lys
                645                 650                 655

Ser Gln Val Val Leu Thr Met Thr Asn Met Asp Pro Val Asp Thr Ala
            660                 665                 670

Thr Tyr Tyr Cys Ala Lys His Pro Tyr Gly His Phe Gly Met Asp Tyr
        675                 680                 685

Trp Gly Gln Gly Thr Thr Val Thr Val Ser Ser
    690                 695
```

<210> SEQ ID NO 107
<211> LENGTH: 357
<212> TYPE: PRT
<213> ORGANISM: Artificial sequence
<220> FEATURE:
<223> OTHER INFORMATION: Synthesized

<400> SEQUENCE: 107

```
Gly Glu Ile Asn Gly Ser Ala Asn Tyr Glu Met Phe Ile Phe His Asn
1               5                   10                  15

Gly Gly Val Gln Ile Leu Cys Lys Tyr Pro Asp Ile Val Gln Gln Phe
            20                  25                  30

Lys Met Gln Leu Leu Lys Gly Gly Gln Ile Leu Cys Asp Leu Thr Lys
        35                  40                  45

Thr Lys Gly Ser Gly Asn Thr Val Ser Ile Lys Ser Leu Lys Phe Cys
    50                  55                  60

His Ser Gln Leu Ser Asn Asn Ser Val Ser Phe Phe Leu Tyr Asn Leu
65                  70                  75                  80

Asp His Ser His Ala Asn Tyr Tyr Phe Cys Asn Leu Ser Ile Phe Asp
                85                  90                  95

Pro Pro Pro Phe Lys Val Thr Leu Thr Gly Gly Tyr Leu His Ile Tyr
            100                 105                 110

Glu Ser Gln Leu Cys Cys Gln Leu Lys Thr Gly Gly Gly Glu Pro Lys
        115                 120                 125

Ser Cys Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285
```

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 108
<211> LENGTH: 136
<212> TYPE: PRT
<213> ORGANISM: Artificial sequence
<220> FEATURE:
<223> OTHER INFORMATION: Synthesized

<400> SEQUENCE: 108

Met Ala Val Leu Val Leu Leu Leu Cys Leu Val Thr Phe Pro Ser Cys
1               5                   10                  15

Ala Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Ile
        35                  40                  45

Ser Ser Asn Ser Val Ser Trp Val Arg Gln Pro Pro Gly Lys Gly Leu
    50                  55                  60

Glu Trp Met Gly Ala Ile Trp Ser Gly Gly Ser Thr Asp Tyr Asn Ser
65                  70                  75                  80

Ala Leu Lys Ser Arg Val Thr Ile Ser Arg Asp Thr Ser Lys Asn Gln
                85                  90                  95

Val Ser Leu Lys Leu Ser Ser Val Thr Ala Ala Asp Thr Ala Val Tyr
            100                 105                 110

Tyr Cys Thr Arg Trp Glu Gln Pro Tyr Tyr Phe Asp Tyr Trp Gly Gln
        115                 120                 125

Gly Thr Met Val Thr Val Ser Ser
    130                 135

<210> SEQ ID NO 109
<211> LENGTH: 5
<212> TYPE: PRT
<213> ORGANISM: Artificial sequence
<220> FEATURE:
<223> OTHER INFORMATION: Synthesized

<400> SEQUENCE: 109

Ser Asn Ser Val Ser
1               5

<210> SEQ ID NO 110
<211> LENGTH: 16
<212> TYPE: PRT
<213> ORGANISM: Artificial sequence
<220> FEATURE:
<223> OTHER INFORMATION: Synthesized

<400> SEQUENCE: 110

Ala Ile Trp Ser Gly Gly Ser Thr Asp Tyr Asn Ser Ala Leu Lys Ser
1               5                   10                  15

<210> SEQ ID NO 111
<211> LENGTH: 9
<212> TYPE: PRT
<213> ORGANISM: Artificial sequence
<220> FEATURE:
<223> OTHER INFORMATION: Synthesized

<400> SEQUENCE: 111

```
Trp Glu Gln Pro Tyr Tyr Phe Asp Tyr
1               5
```

<210> SEQ ID NO 112
<211> LENGTH: 126
<212> TYPE: PRT
<213> ORGANISM: Artificial sequence
<220> FEATURE:
<223> OTHER INFORMATION: Synthesized

<400> SEQUENCE: 112

```
Met Arg Thr Ser Ile Gln Leu Leu Gly Leu Leu Leu Phe Trp Leu His
1               5                   10                  15

Asp Ala Gln Cys Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asn
        35                  40                  45

Ile Tyr Lys Tyr Ile Ala Trp Tyr Gln Gln Lys Pro Gly Lys Ala Pro
    50                  55                  60

Lys Leu Leu Ile Arg Tyr Thr Ser Thr Leu Glu Ser Gly Thr Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Leu Gln Tyr Val
            100                 105                 110

Asn Leu Tyr Thr Phe Gly Gly Gly Thr Lys Val Glu Ile Lys
        115                 120                 125
```

<210> SEQ ID NO 113
<211> LENGTH: 11
<212> TYPE: PRT
<213> ORGANISM: Artificial sequence
<220> FEATURE:
<223> OTHER INFORMATION: Synthesized

<400> SEQUENCE: 113

```
Gln Ala Ser Gln Asn Ile Tyr Lys Tyr Ile Ala
1               5                   10
```

<210> SEQ ID NO 114
<211> LENGTH: 7
<212> TYPE: PRT
<213> ORGANISM: Artificial sequence
<220> FEATURE:
<223> OTHER INFORMATION: Synthesized

<400> SEQUENCE: 114

```
Tyr Thr Ser Thr Leu Glu Ser
1               5
```

<210> SEQ ID NO 115
<211> LENGTH: 8
<212> TYPE: PRT
<213> ORGANISM: Artificial sequence
<220> FEATURE:
<223> OTHER INFORMATION: Synthesized

<400> SEQUENCE: 115

Leu Gln Tyr Val Asn Leu Tyr Thr
1 5

<210> SEQ ID NO 116
<211> LENGTH: 199
<212> TYPE: PRT
<213> ORGANISM: Homo sapiens

<400> SEQUENCE: 116

Met Lys Ser Gly Leu Trp Tyr Phe Phe Leu Phe Cys Leu Arg Ile Lys
1 5 10 15

Val Leu Thr Gly Glu Ile Asn Gly Ser Ala Asn Tyr Glu Met Phe Ile
20 25 30

Phe His Asn Gly Gly Val Gln Ile Leu Cys Lys Tyr Pro Asp Ile Val
35 40 45

Gln Gln Phe Lys Met Gln Leu Leu Lys Gly Gly Gln Ile Leu Cys Asp
50 55 60

Leu Thr Lys Thr Lys Gly Ser Gly Asn Thr Val Ser Ile Lys Ser Leu
65 70 75 80

Lys Phe Cys His Ser Gln Leu Ser Asn Asn Ser Val Ser Phe Phe Leu
85 90 95

Tyr Asn Leu Asp His Ser His Ala Asn Tyr Tyr Phe Cys Asn Leu Ser
100 105 110

Ile Phe Asp Pro Pro Pro Phe Lys Val Thr Leu Thr Gly Gly Tyr Leu
115 120 125

His Ile Tyr Glu Ser Gln Leu Cys Cys Gln Leu Lys Phe Trp Leu Pro
130 135 140

Ile Gly Cys Ala Ala Phe Val Val Val Cys Ile Leu Gly Cys Ile Leu
145 150 155 160

Ile Cys Trp Leu Thr Lys Lys Lys Tyr Ser Ser Ser Val His Asp Pro
165 170 175

Asn Gly Glu Tyr Met Phe Met Arg Ala Val Asn Thr Ala Lys Lys Ser
180 185 190

Arg Leu Thr Asp Val Thr Leu
195

<210> SEQ ID NO 117
<211> LENGTH: 238
<212> TYPE: PRT
<213> ORGANISM: Artificial sequence
<220> FEATURE:
<223> OTHER INFORMATION: Synthesized

<400> SEQUENCE: 117

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asn Ile Tyr Lys Tyr
20 25 30

Ile Ala Trp Tyr Gln Gln Lys Pro Gly Lys Ala Pro Lys Leu Leu Ile
35 40 45

Arg Tyr Thr Ser Thr Leu Glu Ser Gly Thr Pro Ser Arg Phe Ser Gly
50 55 60

Ser Gly Ser Gly Thr Asp Tyr Thr Leu Thr Ile Ser Ser Leu Gln Pro
65 70 75 80

```
Glu Asp Phe Ala Thr Tyr Tyr Cys Leu Gln Tyr Val Asn Leu Tyr Thr
                85                  90                  95

Phe Gly Gly Gly Thr Lys Val Glu Ile Lys Gly Gly Gly Gly Ser Gly
            100                 105                 110

Gly Gly Gly Ser Gly Gly Gly Gly Ser Gln Val Gln Leu Gln Glu Ser
        115                 120                 125

Gly Pro Gly Leu Val Lys Pro Ser Glu Thr Leu Ser Leu Thr Cys Thr
    130                 135                 140

Val Ser Gly Phe Ser Ile Ser Ser Asn Ser Val Ser Trp Val Arg Gln
145                 150                 155                 160

Pro Pro Gly Lys Gly Leu Glu Trp Met Gly Ala Ile Trp Ser Gly Gly
                165                 170                 175

Ser Thr Asp Tyr Asn Ser Ala Leu Lys Ser Arg Val Thr Ile Ser Arg
            180                 185                 190

Asp Thr Ser Lys Asn Gln Val Ser Leu Lys Leu Ser Ser Val Thr Ala
        195                 200                 205

Ala Asp Thr Ala Val Tyr Tyr Cys Thr Arg Trp Glu Gln Pro Tyr Tyr
    210                 215                 220

Phe Asp Tyr Trp Gly Gln Gly Thr Met Val Thr Val Ser Ser
225                 230                 235


<210> SEQ ID NO 118
<211> LENGTH: 355
<212> TYPE: PRT
<213> ORGANISM: Artificial sequence
<220> FEATURE:
<223> OTHER INFORMATION: Synthesized

<400> SEQUENCE: 118

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Ser Gly Gly Gly Gly Ser
            100                 105                 110

Gly Gly Gly Gly Ser Asp Ile Gln Met Thr Gln Ser Pro Ser Ser Leu
        115                 120                 125

Ser Ala Ser Val Gly Asp Arg Val Thr Ile Thr Cys Gln Ala Ser Gln
    130                 135                 140

Asn Ile Tyr Lys Tyr Ile Ala Trp Tyr Gln Gln Lys Pro Gly Lys Ala
145                 150                 155                 160

Pro Lys Leu Leu Ile Arg Tyr Thr Ser Thr Leu Glu Ser Gly Thr Pro
                165                 170                 175

Ser Arg Phe Ser Gly Ser Gly Ser Gly Thr Asp Tyr Thr Leu Thr Ile
            180                 185                 190

Ser Ser Leu Gln Pro Glu Asp Phe Ala Thr Tyr Tyr Cys Leu Gln Tyr
        195                 200                 205
```

```
Val Asn Leu Tyr Thr Phe Gly Gly Gly Thr Lys Val Glu Ile Lys Gly
    210                 215                 220

Gly Gly Gly Ser Gly Gly Gly Gly Ser Gly Gly Gly Gly Ser Gln Val
225                 230                 235                 240

Gln Leu Gln Glu Ser Gly Pro Gly Leu Val Lys Pro Ser Glu Thr Leu
                245                 250                 255

Ser Leu Thr Cys Thr Val Ser Gly Phe Ser Ile Ser Ser Asn Ser Val
            260                 265                 270

Ser Trp Val Arg Gln Pro Pro Gly Lys Gly Leu Glu Trp Met Gly Ala
        275                 280                 285

Ile Trp Ser Gly Gly Ser Thr Asp Tyr Asn Ser Ala Leu Lys Ser Arg
    290                 295                 300

Val Thr Ile Ser Arg Asp Thr Ser Lys Asn Gln Val Ser Leu Lys Leu
305                 310                 315                 320

Ser Ser Val Thr Ala Ala Asp Thr Ala Val Tyr Tyr Cys Thr Arg Trp
                325                 330                 335

Glu Gln Pro Tyr Tyr Phe Asp Tyr Trp Gly Gln Gly Thr Met Val Thr
            340                 345                 350

Val Ser Ser
        355


<210> SEQ ID NO 119
<211> LENGTH: 697
<212> TYPE: PRT
<213> ORGANISM: Artificial sequence
<220> FEATURE:
<223> OTHER INFORMATION: Synthesized

<400> SEQUENCE: 119

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Ser Ser
            20                  25                  30

Tyr Ile Ser Trp Val Arg Gln Ala Pro Gly Gln Gly Leu Glu Trp Ile
        35                  40                  45

Ala Trp Ile Tyr Ala Gly Thr Gly Gly Thr Ser Tyr Asn Gln Lys Phe
    50                  55                  60

Thr Gly Arg Ala Thr Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Gly Val Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Asp Ile Gln Met Thr
    450                 455                 460

Gln Ser Pro Ser Ser Leu Ser Ala Ser Val Gly Asp Arg Val Thr Ile
465                 470                 475                 480

Thr Cys Gln Ala Ser Gln Asn Ile Tyr Lys Tyr Ile Ala Trp Tyr Gln
                485                 490                 495

Gln Lys Pro Gly Lys Ala Pro Lys Leu Leu Ile Arg Tyr Thr Ser Thr
            500                 505                 510

Leu Glu Ser Gly Thr Pro Ser Arg Phe Ser Gly Ser Gly Ser Gly Thr
        515                 520                 525

Asp Tyr Thr Leu Thr Ile Ser Ser Leu Gln Pro Glu Asp Phe Ala Thr
    530                 535                 540

Tyr Tyr Cys Leu Gln Tyr Val Asn Leu Tyr Thr Phe Gly Gly Gly Thr
545                 550                 555                 560

Lys Val Glu Ile Lys Gly Gly Gly Gly Ser Gly Gly Gly Gly Ser Gly
                565                 570                 575

Gly Gly Gly Ser Gln Val Gln Leu Gln Glu Ser Gly Pro Gly Leu Val
            580                 585                 590

Lys Pro Ser Glu Thr Leu Ser Leu Thr Cys Thr Val Ser Gly Phe Ser
        595                 600                 605

Ile Ser Ser Asn Ser Val Ser Trp Val Arg Gln Pro Pro Gly Lys Gly
    610                 615                 620
```

```
Leu Glu Trp Met Gly Ala Ile Trp Ser Gly Gly Ser Thr Asp Tyr Asn
625                 630                 635                 640

Ser Ala Leu Lys Ser Arg Val Thr Ile Ser Arg Asp Thr Ser Lys Asn
                645                 650                 655

Gln Val Ser Leu Lys Leu Ser Ser Val Thr Ala Ala Asp Thr Ala Val
            660                 665                 670

Tyr Tyr Cys Thr Arg Trp Glu Gln Pro Tyr Tyr Phe Asp Tyr Trp Gly
        675                 680                 685

Gln Gly Thr Met Val Thr Val Ser Ser
    690                 695


<210> SEQ ID NO 120
<211> LENGTH: 699
<212> TYPE: PRT
<213> ORGANISM: Artificial sequence
<220> FEATURE:
<223> OTHER INFORMATION: Synthesized

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Gly Leu Glu Trp Ile
        35                  40                  45

Gly Tyr Ile Tyr Pro Gly Ser Gly Gly Pro Val Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asn Tyr Arg Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Asp Ile Gln Met Thr
    450                 455                 460

Gln Ser Pro Ser Ser Leu Ser Ala Ser Val Gly Asp Arg Val Thr Ile
465                 470                 475                 480

Thr Cys His Ala Ser Gln Asn Ile Asn Val Trp Leu Ser Trp Tyr Gln
                485                 490                 495

Gln Lys Pro Gly Lys Val Pro Lys Leu Leu Ile Tyr Lys Ala Ser Asn
            500                 505                 510

Leu His Thr Gly Val Pro Ser Arg Phe Ser Gly Ser Gly Ser Gly Thr
        515                 520                 525

Asp Phe Thr Leu Thr Ile Ser Ser Leu Gln Pro Glu Asp Val Ala Thr
    530                 535                 540

Tyr Tyr Cys Gln Gln Gly Gln Ser Tyr Pro Leu Thr Phe Gly Gly Gly
545                 550                 555                 560

Thr Lys Val Glu Ile Lys Gly Gly Gly Gly Ser Gly Gly Gly Gly Ser
                565                 570                 575

Gly Gly Gly Gly Ser Gln Val Thr Leu Lys Glu Ser Gly Pro Val Leu
            580                 585                 590

Val Lys Pro Thr Glu Thr Leu Thr Leu Thr Cys Thr Val Ser Gly Phe
        595                 600                 605

Ser Leu Thr Asp Tyr Gly Val Ser Trp Ile Arg Gln Pro Pro Gly Lys
    610                 615                 620

Ala Leu Glu Trp Leu Gly Val Ile Trp Gly Gly Gly Gly Thr Tyr Tyr
625                 630                 635                 640

Asn Ser Ala Leu Lys Ser Arg Leu Thr Ile Ser Lys Asp Thr Ser Lys
                645                 650                 655

Ser Gln Val Val Leu Thr Met Thr Asn Met Asp Pro Val Asp Thr Ala
            660                 665                 670

Thr Tyr Tyr Cys Ala Lys His Pro Tyr Gly His Phe Gly Met Asp Tyr
        675                 680                 685

Trp Gly Gln Gly Thr Thr Val Thr Val Ser Ser
    690                 695
```

<210> SEQ ID NO 121
<211> LENGTH: 699
<212> TYPE: PRT
<213> ORGANISM: Artificial sequence
<220> FEATURE:
<223> OTHER INFORMATION: Synthesized

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Ser Ser
            20                  25                  30

Tyr Ile Ser Trp Val Arg Gln Ala Pro Gly Gln Gly Leu Glu Trp Ile
        35                  40                  45

Ala Trp Ile Tyr Ala Gly Thr Gly Gly Thr Ser Tyr Asn Gln Lys Phe
    50                  55                  60

Thr Gly Arg Ala Thr Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Gly Val Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Ser Gly Gly Gly Gly Ser Gly Gly Gly Gly Ser Glu Ile Val Leu Thr
450 455 460

Gln Ser Pro Ala Thr Leu Ser Leu Ser Pro Gly Glu Arg Ala Thr Leu
465 470 475 480

Ser Cys Ser Ala Ser Ser Ser Val Ser Tyr Met His Trp Tyr Gln Gln
485 490 495

Lys Pro Gly Gln Ala Pro Arg Arg Trp Ile Tyr Asp Thr Ser Lys Leu
500 505 510

Ala Ser Gly Val Pro Ala Arg Phe Ser Gly Ser Gly Ser Gly Thr Asp
515 520 525

Tyr Thr Leu Thr Ile Ser Ser Leu Glu Pro Glu Asp Phe Ala Val Tyr
530 535 540

Tyr Cys Gln Gln Trp Ser Ser Asn Pro Leu Thr Phe Gly Gly Gly Thr
545 550 555 560

Lys Val Glu Ile Lys Gly Gly Gly Gly Ser Gly Gly Gly Gly Ser Gly
565 570 575

Gly Gly Gly Ser Gln Val Gln Leu Val Gln Ser Gly Ala Glu Val Lys
580 585 590

Lys Pro Gly Ser Ser Val Lys Val Ser Cys Lys Ala Ser Gly Tyr Thr
595 600 605

Phe Thr Ser Tyr Trp Leu His Trp Val Arg Gln Ala Pro Gly Gln Gly
610 615 620

Leu Glu Trp Ile Gly Arg Ile Asp Pro Asn Ser Gly Asp Thr Lys Tyr
625 630 635 640

Asn Glu Lys Phe Lys Ser Arg Ala Thr Ile Thr Val Asp Lys Ser Thr
645 650 655

Ser Thr Ala Tyr Met Glu Leu Ser Ser Leu Arg Ser Glu Asp Thr Ala
660 665 670

Val Tyr Tyr Cys Ala Arg Tyr Tyr Tyr Gly Arg Ser Tyr Phe Asp Tyr
675 680 685

Trp Gly Gln Gly Thr Thr Val Thr Val Ser Ser
690 695

<210> SEQ ID NO 122
<211> LENGTH: 241
<212> TYPE: PRT
<213> ORGANISM: Artificial sequence
<220> FEATURE:
<223> OTHER INFORMATION: Synthesized

<400> SEQUENCE: 122

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Arg Thr Tyr
20 25 30

Leu Asn Trp Tyr Gln Gln Lys Pro Gly Lys Val Pro Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Val Ala Thr Tyr Tyr Cys Gln Gln Gly Asn Thr Leu Pro Trp
85 90 95

Thr Phe Gly Cys Gly Thr Lys Val Glu Ile Lys Gly Gly Gly Gly Ser
100 105 110

Gly Gly Gly Gly Ser Gly Gly Gly Gly Ser Gln Val Gln Leu Val Gln
115 120 125

Ser Gly Ala Glu Val Lys Lys Pro Gly Ser Ser Val Lys Val Ser Cys
130 135 140

Lys Ala Ser Gly Tyr Thr Phe Thr Ser Tyr Ile Met His Trp Val Arg
145 150 155 160

Gln Ala Pro Gly Gln Cys Leu Glu Trp Ile Gly Tyr Ile Asn Pro Tyr
165 170 175

Asn Ser Gly Thr Lys Tyr Asn Glu Lys Phe Lys Gly Arg Val Thr Ile
180 185 190

Thr Ser Asp Lys Ser Thr Ser Thr Ala Tyr Met Glu Leu Ser Ser Leu
195 200 205

Arg Ser Glu Asp Thr Ala Val Tyr Tyr Cys Ala His Tyr Tyr Gly Ser
210 215 220

Thr Phe Thr Met Asp Tyr Trp Gly Gln Gly Thr Thr Val Thr Val Ser
225 230 235 240

Ser

<210> SEQ ID NO 123
<211> LENGTH: 240
<212> TYPE: PRT
<213> ORGANISM: Artificial sequence
<220> FEATURE:
<223> OTHER INFORMATION: Synthesized

<400> SEQUENCE: 123

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Tyr Met
20 25 30

His Trp Tyr Gln Gln Lys Pro Gly Gln Ala Pro Arg Arg Trp Ile Tyr
35 40 45

Asp Thr Ser Lys Leu Ala Ser Gly Val Pro Ala Arg Phe Ser Gly Ser
50 55 60

Gly Ser Gly Thr Asp Tyr Thr Leu Thr Ile Ser Ser Leu Glu Pro Glu
65 70 75 80

Asp Phe Ala Val Tyr Tyr Cys Gln Gln Trp Ser Ser Asn Pro Leu Thr
85 90 95

Phe Gly Cys Gly Thr Lys Val Glu Ile Lys Gly Gly Gly Gly Ser Gly
100 105 110

Gly Gly Gly Ser Gly Gly Gly Gly Ser Gln Val Gln Leu Val Gln Ser
115 120 125

Gly Ala Glu Val Lys Lys Pro Gly Ser Ser Val Lys Val Ser Cys Lys
130 135 140

```
Ala Ser Gly Tyr Thr Phe Thr Ser Tyr Trp Leu His Trp Val Arg Gln
145                 150                 155                 160

Ala Pro Gly Gln Cys Leu Glu Trp Ile Gly Arg Ile Asp Pro Asn Ser
                165                 170                 175

Gly Asp Thr Lys Tyr Asn Glu Lys Phe Lys Ser Arg Ala Thr Ile Thr
            180                 185                 190

Val Asp Lys Ser Thr Ser Thr Ala Tyr Met Glu Leu Ser Ser Leu Arg
        195                 200                 205

Ser Glu Asp Thr Ala Val Tyr Tyr Cys Ala Arg Tyr Tyr Tyr Gly Arg
    210                 215                 220

Ser Tyr Phe Asp Tyr Trp Gly Gln Gly Thr Thr Val Thr Val Ser Ser
225                 230                 235                 240


<210> SEQ ID NO 124
<211> LENGTH: 238
<212> TYPE: PRT
<213> ORGANISM: Artificial sequence
<220> FEATURE:
<223> OTHER INFORMATION: Synthesized

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Lys Tyr
            20                  25                  30

Ile Ala Trp Tyr Gln Gln Lys Pro Gly Lys Ala Pro Lys Leu Leu Ile
        35                  40                  45

Arg Tyr Thr Ser Thr Leu Glu Ser Gly Thr Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Val Asn Leu Tyr Thr
                85                  90                  95

Phe Gly Cys Gly Thr Lys Val Glu Ile Lys Gly Gly Gly Gly Ser Gly
            100                 105                 110

Gly Gly Gly Ser Gly Gly Gly Gly Ser Gln Val Gln Leu Gln Glu Ser
        115                 120                 125

Gly Pro Gly Leu Val Lys Pro Ser Glu Thr Leu Ser Leu Thr Cys Thr
    130                 135                 140

Val Ser Gly Phe Ser Ile Ser Ser Asn Ser Val Ser Trp Val Arg Gln
145                 150                 155                 160

Pro Pro Gly Lys Cys Leu Glu Trp Met Gly Ala Ile Trp Ser Gly Gly
                165                 170                 175

Ser Thr Asp Tyr Asn Ser Ala Leu Lys Ser Arg Val Thr Ile Ser Arg
            180                 185                 190

Asp Thr Ser Lys Asn Gln Val Ser Leu Lys Leu Ser Ser Val Thr Ala
        195                 200                 205

Ala Asp Thr Ala Val Tyr Tyr Cys Thr Arg Trp Glu Gln Pro Tyr Tyr
    210                 215                 220

Phe Asp Tyr Trp Gly Gln Gly Thr Met Val Thr Val Ser Ser
225                 230                 235


<210> SEQ ID NO 125
<211> LENGTH: 240
<212> TYPE: PRT
<213> ORGANISM: Artificial sequence
<220> FEATURE:
```

<223> OTHER INFORMATION: Synthesized

<400> SEQUENCE: 125

Asp Ile Gln Met Thr Gln Ser Pro Ser Ser Leu Ser Ala Ser Val Gly
1 5 10 15

Asp Arg Val Thr Ile Thr Cys His Ala Ser Gln Asn Ile Asn Val Trp
20 25 30

Leu Ser Trp Tyr Gln Gln Lys Pro Gly Lys Val Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Gln Gly Gln Ser Tyr Pro Leu
85 90 95

Thr Phe Gly Cys Gly Thr Lys Val Glu Ile Lys Gly Gly Gly Gly Ser
100 105 110

Gly Gly Gly Gly Ser Gly Gly Gly Gly Ser Gln Val Thr Leu Lys Glu
115 120 125

Ser Gly Pro Val Leu Val Lys Pro Thr Glu Thr Leu Thr Leu Thr Cys
130 135 140

Thr Val Ser Gly Phe Ser Leu Thr Asp Tyr Gly Val Ser Trp Ile Arg
145 150 155 160

Gln Pro Pro Gly Lys Cys Leu Glu Trp Leu Gly Val Ile Trp Gly Gly
165 170 175

Gly Gly Thr Tyr Tyr Asn Ser Ala Leu Lys Ser Arg Leu Thr Ile Ser
180 185 190

Lys Asp Thr Ser Lys Ser Gln Val Val Leu Thr Met Thr Asn Met Asp
195 200 205

Pro Val Asp Thr Ala Thr Tyr Tyr Cys Ala Lys His Pro Tyr Gly His
210 215 220

Phe Gly Met Asp Tyr Trp Gly Gln Gly Thr Thr Val Thr Val Ser Ser
225 230 235 240

<210> SEQ ID NO 126
<211> LENGTH: 405
<212> TYPE: PRT
<213> ORGANISM: Artificial sequence
<220> FEATURE:
<223> OTHER INFORMATION: Synthesized

<400> SEQUENCE: 126

Phe Glu Arg Thr Arg Ser Leu Gln Asp Pro Cys Ser Asn Cys Pro Ala
1 5 10 15

Gly Thr Phe Cys Asp Asn Asn Arg Asn Gln Ile Cys Ser Pro Cys Pro
20 25 30

Pro Asn Ser Phe Ser Ser Ala Gly Gly Gln Arg Thr Cys Asp Ile Cys
35 40 45

Arg Gln Cys Lys Gly Val Phe Arg Thr Arg Lys Glu Cys Ser Ser Thr
50 55 60

Ser Asn Ala Glu Cys Asp Cys Thr Pro Gly Phe His Cys Leu Gly Ala
65 70 75 80

Gly Cys Ser Met Cys Glu Gln Asp Cys Lys Gln Gly Gln Glu Leu Thr
85 90 95

Lys Lys Gly Cys Lys Asp Cys Cys Phe Gly Thr Phe Asn Asp Gln Lys
100 105 110

Arg Gly Ile Cys Arg Pro Trp Thr Asn Cys Ser Leu Asp Gly Lys Ser
115 120 125

Val Leu Val Asn Gly Thr Lys Glu Arg Asp Val Val Cys Gly Pro Ser
130 135 140

Pro Ala Asp Leu Ser Pro Gly Ala Ser Ser Val Thr Pro Pro Ala Pro
145 150 155 160

Ala Arg Glu Pro Gly His Ser Pro Gln Thr Gly Gly Gly Glu Pro Lys
165 170 175

Ser Cys Asp Lys Thr His Thr Cys Pro Pro Cys Pro Ala Pro Glu Leu
180 185 190

Leu Gly Gly Pro Ser Val Phe Leu Phe Pro Pro Lys Pro Lys Asp Thr
195 200 205

Leu Met Ile Ser Arg Thr Pro Glu Val Thr Cys Val Val Val Asp Val
210 215 220

Ser His Glu Asp Pro Glu Val Lys Phe Asn Trp Tyr Val Asp Gly Val
225 230 235 240

Glu Val His Asn Ala Lys Thr Lys Pro Arg Glu Glu Gln Tyr Asn Ser
245 250 255

Thr Tyr Arg Val Val Ser Val Leu Thr Val Leu His Gln Asp Trp Leu
260 265 270

Asn Gly Lys Glu Tyr Lys Cys Lys Val Ser Asn Lys Ala Leu Pro Ala
275 280 285

Pro Ile Glu Lys Thr Ile Ser Lys Ala Lys Gly Gln Pro Arg Glu Pro
290 295 300

Gln Val Tyr Thr Leu Pro Pro Ser Arg Asp Glu Leu Thr Lys Asn Gln
305 310 315 320

Val Ser Leu Thr Cys Leu Val Lys Gly Phe Tyr Pro Ser Asp Ile Ala
325 330 335

Val Glu Trp Glu Ser Asn Gly Gln Pro Glu Asn Asn Tyr Lys Thr Thr
340 345 350

Pro Pro Val Leu Asp Ser Asp Gly Ser Phe Phe Leu Tyr Ser Lys Leu
355 360 365

Thr Val Asp Lys Ser Arg Trp Gln Gln Gly Asn Val Phe Ser Cys Ser
370 375 380

Val Met His Glu Ala Leu His Asn His Tyr Thr Gln Lys Ser Leu Ser
385 390 395 400

Leu Ser Pro Gly Lys
405

<210> SEQ ID NO 127
<211> LENGTH: 138
<212> TYPE: PRT
<213> ORGANISM: Artificial sequence
<220> FEATURE:
<223> OTHER INFORMATION: Synthesized

<400> SEQUENCE: 127

Met Glu Arg His Trp Ile Phe Leu Phe Leu Phe Ser Val Thr Ala Gly
1 5 10 15

Val His Ser Gln Val Gln Leu Val Gln Ser Gly Ala Glu Val Lys Lys
20 25 30

Pro Gly Ser Ser Val Lys Val Ser Cys Lys Ala Ser Gly Tyr Ile Phe
35 40 45

Ile Asn Tyr Trp Met His Trp Val Arg Ala Pro Gly Gln Gly Leu Glu
50 55 60

Trp Ile Gly Tyr Ile Asn Pro Ser Thr Gly Tyr Thr Glu Ser Asn Gln
65 70 75 80

Lys Phe Lys Asp Arg Val Thr Ile Thr Ala Asp Lys Ser Thr Ser Thr
85 90 95

Ala Tyr Met Glu Leu Ser Ser Leu Arg Ser Glu Asp Thr Ala Val Tyr
100 105 110

Tyr Cys Ala Arg Ser Tyr Val Gly Tyr Tyr Tyr Ala Val Asp Tyr Trp
115 120 125

Gly Gln Gly Thr Thr Val Thr Val Ser Ser
130 135

<210> SEQ ID NO 128
<211> LENGTH: 5
<212> TYPE: PRT
<213> ORGANISM: Artificial sequence
<220> FEATURE:
<223> OTHER INFORMATION: Synthesized

<400> SEQUENCE: 128

Asn Tyr Trp Met His
1 5

<210> SEQ ID NO 129
<211> LENGTH: 17
<212> TYPE: PRT
<213> ORGANISM: Artificial sequence
<220> FEATURE:
<223> OTHER INFORMATION: Synthesized

<400> SEQUENCE: 129

Tyr Ile Asn Pro Ser Thr Gly Tyr Thr Glu Ser Asn Gln Lys Phe Lys
1 5 10 15

Asp

<210> SEQ ID NO 130
<211> LENGTH: 11
<212> TYPE: PRT
<213> ORGANISM: Artificial sequence
<220> FEATURE:
<223> OTHER INFORMATION: Synthesized

<400> SEQUENCE: 130

Ser Tyr Val Gly Tyr Tyr Tyr Ala Val Asp Tyr
1 5 10

<210> SEQ ID NO 131
<211> LENGTH: 133
<212> TYPE: PRT
<213> ORGANISM: Artificial sequence
<220> FEATURE:
<223> OTHER INFORMATION: Synthesized

<400> SEQUENCE: 131

Met Asp Ser Gln Ala Gln Val Leu Met Leu Leu Leu Leu Trp Val Ser
1 5 10 15

Gly Thr Cys Gly Asp Ile Val Met Thr Gln Ser Pro Asp Ser Leu Ala
20 25 30

Val Ser Leu Gly Glu Arg Ala Thr Ile Asn Cys Lys Ser Ser Gln Ser
35 40 45

Leu Leu Tyr Ser Asn Asn Glu Lys Asn Tyr Leu Ala Trp Tyr Gln Gln
50 55 60

Lys Pro Gly Gln Pro Pro Lys Leu Leu Ile Tyr Trp Ala Ser Thr Arg
65 70 75 80

Glu Ser Gly Val Pro Asp Arg Phe Ser Gly Ser Gly Ser Gly Thr Ile
85 90 95

Phe Thr Leu Thr Ile Ser Ser Leu Gln Ala Glu Asp Val Ala Val Tyr
100 105 110

Tyr Cys Gln Gln Tyr Tyr Ser Tyr Pro Tyr Thr Phe Gly Gly Gly Thr
115 120 125

Lys Val Glu Ile Lys
130

<210> SEQ ID NO 132
<211> LENGTH: 17
<212> TYPE: PRT
<213> ORGANISM: Artificial sequence
<220> FEATURE:
<223> OTHER INFORMATION: Synthesized

<400> SEQUENCE: 132

Lys Ser Ser Gln Ser Leu Leu Tyr Ser Asn Asn Glu Lys Asn Tyr Leu
1 5 10 15

Ala

<210> SEQ ID NO 133
<211> LENGTH: 7
<212> TYPE: PRT
<213> ORGANISM: Artificial sequence
<220> FEATURE:
<223> OTHER INFORMATION: Synthesized

<400> SEQUENCE: 133

Trp Ala Ser Thr Arg Glu Ser
1 5

<210> SEQ ID NO 134
<211> LENGTH: 9
<212> TYPE: PRT
<213> ORGANISM: Artificial sequence
<220> FEATURE:
<223> OTHER INFORMATION: Synthesized

<400> SEQUENCE: 134

Gln Gln Tyr Tyr Ser Tyr Pro Tyr Thr
1 5

<210> SEQ ID NO 135
<211> LENGTH: 255
<212> TYPE: PRT
<213> ORGANISM: Homo sapiens

<400> SEQUENCE: 135

Met Gly Asn Ser Cys Tyr Asn Ile Val Ala Thr Leu Leu Leu Val Leu
1 5 10 15

Asn Phe Glu Arg Thr Arg Ser Leu Gln Asp Pro Cys Ser Asn Cys Pro
20 25 30

Ala Gly Thr Phe Cys Asp Asn Asn Arg Asn Gln Ile Cys Ser Pro Cys
35 40 45

Pro Pro Asn Ser Phe Ser Ser Ala Gly Gly Gln Arg Thr Cys Asp Ile
50 55 60

Cys Arg Gln Cys Lys Gly Val Phe Arg Thr Arg Lys Glu Cys Ser Ser
65 70 75 80

```
Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255


<210> SEQ ID NO 136
<211> LENGTH: 247
<212> TYPE: PRT
<213> ORGANISM: Artificial sequence
<220> FEATURE:
<223> OTHER INFORMATION: Synthesized

<400> SEQUENCE: 136

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Asn Asn Glu Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Ile Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Tyr Thr Phe Gly Cys Gly Thr Lys Val Glu Ile
            100                 105                 110

Lys Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ser
    130                 135                 140

Ser Val Lys Val Ser Cys Lys Ala Ser Gly Tyr Ile Phe Ile Asn Tyr
145                 150                 155                 160

Trp Met His Trp Val Arg Ala Pro Gly Gln Cys Leu Glu Trp Ile Gly
                165                 170                 175

Tyr Ile Asn Pro Ser Thr Gly Tyr Thr Glu Ser Asn Gln Lys Phe Lys
            180                 185                 190
```

```
Asp Arg Val Thr Ile Thr Ala Asp Lys Ser Thr Ser Thr Ala Tyr Met
        195                 200                 205

Glu Leu Ser Ser Leu Arg Ser Glu Asp Thr Ala Val Tyr Tyr Cys Ala
    210                 215                 220

Arg Ser Tyr Val Gly Tyr Tyr Tyr Ala Val Asp Tyr Trp Gly Gln Gly
225                 230                 235                 240

Thr Thr Val Thr Val Ser Ser
                245


<210> SEQ ID NO 137
<211> LENGTH: 364
<212> TYPE: PRT
<213> ORGANISM: Artificial sequence
<220> FEATURE:
<223> OTHER INFORMATION: Synthesized

<400> SEQUENCE: 137

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Ser Gly Gly Gly Gly Ser
            100                 105                 110

Gly Gly Gly Gly Ser Asp Ile Val Met Thr Gln Ser Pro Asp Ser Leu
        115                 120                 125

Ala Val Ser Leu Gly Glu Arg Ala Thr Ile Asn Cys Lys Ser Ser Gln
    130                 135                 140

Ser Leu Leu Tyr Ser Asn Asn Glu Lys Asn Tyr Leu Ala Trp Tyr Gln
145                 150                 155                 160

Gln Lys Pro Gly Gln Pro Pro Lys Leu Leu Ile Tyr Trp Ala Ser Thr
                165                 170                 175

Arg Glu Ser Gly Val Pro Asp Arg Phe Ser Gly Ser Gly Ser Gly Thr
            180                 185                 190

Ile Phe Thr Leu Thr Ile Ser Ser Leu Gln Ala Glu Asp Val Ala Val
        195                 200                 205

Tyr Tyr Cys Gln Gln Tyr Tyr Ser Tyr Pro Tyr Thr Phe Gly Cys Gly
    210                 215                 220

Thr Lys Val Glu Ile Lys Gly Gly Gly Gly Ser Gly Gly Gly Gly Ser
225                 230                 235                 240

Gly Gly Gly Gly Ser Gln Val Gln Leu Val Gln Ser Gly Ala Glu Val
                245                 250                 255

Lys Lys Pro Gly Ser Ser Val Lys Val Ser Cys Lys Ala Ser Gly Tyr
            260                 265                 270

Ile Phe Ile Asn Tyr Trp Met His Trp Val Arg Ala Pro Gly Gln Cys
        275                 280                 285

Leu Glu Trp Ile Gly Tyr Ile Asn Pro Ser Thr Gly Tyr Thr Glu Ser
    290                 295                 300
```

```
Asn Gln Lys Phe Lys Asp Arg Val Thr Ile Thr Ala Asp Lys Ser Thr
305                 310                 315                 320

Ser Thr Ala Tyr Met Glu Leu Ser Ser Leu Arg Ser Glu Asp Thr Ala
                325                 330                 335

Val Tyr Tyr Cys Ala Arg Ser Tyr Val Gly Tyr Tyr Tyr Ala Val Asp
            340                 345                 350

Tyr Trp Gly Gln Gly Thr Thr Val Thr Val Ser Ser
        355                 360


<210> SEQ ID NO 138
<211> LENGTH: 706
<212> TYPE: PRT
<213> ORGANISM: Artificial sequence
<220> FEATURE:
<223> OTHER INFORMATION: Synthesized

<400> SEQUENCE: 138

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ser Ser Ser
            20                  25                  30

Tyr Ile Ser Trp Val Arg Gln Ala Pro Gly Gln Gly Leu Glu Trp Ile
        35                  40                  45

Ala Trp Ile Tyr Ala Gly Thr Gly Gly Thr Ser Tyr Asn Gln Lys Phe
    50                  55                  60

Thr Gly Arg Ala Thr Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Gly Val Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Asp Ile Val Met Thr
    450                 455                 460

Gln Ser Pro Asp Ser Leu Ala Val Ser Leu Gly Glu Arg Ala Thr Ile
465                 470                 475                 480

Asn Cys Lys Ser Ser Gln Ser Leu Leu Tyr Ser Asn Asn Glu Lys Asn
                485                 490                 495

Tyr Leu Ala Trp Tyr Gln Gln Lys Pro Gly Gln Pro Pro Lys Leu Leu
            500                 505                 510

Ile Tyr Trp Ala Ser Thr Arg Glu Ser Gly Val Pro Asp Arg Phe Ser
        515                 520                 525

Gly Ser Gly Ser Gly Thr Ile Phe Thr Leu Thr Ile Ser Ser Leu Gln
    530                 535                 540

Ala Glu Asp Val Ala Val Tyr Tyr Cys Gln Gln Tyr Tyr Ser Tyr Pro
545                 550                 555                 560

Tyr Thr Phe Gly Cys Gly Thr Lys Val Glu Ile Lys Gly Gly Gly Gly
                565                 570                 575

Ser Gly Gly Gly Gly Ser Gly Gly Gly Gly Ser Gln Val Gln Leu Val
            580                 585                 590

Gln Ser Gly Ala Glu Val Lys Lys Pro Gly Ser Ser Val Lys Val Ser
        595                 600                 605

Cys Lys Ala Ser Gly Tyr Ile Phe Ile Asn Tyr Trp Met His Trp Val
    610                 615                 620

Arg Ala Pro Gly Gln Cys Leu Glu Trp Ile Gly Tyr Ile Asn Pro Ser
625                 630                 635                 640

Thr Gly Tyr Thr Glu Ser Asn Gln Lys Phe Lys Asp Arg Val Thr Ile
                645                 650                 655

Thr Ala Asp Lys Ser Thr Ser Thr Ala Tyr Met Glu Leu Ser Ser Leu
            660                 665                 670

Arg Ser Glu Asp Thr Ala Val Tyr Tyr Cys Ala Arg Ser Tyr Val Gly
        675                 680                 685

Tyr Tyr Tyr Ala Val Asp Tyr Trp Gly Gln Gly Thr Thr Val Thr Val
    690                 695                 700

Ser Ser
705
```

<210> SEQ ID NO 139
<211> LENGTH: 247
<212> TYPE: PRT
<213> ORGANISM: Artificial sequence
<220> FEATURE:
<223> OTHER INFORMATION: Synthesized

<400> SEQUENCE: 139

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ile Phe Ile Asn Tyr
            20                  25                  30

Trp Met His Trp Val Arg Ala Pro Gly Gln Cys Leu Glu Trp Ile Gly
        35                  40                  45

Tyr Ile Asn Pro Ser Thr Gly Tyr Thr Glu Ser Asn Gln Lys Phe Lys
    50                  55                  60

Asp Arg Val Thr Ile Thr Ala Asp Lys Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ser Tyr Val Gly Tyr Tyr Tyr Ala Val Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Tyr Ser Asn Asn Glu Lys Asn Tyr Leu Ala Trp Tyr
                165                 170                 175

Gln Gln Lys Pro Gly Gln Pro Pro Lys Leu Leu Ile Tyr Trp Ala Ser
            180                 185                 190

Thr Arg Glu Ser Gly Val Pro Asp Arg Phe Ser Gly Ser Gly Ser Gly
        195                 200                 205

Thr Ile Phe Thr Leu Thr Ile Ser Ser Leu Gln Ala Glu Asp Val Ala
    210                 215                 220

Val Tyr Tyr Cys Gln Gln Tyr Tyr Ser Tyr Pro Tyr Thr Phe Gly Cys
225                 230                 235                 240

Gly Thr Lys Val Glu Ile Lys
                245

<210> SEQ ID NO 140
<211> LENGTH: 364
<212> TYPE: PRT
<213> ORGANISM: Artificial sequence
<220> FEATURE:
<223> OTHER INFORMATION: Synthesized

<400> SEQUENCE: 140

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65 70 75 80

Asn Val Phe Ser Cys Ser Val Met His Glu Ala Leu His Asn His Tyr
85 90 95

Thr Gln Lys Ser Leu Ser Leu Ser Pro Gly Ser Gly Gly Gly Gly Ser
100 105 110

Gly Gly Gly Gly Ser Gln Val Gln Leu Val Gln Ser Gly Ala Glu Val
115 120 125

Lys Lys Pro Gly Ser Ser Val Lys Val Ser Cys Lys Ala Ser Gly Tyr
130 135 140

Ile Phe Ile Asn Tyr Trp Met His Trp Val Arg Ala Pro Gly Gln Cys
145 150 155 160

Leu Glu Trp Ile Gly Tyr Ile Asn Pro Ser Thr Gly Tyr Thr Glu Ser
165 170 175

Asn Gln Lys Phe Lys Asp Arg Val Thr Ile Thr Ala Asp Lys Ser Thr
180 185 190

Ser Thr Ala Tyr Met Glu Leu Ser Ser Leu Arg Ser Glu Asp Thr Ala
195 200 205

Val Tyr Tyr Cys Ala Arg Ser Tyr Val Gly Tyr Tyr Tyr Ala Val Asp
210 215 220

Tyr Trp Gly Gln Gly Thr Thr Val Thr Val Ser Ser Gly Gly Gly Gly
225 230 235 240

Ser Gly Gly Gly Gly Ser Gly Gly Gly Gly Ser Asp Ile Val Met Thr
245 250 255

Gln Ser Pro Asp Ser Leu Ala Val Ser Leu Gly Glu Arg Ala Thr Ile
260 265 270

Asn Cys Lys Ser Ser Gln Ser Leu Leu Tyr Ser Asn Asn Glu Lys Asn
275 280 285

Tyr Leu Ala Trp Tyr Gln Gln Lys Pro Gly Gln Pro Pro Lys Leu Leu
290 295 300

Ile Tyr Trp Ala Ser Thr Arg Glu Ser Gly Val Pro Asp Arg Phe Ser
305 310 315 320

Gly Ser Gly Ser Gly Thr Ile Phe Thr Leu Thr Ile Ser Ser Leu Gln
325 330 335

Ala Glu Asp Val Ala Val Tyr Tyr Cys Gln Gln Tyr Tyr Ser Tyr Pro
340 345 350

Tyr Thr Phe Gly Cys Gly Thr Lys Val Glu Ile Lys
355 360

<210> SEQ ID NO 141
<211> LENGTH: 706
<212> TYPE: PRT
<213> ORGANISM: Artificial sequence
<220> FEATURE:
<223> OTHER INFORMATION: Synthesized

<400> SEQUENCE: 141

Gln Val Gln Leu Val Gln Ser Gly Ala Glu Val Lys Lys Pro Gly Ser
1 5 10 15

Ser Val Lys Val Ser Cys Lys Ala Ser Gly Phe Thr Phe Ser Ser Ser
20 25 30

Tyr Ile Ser Trp Val Arg Gln Ala Pro Gly Gln Gly Leu Glu Trp Ile
35 40 45

Ala Trp Ile Tyr Ala Gly Thr Gly Gly Thr Ser Tyr Asn Gln Lys Phe
50 55 60

```
Thr Gly Arg Ala Thr Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Glu Gly Val Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ser Gly Gly Gly Gly Ser Gly Gly Gly Gly Ser Gln Val Gln Leu Val
    450                 455                 460

Gln Ser Gly Ala Glu Val Lys Lys Pro Gly Ser Ser Val Lys Val Ser
465                 470                 475                 480
```

Cys Lys Ala Ser Gly Tyr Ile Phe Ile Asn Tyr Trp Met His Trp Val
485 490 495

Arg Ala Pro Gly Gln Cys Leu Glu Trp Ile Gly Tyr Ile Asn Pro Ser
500 505 510

Thr Gly Tyr Thr Glu Ser Asn Gln Lys Phe Lys Asp Arg Val Thr Ile
515 520 525

Thr Ala Asp Lys Ser Thr Ser Thr Ala Tyr Met Glu Leu Ser Ser Leu
530 535 540

Arg Ser Glu Asp Thr Ala Val Tyr Tyr Cys Ala Arg Ser Tyr Val Gly
545 550 555 560

Tyr Tyr Tyr Ala Val Asp Tyr Trp Gly Gln Gly Thr Thr Val Thr Val
565 570 575

Ser Ser Gly Gly Gly Gly Ser Gly Gly Gly Gly Ser Gly Gly Gly Gly
580 585 590

Ser Asp Ile Val Met Thr Gln Ser Pro Asp Ser Leu Ala Val Ser Leu
595 600 605

Gly Glu Arg Ala Thr Ile Asn Cys Lys Ser Ser Gln Ser Leu Leu Tyr
610 615 620

Ser Asn Asn Glu Lys Asn Tyr Leu Ala Trp Tyr Gln Gln Lys Pro Gly
625 630 635 640

Gln Pro Pro Lys Leu Leu Ile Tyr Trp Ala Ser Thr Arg Glu Ser Gly
645 650 655

Val Pro Asp Arg Phe Ser Gly Ser Gly Ser Gly Thr Ile Phe Thr Leu
660 665 670

Thr Ile Ser Ser Leu Gln Ala Glu Asp Val Ala Val Tyr Tyr Cys Gln
675 680 685

Gln Tyr Tyr Ser Tyr Pro Tyr Thr Phe Gly Cys Gly Thr Lys Val Glu
690 695 700

Ile Lys
705

<210> SEQ ID NO 142
<211> LENGTH: 288
<212> TYPE: PRT
<213> ORGANISM: Homo sapiens

<400> SEQUENCE: 142

Met Gln Ile Pro Gln Ala Pro Trp Pro Val Val Trp Ala Val Leu Gln
1 5 10 15

Leu Gly Trp Arg Pro Gly Trp Phe Leu Asp Ser Pro Asp Arg Pro Trp
20 25 30

Asn Pro Pro Thr Phe Ser Pro Ala Leu Leu Val Val Thr Glu Gly Asp
35 40 45

Asn Ala Thr Phe Thr Cys Ser Phe Ser Asn Thr Ser Glu Ser Phe Val
50 55 60

Leu Asn Trp Tyr Arg Met Ser Pro Ser Asn Gln Thr Asp Lys Leu Ala
65 70 75 80

Ala Phe Pro Glu Asp Arg Ser Gln Pro Gly Gln Asp Cys Arg Phe Arg
85 90 95

Val Thr Gln Leu Pro Asn Gly Arg Asp Phe His Met Ser Val Val Arg
100 105 110

Ala Arg Arg Asn Asp Ser Gly Thr Tyr Leu Cys Gly Ala Ile Ser Leu
115 120 125

Ala Pro Lys Ala Gln Ile Lys Glu Ser Leu Arg Ala Glu Leu Arg Val
130 135 140

Thr Glu Arg Arg Ala Glu Val Pro Thr Ala His Pro Ser Pro Ser Pro
145 150 155 160

Arg Pro Ala Gly Gln Phe Gln Thr Leu Val Val Gly Val Val Gly Gly
165 170 175

Leu Leu Gly Ser Leu Val Leu Leu Val Trp Val Leu Ala Val Ile Cys
180 185 190

Ser Arg Ala Ala Arg Gly Thr Ile Gly Ala Arg Arg Thr Gly Gln Pro
195 200 205

Leu Lys Glu Asp Pro Ser Ala Val Pro Val Phe Ser Val Asp Tyr Gly
210 215 220

Glu Leu Asp Phe Gln Trp Arg Glu Lys Thr Pro Glu Pro Pro Val Pro
225 230 235 240

Cys Val Pro Glu Gln Thr Glu Tyr Ala Thr Ile Val Phe Pro Ser Gly
245 250 255

Met Gly Thr Ser Ser Pro Ala Arg Arg Gly Ser Ala Asp Gly Pro Arg
260 265 270

Ser Ala Gln Pro Leu Arg Pro Glu Asp Gly His Cys Ser Trp Pro Leu
275 280 285

<210> SEQ ID NO 143
<211> LENGTH: 379
<212> TYPE: PRT
<213> ORGANISM: Artificial sequence
<220> FEATURE:
<223> OTHER INFORMATION: Synthesized

<400> SEQUENCE: 143

Leu Asp Ser Pro Asp Arg Pro Trp Asn Pro Pro Thr Phe Ser Pro Ala
1 5 10 15

Leu Leu Val Val Thr Glu Gly Asp Asn Ala Thr Phe Thr Cys Ser Phe
20 25 30

Ser Asn Thr Ser Glu Ser Phe Val Leu Asn Trp Tyr Arg Met Ser Pro
35 40 45

Ser Asn Gln Thr Asp Lys Leu Ala Ala Phe Pro Glu Asp Arg Ser Gln
50 55 60

Pro Gly Gln Asp Cys Arg Phe Arg Val Thr Gln Leu Pro Asn Gly Arg
65 70 75 80

Asp Phe His Met Ser Val Val Arg Ala Arg Arg Asn Asp Ser Gly Thr
85 90 95

Tyr Leu Cys Gly Ala Ile Ser Leu Ala Pro Lys Ala Gln Ile Lys Glu
100 105 110

Ser Leu Arg Ala Glu Leu Arg Val Thr Glu Arg Arg Ala Glu Val Pro
115 120 125

Thr Ala His Pro Ser Pro Ser Pro Arg Pro Ala Gly Gln Phe Gln Thr
130 135 140

Gly Gly Gly Glu Pro Lys Ser Cys Asp Lys Thr His Thr Cys Pro Pro
145 150 155 160

Cys Pro Ala Pro Glu Leu Leu Gly Gly Pro Ser Val Phe Leu Phe Pro
165 170 175

Pro Lys Pro Lys Asp Thr Leu Met Ile Ser Arg Thr Pro Glu Val Thr
180 185 190

Cys Val Val Val Asp Val Ser His Glu Asp Pro Glu Val Lys Phe Asn
195 200 205

-continued

```
Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Asp
        275                 280                 285

Glu Leu Thr Lys Asn Gln Val Ser Leu Thr Cys Leu Val Lys Gly Phe
    290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
        355                 360                 365

Thr Gln Lys Ser Leu Ser Leu Ser Pro Gly Lys
    370                 375
```

ANTIBODIES AGAINST OX40

CROSS-REFERENCE TO RELATED APPLICATIONS

The present application is a divisional application of U.S. application Ser. No. 16/683,073 filed on Nov. 13, 2019, which claims the benefit of U.S. provisional application 62/760,328 filed Nov. 13, 2018, and U.S. provisional application 62/838,579 filed Apr. 25, 2019, each of which is incorporated by reference in its entirety for all purposes.

INCORPORATION BY REFERENCE OF A SEQUENCE LISTING

The present application includes sequences in txt file 557173SEQLIST.TXT of 236,132 bytes, which is incorporated by reference.

BACKGROUND

The antigen-specific immune response is a complex biological process that is controlled by multiple layers of positive and negative regulators. T cells are initially stimulated through the T cell receptor (TCR) by the recognition of their cognate peptide antigen presented by major histocompatibility complex (MHC) molecules on antigen-presenting cells (APCs). Optimal T cell activation requires a second signal provided by costimulatory molecules such as CD28 and ICOS that belong to the CD28 superfamily. The immune response is further regulated positively by other costimulatory molecules such as CD40, OX40, GITR, CD27, HVEM and 4-1BB that belong to the TNF receptor superfamily, which are expressed in a cell type- and development stage-dependent manner, and negatively regulated by checkpoint molecules such as PD-1, TIGIT, TIM-3, LAG-3, BTLA, VISTA, CD96 and CD112R. The function of checkpoint molecules is to prevent undesired overreaction of the immune system in the body; however, they also restrict the ability of the immune system to effectively fight against cancer and infectious disease. For reviews, see Pardoll, Nat. Rev. Cancer, 12:252-264, 2012; Mahoney et al., Nat. Rev. Drug Discov. 14:561-584, 2015; Shin et al., Curr. Opin. Immunol. 33:23-35, 2015; Marquez-Rodas et al. Ann. Transl. Med. 3:267, 2015; Mercier et al., Front. Immunol. 6:418, 2015; Topalian et al., Cancer Cell 27: 450-461, 2015; Baumeister et al., Annu. Rev. Immunol. 34:539-573, 2016; Ward-Kavanagh et al., Immunity 44:1005-1019, 2016; Torphy et al., Int. J. Mol. Sci. 18:2642, 2017.

Blocking the function of a checkpoint molecule by an antagonistic monoclonal antibody has been reported to be effective for boosting the immune system (Mercier et al., supra; Baumeister et al., supra). For example, interaction of PD-1 (also known as CD279) expressed on the surface of T cells with its ligand PD-L1 (also known as CD274) expressed on antigen-presenting cells suppresses immune reactions in the body. Ligands of checkpoint molecules expressed on cancer cells interact with their respective receptors on immune cells and weaken immune reactions in the body, thus allowing the survival and expansion of cancer cells. Inhibition of the interaction between PD-1 and PD-L1 by a monoclonal antibody has been shown to be effective for treatment of cancer. To date, three anti-PD-1 monoclonal IgG antibodies (nivolumab, pembrolizumab and cemiplimab) and three anti-PD-L1 monoclonal IgG antibodies (durvalumab, atezolizumab and avelumab) have been approved as cancer therapeutics by the FDA in the United States. Moreover, monoclonal IgG antibodies against other checkpoint molecules, including TIGIT, TIM-3, LAG-3 and VISTA, that block the interaction with their respective ligands, are investigated for their therapeutic efficacy in clinical studies (Marin-Acevedo et al., J. Hematol. Oncol. 11:39, 2018).

A monoclonal IgG antibody against CTLA-4 (ipilimumab), which blocks the interaction of CTLA-4 on T cells with B7-1 and B7-2 (also called CD80 and CD86, respectively, that are ligands of a costimulatory molecule CD28) on antigen-presenting cells and thus stimulates CD28-mediated activation of T cells, has been used as cancer therapeutics. Agonist IgG antibodies against costimulatory molecules, such as ICOS, CD40, OX40, GITR, CD27 and 4-1BB, are also capable to activate immune cells (Peggs et al., Clin. Exp. Immunol. 157:9-19, 2009; Melero et al., Clin. Cancer Res. 19:1044-1053, 2013; Attanasio et al., Immunity 44:1053-1068, 2016; Strugill et al., Am. J. Hematol. Oncol. 13:4-15, 2017). Costimulatory molecules belonging to the TNF receptor superfamily as well as ICOS require multimeric cross-linking on the surface of immune cells to initiate intracellular signal transduction to enhance immune responses (Watanabe et al., Int. Immunol. 17:269-278, 2005; Croft et al., Nat. Rev. Drug Discov. 12:147-168, 2013; Wikenheiser et al., Front. Immunol. 7: Article 304, 2016). As IgG is divalent for antigen binding, it cannot efficiently trigger signal transduction through these costimulatory molecules unless IgG molecules bound on the cell surface are conjugated, for example, via binding to Fcγ receptors on another cell. An anti-CD40 IgG2 antibody with Fc mutations to enhance the binding to FcγRIIB (also known as CD32B) exhibited anti-tumor activities superior to the parental IgG2 antibody in mouse xenograft tumor models (Dahan et al., Cancer Cell 29:820-831, 2016). As an alternative approach to promote multivalent conjugation of surface molecules, Tso et al. engineered IgG antibodies by fusing the CH3 and CH4 regions of the human mu heavy chain at the C-terminus of the human gamma heavy chain (U.S. Pat. No. 10,053,517). Such engineered hexameric IgG antibodies efficiently cross-linked costimulatory molecules on the cell surface to trigger intracellular signal transduction.

A bispecific antibody is an artificially engineered antibody that is capable to bind to two different antigens or two distinct epitopes on the same antigen. Various forms of bispecific antibodies have been generated (Lameris et al., Crit. Rev. Oncol. Hematol. 92:153-165, 2014; Kontermann et al., Drug Dicov. Today 20:838-847, 2015; Spiess et al., Mol. Immunol. 67:95-106, 2015; Brinkmann et al., MAbs 9:182-212, 2017; Sedykh et al., Drug Des. Dev. Ther. 12:195-208, 2018). Some of the bispecific antibodies, such as blinatumomab that binds to CD3 and CD19, are designed to bring T cells to the proximity of CD19-bearing cancer cells and trigger T cell-mediated cytotoxicity against the cancer cells (Viardot et al., Cancer Treat. Rev. 65:87-95, 2018).

SUMMARY OF THE CLAIMED INVENTION

The invention provides a bispecific antibody comprising a first binding site specifically binding to CD33 and a second binding site specifically binding GITR, OX40, CD40, ICOS or 4-1BB. Optionally, the bispecific antibody further comprises an IgG Fc region. Optionally, the second binding site agonizes OX40 or CD40. Optionally, the first binding site comprises a mature heavy chain variable region comprising CDRs H1, H2 and H3 of SEQ ID NOS. 94-96 respectively and a mature light chain variable region comprising CDRs L1, L2 and L3 of SEQ ID NOS. 97-99 respectively, and the second binding region comprises a mature heavy chain variable region comprising CDRs of H1, H2 and H3 of SEQ ID NOS. 33-35 respectively and a mature light chain variable region comprising CDRs L1, L2 and L3 of SEQ ID NOS. 37-39 respectively, or a mature heavy chain variable region comprising CDRs H1, H2 and H3 of SEQ ID NOS. 13-15 respectively and a mature light chain variable region comprising CDRs L1, L2 and L3 of SEQ ID NOS. 17-19 respectively, or a mature heavy chain variable region comprising CDRs H1, H2 and H3 of SEQ ID NOS. 49-51 respectively and a mature light chain variable region comprising CDRs L1, L2 and L3 of SEQ ID NOS. 53-55 respectively, or a mature heavy chain variable region comprising CDRs H1, H2 and H3 of SEQ ID NOS. 109-111 respectively and a mature light chain variable region comprising CDRs L1, L2 and L3 of SEQ ID NOS. 113-115 respectively, or a mature heavy chain variable region comprising CDRs H1, H2 and H3 of SEQ ID NOS. 128-130 respectively and a mature light chain variable region comprising CDRs L1, L2 and L3 of SEQ ID NOS. 132-134 respectively. Optionally, the first binding site comprises a mature heavy chain variable region comprising residues 20 to 135 of SEQ ID NO:2 and a mature light chain variable region comprising residues 20-131 of SEQ ID NO:7, and the second binding region comprises a mature heavy chain variable region comprising residues 20-137 of SEQ ID NO:32 and a mature light chain variable region comprising residues 21-127 of SEQ ID NO:36, or a mature heavy chain variable region comprising residues 20-138 of SEQ ID NO:12 and a mature light chain variable region comprising residues 21-127 of SEQ ID NO:16, or a mature heavy chain variable region comprising residues 20-138 of SEQ ID NO:48 and a mature light chain variable region comprising residues 23-127 of SEQ ID NO:52, or a mature heavy chain variable region comprising residues 20-136 of SEQ ID NO:108 and a mature light chain variable region comprising residues 21-126 of SEQ ID NO:112, or a mature heavy chain variable region comprising residues 20-138 of SEQ ID NO:127 and a mature light chain variable region comprising residues 21-133 of SEQ ID NO:131. Optionally, the first binding site comprises a mature heavy chain variable region comprising residues 20 to 135 of SEQ ID NO:2 and a mature light chain variable region comprising residues 20-131 of SEQ ID NO:7, and the second binding region comprises a single-chain Fv fragment comprising SEQ ID No: 22, 41, 57, 117, 122, 123, 124, 125, 136 or 139.

The invention further provides a first binding site specifically binding to EGFR, a second binding site specifically binding to GITR, OX40, CD40, ICOS or 4-1BB. Optionally, the bispecific antibody further comprises an Fc region. Optionally, the first binding site antagonizes binding of EGFR to EGF and the second binding site agonizes GITR. Optionally, the first binding site comprises a mature heavy chain variable region comprising CDRs H1, H2 and H3 of SEQ ID NOS. 100-102 respectively and a mature light chain variable region comprising CDRs L1, L2 and L3 of SEQ ID NOS. 103-105 respectively, and the second binding region comprises a mature heavy chain variable region comprising CDRs of H1, H2 and H3 of SEQ ID NOS. 33-35 respectively and a mature light chain variable region comprising CDRs L1, L2 and L3 of SEQ ID NOS. 37-39 respectively, or a mature heavy chain variable region comprising CDRs H1, H2 and H3 of SEQ ID NOS. 13-15 respectively and a mature light chain variable region comprising CDRs L1, L2 and L3 of SEQ ID NOS. 17-19 respectively, or a mature heavy chain variable region comprising CDRs H1, H2 and H3 of SEQ ID NOS. 49-51 respectively and a mature light chain variable region comprising CDRs L1, L2 and L3 of SEQ ID NOS. 53-55 respectively, or a mature heavy chain variable region comprising CDRs H1, H2 and H3 of SEQ ID NOS. 109-111 respectively and a mature light chain variable region comprising CDRs L1, L2 and L3 of SEQ ID NOS. 113-115 respectively, or a mature heavy chain variable region comprising CDRs H1, H2 and H3 of SEQ ID NOS. 128-130 respectively and a mature light chain variable region comprising CDRs L1, L2 and L3 of SEQ ID NOS. 132-134 respectively. Optionally, the first binding site comprises a mature heavy chain variable region comprising residues 20-138 of SEQ ID NO:29 and a mature light chain variable region comprising residues 21-127 of SEQ ID NO:30, and the second binding region comprises a mature heavy chain variable region comprising residues 20-137 of SEQ ID NO:32 and a mature light chain variable region comprising residues 21-127 of SEQ ID NO:36, or a mature heavy chain variable region comprising residues 20-138 of SEQ ID NO:12 and a mature light chain variable region comprising residues 21-127 of SEQ ID NO:16, or a mature heavy chain variable region comprising residues 20-138 of SEQ ID NO:48 and a mature light chain variable region comprising residues 23-127 of SEQ ID NO:52, or a mature heavy chain variable region comprising residues 20-136 of SEQ ID NO:108 and a mature light chain variable region comprising residues 21-126 of SEQ ID NO:112, or a mature heavy chain variable region comprising residues 20-138 of SEQ ID NO:127 and a mature light chain variable region comprising residues 21-133 of SEQ ID NO:131. Optionally, the first binding site comprises a mature heavy chain variable region comprising residues 20-138 of SEQ ID NO:29 and a mature light chain variable region comprising residues 21-127 of SEQ ID NO:30, and the second binding region comprises a single-chain Fv fragment comprising SEQ ID No: 22, 41, 57, 117, 122, 123, 124, 125, 136 or 139.

The invention further provides a monoclonal antibody comprising a mature heavy chain variable region comprising CDRs H1, H2 and H3 of SEQ ID NOS. 13-15 respectively and a mature light chain variable region comprising CDRs L1, L2 and L3 of SEQ ID NOS. 17-19 respectively, or a mature heavy chain variable region comprising CDRs H1, H2 and H3 of SEQ ID NOS. 49-51 respectively and a mature light chain variable region comprising CDRs L1, L2 and L3 of SEQ ID NOS. 53-55 respectively, or a mature heavy chain variable region comprising CDRs H1, H2 and H3 of SEQ ID NOS. 109-111 respectively and a mature light chain variable region comprising CDRs L1, L2 and L3 of SEQ ID NOS. 113-115 respectively, or a mature heavy chain variable region comprising CDRs H1, H2 and H3 of SEQ ID NOS. 128-130 respectively and a mature light chain variable region comprising CDRs L1, L2 and L3 of SEQ ID NOS. 132-134 respectively. Optionally, the monoclonal antibody comprises a mature heavy chain variable region comprising residues 20-137 of SEQ ID NO:32 and a mature light chain variable region comprising residues 21-127 of SEQ ID NO:36, or a mature heavy chain variable region comprising residues 20 to 138 of SEQ ID NO:12 and a mature light chain variable region comprising residues 21-127 of SEQ ID NO:16, or a mature heavy chain variable region comprising residues 20-138 of SEQ ID NO:48 a mature light chain variable region comprising residues 23-127 of SEQ ID NO:52, or a mature heavy chain variable region comprising residues 20 to 136 of SEQ ID NO:108 and a mature light chain variable region comprising residues 21-126 of SEQ ID NO:112, or a mature heavy chain variable region comprising residues 20 to 138 of SEQ ID NO:127 and a mature light chain variable region comprising residues 21-133 of SEQ ID NO:131.

The invention further provides a bispecific antibody comprising a first binding site specifically binding to PD-L1, a second binding site specifically binding to GITR, OX40, CD40, ICOS or 4-1BB. Optionally, the bispecific antibody further comprises an Fc region. Optionally the first binding site antagonizes binding of PD-L1 to PD1 and the second binding site agonizes GITR, OX40, CD40, ICOS or 4-1BB. Optionally, the first binding cite comprises a mature heavy chain variable region comprising CDRs H1, H2 and H3 of SEQ ID NOS. 62-64, 75-77 or 85-87 respectively and a mature light chain variable region comprising CDRs L1, L2 and L3 of SEQ ID NOS. 66-68, 79-81 or 89-91 respectively, and the second binding region comprises a mature heavy chain variable region comprising CDRs of H1, H2 and H3 of SEQ ID NOS. 33-35 respectively and a mature light chain variable region comprising CDRs L1, L2 and L3 of SEQ ID NOS. 37-39 respectively, or a mature heavy chain variable region comprising CDRs H1, H2 and H3 of SEQ ID NOS. 13-15 respectively and a mature light chain variable region comprising CDRs L1, L2 and L3 of SEQ ID NOS. 17-19 respectively, or a mature heavy chain variable region comprising CDRs H1, H2 and H3 of SEQ ID NOS. 49-51 respectively and a mature light chain variable region comprising CDRs L1, L2 and L3 of SEQ ID NOS. 53-55 respectively, or a mature heavy chain variable region comprising CDRs H1, H2 and H3 of SEQ ID NOS. 109-111 respectively and a mature light chain variable region comprising CDRs L1, L2 and L3 of SEQ ID NOS. 113-115 respectively, or a mature heavy chain variable region comprising CDRs H1, H2 and H3 of SEQ ID NOS. 128-130 respectively and a mature light chain variable region comprising CDRs L1, L2 and L3 of SEQ ID NOS. 132-134 respectively. Optionally, the first binding site comprises a mature heavy chain variable region comprising residues 20-138 of SEQ ID NO:61, 20-138 of SEQ ID NO:74, 19-137 of SEQ ID NO:84 and a mature light chain variable region comprising residues 23-127 of SEQ ID NO:65, residues 23-128 of SEQ ID NO:78 or residues 23-128 of SEQ ID NO:88 respectively, and the second binding region comprises a mature heavy chain variable region comprising residues 20-137 of SEQ ID NO:32 and a mature light chain variable region comprising residues 21-127 of SEQ ID NO:36, or a mature heavy chain variable region comprising residues 20-138 of SEQ ID NO:12 and a mature light chain variable region comprising residues 21-127 of SEQ ID NO:16, or a mature heavy chain variable region comprising residues 20-138 of SEQ ID NO:48 and a mature light chain variable region comprising residues 23-127 of SEQ ID NO:52, or a mature heavy chain variable region comprising residues 20-136 of SEQ ID NO:108 and a mature light chain variable region comprising residues 21-126 of SEQ ID NO:112, or a mature heavy chain variable region comprising residues 20-138 of SEQ ID NO:127 and a mature light chain variable region comprising residues 21-133 of SEQ ID NO:131. Optionally, the first binding site comprises a mature heavy chain variable region comprising residues 20-138 of SEQ ID NO:61, 20-138 of SEQ ID NO:74, 19-137 of SEQ ID NO:84 and a mature light chain variable region comprising residues 23-127 of SEQ ID NO:65, residues 23-128 of SEQ ID NO:78 or residues 23-128 of SEQ ID NO:88 respectively, and the second binding region comprises a single-chain Fv fragment comprising SEQ ID No: 22, 41, 57, 117, 122, 123, 124, 125, 136 or 139.

Some bispecific antibodies described above comprises first paired heavy and light chain variable regions forming a first binding site and second paired heavy and light chain variable regions forming a second binding site, wherein the C-termini of the first paired heavy and light chain variable regions are fused to the N-termini of heavy and light chain constant regions and the second paired heavy and light chain variable regions form an scFv fused to the C-terminus of the heavy chain constant region, or vice versa. In some bispecific antibodies the C-termini of the first paired heavy and light chain variable regions are fused to the N-termini of heavy and light chain constant regions and the second paired heavy and light chain variable regions form an scFv fused to the C-terminus of the heavy chain constant region. In some bispecific antibodies, the light chain variable region of scFv is fused to the C-terminus of the heavy chain constant region. In some bispecific antibodies, the first and second binding sites are humanized, veneered or human and the heavy and light chain constant regions are human. In some bispecific antibodies the isotype of the heavy chain constant region is human IgG1 and the light chain constant region is kappa. Some bispecific antibodies comprise two first binding and two second binding sites. In some bispecific antibodies, the heavy chain constant region has at least one mutation reducing or increasing FcRγ binding. In some bispecific antibodies, the heavy chain constant region has at least one mutation increasing binding to FcRn.

The invention further provides a bispecific antibody comprising a first binding site specifically binding to an antigen on a cancer cell, a pathogen-infected cell or an immune cell and a second binding site specifically binding to a co-stimulating molecule, wherein first paired heavy and light chain variable regions form the first binding site and second paired heavy and light chain variable regions form the second binding site, wherein the C-termini of the first paired heavy and light chain variable regions are fused to the N-termini of heavy and light chain constant regions and the second paired heavy and light chain variable regions form an scFv fused to the C-terminus of the heavy chain constant region, or vice versa. Optionally, the first binding site is linked to the N-termini of the heavy and light chain constant regions and the second binding site is linked to the C-terminus of the heavy chain constant region.

The invention further provides a monoclonal antibody specifically binding to PD-L1 comprising a mature heavy chain variable region comprising CDRs H1, H2 and H3 of SEQ ID NOS. 62-64, 75-77 or 85-87 respectively and a mature light chain variable region comprising CDRs L1, L2 and L3 of SEQ ID NOS. 66-68, 79-81 or 89-91 respectively. Optionally, the monoclonal antibody comprises a mature heavy chain variable region comprising residues 20-138 of SEQ ID NO:61, 20-138 of SEQ ID NO:74 or 19-137 of SEQ ID NO:84 and a mature light chain variable region comprising residues 23-127 of SEQ ID NO:65, residues 23-128 of SEQ ID NO:78 or residues 23-128 of SEQ ID NO:88 respectively.

The invention further provides a pharmaceutical composition comprising any of the bispecific or monoclonal antibodies and a pharmaceutically acceptable carrier.

The invention further provides a method of treating or effecting prophylaxis of cancer, comprising administering an effective regime of a bispecific or monoclonal antibody as defined above to a subject having or at risk of cancer.

The invention further provides a method of treating an infection, comprising administering an effective regime of a bispecific antibody or monoclonal antibody as defined above to a subject having or at risk of infection.

DEFINITIONS

Figure 1:
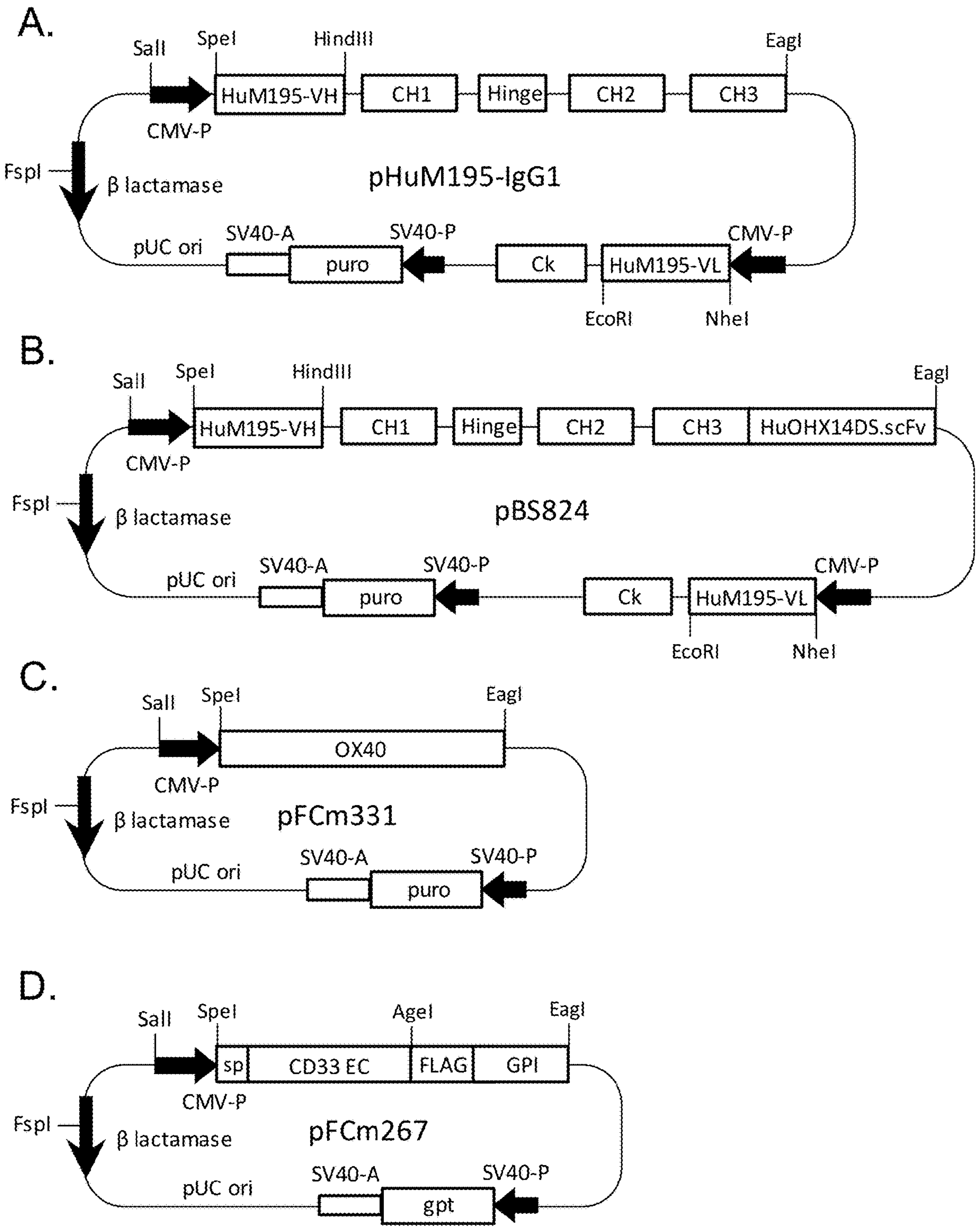
FIGS. 1A-D: Schematic structure of the expression vectors pHuM195-IgG1 (A), pBS824 (B), pFCm331 (C), and pFCm267 (D). Relevant restriction enzyme sites are shown. Figures are not drawn to scale.

Bispecific antibodies of the invention are typically provided in isolated form. This means that a bispecific antibody is typically at least 50% w/w pure of interfering proteins and other contaminants arising from its production or purification but does not exclude the possibility that the bispecific antibody is combined with an excess of pharmaceutical acceptable carrier(s) or other vehicle intended to facilitate its use. Sometimes bispecific antibodies are at least 60, 70, 80, 90, 95 or 99% w/w pure of interfering proteins and contaminants from production or purification. Often a bispecific antibody is the predominant macromolecular species remaining after its purification.

Specific binding of bispecific antibody to its target antigens means an affinity of at least $10^6$, $10^7$, $10^8$, $10^9$, or $10^{10}$ $M^{-1}$. Affinities can be different for the different targets. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that a bispecific antibody with two different binding sites binds only against targets for these two binding sites.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the bispecific antibodies of the invention have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. In IgA, the heavy chain constant region is divided into CH1, CH2 and CH3. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcRn binding.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, in bispecific antibodies, these binding sites can be the same or different depending on the format (see, e.g., Songsivilai and Lachmann, Clin. Exp. Immunol., 79:315-321 (1990); Kostelny et al., J. Immunol., 148:1547-53 (1992)). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chain variable regions or between different light chain variable regions are assigned the same number. Although Kabat numbering can be used for antibody constant regions, the EU index (also called EU numbering) is more commonly used, as is the case in this application.

The term "epitope" refers to a site on an antigen to which an arm of a bispecific antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. Some antibodies bind to an end-specific epitope, meaning an antibody binds preferentially to a polypeptide with a free end relative to the same polypeptide fused to another polypeptide resulting in loss of the free end. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

The term "antigen" or "target antigen" indicates a target molecule bound by one binding site of a bispecific antibody. An antigen may be a protein of any length (natural, synthetic or recombinantly expressed), a nucleic acid or carbohydrate among other molecules. Antigens include receptors, ligands, counter receptors, and coat proteins.

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2 times, 5 times, 10 times, 20 times or 100 times) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "subject" includes human and other mammalian subjects that receive either prophylactic or therapeutic treatment. Other mammalian subjects include animal models of a human condition (e.g., rodent, non-human primate) and veterinary subjects.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention for a variable region or EU numbering for a constant region. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

The term "antibody-dependent cellular cytotoxicity", or ADCC, is a mechanism for inducing cell death that depends upon the interaction of antibody-coated target cells (i.e., cells with bound antibody) with immune cells possessing lytic activity (also referred to as effector cells). Such effector cells include natural killer cells, monocytes/macrophages and neutrophils. ADCC is triggered by interactions between the Fc region of an antibody bound to a cell and Fcγ receptors, particularly FcγRI and FcγRIII, on immune effector cells such as neutrophils, macrophages and natural killer cells. The target cell is eliminated by phagocytosis or lysis, depending on the type of mediating effector cell. Death of the antibody-coated target cell occurs as a result of effector cell activity.

The term opsonization also known as "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an immunoglobulin Fc region.

The term "complement-dependent cytotoxicity" or CDC (also called CMC) refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

pH-dependent binding of an antibody to an FcRn receptor means that an antibody binds more strongly to such a receptor at pH 6.0 than at pH 7.5. Binding to FcRn at a low pH in endosomes after internalization by pinocytosis rescues IgG antibodies from catabolic degradation in lysosomes. Rescued IgG antibodies are then released from FcRn at a neutral pH and recycled to the circulation. Such pH-dependent FcRn binding is the basis of the molecular mechanism for a long serum half-life of IgG antibodies (and bispecific antibodies of the invention) (Ghetie et al., Annu. Rev. Immunol. 18:739-766, 2000). For example, human IgG antibodies bind to human neonatal Fc receptors (FcRn) at pH 6.0 while they bind only weakly to FcRn at pH 7.5. The FcRn binding site in IgG antibodies lies at the junction of the CH2 and CH3 domains. Because a mu heavy chain does not bind to FcRn at pH 6.0 or 7.5, natural IgM cannot take advantage of the FcRn-mediated pathway to rescue antibodies from degradation in lysosomes and therefore in general have shorter half-lives than natural IgG antibodies.

Protein A is a 40-60 kDa surface protein originally found in the cell wall of the bacterium *Staphylococcus aureus*. Protein A specifically binds with high affinity to human IgG1, IgG2 and IgG4 as well as mouse IgG2a and IgG2b. It does not bind to human IgG3 or IgA, or IgM. Protein A is used for affinity purification of antibodies.

Protein G is a 65-kDa (G148 protein G) and a 58 kDa (C40 protein G) Streptococcal cell surface protein. It contains a serum albumin binding domain not needed for IgG binding, which is often deleted. Protein G specifically binds to all of the human IgG isotypes but not IgA or IgM. Protein G is also useful for antibody purification.

DETAILED DESCRIPTION

I. General

The invention provides bispecific antibodies having one arm binding to a cancer associated antigen, such as CD33, EGFR or PD-L1, and a second arm binding to a costimulatory molecule, such as OX40, CD40, GITR, ICOS or 4-1BB. Although understanding of mechanism is not required for practice of the invention, it is believed that bridging by the bispecific antibody of this invention between a cancer cell expressing a cancer associated antigen and an immune cell expressing a costimulatory molecule results in clustering of the costimulatory molecules and selective activation of the immune cell at a location proximate to the cancer cell. Thus, the immune cells can exert an immunotherapeutic effect against the cancer cells with reduced toxicity to healthy tissue. The bispecific antibody can have additional activity against cells expressing the cancer associated antigen as a result of antagonizing receptor interaction with a ligand (e.g., EGFR interaction with EGF, PD-L1 interaction with PD1 or CD33 interaction with sialic acid). Some bispecific antibodies of this invention that bind to cancer cells (or pathogen-infected cells) and a costimulatory molecule can make bridges between these two types of cells and trigger immune responses by multivalent cross-linking of costimulatory molecules at the cell-to-cell junction to fight against cancer or infectious disease. Some bispecific antibodies of this invention can also enhance immune responses by inhibiting the function of a checkpoint molecule (e.g., PD-L1) and triggering a signal transduction pathway through multivalent cross-linking of costimulatory molecules (e.g., GITR, OX40, CD40, ICOS, 4-1BB).

II. Targets

Bispecific antibodies of the invention have at least two arms each specifically binding to a different target antigen. One class of protein that can serve as a target is a cancer associated antigen. Such antigens are expressed by a cancer, typically at higher levels than control matched normal tissue (overexpressed). Some examples of cancer associated antigens are CD33, EGFR and PD-L1. Exemplary Swiss Prot numbers for human forms of these targets are P20138, P00533 and Q9NZQ7. CD33 binds sialic acid and is overexpressed primarily in cancers of myeloid origin, such as acute myeloid leukemia. EGFR binds EGF and is overexpressed primarily in gastric, breast, endometrial, colorectal cancer, head and neck cancer, ovarian, cervical, bladder and esophageal cancers. PD-L1 binds PD1 and is overexpressed in cancers such as gastric cancer, hepatocellular carcinoma, renal cell carcinoma, esophageal cancer, pancreatic cancer, ovarian cancer and bladder cancer. Another class of proteins are antigens expressed on the surface of pathogen-infected cells.

Another class of proteins are co-stimulatory molecules including CD40, OX40, GITR, ICOS and 4-1BB. Exemplary Swiss Prot numbers for human forms of these targets are P25942, P23510, Q9Y5U5, Q9Y6W8 and Q07011. Unless otherwise apparent from the context, reference to a specific target should be understood as referring to human forms. However, non-human forms, such as those of laboratory (e.g., mouse, rat), non-human primates, companion animals or farm animals, can also be used.

III. Exemplary Antibodies Against Each Target

The bispecific antibodies are formed from pairs of heavy and light chain variable regions from component antibodies. The component antibodies can be rodent, chimeric, veneered, humanized, primatized, primate or human among others. The component antibodies can be of the same or different types; for example, one can be humanized and the other human.

The production of other non-human monoclonal antibodies, e.g., murine, guinea pig, primate, rabbit or rat, against an antigen can be accomplished by, for example, immunizing the animal with the antigen or a fragment thereof, or cells bearing the antigen. See Harlow & Lane, Antibodies, A Laboratory Manual (CSHP NY, 1988) (incorporated by reference for all purposes). Such an antigen can be obtained from a natural source, by peptide synthesis or by recombinant expression. Optionally, the antigen can be administered fused or otherwise complexed with a carrier protein. Optionally, the antigen can be administered with an adjuvant. Several types of adjuvant can be used as described below. Complete Freund's adjuvant followed by incomplete adjuvant is preferred for immunization of laboratory animals.

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 and 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

A human antibody can be isolated from a human, or otherwise result from expression of human immunoglobulin genes (e.g., in a transgenic mouse, in vitro or by phage display). Methods for producing human antibodies include the trioma method of Oestberg et al., Hybridoma 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, Nature 148, 1547-1553 (1994), Nature Biotechnology 14, 826 (1996), Kucherlapati, WO 91/10741 (1991)) and phage display methods (see, e.g. Dower et al., WO 91/17271 and McCafferty et al., WO 92/01047, U.S. Pat. Nos. 5,877,218, 5,871,907, 5,858,657, 5,837,242, 5,733,743 and 5,565,332).

Antibodies are screened for specific binding to the antigen. Antibodies may be further screened for binding to a specific region of the antigen, competition with a reference antibody, agonism or antagonism of cells bearing the antigen. Non-human antibodies can be converted to chimeric, veneered or humanized forms as described above.

The specification discloses exemplary antibodies specifically binding to CD33, EGFR, PD-L1, CD40, OX40, GITR and ICOS. These antibodies are characterized by the mature heavy and light chain variable region sequences and Kabat CDRs provided in the sequence listing as indicated in Table 1 below.

TABLE 1

| Target | Antibody name | Mature VH | Mature VL | CDRH1-3 SEQ ID NOS. | CDRL1-L3 SEQ ID NOS. |
|---|---|---|---|---|---|
| CD33 | HuM195 | 20 to 135 of SEQ ID NO: 2 | 21 to 131 of SEQ ID NO: 7 | 94-96 | 97-99 |
| EGFR | Ch225 | 20 to 138 of SEQ ID NO: 29 | 21 to 127 of SEQ ID NO: 30 | 100-102 | 103-105 |
| OX40 | HuOHX14DS | 20 to 138 of SEQ ID NO: 12 | 23 to 127 of SEQ ID NO: 16 | 13-15 | 17-19 |
| CD40 | HuACS2 | 20 to 138 of SEQ ID NO: 48 | 23 to 127 of SEQ ID NO: 52 | 49-51 | 53-55 |
| GITR | HuGAB11 | 20 to 137 of SEQ ID NO: 32 | 21 to 127 of SEQ ID NO: 36 | 33-35 | 37-39 |
| PD-L1 | HuPRO1 | 20 to 138 of SEQ ID NO: 61 | 23 to 127 of SEQ ID NO: 65 | 62-64 | 66-68 |
| PD-L1 | HuPRO2 | 20 to 138 of SEQ ID NO: 74 | 23 to 128 of SEQ ID NO: 78 | 75-77 | 79-81 |
| PD-L1 | HuPRO5 | 19 to 137 of SEQ ID NO: 84 | 23 to 128 of SEQ ID NO: 88 | 85-87 | 89-91 |
| ICOS | HuTAM14 | 20 to 136 of SEQ ID NO: 108 | 21 to 126 of SEQ ID NO: 112 | 109-111 | 113-115 |
| 4-1BB | HuFOB5 | 20 to 138 of SEQ ID NO: 127 | 21 to 133 of SEQ ID NO: 131 | 128-130 | 132-134 |

The specification discloses exemplary single-chain Fv (scFv) antibodies binding to CD40, OX40, GITR, ICOS and 4-1BB. These scFv antibodies are listed in Table 2 below.

TABLE 2

| Target | Antibody name | SEQ ID NO |
|---|---|---|
| OX40 | HuOHX14DS.scFv | 22 |
| OX40 | HuOHX14DS.scFv.ds | 122 |
| CD40 | HuACS2.scFv | 57 |
| CD40 | HuACS2.scFv.ds | 123 |
| GITR | HuGAB11.scFv | 41 |
| GITR | HuGAB11.scFv.ds | 125 |
| ICOS | HuTAM14.scFv | 117 |
| ICOS | HuTAM14.scFv.ds | 124 |
| 4-1BB | HuFOB5.scFv.LH.ds | 136 |
| 4-1BB | HuFOB5.scFv.HL.ds | 139 |

Other antibodies having the same CDRs as defined by Kabat, or alternative definitions, such as Chothia, composite of Chothia and Kabat, AbM or Contact (see world wide web bioinf.org.uk/abs), or binding to the same epitope or competing for binding with any of these antibodies to their target protein can also be used. Other means for binding to any of the above targets can also be used in place of the above antibodies. Antibodies binding to CD40, OX40, GITR, ICOS and 4-1BB can agonize their receptor and thereby activate immune cells expressing the receptor. Antibodies binding to a cancer associated antigen may or may not antagonize the interaction of the cancer associated antigen with its ligand or counterreceptor. Antagonism provides an additional mechanism of cytotoxicity against a cancer cell but is not necessary for activation of immune cells by the binding arm of a bispecific antibody binding to a costimulatory receptor.

Other antibodies against CD33 include gentuzumab, lintuzumab, and BI836858 (Heider Blood 2011; 118(15):4159-4168). Antibodies against EGFR include C225, a chimeric version of which is marketed as cetuximab, panitumumab, matuzumab and necitumumab. Antibodies against PD-L1 include durvalumab, avelumab, atezolizumab and MDX-1105/BMS936559. Agonist antibodies against CD40 include CP-870,893 (Pfizer and VLST), dacetuzumab (Seattle Genetics), Chi Lob 7/4 (University of Southampton), and lucatumumab (Novartis) (Vonderheide et al., Clin Cancer Res 19, 1035-1043 (2013)). Agonist OX40 antibodies include MOXR0916 (Infante et al., Journal of Clinical Oncology 2016 34:15_suppl 101-101), PF-04518600 (Long et al., Journal of Clinical Oncology 2016 34:15_suppl, e14518-e14518), MEDI0562 (Glisson et al., Annals of Oncology, Volume 27, Issue suppl_6, 1 Oct. 2016, 1052PD), MEDI6469 (Bell et al., Clin Cancer Res 2017; 23(23_Suppl):Abstract nr 37). Agonist antibodies against GITR include DTA-1 (Shimizu et al., Nat Immunol. 3, 135-142, 2002), INCAGN01876 (Gonzalez et al. Cancer Res. 2016 Volume 76, Issue 14, Abstract 3220), and 28F3, 19D3, 18E10, 3C3, 2G6, 8A6, 9G7, 14E3, 19H8, and 6G10 (WO2017087678). Agonist antibodies against ICOS include MEDI-570 (Medimmune; Nicholson et al. Reprod. Toxicol. 2017 74:116-133), GSK3359609 (GlaxoSmithKline; Angevin et al. 2017 Cancer Res. Volume 77, Issue 13 Supplement, Abstract CT039), BMS-986226 (Bristol-Myers Squib; Wang et al. 2019 BBA Rev. Cancer 1871:199-224) and JTX-2011 (Jounce Therapeutics; Michaelson et al. 2016 Cancer Res. Volume 76, Issue 14 Supplement, Abstract 573). Agonist antibodies against 4-1BB include urelumab (Bristol-Myers Squib), utomilumab (Pfizer) and AGEN2373 (Agenus; Galand et al. 2019 J. Clin. Oncol. 37, no. 15 suppl.e14005).

Any of these antibodies or other antibodies having the same CDRs as defined by Kabat, or alternative definitions, such as Chothia, composite of Chothia and Kabat, AbM or Contact, binding to the same epitope, or competing for binding with any of these antibodies to their target protein can also be incorporated into the bispecific antibodies of the invention. Other means for binding to any of the above targets can also be used in place of the above antibodies.

The invention also provides monoclonal antibodies specifically binding to human PD-L1 including HuPRO1, HuPRO2 and HuPRO5 and other antibodies sharing the same six CDRs (by any conventional definition) as one of these antibodies or the same pair of mature heavy and light chain variable regions as monoclonal antibodies. Such antibodies can inhibit PD-L1 interaction with PD1. The invention also provides monoclonal antibodies specifically binding to human OX40 including HuOHX14DS and other antibodies sharing the same six CDRs (by any conventional definition) or the same pair of mature heavy and light chain variable regions. The invention also provides monoclonal antibodies specifically binding to human CD40 including HuACS2 and other antibodies sharing the same six CDRs (by any conventional definition) or the same pair of mature heavy and light chain variable regions. The invention also provides monoclonal antibodies specifically binding to human ICOS including HuTAM14 and other antibodies sharing the same six CDRs (by any conventional definition) or the same pair of mature heavy and light chain variable regions. The invention also provides monoclonal antibodies specifically binding to human 4-1BB including HuFOB5 and other antibodies sharing the same six CDRs (by any conventional definition) or the same pair of mature heavy and light chain variable regions.

IV. Formats for Bispecific Antibodies

Over 100 formats have been described for bispecific antibodies (e.g., Kontermann et al., Drug Discovery Today 20, 838-847 (2015); Sedykh et al., Drug Des. Devel. Ther. 2, 195-209 (2018)). Such formats include at least one binding site for each of two targets. Preferred formats include two or more binding sites for each target.

Some formats have a similar tetrameric structure to a normal antibody with two binding regions, one for each target. Each binding region is formed from paired heavy and light chain variable regions, which are linked to heavy and light chain constant regions respectively. Such bispecific antibodies differ from a normal antibody in that the two binding sites and pairs of heavy and light chains forming them are different. Thus, such antibodies require association of two different pairs of heavy and light chains.

The "knobs-into-holes" approach has been adopted to reduce formation of homodimers and mispairing of heavy chains by substituting a large amino acid for a small one in the CH3 domain (the "knob") of one antibody and vice versa (the "hole") of the other antibody (Ridgway et al., Protein Eng 9:617-21, 1996; Atwell et al., J Mol Biol 270:26-35, 1997; and U.S. Pat. No. 7,695,936). Light chain mispairing in such formats can be reduced by a number of strategies. One strategy is to use a common light chain variable region for two different heavy chain variable regions. But this is applicable only to some antibodies. Another approach has been to express the knob- and the hole-containing half-molecules separately in different bacteria. Another approach termed CrossMab swaps the CH1 domain of one of the heavy chain with the constant CL domain of the corresponding light chain to induce the right pairing between the engineered heavy and light chains (Schaefer et al., Proc Natl Acad Sci USA 108:11187-92, 2011; WO 2009/080251; WO 2009/080252; WO 2009/080253). Another approach has been to introduce additional mutations into VH-VL and CH1-CL interfaces (Lewis et al., Nat. Biotechnol., 32 (2014), pp. 191-198). These mutations encourage a heavy chain to preferentially pair with a light chain. Another approach has been to introduce mutations promoting protein A binding into one of the Fc regions and select heterodimeric pairing having intermediate protein A binding from homodimers having higher or lower protein A binding by affinity chromatography (Tusdian et al, MAbs. 2016 May-June; 8(4):828-38).

Other bispecific antibodies avoid the problem of mispairing by combining multiple binding specificities in the same heavy and light chain pair. One approach for doing this, termed dual variable domains, is to link two different heavy chain variable regions in tandem to a heavy chain constant region and two different light chain variable regions in tandem to a light chain constant region (Correia et al., MAbs. 2013 May 1; 5(3): 364-372). Such an antibody can assemble as tetramer by association of two identical paired heavy and light chains. The assembled antibody includes two different binding sites for each target.

Another approach, which is followed in the examples of the present invention, is to incorporate a second binding specificity by linking a single-chain Fv (scFv) to the C-terminus of a heavy chain constant region. Such a bispecific antibody includes a first binding site formed by heavy and light chain variable regions attached to the N-termini of heavy and light chain constant regions as in a standard antibody. The C-terminus of the heavy chain is attached to a scFv providing the second binding site. The scFv is usually attached via a linker and a further linker connects the heavy and light chain variable regions in the scFv. The scFv can be attached either through its light chain variable region or heavy chain variable region end via the linker to the Fc region. When assembled by complexing of two identical paired heavy and light chains, such a bispecific antibody includes two binding sites for each of two different specificities. The cancer-associated antigen or infected-cell antigen and costimulatory antigen-binding arms of such a bispecific antibody can be attached in either orientation. The arm to be attached to the N-termini of the heavy and light chain constant regions is provided as separate heavy and light chain variable regions, and that to be attached to the C-terminus is provided as an scFv fragment. An advantage of this format is that the two different binding spaces are separated by the entire heavy chain constant region, which may promote cell-to-cell bridging.

Another format links an scFv specifically binding to a first target to a heavy chain constant region and an scFv specifically binding to another target to a light chain constant region. Such an antibody assembles into a tetramer including two copies of each binding site (Bs(scFv)4-IgG) (Zuo et al., Protein Eng 13: 361-367, 2000).

Other formats link scFv binding regions on a single chain without a constant region. For example, the BiTe format links two scFv fragments through a linker (see, e.g., Ross et al., PLoS ONE 12(8): e0183390, 2017). Such formats lack effector functions and tend to have a short half-life but may have advantages of accessability and ease of manufacture due to their small size.

Many of the above formats include linker peptides between heavy and light variable regions or between variable regions and a constant region. Linkers are short peptide conferring flexibility often predominantly occupied by Gly, Ala and/or Ser. Some exemplary linkers are Gly-Gly-Ala-Ala, Gly-Gly-Gly-Gly-Ser, Leu-Ala-Ala-Ala-Ala and multimers thereof.

V. Selection of Constant Region

Many of the formats for a bispecific antibody include at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Light chain constant regions can be lambda or kappa. Human IgG1 and IgG3 also induce stronger cell mediated effector functions than human IgG2 and IgG4. Here although ADCC, ADCP and CDC may be useful in providing an additional mechanism of action against cancer or infected cells bound by one arm of the bispecific antibodies, it is not useful for agonizing costimulatory molecules by the other arm to activate immune cells.

One or several amino acids at the amino or carboxy terminus of the light and/or heavy chain, such as the C-terminal lysine of the heavy chain, may be missing or derivatized in a proportion or all of the molecules. Amino acid substitutions can be made in the constant regions to reduce or increase effector functions such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). For example, there are many known mutations in IgG Fc that increase FcRn binding. Exemplary substitutions include Gln at position 250 and/or Leu at position 428, Ser or Asn at position 434, Tyr at position 252, Thr at position 254, Glu at position 256, and Ala at position 434 (EU numbering). Increased FcRn binding is advantageous in making the hybrid proteins of the present invention compete more strongly with endogenous IgG for binding to FcRn. Also numerous mutations are known for reducing any of ADCC, ADCP or CDC. (see, e.g., Winter et al., U.S. Pat. No. 5,624,821; Tso et al., U.S. Pat. No. 5,834,597; and Lazar et al., Proc. Natl. Acad. Sci. USA 103:4005, 2006). For example, substitution of any of amino acid residues at positions 234, 235, 236 and/or 237 reduce affinity for Fcγ receptors, particularly FcγRI receptor (see, e.g., U.S. Pat. No. 6,624,821). Optionally, amino acid residues at positions 234, 236 and/or 237 in human IgG2 are substituted with Ala and at position 235 with Gln or Glu (See, e.g., U.S. Pat. No. 5,624,821). Other substitutions reducing effector functions include Ala at position 268, Gly or Ala at position 297, Leu at position 309, Ala at position 322, Gly at position 327, Ser at position 330, Ser at position 331, Ser at position 238, Ala at position 268, Leu at position 309.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of one or more other isotypes.

VI. Expression of Recombinant Antibodies

Bispecific antibodies are typically produced by recombinant expression. Depending on the bispecific format, expression may be required for one, two or more antibody chains.

If multiple chains are expressed, they can be expressed from the same or different vectors. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of bispecific antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., J. Immunol. 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for productivity and quality of antibodies in serum-free media. Top-producing cell pools can then be subjected to FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, bispecific antibodies can be purified according to standard procedures of the art, including protein A capture, HPLC purification, column chromatography, gel electrophoresis and the like (see generally, Scopes, Protein Purification (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

VII. Nucleic Acids

The invention further provides nucleic acids encoding any of the heavy and light chains described above. Optionally, such nucleic acids further encode a signal peptide and can be expressed with the signal peptide linked to the constant region coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

VIII. Methods of Treatment and Pharmaceutical Compositions

The bispecific antibodies of the invention can be used for treating cancers including any of those in which one arm of the bispecific antibody binds to a target expressed or over-expressed in the cancer, such as those disclosed above. The bispecific antibodies can be used to treat solid tumors, and hematological malignancies. Hematological malignancies include leukemia (e.g., T cell large granular lymphocyte leukemia), lymphoma (Hodgkin's or Non-Hodgkin's), or multiple myeloma. Solid tumors include skin (e.g., melanoma), ovarian, endometrial, kidney, liver, pancreas, bladder, breast, ovarian, prostate, rectum, colon, gastric, intestinal, pancreatic, lung, thymus, thyroid, kidney and brain.

Bispecific antibodies of the invention can also be used for treating pathogenic infections when the bispecific antibody has one arm specifically binding to an antigen expressed in infected cells but not in matched uninfected cells. Such an antigen can be encoded by the pathogen or can be expressed by the cell in response to infection by the pathogen. Examples of such antigens expressed in infected cells are human immune deficiency virus (HIV) glycoproteins gp41 and gp120, human T-cell leukemia virus type 1 (HTLV-1) Env protein, herpes simplex virus (HSV) glycoproteins gB and gH, influenza hemagglutinin (HA) and neuraminidase (NA), and respiratory syncytial virus (RSV) F protein. Examples of pathogenic infections treatable with bispecific antibodies include viral, bacterial, protozoan or fungal infection. Some example of viral infections include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related virus, papillomavirus, molluscum virus, poliovirus, rabies virus, JC virus and arboviral encephalitis virus. Some examples of bacterial infections include *Chlamydia*, rickettsial bacteria, mycobacteria, staphylococci, streptococci, pneumonococci, meningococci and conococci, *Klebsiella, Proteus, Serratia, Pseudomonas, Legionella*, diphtheria, *Salmonella*, bacilli, cholera, tetanus, botulism, anthrax, plague, leptospirosis, Lymes disease bacteria, streptococci, or *Neisseria*. Some examples of pathogenic fungi include *Candida, Aspergillus, Cryptococcus, Histoplasma, Pneumocystis* and *Stachybotrys*. Examples of protozoa include *Cryptosporidium, Giardia lamblia* and *Plasmodium*.

Bispecific antibodies are administered in an effective regime meaning a dosage, route of administration and frequency of administration that delays the onset, reduces the severity, inhibits further deterioration, and/or ameliorates at least one sign or symptom of a condition. If a subject is already suffering from a disorder, the regime can be referred to as a therapeutically effective regime. If the subject is at elevated risk of the condition relative to the general population but is not yet experiencing symptoms, the regime can be referred to as a prophylactically effective regime. In some instances, therapeutic or prophylactic efficacy can be observed in an individual subject relative to historical controls or past experience in the same subject. In other instances, therapeutic or prophylactic efficacy can be demonstrated in a preclinical or clinical trial in a population of treated subjects relative to a control population of untreated subjects.

Preferably a bispecific antibody exhibits at least additive and more preferably synergistic activity against a cancer or infected cell compared with its component antibodies individually. Synergy is preferably assessed quantitatively such as discussed by Tallarida, Genes Cancer. 2011 November; 2(11): 1003-1008. Preferably a bispecific antibody also exhibits increased activity compared with a mixture of its component antibodies, each at equimolar concentration with the bispecific antibody. Such activity can be measured, for example, as cytotoxicity or cytostaticity against cancer cells or infected cells expressing an antigen specifically bound by one arm of the bispecific antibody in the presence of immune cell expressing a costimulating molecule specifically bound by the other arm of the bispecific antibody.

Exemplary dosages for a bispecific antibody are 0.01-20, or 0.5-5, or 0.01-1, or 0.01-0.5 or 0.05-0.5 mg/kg body weight (e.g., 0.1, 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the bispecific antibody in the circulation, the condition of the subject and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of chronic disorders, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, a bispecific antibody can be administered at regular intervals, e.g., weekly, fortnightly, monthly, quarterly, every six months for at least 1, 5 or 10 years, or the life of the subject.

Pharmaceutical compositions are preferably suitable for parenteral administration to a human (e.g., according to the standard of the FDA). Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more pharmaceutically acceptable carriers, diluents, excipients or auxiliaries. Pharmaceutically acceptable means suitable for human administration, e.g., approved or approvable by the FDA. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Treatment with the bispecific antibodies of the invention can be combined with other treatments effective against the disorder being treated. When used in treating cancer, the bispecific antibodies of the invention can be combined with chemotherapy, radiation, stem cell treatment, surgery or treatment with other biologics such as Herceptin™ (trastuzumab) against the HER2 antigen, Avastin™ (bevacizumab) against VEGF, or antibodies to the EGF receptor, such as (Erbitux™, cetuximab), and Vectibix™ (panitumumab). Chemotherapy agents include chlorambucil, cyclophosphamide or melphalan, carboplatinum, daunorubicin, doxorubicin, idarubicin, and mitoxantrone, methotrexate, fludarabine, and cytarabine, etoposide or topotecan, vincristine and vinblastine. For infections, treatment can be in combination with antibiotics, anti-virals, anti-fungal or anti-protozoan agents or the like.

IX. Other Methods

The bispecific antibodies of the invention also find use in diagnostic, prognostic and laboratory methods. They may be used to measure the level of an antigen expressed by a cancer or in the circulation of a patient with a cancer, to determine if the level is measurable or even elevated, and therefore to follow and guide treatment of the cancer, because cancers associated with measurable or elevated levels of an antigen are most susceptible to treatment with a bispecific antibody comprising an arm binding to the cancer. The bispecific antibodies can be used for an ELISA assay, radioimmunoassay or immunohistochemistry among others. The bispecific antibodies can be labeled with fluorescent molecules, spin-labeled molecules, enzymes or radioisotopes, and may be provided in the form of a kit with all the necessary reagents to perform the assay.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1: General Methods and Materials

Gene cloning, mutagenesis, plasmid construction, ELISA and FACS were carried out following standard laboratory techniques such as those described by Green and Sambrook (Molecular Cloning, A Laboratory Manual, 4th ed., 2012, Cold Spring Harbor Laboratory Press, Cold Spring Harbor, NY), Greenfield (Antibodies, A Laboratory Manual, 2nd ed., 2014, Cold Spring Harbor Laboratory Press, Cold Spring Harbor, NY), Kostelny et al. (Int. J. Cancer 93:556-565, 2001), Cole et al. (J. Immunol. 159:3613-3621, 1997) and Tsurushita et al. (Methods 36:69-83, 2005), and in vendors' protocols.

Mouse hybridomas producing monoclonal antibodies against a desired antigen were generated at JN Biosciences (Mountain View, CA) following standard cell fusion techniques using GENOMONE™ CF EX-CELL® fusion reagent (Cosmo Bio, Carlsbad, CA). For mouse immunization, a purified soluble form of recombinant antigen, typically a fusion to the human IgG Fc region, or a mouse cell line expressing recombinant antigens on the surface was used. Mouse monoclonal antibodies secreted in culture supernatants of hybridoma cells were subjected to a series of screening to identify the antibodies with the following properties: (1) specific binding to human antigen, (2) specific binding to cynomolgus antigen, and (3) desired biological functions such as blocking of the interaction of the antigen with its ligand or stimulation of cellular activities by conjugation of the antigens on the cell surface. Selected hybridoma cells were expanded in serum-free media such as Hybridoma SFM (Thermo Fisher Scientific, Waltham, MA). Mouse monoclonal IgG antibodies were purified with a protein A affinity column (MABSELECT™ SURE™ resin, GE Healthcare Life Sciences, Marlborough, MA) following the manufacturer's protocol. The buffer of purified antibodies was exchanged to phosphate-buffered saline (PBS) by dialysis. Antibody concentration was determined by measuring absorbance at 280 nm (OD 1.4=1 mg/ml).

Expression level of mouse IgG antibodies in culture supernatants was measured by sandwich ELISA. In a typical experiment, an ELISA plate was coated with goat anti-mouse IgG Fc-specific polyclonal antibody (SouthenBiotech, Birmingham, AL), washed with Wash Buffer (PBS containing 0.05% Tween 20), and blocked with ELISA Buffer (PBS containing 2% skim milk and 0.05% Tween 20). After washing with Wash Buffer, test samples appropriately diluted in ELISA Buffer were applied to the ELISA plate. An appropriate mouse IgG/kappa antibody was used as a standard. After incubating the ELISA plate for 60 min at room temperature and washing with Wash Buffer, bound mouse antibodies were detected using HRP-conjugated goat anti-mouse kappa chain polyclonal antibody (Bethyl Laboratories, Montgomery, TX). After incubating the plate for 30 min at room temperature and washing with Wash Buffer, color development was initiated by adding ABTS substrate (Sigma-Aldrich, St. Louis, MO) and stopped with 2% oxalic acid. Absorbance was read at 405 nm.

Expression of chimeric and humanized IgG/kappa antibodies in culture supernatants was measured by sandwich ELISA as described above, except that goat anti-human IgG Fc-specific polyclonal antibody (Jackson ImmunoResearch, West Grove, PA) was used for coating of ELISA plates and HRP-conjugated goat anti-human kappa chain polyclonal antibody (Bethyl Laboratories) was used for detection of bound antibodies.

Sequencing of heavy and light chain variable regions (VH and VL, respectively) of a mouse monoclonal antibody was performed with standard molecular biology techniques such as the procedure described in Tsurushita et al. (Methods 36: 69-83, 2005). Humanization of VH and VL was carried out with the general procedure described by Tsurushita et al. (supra) as follows. First, a three-dimensional molecular model of the variable regions of a mouse antibody to be humanized was constructed using an appropriate software. Second, the framework amino acid residues important for the formation of the CDR (complementarity-determining region) structure or necessary for antigen binding are identified using the molecular model. In parallel, cDNA-derived human VH and VL amino acid sequences with high homology to the mouse VH and VL amino acid sequences, respectively, are selected. Lastly, CDR sequences together with framework amino acid residues identified to be important for the formation of the antigen-binding site are grafted from the mouse variable regions into the corresponding selected human framework sequences.

Stable transfection into a Chinese hamster ovary cell line CHO-K1 was carried out by electroporation. Before transfection, an expression vector was linearized using an appropriate restriction enzyme. In a typical experiment, approximately $10^7$ CHO-K1 cells were transfected with 20 μg of linearized plasmid, suspended in SFM4CHO media (GE Healthcare Life Sciences), and plated at 100 μl/well in several 96-well plates after appropriate dilutions of cells. After 48 hr, SFM4CHO media containing 20 μg/ml of puromycin was added at 100 μl/well for isolation of stable transfectants. Approximately ten days after the initiation of selection, culture supernatants of transfectants were assayed for antibody production. CHO-K1 stable transfectants producing a high level of antibodies were identified by ELISA as described above.

CHO-K1 stable transfectants highly producing a recombinant antibody, such as humanized and bispecific IgG antibodies of this invention, were expanded in SFM4CHO until the cell viability became less than 50%. After centrifugation and filtration, culture supernatants were loaded onto a protein A column (HITRAP® MABSELECT™ SURE™ resin, GE Healthcare Life Sciences). The column was washed with PBS before the antibody was eluted with 0.1 M glycine-HCl (pH 3.0) containing 0.1M NaCl or 0.1M sodium acetate (pH 3.6). The buffer of eluted antibodies was neutralized with 1 M Tris-HCl (pH 8.0) and then changed to PBS by dialysis. Antibody concentration was determined by measuring absorbance at 280 nm (1 mg/ml=1.4 OD).

Example 2: Construction of a Bispecific Antibody (BS824) that Binds to CD33 and OX40

The mammalian expression vector pHuM195-IgG1 (FIG. 1A), designed for production of humanized anti-CD33 IgG1/kappa antibody (Co et al., J. Immunol. 148:1149-1154, 1992) that binds to human CD33 (also known as Siglec-3; SEQ ID NO:1), contains the following genetic components. Proceeding clockwise from the SalI site in FIG. 1A, the vector contains the heavy chain transcription unit starting with the human cytomegalovirus (CMV) major immediate early promoter and enhancer (CMV-P in the figure) to initiate transcription of the antibody heavy chain gene. The CMV promoter is followed by an exon encoding humanized M195 (HuM195) VH (SEQ ID NO:2) flanked by the SpeI and HindIII sites (HuM195-VH), a genomic sequence containing the exons encoding CH1 (SEQ ID NO:3), hinge (Hinge; SEQ ID NO:4), CH2 (SEQ ID NO:5) and CH3 (SEQ ID NO:6) constant regions of human gamma-1 heavy chain with the intervening introns, and after the EagI site, the polyadenylation site of the human gamma-1 heavy chain gene. After the heavy chain gene sequence, the light chain transcription unit begins with the CMV promoter and enhancer (CMV-P), followed by an exon encoding the humanized M195 (HuM195) VL (SEQ ID NO:7) flanked by the NheI and EcoRI sites (HuM195-VL), a genomic sequence containing the exon encoding human kappa chain constant region exon (Ck) (SEQ ID NO:8) with part of the intron preceding it, and the polyadenylation site of the human kappa chain gene following the Ck exon. The light chain gene is then followed by the SV40 early promoter (SV40-P), the puromycin N-acetyl-transferase gene (puro) for resistance to puromycin, and a segment containing the SV40 polyadenylation site (SV40-A). Finally, pHuM195-IgG1 contains the bacterial origin of replication (pUC ori) and the β lactamase gene (β lactamase). Arrows in the figure indicate the orientation of transcription. Humanized IgG1/kappa monoclonal antibody (HuM195-IgG1) is expressed from pHuM195-IgG1 in mammalian cells.

Mouse hybridoma producing an IgG/kappa monoclonal antibody OHX14 that binds specifically to human and cynomolgus OX40 (also known as TNFRSF4 and CD134) was isolated as described in Example 1. As an immunogen, a mouse myeloma cell line NS0 stably expressing a recombinant human OX40, which is constituted with the extracellular region of human OX40 fused to the FLAG polypeptide (SEQ ID NO:9) and then the glycosylphosphatidylinositol (GPI) anchorage signal of human CD55 (SEQ ID NO:10) (OX40-FLAG-GPI; SEQ ID NO:11), on the surface was used. Sequencing and humanization of OHX14 VH and VL was carried out as described by Tsurushita et al. (supra).

The amino acid sequence of humanized OHX14 (HuOHX14DS) VH is MGRLTSSFLLLIVPAYVLSQVQLVQSGAEVKKPGSSVKVSCKASGYTFTSYIMHWVRQA PGQGLEWIGYINPYNSGTKYNEKFKGRVTITSDKSTSTAYMELSSLRSEDTAVYYCAHY YGSTFTMDYWGQGTTVTVSS (SEQ ID NO:12). The CDR1, 2 and 3 amino acid sequences of HuOHX14DS VH are SYIMH (SEQ ID NO:13), YINPYNSGTKYNEKFKG (SEQ ID NO:14) and YYGSTFTMDY (SEQ ID NO:15), respectively, according to the definition by Kabat et al. (Sequences of Proteins of Immunological Interests, Fifth edition, NIH Publication No. 91-3242, U.S. Department of Health and Human Services, 1991). A gene encoding HuOHX14DS VH was synthesized as an exon including a splice donor signal at the 3' end of the coding region, a SpeI site at the 5' end of the fragment, and a HindIII site at the 3' end of the fragment.

The amino acid sequence of humanized OHX14 (HuOHX14DS) VL is MMSSAQFLGLLLLCFQGTRCDIQMTQSPSSLSASVGDRVTITCRASQDIRTYLNWYQQK PGKVPKLLIYYTSRLHSGVPSRFSGSGSGTDYTLTISSLQPEDVATYYCQQGNTLPWTFG GGTKVEIK (SEQ ID NO:16). The CDR1, 2 and 3 amino acid sequences of HuOHX14DS VL are RASQDIRTYLN (SEQ ID NO:17), YTSRLHS (SEQ ID NO:18) and QQGNTLPWT (SEQ ID NO:19), respectively, according to the definition by Kabat et al. (supra). A gene encoding HuOHX14DS VL was synthesized as an exon including a splice donor signal at the 3' end of the coding region, a NheI site at the 5' end of the fragment, and an EcoRI site at the 3' end of the fragment.

The expression vector pHuOHX14DS-IgG1.AA has the same structure as pHuM195-IgG1 (FIG. 1A), except that (i) the HuOHX14DS VH exon was placed between the SpeI and HindIII sites, (ii) the HuOHX14DS VL exon was placed between the NheI and EcoRI sites, and (iii) two leucine residues at positions 234 and 235 (EU numbering of Kabat et al. supra) were substituted to alanine residues in CH2 (L234A and L235A, respectively) (SEQ ID NO:20) for elimination of effector functions (Hezareh et al., *J. Virol.* 75:12161-12168, 2001). The new vector pHuOHX14DS-IgG1.AA expresses humanized anti-OX40 IgG1/kappa antibody (HuOHX14DS-IgG1.AA) in mammalian cells.

The mammalian expression vector pBS824 (FIG. 1B), designed for expression of a bispecific antibody that binds to both human CD33 (SEQ ID NO:1) and human OX40 (SEQ ID NO:21), was constructed by modifying pHuM195-IgG1 as follows. The VL and VH coding regions of a humanized anti-human OX40 monoclonal antibody in pHuOHX14DS-IgG1.AA were converted to a single-chain Fv (scFv) form in the order of VL, a polypeptide linker and VH from the N- to C-terminus (HuOHX14DS.scFv; SEQ ID NO:22). The N-terminus of HuOHX14DS.scFv was fused to the penultimate glycine residue in CH3 of pHuM195-IgG1 with a polypeptide linker separating them (CH3-HuOHX14D.scFv; SEQ ID NO:23). In addition, two leucine residues at positions 234 and 235 (EU numbering) were substituted to alanine residues in CH2 (L234A and L235A, respectively). The resultant vector pBS824 expresses a bispecific IgG antibody termed BS824 which binds to both human CD33 and OX40.

The amino acid sequence of the mature heavy chain encoded in pBS824 is

```
                                            (SEQ ID NO: 24)
QVQLVQSGAEVKKPGSSVKVSCKASGYTFTDYNMHWVRQAPGQGLEWIGYI

YPYNGGTGYNQKFKSKATITADESTNTAYMELSSLRSEDTAVYYCARGRPA

MDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPEAAGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGSGGGGSGGGGSDIQ

MTQSPSSLSASVGDRVTITCRASQDIRTYLNWYQQKPGKVPKLLIYYTSRL

HSGVPSRFSGSGSGTDYTLTISSLQPEDVATYYCQQGNTLPWTFGGGTKVE

IKGGGGSGGGGSGGGGSQVQLVQSGAEVKKPGSSVKVSCKASGYTFTSYIM

HWVRQAPGQGLEWIGYINPYNSGTKYNEKFKGRVTITSDKSTSTAYMELSS

LRSEDTAVYYCAHYYGSTFTMDYWGQGTTVTVSS.
```

The amino acid sequence of the mature light chain encoded in pBS824 is

```
                                            (SEQ ID NO: 25)
DIQMTQSPSSLSASVGDRVTITCRASESVDNYGISFMNWFQQKPGGAPKLL

IYAASNQGSGVPSRFSGSGSGTDFTLTISSLQPDDFATYYCQQSKEVPWTF

GQGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSFNRGEC.
```

Figure 2:
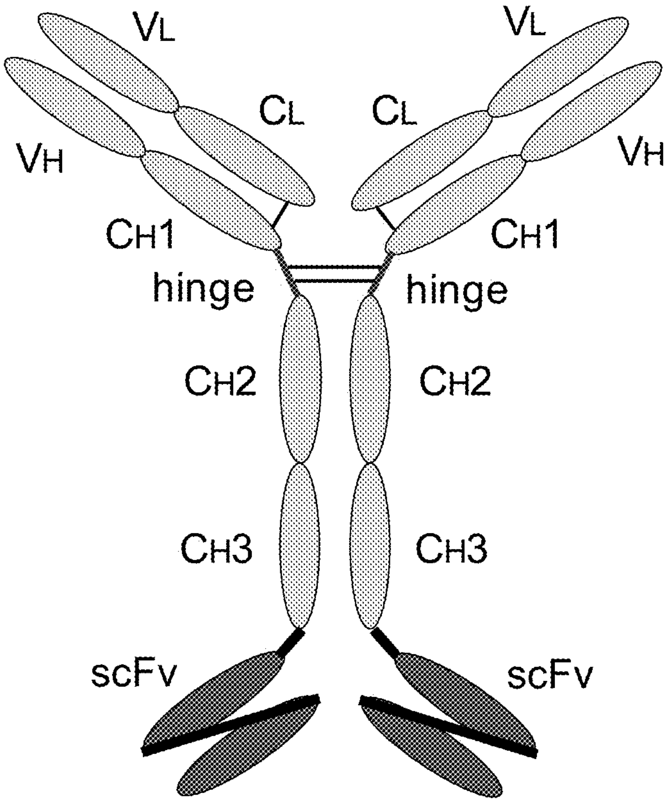
FIG. 2: Schematic structure of the bispecific IgG antibodies of this invention.

The schematic structure of the bispecific IgG antibodies of this invention, such as BS824, is shown in FIG. 2.

Each of the three expression vectors, pHuM195-IgG1, pHuOHX14DS-IgG1.AA and pBS824, was stably transfected into CHO-K1 cells as described above. HuM195-IgG1, HuOHX14DS-IgG1.AA and BS824 were purified from culture supernatants of their respective CHO-K1 stable transfectants with a protein A affinity column as described above. SDS-PAGE analysis under reducing conditions showed only two predominant bands with each of these three antibodies: roughly 50 kD heavy chains and 25 kD light chains (for HuM195-IgG1 and HuOHX14DS-IgG1.AA) or roughly 75 kD heavy chains and 25 kD light chains (for BS824).

Example 3: Biological Activity of a Bispecific Antibody (BS824) that Binds to CD33 and OX40

The biological activity of BS824 that binds to CD33 and OX40 was examined with Jurkat Dual reporter cells (InvivoGen, San Diego, CA) expressing human OX40 on the surface (JD/OX40) and mouse myeloma cell line NS0 expressing human CD33 on the surface (NS0/CD33). Conjugation of OX40 on the cell surface is known to trigger NF-κB signaling (Song et al., J. Immunol. 180:7240-7248, 2008). In Jurkat Dual cells, activation of the intracellular NF-κB signaling pathway leads to expression and secretion of recombinant Lucia luciferase.

JD/OX40 was generated by stably transfecting a vector pFCm331 for expression of human OX40 into Jurkat Dual cells by electroporation. The expression vector pFCm331 (FIG. 1C) has the same structure as pHuM195-IgG1 except that (a) the SpeI-EagI fragment was substituted with a DNA fragment encoding human OX40 (SEQ ID NO:21) and (b) the light chain gene was removed. Puromycin-resistant Jurkat Dual cells expressing OX40 on the surface (JD/OX40) were maintained in RPMI 1640 media containing 10% fetal bovine serum (FBS) at 37° C. in a 7.5% $CO_2$ incubator. No CD33 expression was detected in JD/OX40 cells by flow cytometry using HuM195-IgG1 and secondary PE-labeled goat anti-human IgG antibody.

NS0/CD33 was generated by stably transfecting an expression vector pFCm267 for expression of human CD33 into NS0 cells by electroporation. The expression vector pFCm267 (FIG. 1D) has the same structure as pFCm331 except that (a) the puromycin N-acetyl-transferase gene (puro) was substituted by the *E. coli* xanthine-guanine phosphoribosyltransferase (gpt) and (b) the SpeI-EagI fragment was substituted with a DNA fragment that encodes recombinant human CD33 constituted with, from the N- to C-terminus, a synthetic signal peptide (SEQ ID NO:26), the extracellular region of human CD33 (CD33 EC; SEQ ID NO:27), the FLAG polypeptide (SEQ ID NO:9) and the GPI anchorage signal (SEQ ID NO:10) (CD33-FLAG-GPI). NS0 stable transfectants that (i) survived in DME medium containing 10% FBS, 1 μg/ml mycophenolic acid, HT media supplement (Sigma-Aldrich, St. Louis, MO) and 0.25 mg/ml xanthine and (ii) expressed CD33-FLAG-GPI on the surface were maintained in DME medium containing 10% FBS at 37° C. in a 7.5% $CO_2$ incubator.

Figure 3:
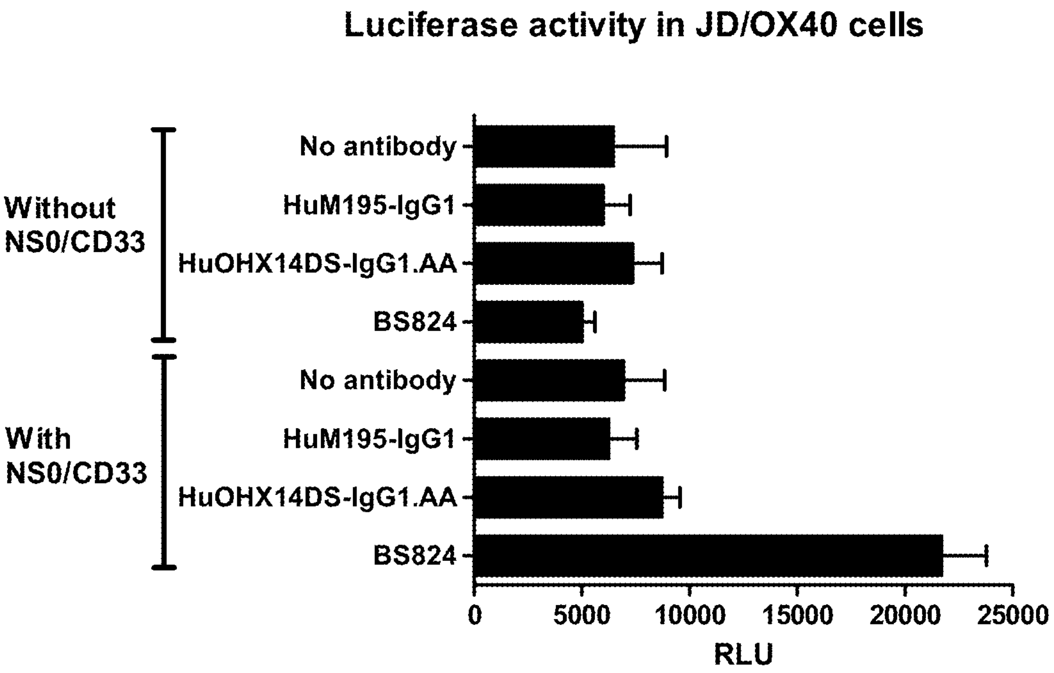
FIG. 3: Analysis of luciferase activities in Jurkat Dual cells expressing OX40 (JD/OX40) with a bispecific antibody binding to CD33 and OX40 (BS824). Average relative luminescence units (RLU) of triplicate analysis are shown with standard deviation bars.

OX40, a member of the TNF receptor superfamily of immune costimulatory molecules, require trimerization on the cell surface to trigger the NF-κB pathway of intracellular signal transduction (Watts, Annu. Immunol. 83:13-22, 2017). In JD/OX40 cells, multimeric cross-linking of OX40 on the surface upregulates expression and secretion of Lucia luciferase. Approximately two hundred thousand JD/OX40 cells were incubated in 200 μl of RPMI 1640 media containing 10% FBS, 0.5 ug/ml of mouse anti-human CD3 IgG antibody OKT3 (BioLegend, San Diego, CA) and 5 μg/ml of goat anti-mouse IgG antibody (human IgG-absorbed) (Jackson ImmunoResearch) to provide the primary signal to activate T cells together with (i) 1 μg/ml of HuM195-IgG1 (anti-CD33), (ii) 1 μg/ml of HuOHX14DS-IgG1.AA (anti-OX40), (iii) 1 μg/ml of BS824, or (iv) no antibody in the presence or absence of approximately two hundred thousand NS0/CD33 cells in a 96-well plate for one day at 37° C. in a 7.5% $CO_2$ incubator. Luciferase activity in culture supernatants was measured in triplicates with QUANTI-LUC™ reagents (InvivoGen) according to the vendor's protocol. Luminescence was measured using a Synergy HT microplate reader (BioTek, Winooski, VT). The result is shown in FIG. 3.

The average relative luciferase unit (RLU) in JD/OX40 cells was 6,458 with no antibody, 5,997 with HuM195-IgG1, 7,361 with HuOHX14DS-IgG1.AA, 5,009 with BS824, 6,918 with NS0/CD33, 6,240 with HuM195-IgG1 and NS0/CD33, 8,698 with HuOHX14DS-IgG1.AA and NS0/CD33, and 21,684 with BS824 and NS0/CD33. Only in the presence of both bispecific antibody binding to CD33 and OX40 (BS824) and CD33-expressing cells (NS0/CD33), the luciferase activity in JD/OX40 cells was significantly increased. This result indicates that only BS824 that can make bridges between JD/OX40 and NS0/CD33 cells, but neither HuM195-IgG1 nor HuOHX14DS-IgG1.AA, causes clustering of OX40 on the surface of JD/OX40 cells at locations proximate to NS0/CD33 cells and leads to activation of JD/OX40 cells to increase the expression of luciferase.

Example 4: Construction of a Bispecific Antibody (BS827) that Binds to EGFR and GITR The mammalian expression vector pCh225-IgG1 for expression of chimeric IgG1/kappa antibody that binds to human epidermal growth factor receptor (EGFR; SEQ ID NO:28) was generated as follows. A gene encoding mouse 225 (Ch225) VH (SEQ ID NO:29) was synthesized as an exon including a splice donor signal at the 3' end of the coding region, a SpeI site at the 5' end of the fragment, and a HindIII site at the 3' end of the fragment. A gene encoding mouse 225 (Ch225) VL (SEQ ID NO:30) was also synthesized as an exon including a splice donor signal at the 3' end of the coding region, a NheI site at the 5' end of the fragment, and an EcoRI site at the 3' end of the fragment. The Ch225 VH and VL exons were cloned into the corresponding sites into an antibody expression vector. The resultant plasmid pCh225-IgG1 for expression of anti-EGFR antibody Ch225-IgG1 has the same structure as pHuM195-IgG1 (FIG. 1A) except that the VH and VL coding regions were substituted by Ch225 VH and VL, respectively.

Mouse hybridoma producing an IgG/kappa monoclonal antibody GAB11 that binds specifically to human and cynomolgus GITR (also known as TNFRSF18 and CD357) was isolated as described in Example 1. As an immunogen, the extracellular region of human GITR fused to the Fc region of the human gamma-1 heavy chain (hGITR-Fc; SEQ ID NO:31) was used. Sequencing and humanization of GAB11 VH and VL was carried out as described in Tsurushita et al. (supra).

The amino acid sequence of humanized GAB11 (HuGAB11) VH is MAVLGLLLCLVTFPSCVLSQVTLKESGPVLVKPTETLTLTCTVSGFSLTDYGVSWIRQPP GKALEWLGVIWGGGGTYYNSALKSRLTISKDTSKSQVVLTMTNMDPVDTATYYCAKH PYGHFGMDYWGQGTTVTVSS (SEQ ID NO:32). The CDR1, 2 and 3 amino acid sequences of HuGAB11 VH are DYGVS (SEQ ID NO:33), VIWGGGGTYYNSALKS (SEQ ID NO:34) and HPYGHFGMDY (SEQ ID NO:35), respectively, according to the definition by Kabat et al. (supra). A gene encoding HuGAB11 VH was synthesized as an exon including a splice donor signal at the 3' end of the coding region, a SpeI site at the 5' end of the fragment, and a HindIII site at the 3' end of the fragment.

The amino acid sequence of humanized GAB11 (HuGAB11) VL is MRVLAELLGLLLFCFLGVRCDIQMTQSPSSLSASVGDRVTITCHASQNINVWLSWYQQK PGKVPKLLIYKASNLHTGVPSRFSGSGSGTDFTLTISSLQPEDVATYYCQQGQSYPLTFG GGTKVEIK (SEQ ID NO:36). The CDR1, 2 and 3 amino acid sequences of HuGAB11 VL are HASQNINVWLS (SEQ ID NO:37), KASNLHT (SEQ ID NO:38) and QQGQSYPLT (SEQ ID NO:39), respectively, according to the definition by Kabat et al. (supra). A gene encoding HuGAB11 VL was synthesized as an exon including a splice donor signal at the 3' end of the coding region, a NheI site at the 5' end of the fragment, and an EcoRI site at the 3' end of the fragment.

The expression vector pHuGAB11-IgG1.AA has the same structure as pHuM195-IgG1 (FIG. 1A), except that (i) the HuGAB11 VH exon was placed between the SpeI and HindIII sites, (ii) the HuGAB11 VL exon was placed between the NheI and EcoRI sites, and (iii) two leucine residues at positions 234 and 235 (EU numbering) were substituted to alanine residues in CH2 (L234A and L235A, respectively) (SEQ ID NO:20) for elimination of effector functions (Hezareh et al., supra). The new vector pHuGAB11-IgG1.AA expresses humanized anti-GITR IgG1/kappa antibody (HuGAB11-IgG1.AA) in mammalian cells.

The mammalian expression vector pBS827, designed for expression of a bispecific antibody that binds to both human EGFR (SEQ ID NO:28) and human GITR (SEQ ID NO:40), was constructed by modifying pCh225-IgG1 as follows. The VL and VH coding regions of a humanized anti-human GITR monoclonal antibody in pHuGAB11-Ig1.AA were converted to a scFv form in the order of VL, a polypeptide linker and VH from the N- to C-terminus (HuGAB11.scFv; SEQ ID NO:41). The N-terminus of HuGAB11.scFv was fused to the penultimate glycine residue in CH3 with a polypeptide linker between them (CH3-HuGAB11.scFv; SEQ ID NO:42) in pCh225-IgG1. In addition, two leucine residues at positions 234 and 235 (EU numbering) were substituted to alanine residues in CH2 (L234A and L235A, respectively). The resultant vector pBS827 expresses a bispecific IgG antibody termed BS827 which binds to both human EGFR and GITR.

The amino acid sequence of the mature heavy chain encoded in pBS827 is

```
                                        (SEQ ID NO: 43)
QVQLKQSGPGLVQPSQSLSITCTVSGFSLTNYGVHWVRQSPGKGLEWLGVI
WSGGNTDYNTPFTSRLSINKDNSKSQVFFKMNSLQSNDTAIYYCARALTYY
DYEFAYWGQGTLVTVSAASTKGPSVFPLAPSSKSTSGGTAALGCLVKDYFP
EPVTVSWNSGALTSGVHTFPAVLQSSGLYSLSSVVTVPSSSLGTQTYICNV
NHKPSNTKVDKKVEPKSCDKTHTCPPCPAPEAAGGPSVFLFPPKPKDTLMI
SRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFL
YSKLTVDKSRWQQGNVFSCSVMHEALHNHYTQKSLSLSPGSGGGGSGGGGS
DIQMTQSPSSLSASVGDRVTITCHASQNINVWLSWYQQKPGKVPKWYKASN
LHTGVPSRFSGSGSGTDFTLTISSLQPEDVATYYCQQGQSYPLTFGGGTKV
EIKGGGGSGGGGSGGGGSQVTLKESGPVLVKPTETLTLTCTVSGFSLTDYG
VSWIRQPPGKALEWLGVIWGGGGTYYNSALKSRLTISKDTSKSQVVLTMTN
MDPVDTATYYCAKHPYGHFGMDYWGQGTTVTVSS.
```

The amino acid sequence of the mature light chain encoded in pBS827 is

```
                                    (SEQ ID NO: 44)
DILLTQSPVILSVSPGERVSFSCRASQSIGTNIHWYQQRTNGSPRLLIKYA

SESISGIPSRFSGSGSGTDFTLSINSVESEDIADYYCQQNNNWPTTFGAGT

KLELKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.
```

The schematic structure of BS827 is shown in FIG. 2.

The three expression vectors, pCh225-IgG1, pHuGAB11-IgG1.AA and pBS827, were stably transfected into CHO-K1 as described above. Ch225-IgG1, HuGAB11-IgG1.AA and BS827 were purified from culture supernatants of their respective CHO-K1 stable transfectants with a protein A affinity column as described above. SDS-PAGE analysis under reducing conditions showed only two predominant bands with each of these three antibodies: roughly 50 kD heavy chains and 25 kD light chains (for Ch225-IgG1 and HuGAB11-IgG1.AA) or roughly 75 kD heavy chains and 25 kD light chains (for BS827).

Example 5: Biological Activity of a Bispecific Antibody (BS827) that Binds to EGFR and GITR The biological activity of BS827 that binds to EGFR and GITR was examined with Jurkat Dual cells (InvivoGen) expressing human GITR on the surface (JD/GITR) and mouse myeloma cell line NS0 expressing human EGFR on the surface (NS0/EGFR).

JD/GITR was generated by stably transfecting a vector pFCm343 for expression of human GITR into Jurkat Dual cells by electroporation. The expression vector pFCm343 has the same structure as pFCm331 (FIG. 1C) except that the SpeI-EagI fragment was substituted with a DNA fragment encoding a synthetic signal peptide (SEQ ID NO:26) fused to mature human GITR (SEQ ID NO:45). Puromycin-resistant Jurkat Dual cells expressing GITR on the surface (JD/GITR) were maintained in RPMI 1640 media containing 10% FBS at 37° C. in a 7.5% $CO_2$ incubator. No EGFR expression was detected in JD/GITR cells by flow cytometry using Ch225-IgG1 and secondary PE-labeled goat anti-human IgG antibody.

NS0/EGFR was generated by stably transfecting an expression vector pFCm507 into NS0 cells by electroporation. The expression vector pFCm507 has the same structure as pFCm331 (FIG. 1C) except that the SpeI-EagI fragment was substituted with a DNA fragment that encodes recombinant human EGFR constituted with, from the N- to C-terminus, a synthetic signal peptide (SEQ ID NO:26), the extracellular region of human EGFR (SEQ ID NO:46), the FLAG polypeptide (SEQ ID NO:9) and the GPI anchorage signal of human CD55 (SEQ ID NO:10) (EGFR-FLAG-GPI). Puromycin-resistant NS0 stable transfectants that expressed EGFR-FLAG-GPI on the surface were maintained in DME medium containing 10% FBS at 37° C. in a 7.5% $CO_2$ incubator.

Figure 4:
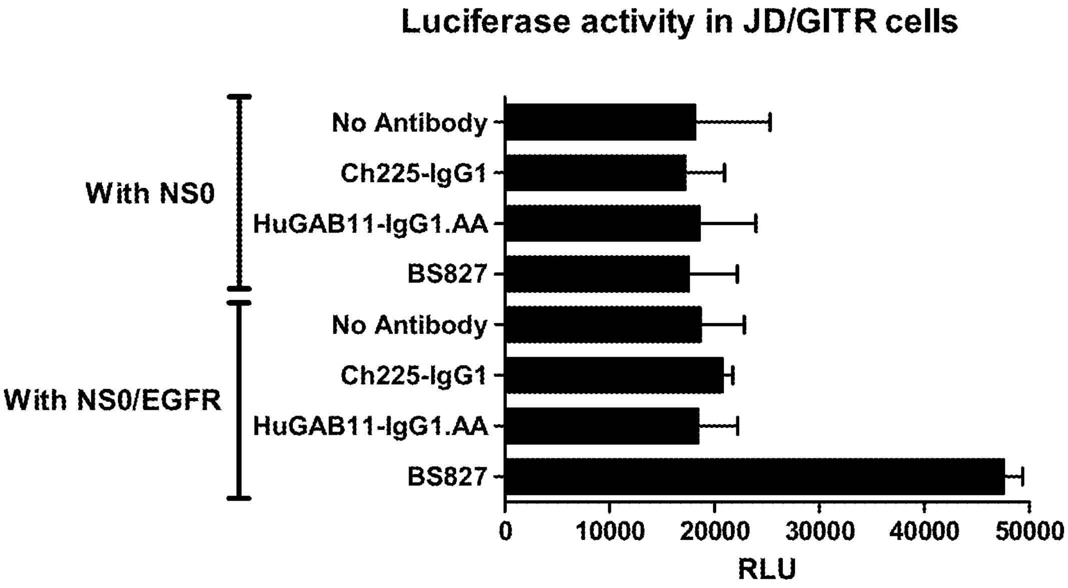
FIG. 4: Analysis of luciferase activity in Jurkat Dual cells expressing GITR (JD/GITR) with a bispecific antibody binding to EGFR and GITR (BS827). Average relative luminescence units (RLU) of triplicate analysis are shown with standard deviation bars.

GITR, a member of the TNF receptor superfamily of immune costimulatory molecules, require trimerization on the cell surface to trigger the NF-κB pathway of intracellular signal transduction (Watts, Annu. Rev. Immunol. 23:23-68, 2005; Chattopadhyay et al., Proc. Natl. Acad. Sci. 104: 19452-19457, 2007; Croft et al., Nat. Rev. Drug Discov. 12:147-168, 2013). In JD/GITR cells, multimeric cross-linking of GITR on the surface upregulates expression and secretion of Lucia luciferase. Approximately two hundred thousand JD/GITR cells were incubated in 200 μl of RPMI 1640 media containing 10% FBS, 0.5 μg/ml of mouse anti-human CD3 IgG antibody OKT3 (BioLegend) and 5 μg/ml of goat anti-mouse IgG antibody (human IgG-absorbed) (Jackson ImmunoResearch) to provide the primary signal to activate T cells together with (i) 1 μg/ml of Ch225-IgG1 (anti-EGFR), (ii) 1 μg/ml of HuGAB11-IgG1.AA (anti-GITR), (iii) 1 μg/ml of BS827, or (iv) no antibody with approximately two hundred thousand NS0 or NS0/EGFR cells in a 96-well plate for one day at 37° C. in a 7.5% $CO_2$ incubator. Luciferase activity in culture supernatants was measured in triplicates with QUANTI-Luc reagents (InvivoGen) according to the vendor's protocol. Luminescence was measured using a Synergy HT microplate reader (BioTek). The result is shown in FIG. 4.

The average relative luciferase unit (RLU) in JD/GITR cells was 18,086 with NS0 cells alone, 17,183 with Ch225-IgG1 and NS0 cells, 18,504 with HuGAB11-IgG1.AA and NS0 cells, 17,490 with BS827 and NS0 cells, 18,662 with NS0/EGFR cells alone, 20,748 with Ch225-IgG1 and NS0/EGFR cells, 18,391 with HuGAB11-IgG1.AA and NS0/EGFR cells, and 47,523 with BS827 and NS0/EGFR cells. The luciferase activity in JD/GITR cells was significantly increased only in the presence of both bispecific antibody binding to EGFR and GITR (BS827) and EGFR-expressing cells (NS0/EGFR). The result indicates that only BS827 which can make bridges between JD/GITR and NS0/EGFR cells, but neither Ch225-IgG1 nor HuGAB11-IgG1.AA, causes clustering of GITR on the surface of JD/GITR cells at locations proximate to NS0/EGFR cells and leads to activation of JD/GITR cells to increase the expression of luciferase.

Example 6: Bispecific Antibody (BS828) that Binds to CD33 and CD40

Mouse hybridoma producing an IgG/kappa monoclonal antibody ACS2 that binds to human and cynomolgus CD40 (also known as TNFRSF5) was isolated as described in Example 1. As an immunogen, the extracellular region of human CD40 fused to the Fc region of the human gamma-1 heavy chain (hCD40-Fc; SEQ ID NO:47) was used. Sequencing and humanization of ACS2 VH and VL was carried out as described by Tsurushita et al. (Methods 36:69-83, 2005).

The amino acid sequence of humanized ACS2 (HuACS2) VH is MKLWLNWVFLLTLLHGIQCQVQLVQSGAEVKKPGSSVKVSCKASGYTFTSYWLHWVR QAPGQGLEWIGRIDPNSGDTKYNEKFKSRATITVDKSTSTAYMELSSLRSEDTAVYYCA RYYYGRSYFDYWGQGTTVTVSS (SEQ ID NO:48). The CDR1, 2 and 3 amino acid sequences of HuACS2 VH are SYWLH (SEQ ID NO:49), RIDPNSGDTKYNEKFKS (SEQ ID NO:50) and YYYGRSYFDY (SEQ ID NO:51), respectively, according to the definition by Kabat et al. (supra). A gene encoding HuACS2 VH was synthesized as an exon including a splice donor signal at the 3' end of the coding region, a SpeI site at the 5' end of the fragment, and a HindIII site at the 3' end of the fragment.

The amino acid sequence of mature humanized ACS2 (HuACS2) VL is MDFQVQIFSFLLISAVIISRGEIVLTQSPATLSLSPGERATLSCSASSSVSYMHWYQQKPG QAPRRWIYDTSKLASGVPARFSGSGSGTDYTLTISSLEPEDFAVYYCQQWSSN- PLTFGGG TKVEIK (SEQ ID NO:52). The CDR1, 2 and 3 amino acid sequences of HuACS2 VL are SASSSVSYMH (SEQ ID NO:53), DTSKLAS (SEQ ID NO:54) and QQWSSNPLT (SEQ ID NO:55), respectively, according to the definition by Kabat et al. (supra). A gene encoding HuACS2 VL was synthesized as an exon including a splice donor signal at the 3' end of the coding region, a NheI site at the 5' end of the fragment, and an EcoRI site at the 3' end of the fragment.

The expression vector pHuACS2-IgG1.AA has the same structure as pHuM195-IgG1 (FIG. 1A), except that (i) the HuACS2 VH exon was placed between the SpeI and HindIII sites, (ii) the HuACS2 VL exon was placed between the NheI and EcoRI sites, and (iii) two leucine residues at positions 234 and 235 (EU numbering) were substituted to alanine residues in CH2 (L234A and L235A, respectively) (SEQ ID NO:20) for elimination of effector functions (Hezareh et al., supra). The new vector pHuACS2-IgG1.AA expresses humanized anti-CD40 IgG1/kappa antibody (HuACS2-IgG1.AA) in mammalian cells.

The mammalian expression vector pBS828, designed for expression of a bispecific antibody that binds to both human CD33 (SEQ ID NO:1) and human CD40 (SEQ ID NO:56), was constructed by modifying pHuM195-IgG1 as follows. The VL and VH coding regions of a humanized anti-human CD40 monoclonal antibody in pHuACS2-Ig1.AA were converted to a single-chain Fv (scFv) form in the order of VL, a polypeptide linker and VH from the N- to C-terminus (HuACS2.scFv; SEQ ID NO:57). The N-terminus of HuACS2.scFv was fused to the penultimate glycine residue in CH3 with a polypeptide linker between them (CH3-HuACS2.scFv; SEQ ID NO:58) in pHuM195-IgG1. In addition, two leucine residues at positions 234 and 235 (Eu numbering) were substituted to alanine residues in CH2 (L234A and L235A, respectively). The resultant vector pBS828 expresses a bispecific IgG antibody termed BS828 which binds to both human CD33 and CD40.

The amino acid sequence of the mature heavy chain encoded in pBS828 is

```
                                               (SEQ ID NO: 59)
QVQLVQSGAEVKKPGSSVKVSCKASGYTFTDYNMHWVRQAPGQGLEWIGYI

YPYNGGTGYNQKFKSKATITADESTNTAYMELSSLRSEDTAVYYCARGRPA

MDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPEAAGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGSGGGGSGGGGSEIV

LTQSPATLSLSPGERATLSCSASSSVSYMEIWYQQKPGQAPRRWIYDTSKL

ASGVPARFSGSGSGTDYTLTISSLEPEDFAVYYCQQWSSNPLTFGGGTKVE

IKGGGGSGGGGSGGGGSQVQLVQSGAEVKKPGSSVKVSCKASGYTFTSYWL

HWVRQAPGQGLEWIGRIDPNSGDTKYNEKFKSRATITVDKSTSTAYMELSS

LRSEDTAVYYCARYYYGRSYFDYWGQGTTVTVSS.
```

The amino acid sequence of the mature light chain encoded in pBS828 is same as the mature light chain sequence encoded in pBS824 (SEQ ID NO:25).

The schematic structure of BS828 is shown in FIG. 2.

Each of the three expression vectors, pHuM195-IgG1, pHuACS2-IgG1.AA and pBS828, was stably transfected into CHO-K1 cells as described above. HuM195-IgG1, HuACS2-IgG1.AA and BS828 were purified from culture supernatants of their respective CHO-K1 stable transfectants with a protein A affinity column as described above. SDS-PAGE analysis under reducing conditions showed only two predominant bands with each of these three antibodies: roughly 50 kD heavy chains and 25 kD light chains (for HuM195-IgG1 and HuACS2-IgG1.AA) or roughly 75 kD heavy chains and 25 kD light chains (for BS828).

Human Burkitt's B lymphoma cell line Ramos expresses CD40 on the surface. Cross-linking of CD40 on the surface of Ramos cells with soluble trimeric CD154 (also called CD40L and TNFSF5), which is a natural CD40 ligand, is known to induce elevated expression of CD95 (Henriquez et al., J. Immunol. 162:3298-3307, 1999). The biological activity of BS828 to upregulate CD95 expression in Ramos cells was examined in the presence or absence of human promyelocytic leukemia cell line HL-60 that expresses CD33 on the surface.

Figure 5:
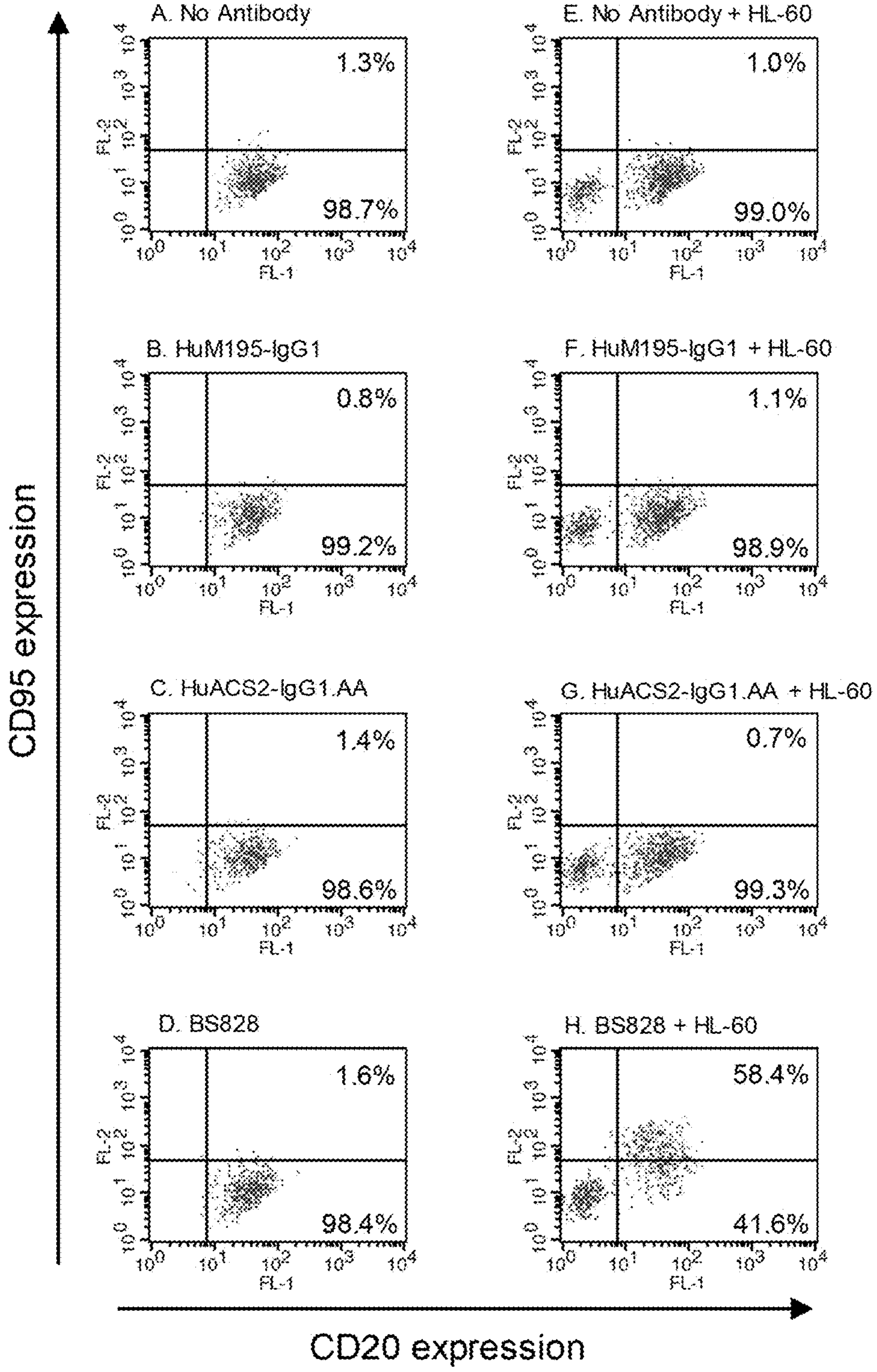
FIG. 5: FACS analysis of CD95 expression in Ramos cells with a bispecific antibody binding to CD33 and CD40 (BS828). X-axis and Y-axis indicate the expression level of CD20 and CD95, respectively. The numbers in the upper right and lower right quadrants show the percentage of CD20-positive cells in each quadrant.

Approximately one hundred thousand Ramos cells were incubated in 200 μl of RPMI 1640 media containing 10% FBS with (i) 0.5 μg/ml of HuM195-IgG1 (anti-CD33), (ii) 0.5 μg/ml of HuACS2-IgG1.AA (anti-CD40), (iii) 0.5 μg/ml of BS828, or (iv) no antibody in the presence or absence of approximately fifty thousand HL-60 cells in a 96-well plate for three days at 37° C. in a 7.5% $CO_2$ incubator. Expression of CD95 in Ramos cells was analyzed by flow cytometry using FITC-labeled mouse anti-human CD20 monoclonal antibody (Clone 2H7, BioLegend) to detect Ramos cells and PE-labeled mouse anti-human CD95 antibody (Clone DX2, BioLegend). Ramos cells are CD20-positive and HL-60 cells are CD20-negative. The result of the FACS analysis is shown in FIG. 5.

The percentage of CD95-positive population among CD20-positive Ramos cells was 1.3% with no antibody, 0.8% with HuM195-IgG1, 1.4% with HuACS2-IgG1.AA, and 1.6% with BS828. When Ramos cells were incubated in the presence of HL-60 cells, the percentage of CD95-positive population among Ramos cells was 1.0% with no antibody, 1.1% with HuM195-IgG1, 0.7% with HuACS2-IgG1.AA, and 58.4% with BS828. The expression of CD95 in Ramos cells was significantly upregulated only in the presence of both the bispecific antibody binding to CD33 and CD40 (BS828) and CD33-expressing cells (HL-60 cells). This result indicates that only BS828 which can make bridges between Ramos and HL-60 cells, but neither HuM195-IgG1 nor HuACS2-IgG1.AA, causes multimeric cross-linking of CD40 on the surface of Ramos cells at locations proximate to HL-60 cells and leads to upregulation of CD95 in Ramos cells.

Example 7: Bispecific Antibody (BS809) that Binds to PD-L1 and GITR

PD-L1 (also known as B7H1 and CD274) is a type I transmembrane protein that functions as a ligand of a checkpoint molecule PD-1. Binding of PD-L1 to PD-1 on T cells suppresses immune reactions. PD-L1 is often expressed on cancer cells (Patel et 1. 2015 Mol. Cancer Ther. 14:847-856; Brody et al. 2017 Lung Cancer 112:200-215; Sun et al. 2018 Immunity 48:434-452). Mouse hybridoma producing an IgG/kappa monoclonal antibody PRO1 that binds to human and cynomolgus PD-L1 and blocks the interaction between PD-1 and PD-L1 was isolated as described in Example 1. As an immunogen, the extracellular region of human PD-L1 fused to the Fc region of the human gamma-1 heavy chain (hPD-L1-Fc; SEQ ID NO:60) was used. Sequencing and humanization of PRO1 VH and VL was carried out as described by Tsurushita et al. (supra).

The amino acid sequence of humanized PRO1 (HuPRO1) VH is MEWNWVVLFLLSLTAGVYAQVQLVQS-GAEVKKPGSSVKVSCKASGFTFSSSYISWVRQ APGQGLEWIAWIYAGTGGTSYNQKFT-GRATITVDESTSTAYMELSSLRSEDTAVYYCAR HEGVYWYFDVWGQGTTVTVSS (SEQ ID NO:61). The CDR1, 2 and 3 amino acid sequences of HuPRO1 VH are SSYIS (SEQ ID NO:62), WIYAGTGGTSYNQKFTG (SEQ ID NO:63) and HEGVYWYFDV (SEQ ID NO:64), respectively, according to the definition by Kabat et al. (supra). A gene encoding HuPRO1 VH was synthesized as an exon including a splice donor signal at the 3' end of the coding region, a SpeI site at the 5' end of the fragment, and a HindIII site at the 3' end of the fragment.

The amino acid sequence of humanized PRO1 (HuPRO1) VL is MDFQVQIFSFLLISAVIMSRGEIVLTQSPATLSL-SPGERATLSCSASSSVSYMHWYQQKPG QAPRP-WIYDTSNLASGFPARFSGSGSGTDFTLTISSLEPED-FAVYYCHQRSSYPWTFGGG TKVEIK (SEQ ID NO:65). The CDR1, 2 and 3 amino acid sequences of HuPRO1 VL are SASSSVSYMH (SEQ ID NO:66), DTSNLAS (SEQ ID NO:67) and HQRSSYPWT (SEQ ID NO:68), respectively, according to the definition by Kabat et al. (supra). A gene encoding HuPRO1 VL was synthesized as an exon including a splice donor signal at the 3' end of the coding region, a NheI site at the 5' end of the fragment, and an EcoRI site at the 3' end of the fragment.

The expression vector pHuPRO1-IgG1.AA has the same structure as pHuM195-IgG1 (FIG. 1A), except that (i) the HuPRO1 VH exon was placed between the SpeI and HindIII sites, (ii) the HuPRO1 VL exon was placed between the NheI and EcoRI sites, and (iii) two leucine residues at positions 234 and 235 (EU numbering) were substituted to alanine residues in CH2 (L234A and L235A, respectively) (SEQ ID NO:20) for elimination of effector functions (Hezareh et al., supra). The new vector pHuPRO1-IgG1.AA expresses humanized anti-PD-L1 IgG1/kappa antibody (HuPRO1-IgG1.AA) in mammalian cells.

The mammalian expression vector pBS809, designed for expression of a bispecific antibody that binds to both human PD-L1 (SEQ ID NO:69) and human GITR (SEQ ID NO:45), was constructed by replacing the CH3 coding region with the coding region of CH3-HuGAB11.scFv (SEQ ID NO:42) in pHuPRO1-IgG1.AA.

The amino acid sequence of the mature heavy chain encoded in pBS809 is

```
                                        (SEQ ID NO:70)
QVQLVQSGAEVKKPGSSVKVSCKASGFTFSSSYISWVRQAPGQGLEWIAWI

YAGTGGTSYNQKFTGRATITVDESTSTAYMELSSLRSEDTAVYYCARHEGV

YWYFDVWGQGTTVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKKVEPKSCDKTHTCPPCPAPEAAGGPSVFLFPPKPKDTLMI

SRTPEVTCVVVDVSHEDPEVKFNWYVDGVEVHNAKTKPREEQYNSTYRVVS
```

-continued

```
VLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFL

YSKLTVDKSRWQQGNVFSCSVMHEALHNHYTQKSLSLSPGSGGGGSGGGGS

DIQMTQSPSSLSASVGDRVTITCHASQNINVWLSWYQQKPGKVPKLLIYKA

SNLHTGVPSRFSGSGSGTDFTLTISSLQPEDVATYYCQQGQSYPLTFGGGT

KVEIKGGGGSGGGGSGGGGSQVTLKESGPVLVKPTETLTLTCTVSGFSLTD

YGVSWIRQPPGKALEWLGVIWGGGGTYYNSALKSRLTISKDTSKSQVVLTM

TNMDPVDTATYYCAKHPYGHFGMDYWGQGTTVTVSS.
```

The amino acid sequence of the mature light chain encoded in pBS809 is

```
                                        (SEQ ID NO:71)
EIVLTQSPATLSLSPGERATLSCSASSSVSYMTIWYQQKPGQAPRPWIYDT

SNLASGFPARFSGSGSGTDFTLTISSLEPEDFAVYYCHQRSSYPWTFGGGT

KVEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSP

VTKSFNRGEC.
```

The schematic structure of BS809 is shown in FIG. 2.

Each of the three expression vectors, pHuPRO1-IgG1.AA, pHuGAB11-IgG1.AA and pBS809, was stably transfected into CHO-K1 as described above. HuPRO1-IgG1.AA, HuGAB11-IgG1.AA and BS809 were purified from culture supernatants of their respective CHO-K1 stable transfectants with a protein A affinity column as described above. SDS-PAGE analysis under reducing conditions showed only two predominant bands with each of these three antibodies: roughly 50 kD heavy chains and 25 kD light chains (for HuPRO1-IgG1.AA and HuGAB11-IgG1.AA) or roughly 75 kD heavy chains and 25 kD light chains (for BS809).

Figure 6:
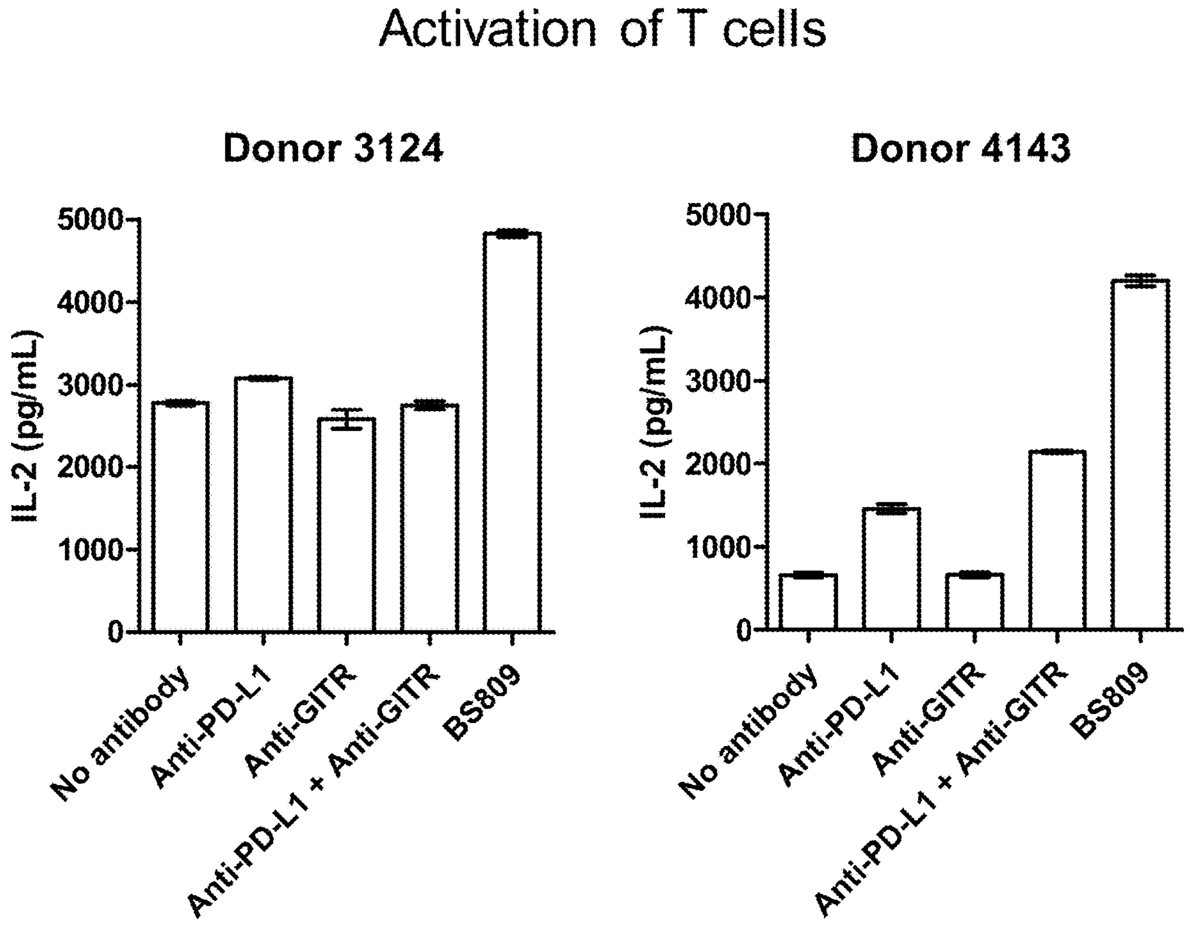
FIG. 6: Activation of T cells with a bispecific antibody binding to PD-L1 and GITR (BS809). Average expression levels of IL-2 are shown with standard deviation bars.

The biological activity of BS809 to enhance immune responses was analyzed by measuring the expression level of IL-2 in human T cells (Malek, Annu. Rev. Immunol. 26:453-79, 2008; Liao et al., Immunity 38:13-25, 2013). Human peripheral blood mononuclear cells (PBMC) from two donors (3124 and 4143) were obtained from iQ Biosciences (Berkeley, CA). PBMC were grown in RPMI-1640 containing 10% FBS and 5 μg/ml of phytohemagglutinin-L (PHA-L) for three days at 37° C. in a 7.5% $CO_2$ incubator to enrich T cells (3-day old PBMC). Expression of PD-1, PD-L1 and GITR in the 3-day old PBMC was confirmed by flow cytometry. Approximately one hundred thousand cells of the 3-day old PBMC were incubated in a well of a 96-well plate, which had been precoated with 1 μg/ml of mouse anti-human CD3 monoclonal antibody OKT3, in the presence of (i) no additional antibody (control), (ii) 1 μg/ml of HuPRO1-IgG1.AA (anti-PD-L1), (iii) 1 μg/ml of HuGAB11-IgG1.AA (anti-GITR), (iv) 1 μg/ml of HuPRO1-IgG1.AA and 1 μg/ml of HuGAB11-IgG1.AA, and (v) 1 μg/ml of BS809 for one day at 37° C. in a 7.5% $CO_2$ incubator. IL-2 concentration in culture supernatants was measured using the Human IL-2 ELISA MAX Standard Kit (BioLegend, San Diego, CA). The result is shown in FIG. 6.

The average IL-2 concentration in PBMC-derived T cells of donor 3124 was (i) 2,776 pg/ml without antibody (control), (ii) 3,075 pg/ml with HuPRO1-IgG1.AA, (iii) 2,577 pg with HuGAB11-IgG1.AA, (iv) 2,747 pg/ml with a mixture of HuPRO1-IgG1.AA and HuGAB11-IgG1.AA, and (v) 4,826 pg/ml with BS809. IL-2 expression significantly increased only in the presence of the bispecific antibody that binds to both PD-L1 and GITR when compared to the IL-2 level in the untreated control cells. This is due to bridging between PD-L1-expressing cells and GITR-expressing T cells by BS809, which causes multimeric cross-linking of GITR on the surface at locations proximate to PD-L1-expressing cells and leads to activation of T cells to upregulate IL-2 expression.

The average IL-2 concentration in PBMC-derived T cells of donor 4143 was (i) 658 pg/ml without antibody, (ii) 1,453 pg/ml with HuPRO1-IgG1.AA, (iii) 659 pg/ml with HuGAB11-IgG1.AA, (iv) 2,136 pg/ml with a mixture of HuPRO1-IgG1.AA and HuGAB11-IgG1.AA, and (v) 4,196 pg/ml with BS809. IL-2 expression increased in the presence of HuPRO1-IgG1.AA when compared to the IL-2 level in the untreated control cells, most probably because the interaction of PD-L1 with PD-1 to suppress immune responses was blocked by HuPRO1-IgG1.AA. IL-2 expression was further increased significantly in the presence of BS809 due to (a) its anti-PD-L1 antagonist activity and (b) the ability of bridging between PD-L1-expressing cells and GITR-expressing T cells for multimeric cross-linking of GITR on the surface, which results in potent activation of T cells.

Example 8: Bispecific Antibody (BS813) that Binds to PD-L1 and OX40

The mammalian expression vector pBS813, designed for expression of a bispecific antibody that binds to both human PD-L1 (SEQ ID NO:69) and human OX40 (SEQ ID NO:21), was constructed by replacing the CH3 coding region in pHuPRO1-IgG1.AA with the coding region of CH3-HuOHX14DS.scFv (SEQ ID NO:23).

The amino acid sequence of the mature heavy chain encoded in pBS813 is

```
                                      (SEQ ID NO: 72)
QVQLVQSGAEVKKPGSSVKVSCKASGFTFSSSYISWVRQAPGQGLEWIAW

IYAGTGGTSYNQKFTGRATITVDESTSTAYMELSSLRSEDTAVYYCARHE

GVYWYFDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGSG

GGGSGGGGSDIQMTQSPSSLSASVGDRVTITCRASQDIRTYLNWYQQKPG

KVPKLLIYYTSRLHSGVPSRFSGSGSGTDYTLTISSLQPEDVATYYCQQG

NTLPWTFGGGTKVEIKGGGGSGGGGSGGGGSQVQLVQSGAEVKKPGSSVK

VSCKASGYTFTSYIMHWVRQAPGQGLEWIGYINPYNSGTKYNEKFKGRVT

ITSDKSTSTAYMELSSLRSEDTAVYYCAHYYGSTFTMDYWGQGTTVTVSS.
```

The amino acid sequence of the mature light chain encoded in pBS813 is same as the mature light chain sequence encoded in pBS809 (SEQ ID NO:71).

The schematic structure of BS813 is shown in FIG. 2.

Each of the three expression vectors, pHuPRO1-IgG1.AA, pHuOHX14DS-IgG1.AA and pBS813, was stably transfected into CHO-K1 cells as described above. HuPRO1-IgG1.AA, HuOHX14DS-IgG1.AA and BS813 were purified from culture supernatants of their respective CHO-K1 stable transfectants with a protein A affinity column as described above. SDS-PAGE analysis under reducing conditions showed only two predominant bands with each of these three antibodies: roughly 50 kD heavy chains and 25 kD light chains (for HuPRO1-IgG1.AA and HuOHX14DS-IgG1.AA) or roughly 75 kD heavy chains and 25 kD light chains (for BS813). NS0/PD-L1 cells, which express recombinant human PD-L1 on the surface, was generated by stably transfecting an expression vector pFCm370 into NS0 cells by electroporation. The expression vector pFCm370 has the same structure as pFCm331 except that the SpeI-EagI fragment was substituted with a DNA fragment that encodes recombinant human PD-L1 constituted with, from the N- to C-terminus, a synthetic signal peptide (SEQ ID NO:26), the extracellular region of human PD-L1 (SEQ ID NO:73), the FLAG polypeptide (SEQ ID NO:9) and the GPI anchorage signal of human CD55 (SEQ ID NO:10) (PD-L1-FLAG-GPI). NS0 stable transfectants that (i) survived in DME medium containing 10% FBS, 1 μg/ml mycophenolic acid, HT media supplement and 0.25 mg/ml xanthine, and (ii) expressed PD-L1-FLAG-GPI on the surface were maintained in DME medium containing 10% FBS at 37° C. in a 7.5% $CO_2$ incubator.

Figure 7:
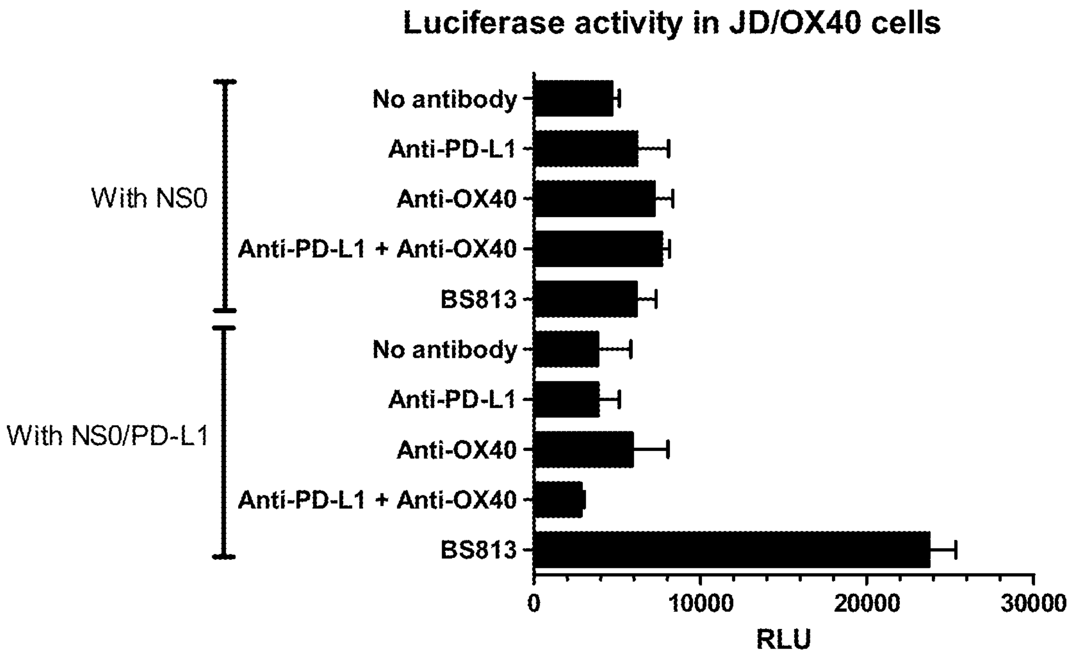
FIG. 7: Analysis of luciferase activities in Jurkat Dual cells expressing OX40 (JD/OX40) with a bispecific antibody binding to PD-L1 and OX40 (BS813). Average relative luminescence units (RLU) of triplicate analysis are shown with standard deviation bars.

Approximately two hundred thousand JD/OX40 cells were incubated in 200 μl of RPMI 1640 media containing 10% FBS, 0.5 μg/ml of mouse anti-human CD3 IgG antibody OKT3 (BioLegend, San Diego, CA) and 5 μg/ml of goat anti-mouse IgG antibody (human IgG-absorbed) (Jackson ImmunoResearch) to provide the primary signal to activate T cells together with no antibody (a and f), 1 μg/ml of HuPRO1-IgG1.AA (anti-PD-L1) (b and g), 1 μg/ml of HuOHX14DS-IgG1.AA (anti-OX40) (c and h), 1 μg/ml of HuPRO1-IgG1.AA and 1 μg/ml of HuOHX14DS-IgG1.AA (d and i), and 1 μg/ml of BS813 (e and j) in a 96-well plate for one day at 37° C. in a 7.5% $CO_2$ incubator. Two hundred thousand NS0 cells were added to the reactions a, b, c, d and e. Two hundred thousand NS0/PD-L1 cells were added to the reaction f, g, h, i and j. Luciferase activity in culture supernatants was measured in triplicates with QUANTI-Luc reagents (InvivoGen) according to the vendor's protocol. Luminescence was measured using a Synergy HT microplate reader (BioTek, Winooski, VT). The result is shown in FIG. 7.

The average relative luciferase unit (RLU) in JD/OX40 cells was 4,683 with NS0 cells (a), 6,193 with HuPRO1-IgG1.AA and NS0 cells (b), 7,230 with HuOHX14DS-IgG1.AA (c), 7,671 with HuPRO1-IgG1.AA, HuOHX14DS-Ig1.AA and NS0 cells (d), 6,146 with BS813 and NS0 cells (e), 3,842 with NS0/PD-L1 cells (f), 3,866 with HuPRO1-IgG1.AA and NS0/PD-L1 cells (g), 5,921 with HuOHX14DS-IgG1.AA and NS0/PD-L1 cells (h), 2,836 with HuPRO1-IgG1.AA, HuOHX14DS-Ig1.AA and NS0/PD-L1 cells (i), and 23,715 with BS813 and NS0/PD-L1 cells (j). Only in the presence of both bispecific antibody binding to PD-L1 and OX40 (BS813) and PD-L1-expressing cells (NS0/PD-L1), the luciferase activity in JD/OX40 cells was significantly increased. This result indicates that only BS813 that can make bridges between JD/OX40 and NS0/PD-L1 cells, but neither HuPRO1-IgG1.AA, HuOHX14DS-IgG1.AA nor the combination of these two monospecific antibodies, causes multimeric cross-linking of OX40 on the surface of JD/OX40 cells at locations proximate to NS0/PD-L1 cells, which results in activation of JD/OX40 cells to increase the expression of luciferase.

Example 9: Generation of a Bispecific Antibody (BS841) that Binds to PD-L1 and OX40

Mouse hybridoma producing an IgG/kappa monoclonal antibody PRO2 that (i) binds to human and cynomolgus PD-L1 and (ii) blocks the interaction between PD-1 and PD-L1 was isolated as described in Example 1. Sequencing and humanization of VH and VL of PRO2 was carried out as described in Tsurushita et al. (supra).

The amino acid sequence of humanized PRO2 (HuPRO2) VH is MGWNWIFLFLSGTAGVHCQVQLVQSGAEVKKPGSSVKVSCKASGYTFTSYGINWVRQAPGQGLEWIGYIYPGSGGPVYNQKFKGRVTLTADKSTSTAYMELSSLRSEDTAVYYCARENYRYWYFDVWGQGTTVTVSS (SEQ ID NO:74). The CDR1, 2 and 3 amino acid sequences of HuPRO2 VH are SYGIN (SEQ ID NO:75), YIYPGSGGPVYNQKFKG (SEQ ID NO:76) and ENYRYWYFDV (SEQ ID NO:77), respectively, according to the definition by Kabat et al. (supra). A gene encoding HuPRO2 VH was synthesized as an exon including a splice donor signal at the 3' end of the coding region, a SpeI site at the 5' end of the fragment, and a HindIII site at the 3' end of the fragment.

The amino acid sequence of humanized PRO2 (HuPRO2) VL is MHFQVQIFSFLLISASVIMSRGDIQLTQSPSFLSASVGDRVTITCSASSSVNYMHWFQQKPGKAPKLWIYSTSNLASGVPSRFSGSGSGTEFTLTISSLQPEDFATYYCQQRSSYPLTFGGG TKVEIK (SEQ ID NO:78). The CDR1, 2 and 3 amino acid sequences of HuPRO2 VL are SASSSVNYMH (SEQ ID NO:79), STSNLAS (SEQ ID NO:80) and QQRSSYPLT (SEQ ID NO:81), respectively, according to the definition by Kabat et al. (supra). A gene encoding HuPRO2 VL was synthesized as an exon including a splice donor signal at the 3' end of the coding region, a NheI site at the 5' end of the fragment, and an EcoRI site at the 3' end of the fragment.

The expression vector pHuPRO2-IgG1.AA has the same structure as pHuM195-IgG1 (FIG. 1A), except that (i) the HuPRO2 VH exon was placed between the SpeI and HindIII sites, (ii) the HuPRO2 VL exon was placed between the NheI and EcoRI sites, and (iii) two leucine residues at positions 234 and 235 (Eu numbering) were substituted to alanine residues in CH2 (L234A and L235A, respectively) (SEQ ID NO:20) for elimination of effector functions (Hezareh et al., supra). The new vector pHuPRO2-IgG1.AA expresses humanized anti-PD-L1 IgG1/kappa antibody (HuPRO2-IgG1.AA) in mammalian cells.

The mammalian expression vector pBS841, designed for expression of a bispecific antibody that binds to both human PD-L1 (SEQ ID NO:69) and human OX40 (SEQ ID NO:21), was constructed by replacing the CH3 coding region in pHuPRO2-IgG1.AA with the coding region of CH3-HuOHX14DS.scFv (SEQ ID NO:23).

The amino acid sequence of the mature heavy chain encoded in pBS841 is

```
                                            (SEQ ID NO: 82)
QVQLVQSGAEVKKPGSSVKVSCKASGYTFTSYGINWVRQAPGQGLEWIGY

IYPGSGGPVYNQKFKGRVTLTADKSTSTAYMELSSLRSEDTAVYYCAREN
```

-continued

```
YRYWYFDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGSG

GGGSGGGGSDIQMTQSPSSLSASVGDRVTITCRASQDIRTYLNWYQQKPG

KVPKLLIYYTSRLHSGVPSRFSGSGSGTDYTLTISSLQPEDVATYYCQQG

NTLPWTFGGGTKVEIKGGGGSGGGGSGGGGSQVQLVQSGAEVKKPGSSVK

VSCKASGYTFTSYIMHWVRQAPGQGLEWIGYINPYNSGTKYNEKFKGRVT

ITSDKSTSTAYMELSSLRSEDTAVYYCAHYYGSTFTMDYWGQGTTVTVSS.
```

The amino acid sequence of the mature light chain encoded in pBS841 is

```
                                            (SEQ ID NO: 83)
DIQLTQSPSFLSASVGDRVTITCSASSSVNYMHWFQQKPGKAPKLWIYST

SNLASGVPSRFSGSGSGTEFTLTISSLQPEDFATYYCQQRSSYPLTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC.
```

Example 10: Generation of a Bispecific Antibody (BS839) that Binds to PD-L1 and OX40

Mouse hybridoma producing an IgG/kappa monoclonal antibody PRO5 that (i) binds to human and cynomolgus PD-L1 and (ii) blocks the interaction between PD-1 and PD-L1 was isolated as described in Example 1. Sequencing and humanization of VH and VL of PRO5 was carried out as described in Tsurushita et al. (supra).

The amino acid sequence of humanized PRO5 (HuPRO5) VH is MMVLSLLYLLTALPGILSQVQLQESGPGLVKPSQTLSLTCTVSGDSISSGYWNWIRQPPGKGLEYMGYISYTGSTYSNPSLKSRVTISRDTSKNQFSLKLSSVTAADTAVYYCARSQNW ERAWFAYWGQGTLVTVSS (SEQ ID NO:84). The CDR1, 2 and 3 amino acid sequences of HuPRO5 VH are SGYWN (SEQ ID NO:85), YISYTGSTYSNPSLKS (SEQ ID NO:86) and SQNWERAWFAY (SEQ ID NO:87), respectively, according to the definition by Kabat et al. (supra). A gene encoding HuPRO5 VH was synthesized as an exon including a splice donor signal at the 3' end of the coding region, a SpeI site at the 5' end of the fragment, and a HindIII site at the 3' end of the fragment.

The amino acid sequence of humanized PRO5 (HuPRO5) VL is MDFQVQIFSFLLISASVIMSRGDIQMTQSPSSLSASVGDRVTITCSASSSVSYMHWYQQKPGKAPKLWIYDTSKLASGVPSRFSGSGSGTDFTLTISSLQPEDFATYYCFQGSGYPFTFGG GTKVEIK (SEQ ID NO:88). The CDR1, 2 and 3 amino acid sequences of HuPRO5 VL are SASSSVSYMH (SEQ ID NO:89), DTSKLAS (SEQ ID NO:90) and FQGSGYPFT (SEQ ID NO:91), respectively, according to the definition by Kabat et al. (supra). A gene encoding HuPRO5 VL was synthesized as an exon including a splice donor signal at the 3' end of the coding region, a NheI site at the 5' end of the fragment, and an EcoRI site at the 3' end of the fragment.

The expression vector pHuPRO5-IgG1.AA has the same structure as pHuM195-IgG1 (FIG. 1A), except that (i) the HuPRO5 VH exon was placed between the SpeI and HindIII sites, (ii) the HuPRO5 VL exon was placed between the NheI and EcoRI sites, and (iii) two leucine residues at positions 234 and 235 (Eu numbering) were substituted to alanine residues in CH2 (L234A and L235A, respectively) (SEQ ID NO:20) for elimination of effector functions (Hezareh et al., supra). The new vector pHuPRO5-IgG1.AA expresses humanized anti-PD-L1 IgG1/kappa antibody (HuPRO5-IgG1.AA) in mammalian cells.

The mammalian expression vector pBS839, designed for expression of a bispecific antibody that binds to both human PD-L1 (SEQ ID NO:69) and human OX40 (SEQ ID NO:21), was constructed by replacing the CH3 coding region in pHuPRO5-IgG1.AA with the coding region of CH3-HuOHX14DS.scFv (SEQ ID NO:23).

The amino acid sequence of the mature heavy chain encoded in pBS839 is

```
                                        (SEQ ID NO: 92)
QVQLQESGPGLVKPSQTLSLTCTVSGDSISSGYWNWIRQPPGKGLEYMGY

ISYTGSTYSNPSLKSRVTISRDTSKNQFSLKLSSVTAADTAVYYCARSQN

WERAWFAYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGSG

GGGSGGGGSDIQMTQSPSSLSASVGDRVTITCRASQDIRTYLNWYQQKPG

KVPKLLIYYTSRLHSGVPSRFSGSGSGTDYTLTISSLQPEDVATYYCQQG

NTLPWTFGGGTKVEIKGGGGSGGGGSGGGGSQVQLVQSGAEVKKPGSSVK

VSCKASGYTFTSYIMHWVRQAPGQGLEWIGYINPYNSGTKYNEKFKGRVT

ITSDKSTSTAYMELSSLRSEDTAVYYCAHYYGSTFTMDYWGQGTTVTVSS.
```

The amino acid sequence of the mature light chain encoded in pBS839 is

```
                                        (SEQ ID NO: 93)
DIQMTQSPSSLSASVGDRVTITCSASSSVSYMHWYQQKPGKAPKLWIYDT

SKLASGVPSRFSGSGSGTDFTLTISSLQPEDFATYYCFQGSGYPFTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC.
```

Example 11: Expression and Characterization of Bispecific Antibodies BS839 and BS841 that Bind to PD-L1 and OX40

The four expression vectors, pHuPRO2-IgG1.AA, pHuPRO5-IgG1.AA, pBS839 and pBS841, are stably transfected into CHO-K1 as described above. HuPRO2-IgG1AA, HuPRO5-IgG1.AA, BS839 and BS841 are purified from culture supernatants of their respective CHO-K1 transfectants with a protein A affinity column as described above. SDS-PAGE analysis under reducing conditions is carried out to examine the size of heavy and light chains of these four antibodies.

The biological activity of BS839 and BS841 to enhance immune responses is analyzed by measuring the expression level of IL-2 in human T cells. Human PBMC are grown in RPMI-1640 containing 10% FBS and 10 μg/ml of PHA-L for three days (3-day old PBMC) as described above. Approximately one hundred thousand cells of the 3-day old PBMC are incubated in a well of a 96-well plate, which is precoated with 1 μg/ml of mouse anti-human CD3 monoclonal antibody OKT3, in the presence of (i) no additional antibody, (ii) 1 μg/ml of HuPRO2-IgG1.AA, (iii) 1 μg/ml of HuPRO5-IgG1.AA, (iv) 1 μg/ml of HuOHX14DS-IgG1.AA, (v) 1 μg/ml of HuPRO2-IgG1.AA and HuOHX14DS-IgG1.AA, (vi) 1 μg/ml of HuPRO5-IgG1.AA and HuOHX14DS-IgG1.AA, (vii) 1 μg/ml of BS841, and (viii) 1 μg/ml of BS839 for one day at 37° C. in a 7.5% $CO_2$ incubator. IL-2 concentration in culture supernatants is measured using the Human IL-2 ELISA MAX Standard Kit (BioLegend).

Example 12: Bispecific Antibody that Binds to a Cancer Cell and a Costimulatory Molecule A monoclonal antibody that binds to a cancer cell is isolated using hybridoma or display technologies (Akamatsu et al., J. Immunol. Methods, 327:40-52, 2007; Bradbury et al., Nat. Biotechnol. 29:245-254, 2011; Hammers et al., J. Invest. Dermatol. 134:e17, 2014; Cherf et al., Methods Mol. Biol. 1319:155-175, 2015; Saeed et al., MOJ Immunol. 3:00099, 2016; Mahmuda et al., Trop. J. Pharm. Res. 16:713-722, 2017). The VH and VL regions of such isolated anti-cancer antibody, or their humanized form, are cloned into an expression vector such as pHuM195-IgG1 (FIG. 1A) as described above. Another monoclonal antibody that binds to an immune costimulatory molecule (Bakdash et al., Front. Immunol. 4: Article 53, 2013; Mahoney et al., Nat. Rev. Drug Discov. 14:561-584, 2015) is isolated using hybridoma or display technologies. The VH and VL regions of such isolated anti-costimulatory molecule antibody, or their humanized form, are converted to a single-chain Fv (scFv) form (Nelson, mAbs 2:77-83, 2010; Ahmad et al., Clin. Dev. Immunol. Article ID 980250, 2012). The scFv form of the anti-costimulatory molecule antibody is fused to the C-terminus of the heavy chain of the anti-cancer antibody to generate a new vector that expresses a bispecific antibody binding to the cancer cells and the costimulatory molecule. The biological activity of such generated bispecific antibody, which can (i) make bridges between cancer cells and immune cells and (ii) activate such immune cells by multimeric cross-linking of the costimulatory molecules, is tested in an appropriate disease model, for example, a tumor xenograft model using humanized mice having human-derived immune cells (Day et al., Cell 163:39-53, 2015; Morton et al., Cancer Res. 76:6153-6158, 2016).

Example 13: Bispecific Antibody that Binds to a Pathogen-Derived Molecule and a Costimulatory Molecule A monoclonal antibody that binds to a pathogen expressed by an infectious agent on the surface of host cells is isolated using hybridoma or display technologies as described above. The VH and VL regions of such isolated anti-pathogen antibody, or their humanized form, are cloned into an expression vector such as pHuM195-IgG1 (FIG. 1A) as described above. Another monoclonal antibody that binds to an immune costimulatory molecule is isolated using hybridoma or display technologies. The VH and VL regions of such isolated anti-costimulatory molecule antibody, or their humanized form, are converted to a scFv form as described above. The scFv form of the anti-costimulatory antibody is fused to the C-terminus of the heavy chain of the anti-pathogen antibody as described above in an expression vector for the anti-pathogen IgG antibody. The resulting new vector expresses a bispecific IgG antibody that is capable of binding to the cell infected by the pathogen and the costimulatory molecule. The biological activity of such generated bispecific antibody, which can (i) make bridges between pathogen-infected cells and immune cells, and (ii) activate such immune cells by multimeric cross-linking of the costimulatory molecules, is tested in an appropriate disease model, for example, humanized mice having human-derived immune cells that are infected by a pathogen (Shultz et al., Ann. N. Y. Acad. Sci. 1245:50-54, 2011; Leung et al., Eur. J. Immunol. 43: 2246-2254, 2013).

Example 14: Replacement of scFv with a Different Format of a Receptor-Binding Module The scFv region of the bispecific antibodies of this invention, which provides a second antigen-binding site to IgG molecules, is replaced with a polypeptide capable of binding to a cell surface receptor, for example, a growth factor, a cytokine, a chemokine, a soluble form of a receptor, a single domain antibody such as VH, VL or VHH (Holt et al., Trends Biotechnol. 21:484-490, 2003; Bannas et al, Front. Immunol. 8: Article 1603, 2017) or an antibody mimetic (Yu et al., Annu. Rev. Anal. Chem. 10: 293-320, 2017). Such generated bispecific antibody is tested for its biological activity to activate immune cells via multivalent cross-linking of costimulatory molecules in appropriate animal disease models such as the ones described above for cancer and infectious disease.

Example 15: Fusion of scFv at the C-Terminus of a Light Chain

The scFv region of an anti-costimulatory molecule is fused to the C-terminus of the light chain of an IgG antibody against a checkpoint molecule, a cancer cell or a pathogen. Such generated bispecific antibody is tested for its biological activity to activate immune cells via multivalent cross-linking of costimulatory molecules in appropriate animal models such as the ones described above for cancer and infectious disease.

Example 16: Activation of T Cells by BS809

Figure 8:
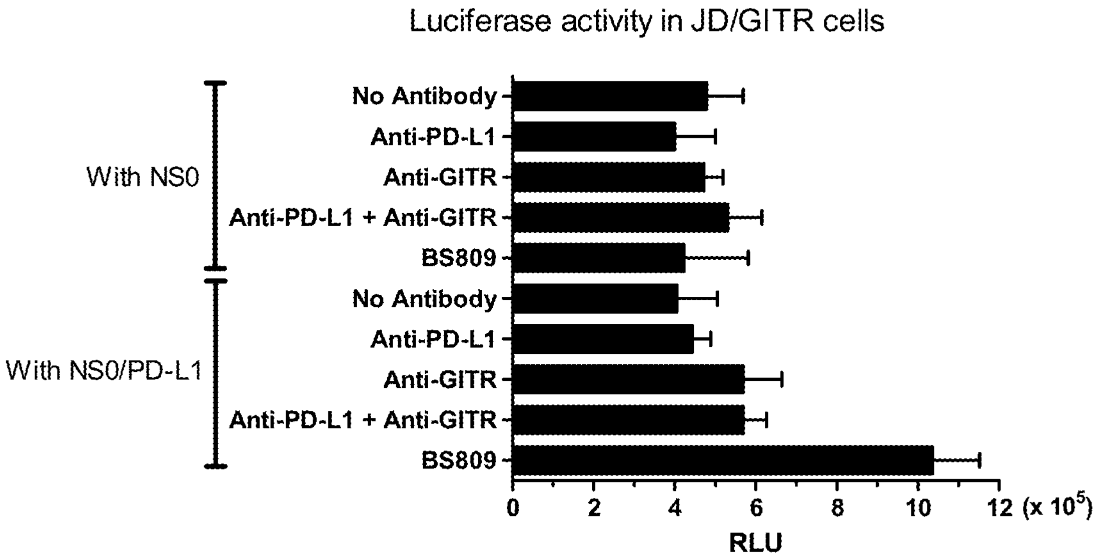
FIG. 8: Analysis of luciferase activities in Jurkat Dual cells expressing GITR (JD/GITR) with a bispecific antibody binding to PD-L1 and GITR (BS809). Average relative luminescence units (RLU) of triplicate analysis are shown with standard deviation bars.

Approximately one hundred thousand JD/GITR cells were incubated in 200 µl/well of RPMI 1640 media containing 10% FBS, 0.5 µg/ml of mouse anti-human CD3 IgG antibody OKT3 (BioLegend, San Diego, CA) and 5 µg/ml of goat anti-mouse IgG antibody (human IgG-absorbed) (Jackson ImmunoResearch) with no antibody (a and f), 1 µg/ml of HuPRO1-IgG1.AA (anti-PD-L1 in FIG. 8) (b and g), 1 µg/ml of HuGAB11-IgG1.AA (anti-GITR in FIG. 8) (c and h), 1 µg/ml of HuPRO1-IgG1.AA and 1 µg/ml of HuGAB11-IgG1.AA (d and i), and 1 µg/ml of BS809 (e and j) in a 96-well plate at 37° C. in a 7.5% $CO_2$ incubator. One hundred thousand NS0 cells were included in the reactions a, b, c, d and e. One hundred thousand NS0/PD-L1 cells were included in the reactions f, g, h, i and j. After incubation for one day, luciferase activity in culture supernatants was measured in triplicates with QUANTI-Luc reagents (InvivoGen) according to the vendor's protocol. Luminescence was measured using a Synergy HT microplate reader with the Gen5 software (BioTek, Winooski, VT). The result is shown in FIG. 8.

The average relative luciferase unit (RLU) in the culture supernatants of JD/GITR cells was: (a) 479,187 with NS0 cells, (b) 400,158 with HuPRO1-IgG1.AA and NS0 cells, (c) 472,050 with HuGAB11-IgG1.AA and NS0 cells, (d) 531,275 with HuPRO1-IgG1.AA, HuGAB11-IgG1.AA and NS0 cells, (e) 422,955 with BS809 and NS0 cells, (f) 405,780 with NS0/PD-L1 cells, (g) 443,588 with HuPRO1-IgG1.AA and NS0/PD-L1 cells, (h) 568,268 with HuGAB11-IgG1.AA and NS0/PD-L1 cells, (i) 569,172 with HuPRO1-IgG1.AA, HuGAB11-Ig1.AA and NS0/PD-L1 cells, and (j) 1,035,453 with BS809 and NS0/PD-L1 cells. Only in the presence of both the bispecific antibody binding to PD-L1 and GITR (BS809) and PD-L1-expressing cells (NS0/PD-L1), the luciferase activity in JD/GITR cells was significantly increased. This result indicates that only BS809 that can make bridges between JD/GITR and NS0/PD-L1 cells, but neither HuPRO1-IgG1.AA, HuGAB11-IgG1.AA nor the combination of these two monospecific antibodies, causes multimeric cross-linking of GITR on the surface of JD/GITR cells at locations proximate to NS0/PD-L1 cells, which results in activation of JD/GITR cells to increase the expression of luciferase.

Example 17: Activation of PHA-L-Treated PBMC by BS813, BS841 and BS839

Figure 9:
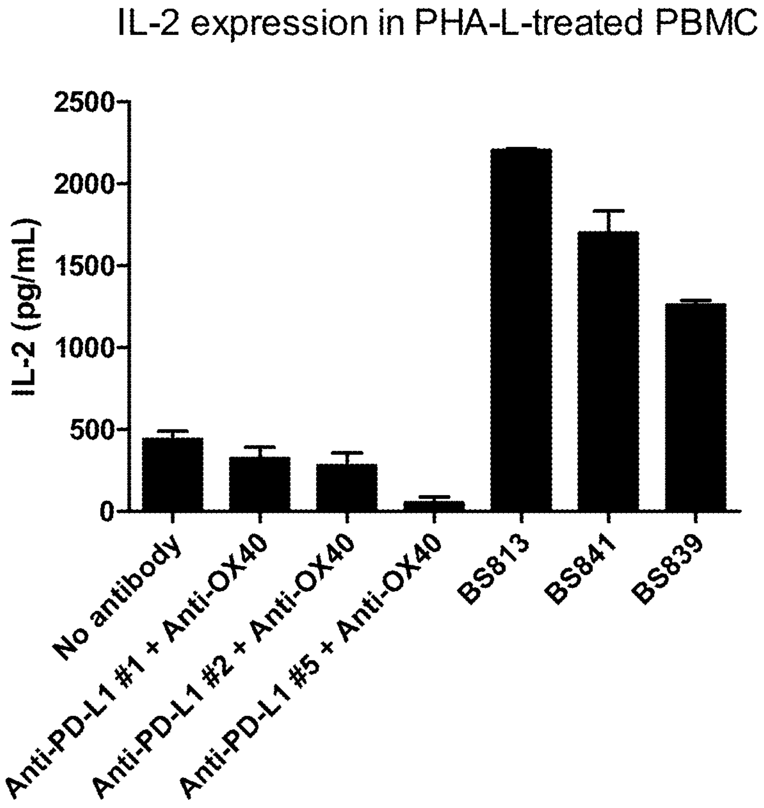
FIG. 9: Activation of human T cells with bispecific antibodies binding to PD-L1 and OX40 (BS813, BS841 and BS839). Average IL-2 expression levels of triplicate analysis are shown with standard deviation bars.

The biological activity of BS813, BS841 and BS839 to enhance immune responses was analyzed by measuring IL-2 expression in human T cells. Bispecific antibodies BS813, BS841 and BS839, each of which binds to PD-L1 and OX40, were purified using a protein A affinity column from culture supernatants of CHO-K1 cells stably transfected with pBS813, pBS841 and pBS839, respectively. Human PBMC were grown in RPMI-1640 media containing 10% FBS and 10 µg/ml of PHA-L for three days (3-day old PBMC) as described above. Approximately one hundred thousand cells of 3-day old PBMC were incubated at 200 µl/well in a 96-well plate, which had been precoated with 1 µg/ml of mouse anti-human CD3 monoclonal antibody OKT3, for one day at 37° C. in a 7.5% $CO_2$ incubator in the presence of (a) no additional antibody, (b) 1 µg/ml of HuPRO1-IgG1.AA (Anti-PD-L1 #1 in FIG. 9) and 1 µg/ml of HuOHX14DS-IgG1.AA (Anti-OX40 in FIG. 9), (c) 1 µg/ml of HuPRO2-IgG1.AA (Anti-PD-L1 #2 in FIG. 9) and 1 µg/ml of HuOHX14DS-IgG1.AA, (d) HuPRO5-IgG1.AA (Anti-PD-L1 #5 in FIG. 9) and 1 µg/ml of HuOHX14DS-IgG1.AA, (e) 1 µg/ml of BS813, (f) 1 µg/ml of BS841, and (g) 1 µg/ml of BS839. IL-2 concentration in culture supernatants was measured in triplicates using the Human IL-2 ELISA MAX Standard Kit (BioLegend). The result is shown in FIG. 9.

The average IL-2 concentration in human PBMC-derived T cells was (a) 439 pg/ml without a test antibody (control), (b) 324 pg/ml with a combination of HuPRO1-IgG1.AA and HuOHX14DS-IgG1.A, (c) 281 pg/ml with a combination of HuPRO2-IgG1.AA and HuOHX14DS-IgG1.AA, (d) 53 pg/ml with a combination of HuPRO5-IgG1.AA and HuOHX14DS-IgG1.AA, (e) 2,202 pg/ml with BS813, (f) 1,698 pg/ml of BS841, and (g) 1,259 pg/ml with BS839. IL-2 expression significantly increased only in the presence of either one of the bispecific antibodies that bind to both PD-L1 and OX40 (BS813, BS841 and BS839) when compared to the IL-2 level in the control or the combination of two parental antibodies of each of BS813, BS841 and BS839. This is due to bridging of PD-L1-expressing cells with OX40-expressing T cells by each of BS813, BS841 and BS839, which causes multimeric cross-linking of OX40 on the cell surface at locations proximate to PD-L1-expressing cells and leads to activation of OX40-expressing T cells to upregulate IL-2 expression.

Example 18: Activation of SEB-Treated PBMC by BS813, BS841 and BS839

Superantigens such as SEB (*Staphylococcus* enterotoxin B) activate T-cells by linking MHC class II molecules on antigen presenting cells to the vβ element of T cell receptors, resulting in the activation of T cells and production of cytokines including interleukin-2 (IL-2), interleukin-6 (IL-6), tumor necrosis factor alpha (TNFα), and interferon gamma (IFNγ) (see, e.g., Krakauer et al., Toxins (Basel). 2010 August; 2(8): 1963-1983). SEB is capable of activating up to 10 to 20% of T cells in human blood depending on the fraction of T cells bearing the vβ3, vβ12, vβ14 and vβ17 found in each particular blood donor. SEB can therefore be used fora T cell-based cytokine secretion assay to monitor activation of immune costimulatory molecules.

Figure 10:
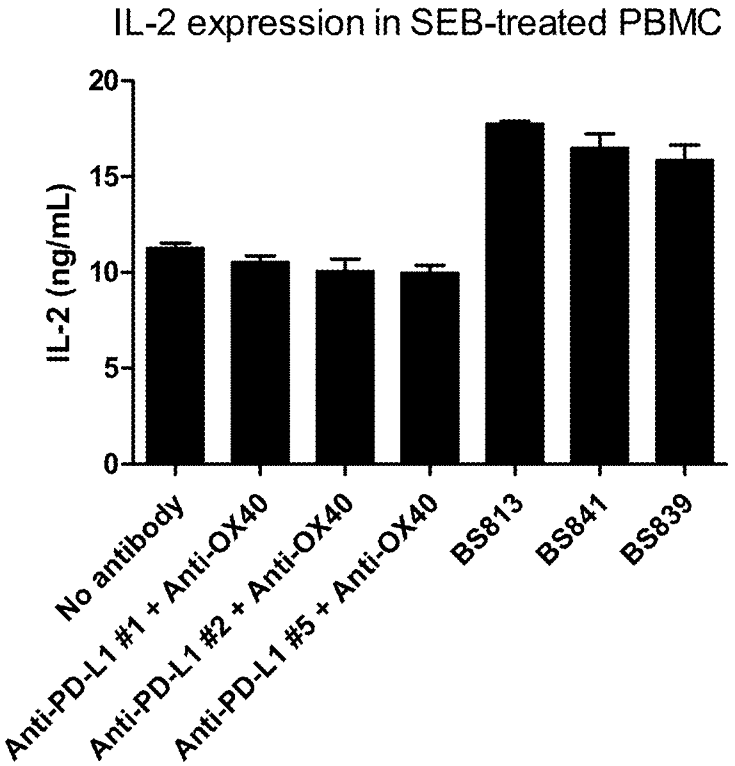
FIG. 10: Activation of SEB-treated human peripheral blood mononuclear cells with bispecific antibodies binding to PD-L1 and OX40 (BS813, BS841 and BS839). Average IL-2 expression levels of triplicate analysis are shown with standard deviation bars.

Approximately four hundred thousand of human PBMC were incubated in 200 μl/well of RPMI-1640 media containing 10% FBS and 1 μg/ml SEB in a 96-well plate with (a) no antibody (control), (b) 1 μg/ml of HuPRO1-IgG1.AA (Anti-PD-L1 #1 in FIG. 10) and 1 μg/ml of HuOHX14DS-IgG1.AA (Anti-OX40 in FIG. 10), (c) 1 μg/ml of HuPRO2-IgG1.AA (Anti-PD-L1 #2 in FIG. 10) and 1 μg/ml of HuOHX14DS-IgG1.AA, (d) HuPRO5-IgG1.AA (Anti-PD-L1 #5 in FIG. 10) and 1 μg/ml of HuOHX14DS-IgG1.AA, (e) 1 μg/ml of BS813, (f) 1 μg/ml of BS841, and (g) 1 μg/ml of BS839. After incubation for one day at 37° C. in a 7.5% $CO_2$ incubator, IL-2 concentration in culture supernatants was measured in triplicates using the Human IL-2 ELISA MAX Standard Kit (BioLegend). The result is shown in FIG. 10.

The average IL-2 concentration was (a) 11.3 ng/ml without a test antibody, (b) 10.5 ng/ml with a combination of HuPRO1-IgG1.AA and HuOHX14DS-IgG1.A, (c) 10.0 ng/ml with a combination of HuPRO2-IgG1.AA and HuOHX14DS-IgG1.AA, (d) 10.0 ng/ml with a combination of HuPRO5-IgG1.AA and HuOHX14DS-IgG1.AA, (e) 17.7 ng/ml with BS813, (f) 16.5 ng/ml of BS841, and (g) 15.8 ng/ml with BS839. IL-2 expression significantly increased only in the presence of either one of the bispecific antibodies that bind to both PD-L1 and OX40 (BS813, BS841 and BS839) when compared to the IL-2 level in the control where no antibody was added to SEB-treated PBMC. The combination of two parental antibodies of each of BS813, BS841 and BS839 did not increase the IL-2 expression over the control level. This result indicates that each of BS813, BS841 and BS839 can make bridging between PD-L1-expressing cells and OX40-expressing T cells, which causes multimeric cross-linking of OX40 on the cell surface at locations proximate to PD-L1-expressing cells and leads to activation of OX40-expressing T cells to upregulate IL-2 expression.

Example 19: Bispecific Antibody with Disulfide-Linked Single-Chain Fv

Brinkman et al. previously reported that the introduction of a disulfide linkage stabilized the association of VH and VL in the Fv format (dsFv) by converting an amino acid residue at position 100 in VL to a cysteine residue and another amino acid residue at position 44 in VH to a cysteine residue (Eu numbering) (Proc. Natl. Acad. Sci. 90:7538-7542, 1993). Use of different VH and VL locations was also reported for introduction of a pair of cysteine residues to stabilize the Fv structure (Brinkman et al. supra; Young et al. FEBS Lett. 377:135-139, 1995; Schmiedl et al. Protein Eng. 13:724-730, 2000).

The bispecific anti-PD-L1/GITR antibody (BS809) of this invention was modified to stabilize the single chain Fv structure by introducing two cysteine residues (underlined) in the anti-GITR variable region, one at position 44 in VH and another at position 100 in VL, by site-directed mutagenesis in pBS809. Although the resulting expression vector, pBS853, has the same structure as pBS809, the amino acid sequence of the anti-GITR single-chain Fv region is different between pBS809 and pBS853. The vectors pBS809 and pBS853 carry the same light chain sequence (SEQ ID NO:71). The amino acid sequence of the mature heavy chain encoded in pBS853 is

```
                                  (SEQ ID NO: 106)
QVQLVQSGAEVKKPGSSVKVSCKASGFTFSSSYISWVRQAPGQGLEWIAW

IYAGTGGTSYNQKFTGRATITVDESTSTAYMELSSLRSEDTAVYYCARHE

GVYWYFDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGSG

GGGSGGGGSDIQMTQSPSSLSASVGDRVTITCHASQNINVWLSWYQQKPG

KVPKLLIYKASNLHTGVPSRFSGSGSGTDFTLTISSLQPEDVATYYCQQG

QSYPLTFGCGTKVEIKGGGGSGGGGSGGGGSQVTLKESGPVLVKPTETLT

LTCTVSGFSLTDYGVSWIRQPPGKCLEWLGVIWGGGGTYYNSALKSRLTI

SKDTSKSQVVLTMTNMDPVDTATYYCAKHPYGHFGMDYWGQGTTVTVSS.

Cysteine substitutions are underlined.
```

The modified bispecific antibody encoded in pBS853 (BS853) was transiently expressed in HEK293 cells following the procedure of Durocher et al. (Nucl. Acids Res. 30:e9, 2002). BS853 showed the same level of binding to PD-L1 and GITR by ELISA as BS809.

Example 20: Bispecific Antibody (BS859) that Binds to PD-L1 and ICOS

ICOS (inducible T-cell costimulatory), also known as CD278, is an immune costimulatory molecule that belongs to the CD28 family. Multimeric cross-linking of ICOS on the cell surface of immune cells is required to initiate intracellular signal transduction to enhance immune responses (Wikenheiser et al., Front. Immunol. 7: Article 304, 2016).

Rat hybridoma producing an IgG/kappa monoclonal antibody TAM14 that binds specifically to human and cynomolgus ICOS was isolated as described in Example 1, except that Sprague Dawley rats were used for immunization. As an immunogen, the extracellular region of human ICOS fused to the Fc region of the human gamma-1 heavy chain (hICOS-Fc; SEQ ID NO:107) was used. Sequencing and humanization of TAM14 VH and VL was carried out as described in Tsurushita et al. (supra).

The amino acid sequence of humanized TAM14 (HuTAM14) VH is MAVLVLLLCLVTFPSCALSQVQLQESGPGLVKPSETLSLTCTVSGFSISSNSVSWVRQPP GKGLEWMGAIWSGGSTDYNSALKSRVTISRDTSKNQVSLKLSSVTAADTAVYYCTRWE QPYYFDYWGQGTMVTVSS (SEQ ID NO:108). The CDR1, 2 and 3 amino acid sequences of HuTAM14 VH are SNSVS (SEQ ID NO:109), AIWSGGSTDYNSALKS (SEQ ID NO:110) and WEQPYYFDY (SEQ ID NO:111), respectively, according to the definition by Kabat et al. (supra). A gene encoding HuTAM14 VH was synthesized as an exon including a splice donor signal at the 3' end of the coding region, a SpeI site at the 5' end of the fragment, and a HindIII site at the 3' end of the fragment.

The amino acid sequence of humanized TAM14 (HuTAM14) VL is MRTSIQLLGLLLFWLHDAQCDIQMTQSPSSLSASVGDRVTITCQASQNIYKYIAWYQQK PGKAPKLLIRYTSTLESGTPSRFSGSGSGTDYTLTISSLQPEDFATYYCLQYVNLYTFGGG TKVEIK (SEQ ID NO: 112). The CDR1, 2 and 3 amino acid sequences of HuTAM14 VL are QASQNIYKYIA (SEQ ID NO:113), YTSTLES (SEQ ID NO:114) and LQYVNLYT (SEQ ID NO:115), respectively, according to the definition by Kabat et al. (supra). A gene encoding HuTAM14 VL was synthesized as an exon including a splice donor signal at the 3' end of the coding region, a NheI site at the 5' end of the fragment, and an EcoRI site at the 3' end of the fragment.

The expression vector pHuTAM14-IgG1.AA has the same structure as pHuM195-IgG1 (FIG. 1A), except that (i) the HuTAM14 VH exon was placed between the SpeI and HindIII sites, (ii) the HuTAM14 VL exon was placed between the NheI and EcoRI sites, and (iii) two leucine residues at positions 234 and 235 (EU numbering of Kabat et al. supra) were substituted to alanine residues in CH2 (L234A and L235A, respectively) (SEQ ID NO:20) for elimination of effector functions (Hezareh et al., J. Virol. 75:12161-12168, 2001). The new vector pHuTAM14-IgG1.AA expresses humanized anti-ICOS IgG1/kappa antibody (HuTAM14-IgG1.AA) in mammalian cells.

The mammalian expression vector, designed for expression of a bispecific antibody that binds to both human PD-L1 (SEQ ID NO:69) and human ICOS (SEQ ID NO:116), was constructed by modifying pHuPRO1-IgG1.AA as follows. The VL and VH coding regions of a humanized anti-human ICOS monoclonal antibody in pHuTAM14-IgG1.AA were converted to a single-chain Fv (scFv) form in the order of VL, a polypeptide linker and VH from the N- to C-terminus (HuTAM14.scFv; SEQ ID NO:117). The N-terminus of HuTAM14.scFv was fused to the penultimate glycine residue in CH3 of pHuPRO1-IgG1.AA with a polypeptide linker separating them (CH3-HuTAM14.scFv; SEQ ID NO:118). The resultant vector pBS859 expresses a bispecific IgG antibody termed BS859 which binds to both human PD-L1 and ICOS.

The amino acid sequence of the mature heavy chain encoded in pBS859 is

```
                                        (SEQ ID NO: 119)
QVQLVQSGAEVKKPGSSVKVSCKASGFTFSSSYISWVRQAPGQGLEWIAW

IYAGTGGTSYNQKFTGRATITVDESTSTAYMELSSLRSEDTAVYYCARHE

GVYWYFDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGSG

GGGSGGGGSDIQMTQSPSSLSASVGDRVTITCQASQNIYKYIAWYQQKPG

KAPKLLIRYTSTLESGTPSRFSGSGSGTDYTLTISSLQPEDFATYYCLQY

VNLYTFGGGTKVEIKGGGGSGGGGSGGGGSQVQLQESGPGLVKPSETLSL

TCTVSGFSISSNSVSWVRQPPGKGLEWMGAIWSGGSTDYNSALKSRVTIS

RDTSKNQVSLKLSSVTAADTAVYYCTRWEQPYYFDYWGQGTMVTVSS.
```

The amino acid sequence of the mature light chain encoded in pBS859 is same as the mature light chain sequence encoded in pBS809 (SEQ ID NO:71).

The schematic structure of the bispecific IgG antibodies of this invention, such as BS859, is shown in FIG. 2.

Each of the three expression vectors, pHuPRO1-IgG1.AA, pHuTAM14-IgG1.AA and pBS859, was stably transfected into CHO-K1 cells as described above. HuPRO1-IgG1.AA, HuTAM14-IgG1.AA and BS859 were purified from culture supernatants of their respective CHO-K1 stable transfectants with a protein A affinity column as described above. SDS-PAGE analysis under reducing conditions showed only two predominant bands with each of these three antibodies: roughly 50 kD heavy chains and 25 kD light chains (for HuPRO1-IgG1.AA and HuTAM14-IgG1.AA) or roughly 75 kD heavy chains and 25 kD light chains (for BS859).

The biological activity of BS859 to enhance immune responses was analyzed by measuring the expression level of IL-2 and IL-10 in human T cells. Human peripheral blood mononuclear cells (PBMC) from two donors (3486 and 4239) were obtained from iQ Biosciences (Berkeley, CA). Human PBMC were grown in RPMI-1640 containing 10% FBS and 10 μg/ml of phytohemagglutinin-L (PHA-L) for three days at 37° C. in a 7.5% $CO_2$ incubator to enrich T cells (3-day old PBMC).

Figure 11:
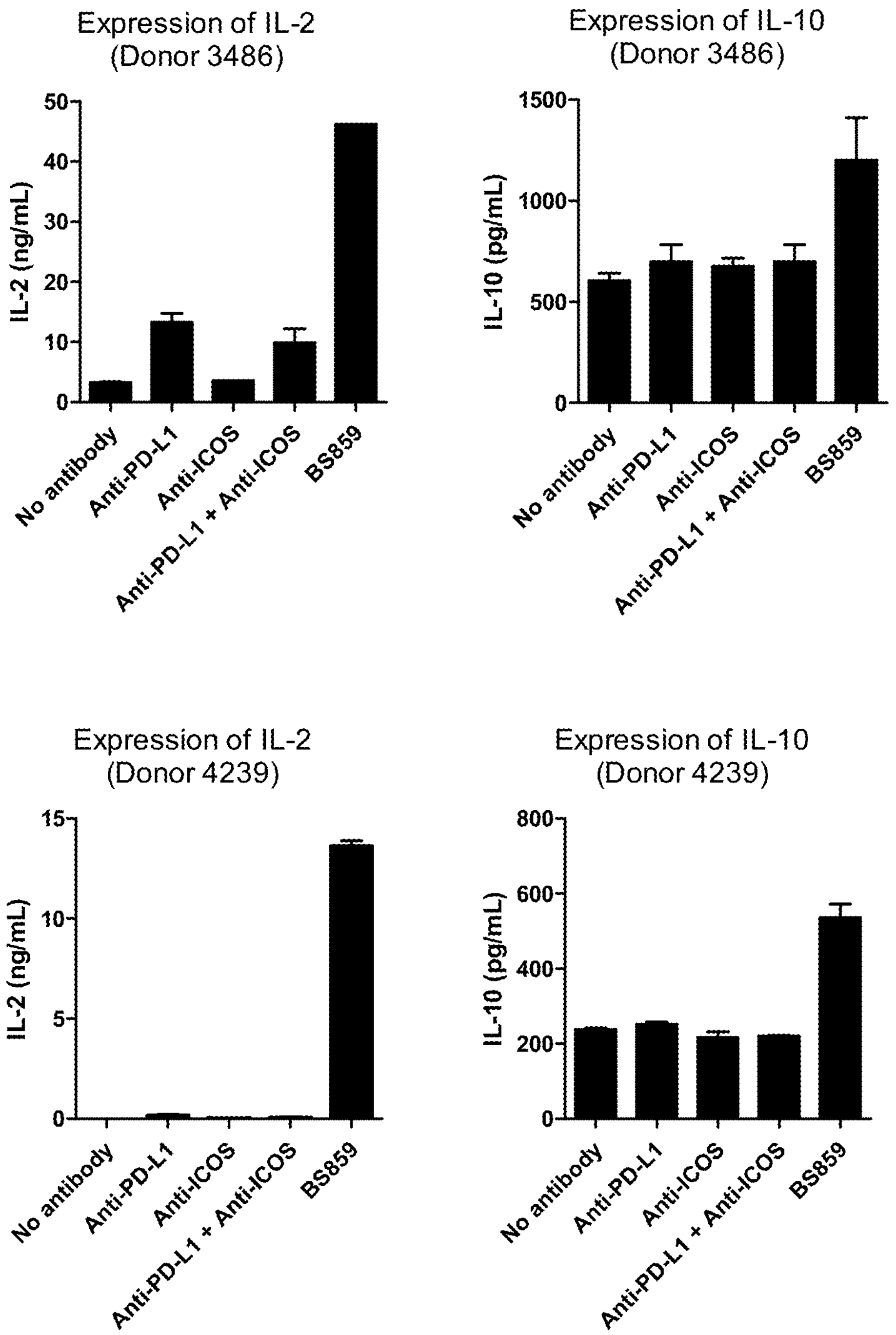
FIG. 11: Activation of human T cells with a bispecific antibody binding to PD-L1 and ICOS (BS859). Average IL-2 and IL-10 expression levels are shown with standard deviation bars.

Approximately two hundred thousand cells of the 3-day old PBMC were incubated in a well of a 96-well plate, which had been precoated with 1 μg/ml of mouse anti-human CD3 monoclonal antibody OKT3 and 1 μg/ml of human PD-L1-Fc fusion proteins (Recombinant Human B7-H1-Fc Chimera, BioLegend, San Diego, CA), in the presence of (i) no additional antibody (control), (ii) 1 μg/ml of HuPRO1-IgG1.AA (anti-PD-L1), (iii) 1 μg/ml of HuTAM14-IgG1.AA (anti-ICOS), (iv) 1 μg/ml of HuPRO1-IgG1.AA and 1 μg/ml of HuTAM14-IgG1.AA, and (v) 1 μg/ml of BS859 for one day at 37° C. in a 7.5% $CO_2$ incubator. Concentrations of IL-2 and IL-10 in culture supernatants were measured using the ELISA MAX Standard Set Human IL-2 and ELISA MAX Standard Set Human IL-10 (BioLegend, San Diego, CA), respectively. The results are shown in FIG. 11.

The average IL-2 concentration in PBMC-derived T cells of donor 3486 was (i) 3.3 ng/ml without antibody (control), (ii) 13.3 ng/ml with HuPRO1-IgG1.AA, (iii) 3.6 ng with HuTAM14-IgG1.AA, (iv) 9.9 ng/ml with a mixture of HuPRO1-IgG1.AA and HuTAM14-IgG1.AA, and (v) 46.2 ng/ml with BS859.

The average IL-10 concentration in PBMC-derived T cells of donor 3486 was (i) 604 pg/ml without antibody (control), (ii) 676 pg/ml with HuPRO1-IgG1.AA, (iii) 527 pg/ml with HuTAM14-IgG1.AA, (iv) 699 pg/ml with a mixture of HuPRO1-IgG1.AA and HuTAM14-IgG1.AA, and (v) 1,201 pg/ml with BS859.

The average IL-2 concentration in PBMC-derived T cells of donor 4239 was (i) 0.01 ng/ml without antibody (control), (ii) 0.15 ng/ml with HuPRO1-IgG1.AA, (iii) 0.01 ng/ml with HuTAM14-IgG1.AA, (iv) 0.06 ng/ml with a mixture of HuPRO1-IgG1.AA and HuTAM14-IgG1.AA, and (v) 13.6 ng/ml with BS859.

The average IL-10 concentration in PBMC-derived T cells of donor 4239 was (i) 238 pg/ml without antibody (control), (ii) 252 pg/ml with HuPRO1-IgG1.AA, (iii) 217 pg/ml with HuTAM14-IgG1.AA, (iv) 220 pg/ml with a mixture of HuPRO1-IgG1.AA and HuTAM14-IgG1.AA, and (v) 537 pg/ml with BS859.

HuPRO1-IgG1.AA alone was able to increase IL-2 expression of PHA-L-treated PBMC from two different donors when compared to their respective control groups with no antibody treatment. BS859 further significantly increased IL-2 expression with these two donors.

Expression of IL-10 in PHA-L-treated PBMC from two different donors significantly increased only in the presence of the bispecific antibody of this invention (BS859) that binds to both PD-L1 and ICOS.

Example 21: Bispecific Antibody (BS840) that Binds to PD-L1 and GITR

The mammalian expression vector pBS840, designed for expression of a bispecific antibody that binds to both human PD-L1 (SEQ ID NO:69) and human GITR (SEQ ID NO:40) has the same structure as pBS841 except that CH3-HuOHX14DS.scFv (SEQ ID NO:23) is substituted by CH3-HuGAB11.scFv (SEQ ID NO:42). The vector pBS840 expresses a bispecific IgG antibody termed BS840 which binds to both human PD-L1 and GITR.

The amino acid sequence of the mature heavy chain encoded in pBS840 is

```
                                        (SEQ ID NO: 120)
QVQLVQSGAEVKKPGSSVKVSCKASGYTFTSYGINWVRQAPGQGLEWIGY

IYPGSGGPVYNQKFKGRVTITADKSTSTAYMELSSLRSEDTAVYYCAREN

YRYWYFDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL
```

-continued

```
DSDGSFELYSKLTVDKSRWQQGNVFSCSVMHEALHNHYTQKSLSLSPGSG

GGGSGGGGSDIQMTQSPSSLSASVGDRVTITCHASQNINVWLSWYQQKPG

KVPKWYKASNLHTGVPSRFSGSGSGTDFTLTISSLQPEDVATYYCQQGQS

YPLTFGGGTKVEIKGGGGSGGGGSGGGGSQVTLKESGPVLVKPTETLTLT

CTVSGFSLTDYGVSWIRQPPGKALEWLGVIWGGGGTYYNSALKSRLTISK

DTSKSQVVLTMTNMDPVDTATYYCAKHPYGHFGMDYWGQGTTVTVSS
```

The amino acid sequence of the mature light chain encoded in pBS840 is same as that of the light chain sequence encoded in pBS841 (SEQ ID NO:83).

The expression vector pBS840 was stably transfected into CHO-K1 cells as described above. BS840 was purified from culture supernatants of the resulting CHO-K1 stable transfectant with a protein A affinity column as described above. Protein A-purified BS840 showed a single dominant peak of the expected size (approximately 200 kDa) by gel filtration using a Superose 6 size exclusion 10/300 column (GE Healthcare Life Sciences, Pittsburgh, PA). SDS-PAGE analysis under reducing conditions showed only two predominant bands of roughly 75 kD heavy chains and 25 kD light chains.

Figure 12:
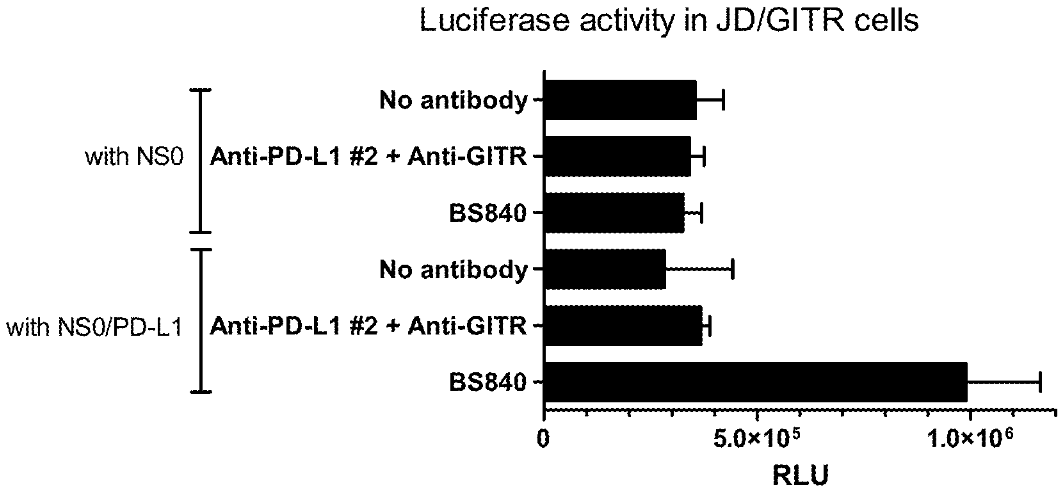
FIG. 12: Analysis of luciferase activities in Jurkat Dual cells expressing GITR (JD/GITR) with a bispecific antibody binding to PD-L1 and GITR (BS840). Average relative luminescence units (RLU) of triplicate analysis are shown with standard deviation bars.

The biological activity of BS840 to enhance immune responses was studied using Jurkat Dual cells stably expressing human GITR (JD/GITR) as described above. The data is shown in FIG. 12. The average relative luciferase unit (RLU) in the culture supernatants of JD/GITR cells was: (a) 354,057 with NS0 cells, (b) 341,277 with HuPRO2-IgG1.AA (Anti-PD-L1 #2 in FIG. 12; the parental monospecific IgG antibody of BS840), HuGAB11-IgG1.AA (Anti-GITR in FIG. 12) and NS0 cells, (c) 326,577 with BS840 and NS0 cells, (d) 282,554 with NS0/PD-L1 cells, (e) 386,137 with HuPRO2-IgG1.AA, HuGAB11-Ig1.AA and NS0/PD-L1 cells, and (f) 989,407 with BS840 and NS0/PD-L1 cells. Only in the presence of both the bispecific antibody binding to PD-L1 and GITR (BS840) and PD-L1-expressing cells (NS0/PD-L1), the luciferase activity in JD/GITR cells was significantly increased.

Example 22: Bispecific Antibody (BS846) that Binds to PD-L1 and CD40

The mammalian expression vector pBS846, designed for expression of a bispecific antibody that binds to both human PD-L1 (SEQ ID NO:69) and human CD40 (SEQ ID NO:56) has the same structure as pBS809 except that CH3-HuGAB11.scFv (SEQ ID NO:42) is substituted by CH3-HuACS2.scFv (SEQ ID NO:58). The vector pBS846 expresses a bispecific IgG antibody termed BS846 which binds to both human PD-L1 and CD40.

The amino acid sequence of the mature heavy chain encoded in pBS846 is

```
                                        (SEQ ID NO: 121)
QVQLVQSGAEVKKPGSSVKVSCKASGFTFSSSYISWVRQAPGQGLEWIAW

IYAGTGGTSYNQKFTGRATITVDESTSTAYMELSSLRSEDTAVYYCARHE

GVYWYFDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK
```

-continued

```
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGSG
GGGSGGGGSEIVLTQSPATLSLSPGERATLSCSASSSVSYMHWYQQKPGQ
APRRWIYDTSKLASGVPARFSGSGSGTDYTLTISSLEPEDFAVYYCQQWS
SNPLTFGGGTKVEIKGGGGSGGGGSGGGGSQVQLVQSGAEVKKPGSSVKV
SCKASGYTFTSYWLHWVRQAPGQGLEWIGRIDPNSGDTKYNEKFKSRATI
TVDKSTSTAYMELSSLRSEDTAVYYCARYYYGRSYFDYWGQGTTVTVSS
```

The amino acid sequence of the mature light chain encoded in pBS846 is same as that of the light chain sequence encoded in pBS809 (SEQ ID NO:71).

The expression vector pBS846 was stably transfected into CHO-K1 cells as described above. BS846 was purified from culture supernatants of the resulting CHO-K1 stable transfectant with a protein A affinity column as described above. Protein A-purified BS846 showed a single dominant peak of the expected size (approximately 200 kDa) by gel filtration using a Superose 6 size exclusion 10/300 column (GE Healthcare Life Sciences, Pittsburgh, PA). SDS-PAGE analysis under reducing conditions showed only two predominant bands of roughly 75 kD heavy chains and 25 kD light chains.

The biological activity of BS846 to enhance CD40-mediated immune responses was studied using Ramos cells as described above. Ramos cells were incubated for three days in DME media with 10% FBS in the presence of (a) no antibody and NS0 cells, (b) 1 μg/ml of HuPRO1-IgG1.AA (Anti-PD-L1) and NS0 cells, (c) 1 μg/ml of HuACS2-IgG1.AA (Anti-CD40) and NS0 cells, (d) 1 μg/ml of HuPRO1-IgG1.AA, 1 μg/ml of HuACS2-IgG1.AA and NS0 cells, (e) 1 μg/ml of BS846 and NS0 cells, (f) no antibody and NS0/PD-L1 cells, (g) 1 μg/ml of HuPRO1-IgG1.AA and NS0/PD-L1 cells, (h) 1 μg/ml of HuACS2-IgG1.AA and NS0/PD-L1 cells, (i) 1 μg/ml of HuPRO1-IgG1.AA, 1 μg/ml of HuACS2-IgG1.AA and NS0/PD-L1 cells, and (j) 1 μg/ml of BS846 and NS0/PD-L1 cells. Expression of CD95 in Ramos cells was analyzed by flow cytometry using FITC-labeled mouse anti-human CD20 monoclonal antibody (Clone 2H7, BioLegend) to detect Ramos cells and PE-labeled mouse anti-human CD95 antibody (Clone DX2, BioLegend) to monitor CD95 expression.

Figure 13:
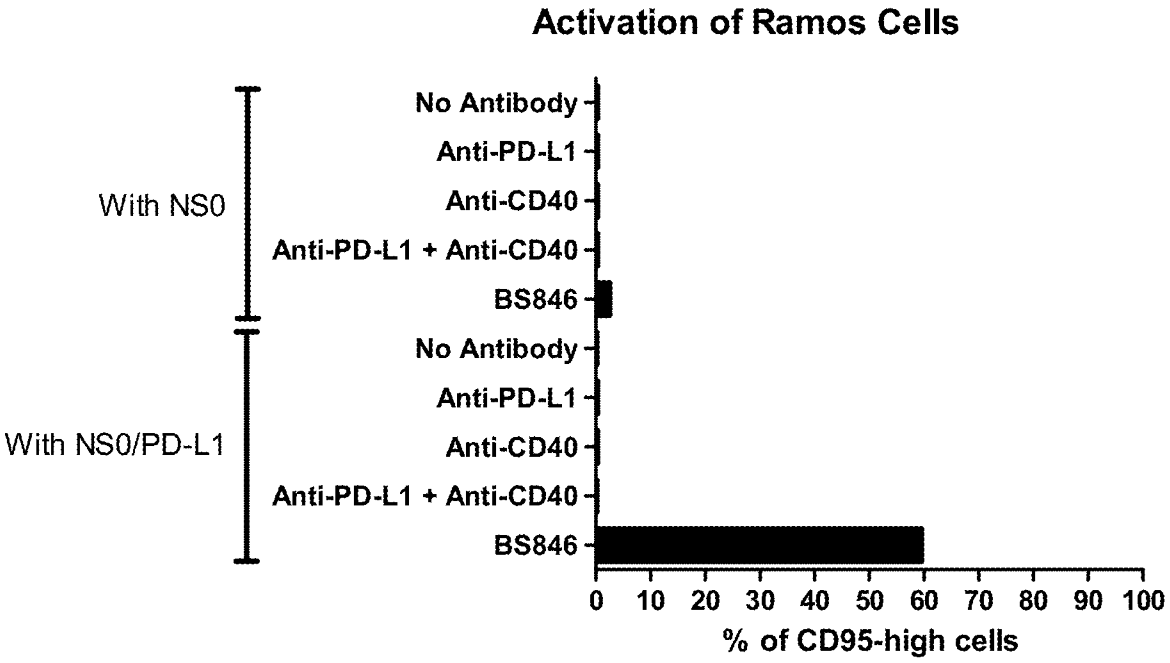
FIG. 13: Activation of Ramos cells with a bispecific antibody binding to PD-L1 and CD40 (BS846).

The percentage of CD95-positive population among CD20-positive Ramos cells was 0.3% with no antibody and NS0 cells (a), 0.3% with 1 μg/ml of HuPRO1-IgG1.AA and NS0 cells (b), 0.3% with 1 μg/ml of HuACS2-IgG1.AA and NS0 cells (c), 0.3% with 1 μg/ml of HuPRO1-IgG1.AA, 1 μg/ml of HuACS2-IgG1.AA and NS0 cells (d), 2.5% with 1 μg/ml of BS846 and NS0 cells (e), 0.2% with no antibody and NS0/PD-L1 cells (f), 0.3% with 1 μg/ml of HuPRO1-IgG1.AA and NS0/PD-L1 cells (g), 0.3% with 1 μg/ml of HuACS2-IgG1.AA and NS0/PD-L1 cells (h), 0.2% with 1 μg/ml of HuPRO1-IgG1.AA, 1 μg/ml of HuACS2-IgG1.AA and NS0/PD-L1 cells (i), and 59.5% with 1 μg/ml of BS846 and NS0/PD-L1 cells (j) (FIG. 13). Only BS846, which can make bridges between Ramos and NS0/PD-L1 cells, was able to significantly increase CD95 expression in Ramos cells, because BS846 can make multimeric cross-linking of CD40 on the surface of Ramos cells at cell-to-cell junctions with NS0/PD-L1 cells and trigger CD40-mediated intracellular signal transduction to upregulate CD95 expression in Ramos cells.

Example 24: Disulfide-Linked Single-Chain Fv

Each of single-chain Fv (scFv) antibodies against OX40 (HuOHX14DS.scFv; SEQ ID NO:22), CD40 (HuACS2.scFv; SEQ ID NO:57) and ICOS (HuTAM14.scFv; SEQ ID NO:117) was modified to stabilize the structure by substituting an amino acid residue at position 44 in VH with a cysteine residue and another amino acid residue at position 100 in VL with a cysteine residue by site-directed mutagenesis (Eu numbering) (Brinkman et al., Proc. Natl. Acad. Sci. 90:7538-7542, 1993).

The amino acid sequence of mature HuOHX14DS.scFv with two cysteine substitutions (HuOHX14DS.scFv.ds) is

```
                                         (SEQ ID NO: 122)
DIQMTQSPSSLSASVGDRVTITCRASQDIRTYLNWYQQKPGKVPKLLIYY
TSRLHSGVPSRFSGSGSGTDYTLTISSLQPEDVATYYCQQGNTLPWTFGC
GTKVEIKGGGGSGGGGSGGGGSQVQLVQSGAEVKKPGSSVKVSCKASGYT
FTSYIMHWVRQAPGQCLEWIGYINPYNSGTKYNEKFKGRVTITSDKSTST
AYMELSSLRSEDTAVYYCAHYYGSTFTMDYWGQGTTVTVSS.
```

The amino acid sequence of mature HuACS2.scFv with two cysteine substitutions (HuACS2.scFv.ds) is

```
                                         (SEQ ID NO: 123)
EIVLTQSPATLSLSPGERATLSCSASSSVSYMHWYQQKPGQAPRRWIYDT
SKLASGVPARFSGSGSGTDYTLTISSLEPEDFAVYYCQQWSSNPLTFGCG
TKVEIKGGGGSGGGGSGGGGSQVQLVQSGAEVKKPGSSVKVSCKASGYTF
TSYWLHWVRQAPGQCLEWIGRIDPNSGDTKYNEKFKSRATITVDKSTSTA
YMELSSLRSEDTAVYYCARYYYGRSYFDYWGQGTTVTVSS.
```

The amino acid sequence of mature HuTAM14.scFv with two cysteine substitutions (HuTAM14.scFv.ds) is

```
                                         (SEQ ID NO: 124)
DIQMTQSPSSLSASVGDRVTITCQASQNIYKYIAWYQQKPGKAPKLLIRY
TSTLESGTPSRFSGSGSGTDYTLTISSLQPEDFATYYCLQYVNLYTFGCG
TKVEIKGGGGSGGGGSGGGGSQVQLQESGPGLVKPSETLSLTCTVSGFSI
SSNSVSWVRQPPGKCLEWMGAIWSGGSTDYNSALKSRVTISRDTSKNQVS
LKLSSVTAADTAVYYCTRWEQPYYFDYWGQGTMVTVSS.
```

The amino acid sequence of mature HuGAB11.scFv with two cysteine substitutions (HuGAB11.scFv.ds), generation of which is described in Example 19, is

```
                                         (SEQ ID NO: 125)
DIQMTQSPSSLSASVGDRVTITCHASQNINVWLSWYQQKPGKVPKLLIYK
ASNLHTGVPSRFSGSGSGTDFTLTISSLQPEDVATYYCQQGQSYPLTFGC
GTKVEIKGGGGSGGGGSGGGGSQVTLKESGPVLVKPTETLTLTCTVSGFS
LTDYGVSWIRQPPGKCLEWLGVIWGGGGTYYNSALKSRLTISKDTSKSQV
VLTMTNMDPVDTATYYCAKHPYGHFGMDYWGQGTTVTVSS.
```

Cysteine substitutions are underlined in the amino acid sequences shown in this Example 24.

Example 25: Construction of Bispecific Antibodies (BS883 and BS884) that Bind to PD-L1 and 4-1BB 4-1BB, also known as CD137 and TNFRSF9, is an immune costimulatory molecule that belongs to the TNF receptor superfamily. Cross-linking of 4-1BB on the cell surface of immune cells is required to initiate intracellular signal transduction to enhance immune responses (Chester et al. 2016 Cancer Immunol. Immunother. 65:1243-1248).

Mouse hybridoma producing an IgG/kappa monoclonal antibody FOB5 that binds specifically to human and cynomolgus 4-1BB was isolated as described in Example 1. As an immunogen, the extracellular region of human 4-1BB fused to the Fc region of the human gamma-1 heavy chain (h4-1BB-Fc; SEQ ID NO:126) was used. Sequencing and humanization of FOB5 VH and VL was carried out as described in Tsurushita et al. (supra).

The amino acid sequence of humanized FOB5 (HuFOB5) VH is MERHWIFLFLFSVTAGVHSQVQLVQSGAEVKKPGSSVKVSCKASGYIFINYWMHWVRAPGQGLEWIGYINPSTGYTESNQKFKDRVTITADKSTSTAYMELSSLRSEDTAVYYCARSYVGYYYAVDYWGQGTTVTVSS (SEQ ID NO:127). The CDR1, 2 and 3 amino acid sequences of HuFOB5 VH are NYWMH (SEQ ID NO:128), YINPSTGYTESNQKFKD (SEQ ID NO:129) and SYVGYYYAVDY (SEQ ID NO:130), respectively, according to the definition by Kabat et al. (supra). A gene encoding HuFOB5 VH was synthesized as an exon including a splice donor signal at the 3' end of the coding region, a SpeI site at the 5' end of the fragment, and a HindIII site at the 3' end of the fragment.

The amino acid sequence of humanized FOB5 (HuFOB5) VL is MDSQAQVLMLLLLWVSGTCGDIVMTQSPDSLAVSLGERATINCKSSQSLLYSNNEKNYLAWYQQKPGQPPKLLIYWASTRESGVPDRFSGSGSGTIFTLTISSLQAEDVAVYYCQQYYSYPYTFGGGTKVEIK (SEQ ID NO:131). The CDR1, 2 and 3 amino acid sequences of HuFOB5 VL are KSSQSLLYSNNEKNYLA (SEQ ID NO:132), WASTRES (SEQ ID NO:133) and QQYYSYPYT (SEQ ID NO:134), respectively, according to the definition by Kabat et al. (supra). A gene encoding HuFOB5 VL was synthesized as an exon including a splice donor signal at the 3' end of the coding region, a NheI site at the 5' end of the fragment, and an EcoRI site at the 3' end of the fragment.

The expression vector pHuFOB5-IgG1.AA has the same structure as pHuM195-IgG1 (FIG. 1A), except that (i) the HuFOB5 VH exon was placed between the SpeI and HindIII sites, (ii) the HuFOB5 VL exon was placed between the NheI and EcoRI sites, and (iii) two leucine residues at positions 234 and 235 (EU numbering of Kabat et al. supra) were substituted to alanine residues in CH2 (L234A and L235A, respectively) (SEQ ID NO:20) for elimination of effector functions (Hezareh et al., *J. Virol.* 75:12161-12168, 2001). The new vector pHuFOB5-IgG1.AA expresses humanized anti-4-1BB IgG1/kappa antibody (HuFOB5-IgG1.AA) in mammalian cells.

The mammalian expression vector, designed for expression of a bispecific antibody that binds to both human PD-L1 (SEQ ID NO:69) and human 4-1BB (SEQ ID NO:135), was constructed by modifying pHuPRO1-IgG1.AA as follows. The VL and VH coding regions of a humanized anti-human 4-1BB monoclonal antibody in pHuFOB5-IgG1.AA were converted to a single-chain Fv (scFv) form in the order of VL, a polypeptide linker and VH from the N- to C-terminus. In addition, a glycine residue at position 44 in HuFOB5 VH was changed to a cysteine residue and a glycine residue at position 100 in HuFOB5 VL was also changed to a cysteine residue to construct a disulfide-linked HuFOB5 scFv (HuFOB5.scFv.LH.ds; SEQ ID NO:136). The N-terminus of HuFOB5.scFv was fused to the penultimate glycine residue in CH3 of pHuPRO1-IgG1.AA with a polypeptide linker separating them (CH3-HuFOB5.scFv.LH.ds; SEQ ID NO:137). The CH3 coding region in pHuPRO1-IgG1.AA was replaced with the coding region of CH3-FOB5.scFv.LH.ds. The resultant vector pBS883 expresses a bispecific IgG antibody termed BS883 which binds to both human PD-L1 and 4-1BB.

The amino acid sequence of the mature heavy chain encoded in pBS883 is

```
                                    (SEQ ID NO: 138)
QVQLVQSGAEVKKPGSSVKVSCKASGFTFSSSYISWVRQAPGQGLEWIAW
IYAGTGGTSYNQKFTGRATITVDESTSTAYMELSSLRSEDTAVYYCARHE
GVYWYFDVWGQGTTVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPEAAGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGSG
GGGSGGGGSDIVMTQSPDSLAVSLGERATINCKSSQSLLYSNNEKNYLAW
YQQKPGQPPKLLIYWASTRESGVPDRFSGSGSGTIFTLTISSLQAEDVAV
YYCQQYYSYPYTFGCGTKVEIKGGGGSGGGGSGGGGSQVQLVQSGAEVKK
PGSSVKVSCKASGYIFINYWMHWVRAPGQCLEWIGYINPSTGYTESNQKF
KDRVTITADKSTSTAYMELSSLRSEDTAVYYCARSYVGYYYAVDYWGQGT
TVTVSS.
```

Cysteine substitutions are underlined.

The amino acid sequence of the mature light chain encoded in pBS883 is same as the mature light chain sequence encoded in pBS809 (SEQ ID NO:71)

Another mammalian expression vector, designed for expression of a bispecific antibody that binds to both human PD-L1 (SEQ ID NO:69) and human 4-1BB (SEQ ID NO:135), was constructed by modifying pHuPRO1-IgG1.AA as follows. The VH and VL coding regions of a humanized anti-human 4-1BB monoclonal antibody in pHuFOB5-IgG1.AA were converted to a scFv form in the order of VH, a polypeptide linker and VL from the N- to C-terminus. In addition, a glycine residue at position 44 in HuFOB5 VH was changed to a cysteine residue and a glycine residue at position 100 in HuFOB5 VL was also changed to a cysteine residue to construct a disulfide-linked HuFOB5 scFv (HuFOB5.scFv.HL.ds; SEQ ID NO:139). The N-terminus of HuFOB5.scFv was fused to the penultimate glycine residue in CH3 of pHuPRO1-IgG1.AA with a polypeptide linker separating them (CH3-FOB5.scFv.HL.ds; SEQ ID NO:140). The CH3 coding region in pHuPRO1-IgG1.AA was replaced with the coding region of CH3-HuFOB5.scFv.HL.ds. The resultant vector pBS884 expresses a bispecific IgG antibody termed BS884 which binds to both human PD-L1 and 4-1BB.

The amino acid sequence of the mature heavy chain encoded in pBS884 is (SEQ ID NO: 141)

QVQLVQSGAEVKKPGSSVKVSCKASGFTFSSSYISWVRQAPGQGLEWIAW

IYAGTGGTSYNQKFTGRATITVDESTSTAYMELSSLRSEDTAVYYCARHE

GVYWYFDVWGQGTTVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGSG

GGGSGGGGSQVQLVQSGAEVKKPGSSVKVSCKASGYIFINYWMHWVRAPG

QCLEWIGYINPSTGYTESNQKFKDRVTITADKSTSTAYMELSSLRSEDTA

VYYCARSYVGYYYAVDYWGQGTTVTVSSGGGGSGGGGSGGGGSDIVMTQS

PDSLAVSLGERATINCKSSQSLLYSNNEKNYLAWYQQKPGQPPKLLIYWA

STRESGVPDRFSGSGSGTIFTLTISSLQAEDVAVYYCQQYYSYPYTFGCG

TKVEIK.

Cysteine substitutions are underlined.

The amino acid sequence of the mature light chain encoded in pBS884 is same as the mature light chain sequence encoded in pBS809 (SEQ ID NO:71)

The schematic structure of the bispecific IgG antibodies of this invention, such as BS883 and BS884, is shown in FIG. 2.

Example 26: Blocking of the Interaction Between PD-L1 and PD-1

The activity of HuPRO1-IgG1.AA, HuPRO2-IgG1.AA and HuPRO5-IgG1.AA to block the interaction of human PD-1 (SEQ ID NO:142) with human PD-L1 was analyzed using NS0/PD-L1 cells and PD-1-Fc fusion proteins by flow cytometry. For the use as a ligand that binds to PD-L1, the extracellular region of human PD-1 was fused to the Fc region of the human gamma-1 heavy chain (hPD-1-Fc; SEQ ID NO:143), expressed in NS0 cells, and purified by protein A affinity chromatography. To monitor the binding to NS0/PD-L1 cells, hPD-1-Fc was labeled with fluorescein isothiocyanate (FITC) using a standard conjugation method. NS0/PD-L1 cells were incubated with a subsaturating concentration of FITC-labeled hPD-1-Fc and various concentrations of a test antibody (HuPRO1-IgG1.AA, HuPRO2-IgG1.AA or HuPRO5-IgG1.AA) in FACS Buffer (PBS containing 0.5% BSA and 0.05% sodium azide) for 60 min at 4° C. After washing with and suspending in FACS Buffer, cells were subjected to flow cytometry analysis. The half-maximal concentration to block the binding of hPD-1-Fc to NS0/PD-L1 cells ($IC_{50}$) was 106 ng/ml for HuPRO1-IgG1.AA, 55 ng/ml for HuPRO2-IgG1.AA, and 87 ng/ml for HuPRO5-IgG1.AA.

SEQUENCE LISTING

Amino acid sequence of human CD33

SEQ ID NO: 1

MPLLLLLPLLWAGALAMDPNFWLQVQESVTVQEGLCVLVPCTFFHPIPYYD

KNSPVHGYWFREGAIISRDSPVATNKLDQEVQEETQGRFRLLGDPSRNNCSLSIVDARRR

DNGSYFFRMERGSTKYSYKSPQLSVHVTDLTHRPKILIPGTLEPGHSKNLTCSVSWACEQ

GTPPIFSWLSAAPTSLGPRTTHSSVLIITPRPQDHGTNLTCQVKFAGAGVTTERTIQLNVT

YVPQNPTTGIFPGDGSGKQETRAGVVHGAIGGAGVTALLALCLCLIFFIVKTHRRKAART

AVGRNDTHPTTGSASPKHQKKSKLHGPTETSSCSGAAPTVEMDEELHYASLNFHGMNP

SKDTSTEYSEVRTQ

Amino acid sequence of HuM195 VH

SEQ ID NO: 2

MGWSWIFFFLLSGTASVLSQVQLVQSGAEVKKPGSSVKVSCKASGYTFTDY

NMHWVRQAPGQGLEWIGYIYPYNGGTGYNQKFKSKATITADESTNTAYMELSSLRSED

TAVYYCARGRPAMDYWGQGTLVTVSS

Amino acid sequence of the CH1 region of
human gamma-1 heavy chain encoded in pHuM195-IgG1

SEQ ID NO: 3

ASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKV

Amino acid sequence of the hinge region (Hinge)
of human gamma-1 heavy chain encoded in pHuM195-IgG1

SEQ ID NO: 4

EPKSCDKTHTCPPCP

-continued

Amino acid sequence of the CH2 region of human gamma-1 heavy chain encoded in pHuM195-IgG1

SEQ ID NO: 5

APELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISKAK

Amino acid sequence of the CH3 region of human gamma-1 heavy chain encoded in pHuM195-IgG1

SEQ ID NO: 6

GQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGK

Amino acid sequence of HuM195 VL

SEQ ID NO: 7

MEKDTLLLWVLLLWVPGSTGDIQMTQSPSSLSASVGDRVTITCRASESVDNY

GISFMNWFQQKPGGAPKLLIYAASNQGSGVPSRFSGSGSGTDFTLTISSLQPDDFATYYC

QQSKEVPWTFGQGTKVEIK

Amino acid sequence of the human kappa constant region encoded in pHuM195-IgG1

SEQ ID NO: 8

RTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

Amino acid sequence of the FLAG peptide

SEQ ID NO: 9

DYKDDDDK

Amino acid sequence of the GPI anchorage signal

SEQ ID NO: 10

PNKGSGTTSGTTRLLSGHTCFTLTGLLGTLVTMGLLT

Amino acid sequence of mature OX40-FLAG-GPI

SEQ ID NO: 11

LHCVGDTYPSNDRCCHECRPGNGMVSRCSRSQNTVCRPCGPGFYNDVVSSK

PCKPCTWCNLRSGSERKQLCTATQDTVCRCRAGTQPLDSYKPGVDCAPCPPGHFSPGD

NQACKPWTNCTLAGKHTLQPASNSSDAICEDRDPPATQPQETQGPPARPITVQPTEAWP

RTSQGPSTRPVEVPGGRATGGGDYKDDDDKGGGPNKGSGTTSGTTRLLSGHTCFTLTG

LLGTLVTMGLLT

Amino acid sequence of HuOHX14DS VH

SEQ ID NO: 12

MGRLTSSELLLIVPAYVLSQVQLVQSGAEVKKPGSSVKVSCKASGYTFTSYIM

HWVRQAPGQGLEWIGYINPYNSGTKYNEKFKGRVTITSDKSTSTAYMELSSLRSEDTAV

YYCAHYYGSTFTMDYWGQGTTVTVSS

Amino acid sequence of CDR1 of HuOHX14DS VH

SEQ ID NO: 13

SYIMH

Amino acid sequence of CDR2 of HuOHX14DS VH

SEQ ID NO: 14

YINPYNSGTKYNEKFKG

Amino acid sequence of CDR3 of HuOHX14DS VH

SEQ ID NO: 15

YYGSTFTMDY

Amino acid sequence of HuOHX14DS VL

SEQ ID NO: 16

MMSSAQFLGLLLLCFQGTRCDIQMTQSPSSLSASVGDRVTITCRASQDIRTYL

NWYQQKPGKVPKLLIYYTSRLHSGVPSRFSGSGSGTDYTLTISSLQPEDVATYYCQQGN

TLPWTFGGGTKVEIK

Amino acid sequence of CDR1 of HuOHX14DS VL

SEQ ID NO: 17

RASQDIRTYLN

-continued

Amino acid sequence of CDR2 of HuOHX14DS VL

SEQ ID NO: 18

YTSRLHS

Amino acid sequence of CDR3 of HuOHX14DS VL

SEQ ID NO: 19

QQGNTLPWT

Amino acid sequence of the CH2 region having L234A and L235 mutations

SEQ ID NO: 20

APEAAGGPSVFLEPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISKAK

Amino acid sequence of human OX40

SEQ ID NO: 21

MCVGARRLGRGPCAALLLLGLGLSTVTGLHCVGDTYPSNDRCCHECRPGNG

MVSRCSRSQNTVCRPCGPGFYNDVVSSKPCKPCTWCNLRSGSERKQLCTATQDTVCRC

RAGTQPLDSYKPGVDCAPCPPGHFSPGDNQACKPWTNCTLAGKHTLQPASNSSDAICED

RDPPATQPQETQGPPARPITVQPTEAWPRTSQGPSTRPVEVPGGRAVAAILGLGLVLGLL

GPLAILLALYLLRRDQRLPPDAHKPPGGGSFRTPIQEEQADAHSTLAKI

Amino acid sequence of HuOHX14DS.scFv

SEQ ID NO: 22

DIQMTQSPSSLSASVGDRVTITCRASQDIRTYLNWYQQKPGKVPKLLIYYTSR

LHSGVPSRFSGSGSGTDYTLTISSLQPEDVATYYCQQGNTLPWTFGGGTKVEIKGGGGS

GGGGSGGGGSQVQLVQSGAEVKKPGSSVKVSCKASGYTFTSYIMHWVRQAPGQGLEW

IGYINPYNSGTKYNEKFKGRVTITSDKSTSTAYMELSSLRSEDTAVYYCAHYYGSTFTM

DYWGQGTTVTVSS

Amino acid sequence of the fusion of CH3 to HuOHX14DS.scFv (CH3-HuOHX14DS.scFv) encoded in pBS824

SEQ ID NO: 23

GQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGSGGG

GSGGGGSDIQMTQSPSSLSASVGDRVTITCRASQDIRTYLNWYQQKPGKVPKLLIYYTSR

LHSGVPSRFSGSGSGTDYTLTISSLQPEDVATYYCQQGNTLPWTFGGGTKVEIKGGGGS

GGGGSGGGGSQVQLVQSGAEVKKPGSSVKVSCKASGYTFTSYIMHWVRQAPGQGLEW

IGYINPYNSGTKYNEKFKGRVTITSDKSTSTAYMELSSLRSEDTAVYYCAHYYGSTFTM

DYWGQGTTVTVSS

Amino acid sequence of the mature heavy chain encoded in pBS824

SEQ ID NO: 24

QVQLVQSGAEVKKPGSSVKVSCKASGYTFTDYNMHWVRQAPGQGLEWIGY

IYPYNGGTGYNQKFKSKATITADESTNTAYMELSSLRSEDTAVYYCARGRPAMDYWGQ

GTLVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPKSCDKTHTCPPC

PAPEAAGGPSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPVLDSDGSFFL

YSKLTVDKSRWQQGNVFSCSVMHEALHNHYTQKSLSLSPGSGGGGSGGGGSDIQMTQS

PSSLSASVGDRVTITCRASQDIRTYLNWYQQKPGKVPKLLIYYTSRLHSGVPSRFSGSGS

-continued

GTDYTLTISSLQPEDVATYYCQQGNTLPWTFGGGTKVEIKGGGGSGGGGSGGGGSQVQ

LVQSGAEVKKPGSSVKVSCKASGYTFTSYIMHWVRQAPGQGLEWIGYINPYNSGTKYN

EKFKGRVTITSDKSTSTAYMELSSLRSEDTAVYYCAHYYGSTFTMDYWGQGTTVTVSS

Amino acid sequence of the mature light chain encoded in pBS824

SEQ ID NO: 25

DIQMTQSPSSLSASVGDRVTITCRASESVDNYGISFMNWFQQKPGGAPKLLIY

AASNQGSGVPSRFSGSGSGTDFTLTISSLQPDDFATYYCQQSKEVPWTFGQGTKVEIKRT

VAAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

Amino acid sequence of the synthetic signal peptide

SEQ ID NO: 26

MGWSWIFFFLLSGTASVLS

Amino acid sequence of the extracellular region of human CD33 encoded in pFCm267

SEQ ID NO: 27

MDPNFWLQVQESVTVQEGLCVLVPCTFFHPIPYYDKNSPVHGYWFREGAIIS

RDSPVATNKLDQEVQEETQGRFRLLGDPSRNNCSLSIVDARRRDNGSYFFRMERGSTKY

SYKSPQLSVHVTDLTHRPKILIPGTLEPGHSKNLTCSVSWACEQGTPPIFSWLSAAPTSLG

PRTTHSSVLIITPRPQDHGTNLTCQVKFAGAGVTTERTIQLNVTYVPQNPTTGIFPGDGSG

KQETRAGVVH

Amino acid sequence of human epidermal growth factor receptor (EGFR)

SEQ ID NO: 28

MRPSGTAGAALLALLAALCPASRALEEKKVCQGTSNKLTQLGTFEDHFLSLQ

RMFNNCEVVLGNLEITYVQRNYDLSFLKTIQEVAGYVLIALNTVERIPLENLQIIRGNMY

YENSYALAVLSNYDANKTGLKELPMRNLQEILHGAVRFSNNPALCNVESIQWRDIVSSD

FLSNMSMDFQNHLGSCQKCDPSCPNGSCWGAGEENCQKLTKIICAQQCSGRCRGKSPS

DCCHNQCAAGCTGPRESDCLVCRKFRDEATCKDTCPPLMLYNPTTYQMDVNPEGKYSF

GATCVKKCPRNYVVTDHGSCVRACGADSYEMEEDGVRKCKKCEGPCRKVCNGIGIGE

FKDSLSINATNIKHFKNCTSISGDLHILPVAFRGDSFTHTPPLDPQELDILKTVKEITGFLLI

QAWPENRTDLHAFENLEIIRGRTKQHGQFSLAVVSLNITSLGLRSLKEISDGDVIISGNKN

LCYANTINWKKLFGTSGQKTKIISNRGENSCKATGQVCHALCSPEGCWGPEPRDCVSCR

NVSRGRECVDKCNLLEGEPREFVENSECIQCHPECLPQAMNITCTGRGPDNCIQCAHYID

GPHCVKTCPAGVMGENNTLVWKYADAGHVCHLCHPNCTYGCTGPGLEGCPTNGPKIP

SIATGMVGALLLLLVVALGIGLFMRRRHIVRKRTLRRLLQERELVEPLTPSGEAPNQALL

RILKETEFKKIKVLGSGAFGTVYKGLWIPEGEKVKIPVAIKELREATSPKANKEILDEAYV

MASVDNPHVCRLLGICLTSTVQLITQLMPFGCLLDYVREHKDNIGSQYLLNWCVQIAKG

MNYLEDRRLVHRDLAARNVLVKTPQHVKITDFGLAKLLGAEEKEYHAEGGKVPIKWM

ALESILHRIYTHQSDVWSYGVTVWELMTFGSKPYDGIPASEISSILEKGERLPQPPICTIDV

YMIMVKCWMIDADSRPKFRELIIEFSKMARDPQRYLVIQGDERMHLPSPTDSNFYRALM

DEEDMDDVVDADEYLIPQQGFFSSPSTSRTPLLSSLSATSNNSTVACIDRNGLQSCPIKED

SFLQRYSSDPTGALTEDSIDDTFLPVPEYINQSVPKRPAGSVQNPVYHNQPLNPAPSRDPH

YQDPHSTAVGNPEYLNTVQPTCVNSTFDSPAHWAQKGSHQISLDNPDYQQDFFPKEAK

PNGIFKGSTAENAEYLRVAPQSSEFIGA

-continued

Amino acid sequence of mouse 225 (Ch225) VH
SEQ ID NO: 29
MAVLALLFCLVTFPSCVLSQVQLKQSGPGLVQPSQSLSITCTVSGFSLTNYGV
HWVRQSPGKGLEWLGVIWSGGNTDYNTPFTSRLSINKDNSKSQVFFKMNSLQSNDTAI
YYCARALTYYDYEFAYWGQGTLVTVSA Amino acid sequence of mouse 225 (Ch225) VL
SEQ ID NO: 30
MRAPAQFLGFLLFWIPASRSDILLTQSPVILSVSPGERVSFSCRASQSIGTNIHW
YQQRTNGSPRLLIKYASESISGIPSRFSGSGSGTDFTLSINSVESEDIADYYCQQNNNWPTT
FGAGTKLELK Amino acid sequence of hGITR-Fc
SEQ ID NO: 31
QRPTGGPGCGPGRLLLGTGTDARCCRVHTTRCCRDYPGEECCSEWDCMCVQ
PEFHCGDPCCTTCRHHPCPPGQGVQSQGKFSFGFQCIDCASGTFSGGHEGHCKPWTDCT
QFGFLTVFPGNKTHNAVCVPGSPPAEPLGTGGGEPKSCDKTHTCPPCPAPELLGGPSVFL
FPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQ
QGNVFSCSVMHEALHNHYTQKSLSLSPGK Amino acid sequence of HuGAB11 VH
SEQ ID NO: 32
MAVLGLLLCLVTFPSCVLSQVTLKESGPVLVKPTETLTLTCTVSGFSLTDYGV
SWIRQPPGKALEWLGVIWGGGGTYYNSALKSRLTISKDTSKSQVVLTMTNMDPVDTAT
YYCAKHPYGHFGMDYWGQGTTVTVSS Amino acid sequence of CDR1 of HuGAB11 VH
SEQ ID NO: 33
DYGVS Amino acid sequence of CDR2 of HuGAB11 VH
SEQ ID NO: 34
VIWGGGGTYYNSALKS Amino acid sequence of CDR3 of HuGAB11 VH
SEQ ID NO: 35
HPYGHFGMDY Amino acid sequence of HuGAB11 VL
SEQ ID NO: 36
MRVLAELLGLLLFCFLGVRCDIQMTQSPSSLSASVGDRVTITCHASQNINVWL
SWYQQKPGKVPKLLIYKASNLHTGVPSRFSGSGSGTDFTLTISSLQPEDVATYYCQQGQS
YPLTFGGGTKVEIK Amino acid sequence of CDR1 of HuGAB11 VL
SEQ ID NO: 37
HASQNINVWLS Amino acid sequence of CDR2 of HuGAB11 VL
SEQ ID NO: 38
KASNLHT Amino acid sequence of CDR3 of HuGAB11 VL
SEQ ID NO: 39
QQGQSYPLT Amino acid sequence of human GITR
SEQ ID NO: 40
MAQHGAMGAFRALCGLALLCALSLGQRPTGGPGCGPGRLLLGTGTDARCCR
VHTTRCCRDYPGEECCSEWDCMCVQPEFHCGDPCCTTCRHHPCPPGQGVQSQGKFSFG
FQCIDCASGTFSGGHEGHCKPWTDCTQFGFLTVFPGNKTHNAVCVPGSPPAEPLGWLTV -continued

VLLAVAACVLLLTSAQLGLHIWQLRSQCMWPRETQLLLEVPPSTEDARSCQFPEEERGE

RSAEEKGRLGDLWV

Amino acid sequence of HuGAB11.scFv

SEQ ID NO: 41

DIQMTQSPSSLSASVGDRVTITCHASQNINVWLSWYQQKPGKVPKLLIYKAS

NLHTGVPSRFSGSGSGTDFTLTISSLQPEDVATYYCQQGQSYPLTFGGGTKVEIKGGGGS

GGGGSGGGGSQVTLKESGPVLVKPTETLTLTCTVSGFSLTDYGVSWIRQPPGKALEWLG

VIWGGGGTYYNSALKSRLTISKDTSKSQVVLTMTNMDPVDTATYYCAKHPYGHFGMD

YWGQGTTVTVSS

Amino acid sequence of the fusion of CH3 to HuGAB11.scFv (CH3-HuGAB11.scFv) encoded in pBS827

SEQ ID NO: 42

GQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGSGGG

GSGGGGSDIQMTQSPSSLSASVGDRVTITCHASQNINVWLSWYQQKPGKVPKLLIYKAS

NLHTGVPSRFSGSGSGTDFTLTISSLQPEDVATYYCQQGQSYPLTFGGGTKVEIKGGGGS

GGGGSGGGGSQVTLKESGPVLVKPTETLTLTCTVSGFSLTDYGVSWIRQPPGKALEWLG

VIWGGGGTYYNSALKSRLTISKDTSKSQVVLTMTNMDPVDTATYYCAKHPYGHFGMD

YWGQGTTVTVSS

Amino acid sequence of the mature heavy chain encoded in pBS827

SEQ ID NO: 43

QVQLKQSGPGLVQPSQSLSITCTVSGFSLTNYGVHWVRQSPGKGLEWLGVIW

SGGNTDYNTPFTSRLSINKDNSKSQVFFKMNSLQSNDTAIYYCARALTYYDYEFAYWG

QGTLVTVSAASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSDIQMT

QSPSSLSASVGDRVTITCHASQNINVWLSWYQQKPGKVPKLLIYKASNLHTGVPSRFSGS

GSGTDFTLTISSLQPEDVATYYCQQGQSYPLTFGGGTKVEIKGGGGSGGGGSGGGGSQV

TLKESGPVLVKPTETLTLTCTVSGFSLTDYGVSWIRQPPGKALEWLGVIWGGGGTYYNS

ALKSRLTISKDTSKSQVVLTMTNMDPVDTATYYCAKHPYGHFGMDYWGQGTTVTVSS

Amino acid sequence of the mature light chain encoded in pBS827

SEQ ID NO: 44

DILLTQSPVILSVSPGERVSFSCRASQSIGTNIHWYQQRTNGSPRLLIKYASESIS

GIPSRFSGSGSGTDFTLSINSVESEDIADYYCQQNNNWPTTFGAGTKLELKRTVAAPSVFI

FPPSDEQLKSGTASVVCLLNNFYPREAKVQWKVDNALQSGNSQESVTEQDSKDSTYSLS

STLTLSKADYEKHKVYACEVTHQGLSSPVTKSFNRGEC

Amino acid sequence of mature human GITR

SEQ ID NO: 45

QRPTGGPGCGPGRLLLGTGTDARCCRVHTTRCCRDYPGEECCSEWDCMCVQ

PEFHCGDPCCTTCRHHPCPPGQGVQSQGKFSFGFQCIDCASGTFSGGHEGHCKPWTDCT

QFGFLTVFPGNKTHNAVCVPGSPPAEPLGWLTVVLLAVAACVLLLTSAQLGLHIWQLRS

QCMWPRETQLLLEVPPSTEDARSCQFPEEERGERSAEEKGRLGDLWV

-continued

Amino acid sequence of the extracellular region of human EGFR encoded in pFCm507

SEQ ID NO: 46

LEEKKVCQGTSNKLTQLGTFEDHFLSLQRMFNNCEVVLGNLEITYVQRNYDL

SFLKTIQEVAGYVLIALNTVERIPLENLQIIRGNMYYENSYALAVLSNYDANKTGLKELP

MRNLQEILHGAVRFSNNPALCNVESIQWRDIVSSDFLSNMSMDFQNHLGSCQKCDPSCP

NGSCWGAGEENCQKLTKIICAQQCSGRCRGKSPSDCCHNQCAAGCTGPRESDCLVCRK

FRDEATCKDTCPPLMLYNPTTYQMDVNPEGKYSFGATCVKKCPRNYVVTDHGSCVRA

CGADSYEMEEDGVRKCKKCEGPCRKVCNGIGIGEFKDSLSINATNIKHFKNCTSISGDLH

ILPVAFRGDSFTHTPPLDPQELDILKTVKEITGFLLIQAWPENRTDLHAFENLEIIRGRTKQ

HGQFSLAVVSLNITSLGLRSLKEISDGDVIISGNKNLCYANTINWKKLFGTSGQKTKIISN

RGENSCKATGQVCHALCSPEGCWGPEPRDCVSCRNVSRGRECVDKCNLLEGEPREFVE

NSECIQCHPECLPQAMNITCTGRGPDNCIQCAHYIDGPHCVKTCPAGVMGENNTLVWK

YADAGHVCHLCHPNC TYGCTGPGLEGCPTNGPKIPS

Amino acid sequence of hCD40-Fc

SEQ ID NO: 47

EPPTACREKQYLINSQCCSLCQPGQKLVSDCTEFTETECLPCGESEFLDTWNR

ETHCHQHKYCDPNLGLRVQQKGTSETDTICTCEEGWHCTSEACESCVLHRSCSPGFGVK

QIATGVSDTICEPCPVGFFSNVSSAFEKCHPWTSCETKDLVVQQAGTNKTDVVCGPQDR

LRTGGGEPKSCDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPSDIAVEWESNG

QPENNYKTTPPVLDSDGSFFLYSKLTVDKSRWQQGNVFSCSVMHEALHNHYTQKSLSL

SPGK

Amino acid sequence of HuACS2 VH

SEQ ID NO: 48

MKLWLNWVFLLTLLHGIQCQVQLVQSGAEVKKPGSSVKVSCKASGYTFTSY

WLHWVRQAPGQGLEWIGRIDPNSGDTKYNEKFKSRATITVDKSTSTAYMELSSLRSEDT

AVYYCARYYYGRSYFDYWGQGTTVTVSS

Amino acid sequence of CDR1 of HuACS2 VH

SEQ ID NO: 49

SYWLH

Amino acid sequence of CDR2 of HuACS2 VH

SEQ ID NO: 50

RIDPNSGDTKYNEKFKS

Amino acid sequence of CDR3 of HuACS2 VH

SEQ ID NO: 51

YYYGRSYFDY

Amino acid sequence of HuACS2VL

SEQ ID NO: 52

MDFQVQIFSFLLISAVIISRGEIVLTQSPATLSLSPGERATLSCSASSSVSYMHW

YQQKPGQAPRRWIYDTSKLASGVPARFSGSGSGTDYTLTISSLEPEDFAVYYCQQWSSN

PLTFGGGTKVEIK

Amino acid sequence of CDR1 of HuACS2 VL

SEQ ID NO: 53

SASSSVSYMH

Amino acid sequence of CDR2 of HuACS2 VL

SEQ ID NO: 54

DTSKLAS

-continued

Amino acid sequence of CDR3 of HuACS2 VL

SEQ ID NO: 55

QQWSSNPLT

Amino acid sequence of human CD40

SEQ ID NO: 56

MVRLPLQCVLWGCLLTAVHPEPPTACREKQYLINSQCCSLCQPGQKLVSDCT

EFTETECLPCGESEFLDTWNRETHCHQHKYCDPNLGLRVQQKGTSETDTICTCEEGWHC

TSEACESCVLHRSCSPGFGVKQIATGVSDTICEPCPVGFFSNVSSAFEKCHPWTSCETKDL

VVQQAGTNKTDVVCGPQDRLRALVVIPIIFGILFAILLVLVFIKKVAKKPTNKAPHPKQEP

QEINFPDDLPGSNTAAPVQETLHGCQPVTQEDGKESRISVQERQ

Amino acid sequence of HuACS2.scFv

SEQ ID NO: 57

EIVLTQSPATLSLSPGERATLSCSASSSVSYMHWYQQKPGQAPRRWIYDTSKL

ASGVPARFSGSGSGTDYTLTISSLEPEDFAVYYCQQWSSNPLTFGGGTKVEIKGGGGSGG

GGSGGGGSQVQLVQSGAEVKKPGSSVKVSCKASGYTFTSYWLHWVRQAPGQGLEWIG

RIDPNSGDTKYNEKFKSRATITVDKSTSTAYMELSSLRSEDTAVYYCARYYYGRSYFDY

WGQGTTVTVSS

Amino acid sequence of the fusion of CH3 to HuACS2.scFv (CH3-HuACS2.scFv) encoded in pBS828

SEQ ID NO: 58

GQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGSGGG

GSGGGGSEIVLTQSPATLSLSPGERATLSCSASSSVSYMHWYQQKPGQAPRRWIYDTSK

LASGVPARFSGSGSGTDYTLTISSLEPEDFAVYYCQQWSSNPLTFGGGTKVEIKGGGGSG

GGGSGGGGSQVQLVQSGAEVKKPGSSVKVSCKASGYTFTSYWLHWVRQAPGQGLEWI

GRIDPNSGDTKYNEKFKSRATITVDKSTSTAYMELSSLRSEDTAVYYCARYYYGRSYFD

YWGQGTTVTVSS

Amino acid sequence of the mature heavy chain encoded in pBS828

SEQ ID NO: 59

QVQLVQSGAEVKKPGSSVKVSCKASGYTFTDYNMHWVRQAPGQGLEWIGY

IYPYNGGTGYNQKFKSKATITADESTNTAYMELSSLRSEDTAVYYCARGRPAMDYWGQ

GTLVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKKVEPKSCDKTHTCPPC

PAPEAAGGPSVFLFPPKPKDTLMISRTPEVTCVVVDVSHEDPEVKFNWYVDGVEVHNA

KTKPREEQYNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPVLDSDGSFFL

YSKLTVDKSRWQQGNVFSCSVMHEALHNHYTQKSLSLSPGSGGGGSGGGGSEIVLTQS

PATLSLSPGERATLSCSASSSVSYMHWYQQKPGQAPRRWIYDTSKLASGVPARFSGSGS

GTDYTLTISSLEPEDFAVYYCQQWSSNPLTFGGGTKVEIKGGGGSGGGGSGGGGSQVQL

VQSGAEVKKPGSSVKVSCKASGYTFTSYWLHWVRQAPGQGLEWIGRIDPNSGDTKYNE

KFKSRATITVDKSTSTAYMELSSLRSEDTAVYYCARYYYGRSYFDYWGQGTTVTVSS

Amino acid sequence of hPD-L1-Fc

SEQ ID NO: 60

FTVTVPKDLYVVEYGSNMTIECKFPVEKQLDLAALIVYWEMEDKNIIQFVHG

EEDLKVQHSSYRQRARLLKDQLSLGNAALQITDVKLQDAGVYRCMISYGGADYKRITV

KVNAPYNKINQRILVVDPVTSEHELTCQAEGYPKAEVIWTSSDHQVLSGKTTTTNSKRE

-continued

EKLFNVTSTLRINTTTNEIFYCTFRRLDPEENHTAELVIPELPLAHPPNERTHTGGGEPKSC

DKTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPGK

Amino acid sequence of HuPRO1 VH

SEQ ID NO: 61

MEWNWVVLFLLSLTAGVYAQVQLVQSGAEVKKPGSSVKVSCKASGFTFSSS

YISWVRQAPGQGLEWIAWIYAGTGGTSYNQKFTGRATITVDESTSTAYMELSSLRSEDT

AVYYCARHEGVYWYFDVWGQGTTVTVSS

Amino acid sequence of CDR1 of HuPRO1 VH

SEQ ID NO: 62

SSYIS

Amino acid sequence of CDR2 of HuPRO1 VH

SEQ ID NO: 63

WIYAGTGGTSYNQKFTG

Amino acid sequence of CDR3 of HuPRO1 VH

SEQ ID NO: 64

HEGVYWYFDV

Amino acid sequence of HuPRO1 VL

SEQ ID NO: 65

MDFQVQIFSFLLISAVIMSRGEIVLTQSPATLSLSPGERATLSCSASSSVSYMH

WYQQKPGQAPRPWIYDTSNLASGFPARFSGSGSGTDFTLTISSLEPEDFAVYYCHQRSSY

PWTFGGGTKVEIK

Amino acid sequence of CDR1 of HuPRO1 VL

SEQ ID NO: 66

SASSSVSYMH

Amino acid sequence of CDR2 of HuPRO1 VL

SEQ ID NO: 67

DTSNLAS

Amino acid sequence of CDR3 of HuPRO1 VL

SEQ ID NO: 68

HQRSSYPWT

Amino acid sequence of human PD-L1

SEQ ID NO: 69

MRIFAVFIFMTWHLLNAFTVTVPKDLYVVEYGSNMTIECKFPVEKQLDLAA

LIVWEMEDKNIIQFVHGEEDLKVQHSSYRQRARLLKDQLSLGNAALQITDVKLQDAG

VYRCMISYGGADYKRITVKVNAPYNKINQRILVVDPVTSEHELTCQAEGYPKAEVIWTS

SDHQVLSGKTTTTNSKREEKLFNVTSTLRINTTTNEIFYCTFRRLDPEENHTAELVIPELPL

AHPPNERTHLVILGAILLCLGVALTFIFRLRKGRMMDVKKCGIQDTNSKKQSDTHLEET

Amino acid sequence of mature heavy chain
encoded in pBS809

SEQ ID NO: 70

QVQLVQSGAEVKKPGSSVKVSCKASGFTFSSSYISWVRQAPGQGLEWIAWIY

AGTGGTSYNQKFTGRATITVDESTSTAYMELSSLRSEDTAVYYCARHEGVYWYFDVWG

QGTTVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSDIQMT

-continued

QSPSSLSASVGDRVTITCHASQNINVWLSWYQQKPGKVPKLLIYKASNLHTGVPSRFSGS

GSGTDFTLTISSLQPEDVATYYCQQGQSYPLTFGGGTKVEIKGGGGSGGGGSGGGGSQV

TLKESGPVLVKPTETLTLTCTVSGFSLTDYGVSWIRQPPGKALEWLGVIWGGGGTYYNS

ALKSRLTISKDTSKSQVVLTMTNMDPVDTATYYCAKHPYGHFGMDYWGQGTTVTVSS

Amino acid sequence of mature light chain encoded in pBS809 and pBS813

SEQ ID NO: 71

EIVLTQSPATLSLSPGERATLSCSASSSVSYMHWYQQKPGQAPRPWIYDTSNL

ASGFPARFSGSGSGTDFTLTISSLEPEDFAVYYCHQRSSYPWTFGGGTKVEIKRTVAAPS

VFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

Amino acid sequence of mature heavy chain encoded in pBS813

SEQ ID NO: 72

QVQLVQSGAEVKKPGSSVKVSCKASGFTFSSSYISWVRQAPGQGLEWIAWIY

AGTGGTSYNQKFTGRATITVDESTSTAYMELSSLRSEDTAVYYCARHEGVYWYFDVWG

QGTTVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSDIQMT

QSPSSLSASVGDRVTITCRASQDIRTYLNWYQQKPGKVPKLLIYYTSRLHSGVPSRFSGS

GSGTDYTLTISSLQPEDVATYYCQQGNTLPWTFGGGTKVEIKGGGGSGGGGSGGGGSQ

VQLVQSGAEVKKPGSSVKVSCKASGYTFTSYIMHWVRQAPGQGLEWIGYINPYNSGTK

YNEKFKGRVTITSDKSTSTAYMELSSLRSEDTAVYYCAHYYGSTFTMDYWGQGTTVTV

SS

Amino acid sequence of the extracellular region of humanPD-L1

SEQ ID NO: 73

FTVTVPKDLYVVEYGSNMTIECKFPVEKQLDLAALIVYWEMEDKNIIQFVHG

EEDLKVQHSSYRQRARLLKDQLSLGNAALQITDVKLQDAGVYRCMISYGGADYKRITV

KVNAPYNKINQRILVVDPVTSEHELTCQAEGYPKAEVIWTSSDHQVLSGKTTTTNSKRE

EKLFNVTSTLRINTTTNEIFYCTFRRLDPEENHTAELVIPELPLAHPPNERTH

Amino acid sequence of HuPRO2 VH

SEQ ID NO: 74

MGWNWIFLFLSGTAGVHCQVQLVQSGAEVKKPGSSVKVSCKASGYTFTSYG

INWVRQAPGQGLEWIGYIYPGSGGPVYNQKFKGRVTLTADKSTSTAYMELSSLRSEDTA

VYYCARENYRYWYFDVWGQGTTVTVSS

Amino acid sequence of CDR1 of HuPRO2 VH

SEQ ID NO: 75

SYGIN

Amino acid sequence of CDR2 of HuPRO2 VH

SEQ ID NO: 76

YIYPGSGGPVYNQKFKG

Amino acid sequence of CDR3 of HuPRO2 VH

SEQ ID NO: 77

ENYRYWYFDV

-continued

Amino acid sequence of HuPRO2VL

SEQ ID NO: 78

MHFQVQIFSFLLISASVIMSRGDIQLTQSPSFLSASVGDRVTITCSASSSVNYM

HWFQQKPGKAPKLWIYSTSNLASGVPSRFSGSGSGTEFTLTISSLQPEDFATYYCQQRSS

YPLTFGGGTKVEIK

Amino acid sequence of CDR1 of HuPRO2 VL

SEQ ID NO: 79

SASSSVNYMH

Amino acid sequence of CDR2 of HuPRO2 VL

SEQ ID NO: 80

STSNLAS

Amino acid sequence of CDR3 of HuPRO2 VL

SEQ ID NO: 81

QQRSSYPLT

Amino acid sequence of mature heavy chain encoded in pBS841

SEQ ID NO: 82

QVQLVQSGAEVKKPGSSVKVSCKASGYTFTSYGINWVRQAPGQGLEWIGYI

YPGSGGPVYNQKFKGRVTITADKSTSTAYMELSSLRSEDTAVYYCARENYRWYFDV

WGQGTTVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTH

TCPPCPAPEAAGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGSGGGGSGGGGSD

IQMTQSPSSLSASVGDRVTITCRASQDIRTYLNWYQQKPGKVPKLLIYYTSRLHSGVPSR

FSGSGSGTDYTLTISSLQPEDVATYYCQQGNTLPWTFGGGTKVEIKGGGGSGGGGSGGG

GSQVQLVQSGAEVKKPGSSVKVSCKASGYTFTSYWIHWVRQAPGQGLEWIGYINPYNS

GTKYNEKFKGRVTITSDKSTSTAYMELSSLRSEDTAVYYCAHYYGSTFTMDWGQGTT

VTVSS

Amino acid sequence of mature light chain encoded in pBS841

SEQ ID NO: 83

DIQLTQSPSFLSASVGDRVTITCSASSSVNYMHWFQQKPGKAPKLWIYSTSNL

ASGVPSRFSGSGSGTEFTLTISSLQPEDFATYYCQQRSSYPLTFGGGTKVEIKRTVAAPSV

FIFPPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC

Amino acid sequence of HuPRO5 VH

SEQ ID NO: 84

MMVLSLLYLLTALPGILSQVQLQESGPGLVKPSQTLSLTCTVSGDSISSGYWNWIRQPPG

KGLEYMGYISYTGSTYSNPSLKSRVTISRDTSKNQFSLKLSSVTAADTAVYYCARSQNW

ERAWFAYWGQGTLVTVSS

Amino acid sequence of CDR1 of HuPRO5 VH

SEQ ID NO: 85

SGYWN

Amino acid sequence of CDR2 of HuPRO5 VH

SEQ ID NO: 86

YISYTGSTYSNPSLKS

Amino acid sequence of CDR3 of HuPRO5 VH

SEQ ID NO: 87

SQNWERAWFAY

-continued

Amino acid sequence of HuPRO5 VL

SEQ ID NO: 88

MDFQVQIFSFLLISASVIMSRGDIQMTQSPSSLSASVGDRVTITCSASSSVSYM

HWYQQKPGKAPKLWIYDTSKLASGVPSRFSGSGSGTDFTLTISSLQPEDFATYYCFQGSG

YPFTFGGGTKVEIK

Amino acid sequence of CDR1 of HuPRO5 VL

SEQ ID NO: 89

SASSSVSYMH

Amino acid sequence of CDR2 of HuPRO5 VL

SEQ ID NO: 90

DTSKLAS

Amino acid sequence of CDR3 of HuPRO5 VL

SEQ ID NO: 91

FQGSGYPFT

Amino acid sequence of mature heavy chain encoded in pBS839

SEQ ID NO: 92

QVQLQESGPGLVKPSQTLSLTCTVSGDSISSGYWNWIRQPPGKGLEYMGYIS

YTGSTYSNPSLKSRVTISRDTSKNQFSLKLSSVTAADTAVYYCARSQNWERAWFAYWG

QGTLVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSDIQMT

QSPSSLSASVGDRVTITCRASQDIRTYLNWYQQKPGKVPKLLIYYTSRLHSGVPSRFSGS

GSGTDYTLTISSLQPEDVATYYCQQGNTLPWTFGGGTKVEIKGGGGSGGGGSGGGGSQ

VQLVQSGAEVKKPGSSVKVSCKASGYTFTSYWIHWVRQAPGQGLEWIGYINPYNSGTK

YNEKFKGRVTITSDKSTSTAYMELSSLRSEDTAVYYCAHYYGSTFTMDYWGQGTTVTV

SS

Amino acid sequence of mature light chain encoded in pBS839

SEQ ID NO: 93

DIQMTQSPSSLSASVGDRVTITCSASSSVSYMHWYQQKPGKAPKLWIYDTSK

LASGVPSRFSGSGSGTDFTLTISSLQPEDFATYYCFQGSGYPFTFGGGTKVEIKRTVAAPS

VFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

Amino acid sequence of CDR1 of HuM195 VH

SEQ ID NO: 94

DYNMH

Amino acid sequence of CDR2 of HuM195 VH

SEQ ID NO: 95

YIYPYNGGTGYNQKFKS

Amino acid sequence of CDR3 of HuM195 VH

SEQ ID NO: 96

GRPAMDY

Amino acid sequence of CDR1 of HuM195 VL

SEQ ID NO: 97

RASESVDNYGISFMN

Amino acid sequence of CDR2 of HuM195 VL

SEQ ID NO: 98

AASNQGS

-continued

Amino acid sequence of CDR3 of HuM195 VL

SEQ ID NO: 99

QQSKEVPWT

Amino acid sequence of CDR1 of Ch225 VH

SEQ ID NO: 100

NYGVH

Amino acid sequence of CDR2 of Ch225 VH

SEQ ID NO: 101

VIWSGGNTDYNTPFTS

Amino acid sequence of CDR3 of Ch225 VH

SEQ ID NO: 102

ALTYYDYEFAY

Amino acid sequence of CDR1 of Ch225 VL

SEQ ID NO: 103

RASQSIGTNIH

Amino acid sequence of CDR2 of Ch225 VL

SEQ ID NO: 104

YASESIS

Amino acid sequence of CDR3 of Ch225 VL

SEQ ID NO: 105

QQNNNWPTT

Amino acid sequence of the mature heavy chain encoded in pBS853

SEQ ID NO: 106

QVQLVQSGAEVKKPGSSVKVSCKASGFTFSSSYISWVRQAPGQGLEWIAWIY

AGTGGTSYNQKFTGRATITVDESTSTAYMELSSLRSEDTAVYYCARHEGVYWYFDVWG

QGTTVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSDIQMT

QSPSSLSASVGDRVTITCHASQNINVWLSWYQQKPGKVPKLLIYKASNLHTGVPSRFSGS

GSGTDFTLTISSLQPEDVATYYCQQGQSYPLTFGCGTKVEIKGGGGSGGGGSGGGGSQV

TLKESGPVLVKPTETLTLTCTVSGFSLTDYGVSWIRQPPGKCLEWLGVIWGGGGTYYNS

ALKSRLTISKDTSKSQVVLTMTNMDPVDTATYYCAKHPYGHFGMDYWGQGTTVTVSS

Amino acid sequence of hICOS-Fc

SEQ ID NO: 107

GEINGSANYEMFIFHNGGVQILCKYPDIVQQFKMQLLKGGQILCDLTKTKGS

GNTVSIKSLKFCHSQLSNNSVSFFLYNLDHSHANYYFCNLSIFDPPPFKVTLTGGYLHIYE

SQLCCQLKTGGGEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMHEALHNHYT

QKSLSLSPGK

Amino acid sequence of HuTAM14 VH

SEQ ID NO: 108

MAVLVLLLCLVTFPSCALSQVQLQESGPGLVKPSETLSLTCTVSGFSISSNSVS

WVRQPPGKGLEWMGAIWSGGSTDYNSALKSRVTISRDTSKNQVSLKLSSVTAADTAVY

YCTRWEQPYYFDYWGQGTMVTVSS

-continued

Amino acid sequence of CDR1 of HuTAM14 VH
SEQ ID NO: 109
SNSVS

Amino acid sequence of CDR2 of HuTAM14 VH
SEQ ID NO: 110
AIWSGGSTDYNSALKS

Amino acid sequence of CDR3 of HuTAM14 VH
SEQ ID NO: 111
WEQPYYFDY

Amino acid sequence of HuTAM14VL
SEQ ID NO: 112
MRTSIQLLGLLLFWLHDAQCDIQMTQSPSSLSASVGDRVTITCQASQNIYKYI

AWYQQKPGKAPKLLIRYTSTLESGTPSRFSGSGSGTDYTLTISSLQPEDFATYYCLQYVN

LYTFGGGTKVEIK

Amino acid sequence of CDR1 of HuTAM14 VL
SEQ ID NO: 113
QASQNIYKYIA

Amino acid sequence of CDR2 of HuTAM14 VL
SEQ ID NO: 114
YTSTLES

Amino acid sequence of CDR3 of HuTAM14 VL
SEQ ID NO: 115
LQYVNLYT

Amino acid sequence of human ICOS
SEQ ID NO: 116
MKSGLWYFFLFCLRIKVLTGEINGSANYEMFIFHNGGVQILCKYPDIVQQFK

MQLLKGGQILCDLTKTKGSGNTVSIKSLKFCHSQLSNNSVSFFLYNLDHSHANYYFCNL

SIFDPPPFKVTLTGGYLHIYESQLCCQLKFWLPIGCAAFVVVCILGCILICWLTKKKYSSS

VHDPNGEYMFMRAVNTAKKSRLTDVTL

Amino acid sequences of HuTAM14.scFv
SEQ ID NO: 117
DIQMTQSPSSLSASVGDRVTITCQASQNIYKYIAWYQQKPGKAPKLLIRYTST

LESGTPSRFSGSGSGTDYTLTISSLQPEDFATYYCLQYVNLYTFGGGTKVEIKGGGGSGG

GGSGGGGSQVQLQESGPGLVKPSETLSLTCTVSGFSISSNSVSWVRQPPGKGLEWMGAI

WSGGSTDYNSALKSRVTISRDTSKNQVSLKLSSVTAADTAVYYCTRWEQPYYFDYWG

QGTMVTVSS

Amino acid sequence of the fusion of CH3
to HuTAM14.scFv (CH3-HuTAM14.scFv) encoded in pBS859
SEQ ID NO: 118
GQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGSGGG

GSGGGGSDIQMTQSPSSLSASVGDRVTITCQASQNIYKYIAWYQQKPGKAPKLLIRYTST

LESGTPSRFSGSGSGTDYTLTISSLQPEDFATYYCLQYVNLYTFGGGTKVEIKGGGGSGG

GGSGGGGSQVQLQESGPGLVKPSETLSLTCTVSGFSISSNSVSWVRQPPGKGLEWMGAI

WSGGSTDYNSALKSRVTISRDTSKNQVSLKLSSVTAADTAVYYCTRWEQPYYFDYWG

QGTMVTVSS

Amino acid sequence of the mature heavy chain
encoded in pBS859
SEQ ID NO: 119
QVQLVQSGAEVKKPGSSVKVSCKASGFTFSSSYISWVRQAPGQGLEWIAWIY

AGTGGTSYNQKFTGRATITVDESTSTAYMELSSLRSEDTAVYYCARHEGVYWYFDVWG

QGTTVTVSSASTKGPSVFPLAPSSKSTSGGTAALGCLVKDYFPEPVTVSWNSGALTSGV

-continued

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSDIQMT

QSPSSLSASVGDRVTITCQASQNIYKYIAWYQQKPGKAPKLLIRYTSTLESGTPSRFSGSG

SGTDYTLTISSLQPEDFATYYCLQYVNLYTFGGGTKVEIKGGGGSGGGGSGGGGSQVQL

QESGPGLVKPSETLSLTCTVSGFSISSNSVSWVRQPPGKGLEWMGAIWSGGSTDYNSAL

KSRVTISRDTSKNQVSLKLSSVTAADTAVYYCTRWEQPYYFDYWGQGTMVTVSS

Amino acid sequence of the mature heavy chain encoded in pBS840

SEQ ID NO: 120

QVQLVQSGAEVKKPGSSVKVSCKASGYTFTSYGINWVRQAPGQGLEWIGYI

YPGSGGPVYNQKFKGRVTITADKSTSTAYMELSSLRSEDTAVYYCARENYRYWYFDV

WGQGTTVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKTH

TCPPCPAPEAAGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGSGGGGSGGGGSD

IQMTQSPSSLSASVGDRVTITCHASQNINVWLSWYQQKPGKVPKWYKASNLHTGVPS

RFSGSGSGTDFTLTISSLQPEDVATYYCQQGQSYPLTFGGGTKVEIKGGGGSGGGGSGG

GGSQVTLKESGPVLVKPTETLTLTCTVSGFSLTDYGVSWIRQPPGKALEWLGVIWGGGG

TYYNSALKSRLTISKDTSKSQVVLTMTNMDPVDTATYYCAKHPYGHFGMDYWGQGTT

VTVSS

Amino acid sequence of the mature heavy chain encoded in pBS846

SEQ ID NO: 121

QVQLVQSGAEVKKPGSSVKVSCKASGFTFSSSYISWVRQAPGQGLEWIAWIY

AGTGGTSYNQKFTGRATITVDESTSTAYMELSSLRSEDTAVYYCARHEGVYWYFDVWG

QGTTVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSEIVLT

QSPATLSLSPGERATLSCSASSSVSYMHWYQQKPGQAPRRWIYDTSKLASGVPARFSGS

GSGTDYTLTISSLEPEDFAVYYCQQWSSNPLTFGGGTKVEIKGGGGSGGGGSGGGGSQV

QLVQSGAEVKKPGSSVKVSCKASGYTFTSYWLHWVRQAPGQGLEWIGRIDPNSGDTKY

NEKFKSRATITVDKSTSTAYMELSSLRSEDTAVYYCARYYYGRSYFDYWGQGTTVTVS

S

Amino acid sequence of HuOHX14DS.scFv.ds

SEQ ID NO: 122

DIQMTQSPSSLSASVGDRVTITCRASQDIRTYLNWYQQKPGKVPKLLIYYTSR

LHSGVPSRFSGSGSGTDYTLTISSLQPEDVATYYCQQGNTLPWTFGCGTKVEIKGGGGS

-continued

GGGGSGGGGSQVQLVQSGAEVKKPGSSVKVSCKASGYTFTSYIMHWVRQAPGQCLEW

IGYINPYNSGTKYNEKFKGRVTITSDKSTSTAYMELSSLRSEDTAVYYCAHYYGSTFTM

DYWGQGTTVTVSS

Amino acid sequence of HuACS2.scFv.ds

SEQ ID NO: 123

EIVLTQSPATLSLSPGERATLSCSASSSVSYMHWYQQKPGQAPRRWIYDTSKL

ASGVPARFSGSGSGTDYTLTISSLEPEDFAVYYCQQWSSNPLTFGCGTKVEIKGGGGSGG

GGSGGGGSQVQLVQSGAEVKKPGSSVKVSCKASGYTFTSYWLHWVRQAPGQCLEWIG

RIDPNSGDTKYNEKFKSRATITVDKSTSTAYMELSSLRSEDTAVYYCARYYYGRSYFDY

WGQGTTVTVSS

Amino acid sequence of HuTAM14.scFv.ds

SEQ ID NO: 124

DIQMTQSPSSLSASVGDRVTITCQASQNIYKYIAWYQQKPGKAPKLLIRYTST

LESGTPSRFSGSGSGTDYTLTISSLQPEDFATYYCLQYVNLYTFGCGTKVEIKGGGGSGG

GGSGGGGSQVQLQESGPGLVKPSETLSLTCTVSGFSISSNSVSWVRQPPGKCLEWMGAI

WSGGSTDYNSALKSRVTISRDTSKNQVSLKLSSVTAADTAVYYCTRWEQPYYFDYWG

QGTMVTVSS

Amino acid sequence of HuGAB11.scFv.ds

SEQ ID NO: 125

DIQMTQSPSSLSASVGDRVTITCHASQNINVWLSWYQQKPGKVPKLLIYKAS

NLHTGVPSRFSGSGSGTDFTLTISSLQPEDVATYYCQQGQSYPLTFGCGTKVEIKGGGGS

GGGGSGGGGSQVTLKESGPVLVKPTETLTLTCTVSGFSLTDYGVSWIRQPPGKCLEWLG

VIWGGGGTYYNSALKSRLTISKDTSKSQVVLTMTNMDPVDTATYYCAKHPYGHFGMD

YWGQGTTVTVSS

Amino acid sequence of h4-1BB-Fc

SEQ ID NO: 126

FERTRSLQDPCSNCPAGTFCDNNRNQICSPCPPNSFSSAGGQRTCDICRQCKG

VFRTRKECSSTSNAECDCTPGFHCLGAGCSMCEQDCKQGQELTKKGCKDCCFGTFNDQ

KRGICRPWTNCSLDGKSVLVNGTKERDVVCGPSPADLSPGASSVTPPAPAREPGHSPQT

GGGEPKSCDKTHTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYTQKSLSLSPG

K

Amino acid sequence of HuFOB5 VH

SEQ ID NO: 127

MERHWIFLFLFSVTAGVHSQVQLVQSGAEVKKPGSSVKVSCKASGYIFINYW

MHWVRAPGQGLEWIGYINPSTGYTESNQKFKDRVTITADKSTSTAYMELSSLRSEDTAV

YYCARSYVGYYYAVDYWGQGTTVTVSS

Amino acid sequence of CDR1 of HuFOB5 VH

SEQ ID NO: 128

NYWMH

Amino acid sequence of CDR2 of HuFOB5 VH

SEQ ID NO: 129

YINPSTGYTESNQKFKD

Amino acid sequence of CDR3 of HuFOB5 VH

SEQ ID NO: 130

SYVGYYYAVDY

-continued

Amino acid sequence of HuFOB5 VL

SEQ ID NO: 131

MDSQAQVLMLLLLWVSGTCGDIVMTQSPD SLAVSLGERATINCKSSQSLLYS

NNEKNYLAWYQQKPGQPPKLLIYWASTRESGVPDRFSGSGSGTIFTLTISSLQAEDVAV

YYCQQYYSYPYTFGGGTKVEIK

Amino acid sequence of CDR1 of HuFOB5 VL

SEQ ID NO: 132

KSSQSLLYSNNEKNYLA

Amino acid sequence of CDR2 of HuFOB5 VL

SEQ ID NO: 133

WASTRES

Amino acid sequence of CDR3 of HuFOB5 VL

SEQ ID NO: 134

QQYYSYPYT

Amino acid sequence of human 4-1BB

SEQ ID NO: 135

MGNSCYNIVATLLLVLNFERTRSLQDPCSNCPAGTFCDNNRNQICSPCPPNSF

SSAGGQRTCDICRQCKGVFRTRKECSSTSNAECDCTPGFHCLGAGCSMCEQDCKQGQE

LTKKGCKDCCFGTFNDQKRGICRPWTNCSLDGKSVLVNGTKERDVVCGPSPADLSPGA

SSVTPPAPAREPGHSPQIISFFLALTSTALLFLLFFLTLRFSVVKRGRKKLLYIFKQPFMRP

VQTTQEEDGCSCRFPEEEEGGCEL

Amino acid sequences of HuFOB5.scFv.LH.ds

SEQ ID NO: 136

DIVMTQSPDSLAVSLGERATINCKSSQSLLYSNNEKNYLAWYQQKPGQPPKL

LIYWASTRESGVPDRFSGSGSGTIFTLTISSLQAEDVAVYYCQQYYSYPYTFGCGTKVEI

KGGGGSGGGGSGGGGSQVQLVQSGAEVKKPGSSVKVSCKASGYIFINYWMHWVRAPG

QCLEWIGYINPSTGYTESNQKFKDRVTITADKSTSTAYMELSSLRSEDTAVYYCARSYV

GYYYAVDYWGQGTTVTVSS

Amino acid sequence of the fusion of CH3 to HuFOB5.scFv.LH.ds (CH3-HuFOB5.scFv.LH.ds) encoded in pBS883

SEQ ID NO: 137

GQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGSGGG

GSGGGGSDIVMTQSPDSLAVSLGERATINCKSSQSLLYSNNEKNYLAWYQQKPGQPPKL

LIYWASTRESGVPDRFSGSGSGTIFTLTISSLQAEDVAVYYCQQYYSYPYTFGCGTKVEI

KGGGGSGGGGSGGGGSQVQLVQSGAEVKKPGSSVKVSCKASGYIFINYWMHWVRAPG

QCLEWIGYINPSTGYTESNQKFKDRVTITADKSTSTAYMELSSLRSEDTAVYYCARSYV

GYYYAVDYWGQGTTVTVSS

Amino acid sequence of the mature heavy chain encoded in pBS883

SEQ ID NO: 138

QVQLVQSGAEVKKPGSSVKVSCKASGFTFSSSYISWVRQAPGQGLEWIAWIY

AGTGGTSYNQKFTGRATITVDESTSTAYMELSSLRSEDTAVYYCARHEGVYWYFDVWG

QGTTVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSDIVMT

QSPDSLAVSLGERATINCKSSQSLLYSNNEKNYLAWYQQKPGQPPKLLIYWASTRESGV

-continued

PDRFSGSGSGTIFTLTISSLQAEDVAVYYCQQYYSYPYTFGCGTKVEIKGGGGSGGGGSG

GGGSQVQLVQSGAEVKKPGSSVKVSCKASGYIFINYWMHWVRAPGQCLEWIGYINPST

GYTESNQKFKDRVTITADKSTSTAYMELSSLRSEDTAVYYCARSYVGYYYAVDYWGQ

GTTVTVSS

Amino acid sequences of HuFOB5.scFv.HL.ds

SEQ ID NO: 139

QVQLVQSGAEVKKPGSSVKVSCKASGYIFINYWMHWVRAPGQCLEWIGYIN

PSTGYTESNQKFKDRVTITADKSTSTAYMELSSLRSEDTAVYYCARSYVGYYYAVDYW

GQGTTVTVSSGGGGSGGGGSGGGGSDIVMTQSPDSLAVSLGERATINCKSSQSLLYSNN

EKNYLAWYQQKPGQPPKLLIYWASTRESGVPDRFSGSGSGTIFTLTISSLQAEDVAVYYC

QQYYSYPYTFGCGTKVEIK

Amino acid sequence of the fusion of CH3 to HuFOB5.scFv.HL.ds (CH3-HuFOB5.scFv.HL.ds) encoded in pBS884

SEQ ID NO: 140

GQPREPQVYTLPPSRDELTKNQVSLTCLVKGFYPSDIAVEWESNGQPENNYK

TTPPVLDSDGSFFLYSKLTVDKSRWQQGNVFSCSVMHEALHNHYTQKSLSLSPGSGGG

GSGGGGSQVQLVQSGAEVKKPGSSVKVSCKASGYIFINYWMHWVRAPGQCLEWIGYIN

PSTGYTESNQKFKDRVTITADKSTSTAYMELSSLRSEDTAVYYCARSYVGYYYAVDYW

GQGTTVTVSSGGGGSGGGGSGGGGSDIVMTQSPDSLAVSLGERATINCKSSQSLLYSNN

EKNYLAWYQQKPGQPPKLLIYWASTRESGVPDRFSGSGSGTIFTLTISSLQAEDVAVYYC

QQYYSYPYTFGCGTKVEIK

Amino acid sequence of the mature heavy chain encoded in pBS884

SEQ ID NO: 141

QVQLVQSGAEVKKPGSSVKVSCKASGFTFSSSYISWVRQAPGQGLEWIAWIY

AGTGGTSYNQKFTGRATITVDESTSTAYMELSSLRSEDTAVYYCARHEGVYWYFDVWG

QGTTVTVSSASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEPKSCDKTHTCP

PCPAPEAAGGPSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGSGGGGSGGGGSQVQL

VQSGAEVKKPGSSVKVSCKASGYIFINYWMHWVRAPGQCLEWIGYINPSTGYTESNQK

FKDRVTITADKSTSTAYMELSSLRSEDTAVYYCARSYVGYYYAVDYWGQGTTVTVSSG

GGGSGGGGSGGGGSDIVMTQSPDSLAVSLGERATINCKSSQSLLYSNNEKNYLAWYQQ

KPGQPPKLLIYWASTRESGVPDRFSGSGSGTIFTLTISSLQAEDVAVYYCQQYYSYPYTF

GCGTKVEIK

Amino acid sequence of human PD-1

SEQ ID NO: 142

MQIPQAPWPVVWAVLQLGWRPGWFLDSPDRPWNPPTFSPALLVVTEGDNAT

FTCSFSNTSESFVLNWYRMSPSNQTDKLAAFPEDRSQPGQDCRFRVTQLPNGRDFHMSV

VRARRNDSGTYLCGAISLAPKAQIKESLRAELRVTERRAEVPTARPSPSPRPAGQFQTLV

VGVVGGLLGSLVLLVWVLAVICSRAARGTIGARRTGQPLKEDPSAVPVFSVDYGELDFQ

WREKTPEPPVPCVPEQTEYATIVFPSGMGTSSPARRGSADGPRSAQPLRPEDGHCSWPL

-continued

Amino acid sequence of hPD-1-Fc

SEQ ID NO: 143

LDSPDRPWNPPTFSPALLVVTEGDNATFTCSFSNTSESFVLNWYRMSPSNQTD

KLAAFPEDRSQPGQDCRFRVTQLPNGRDFHMSVVRARRNDSGTYLCGAISLAPKAQIKE

SLRAELRVTERRAEVPTAHPSPSPRPAGQFQTGGGEPKSCDKTHTCPPCPAPELLGGPSV

FLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSR

WQQGNVFSCSVMHEALHNHYTQKSLSLSPGK

What is claimed is:

1. A bispecific antibody comprising a first binding site and a second binding site, wherein first paired heavy and light chain variable regions respectively fused to heavy and light chain constant regions form the first binding site, an scFv comprising second paired heavy and light chain variable regions forms the second binding site, the N-terminus of the light chain variable region of the scFv is linked to the C-terminus of the heavy chain constant region, and the bispecific antibody comprises two first binding and two second binding sites, wherein the second binding site specifically binds to OX40 and comprises CDRs H1, H2 and H3 of SEQ ID NOS: 13-15 respectively and CDRs L1, L2 and L3 of SEQ ID NOS: 17-19 respectively, and wherein (a) the first binding site specifically binds to CD33 and the first paired heavy chain variable region comprises CDRs H1, H2 and H3 of SEQ ID NOS: 94-96 respectively and the first paired light chain variable region comprises CDRs L1, L2 and L3 of SEQ ID NOS: 97-99 respectively, or (b) the first binding site specifically binds to EGFR and the first paired heavy chain variable region comprises CDRs H1, H2 and H3 of SEQ ID NOS: 100-102 respectively and the first paired light chain variable region comprises CDRs L1, L2 and L3 of SEQ ID NOS: 103-105 respectively.

2. The bispecific antibody of claim 1, wherein the first binding site specifically binds to CD33.

3. The bispecific antibody of claim 2, wherein the first paired heavy chain variable region comprises residues 20 to 135 of SEQ ID NO:2 and the first paired light chain variable region comprises residues 21-131 of SEQ ID NO:7, and the second paired heavy chain variable region comprises residues 20 to 138 of SEQ ID NO:12 and the second paired light chain variable region comprises residues 21-127 of SEQ ID NO:16.

4. The bispecific antibody of claim 2, wherein the first paired heavy chain variable region comprising residues 20 to 135 of SEQ ID NO:2 and the first paired light chain variable region comprises residues 20-131 of SEQ ID NO:7, and the scFv has an amino acid sequence comprising SEQ ID NO:22 or 122.

5. The bispecific antibody of claim 1 wherein the first binding site specifically binds to EGFR.

6. The bispecific antibody of claim 5, wherein the first paired heavy chain variable region comprises residues 20-138 of SEQ ID NO:29 and the first paired light chain variable region comprises residues 21-127 of SEQ ID NO:30, and the second paired heavy chain variable region comprises residues 20 to 138 of SEQ ID NO: 12 and the second paired light chain variable region comprises residues 21-127 of SEQ ID NO:16.

7. The bispecific antibody of claim 5, wherein the first paired heavy chain variable region comprises residues 20-138 of SEQ ID NO:29 and the first paired light chain variable region comprises residues 21-127 of SEQ ID NO:30, and the scFv has an amino acid sequence comprising SEQ ID NO: 22 or 122.

8. A monoclonal antibody specifically binding to OX40 comprising a heavy chain variable region comprising CDRs H1, H2 and H3 of SEQ ID NOS: 13-15 respectively and a light chain variable region comprising CDRs L1, L2 and L3 of SEQ ID NOS: 17-19 respectively.

9. The monoclonal antibody of claim 8, comprising a heavy chain variable region comprising residues 20 to 138 of SEQ ID NO: 12 and a light chain variable region comprising residues 21-127 of SEQ ID NO:16.

10. A pharmaceutical composition comprising athe bispecific antibody of claim 1 and a pharmaceutically acceptable carrier.

11. A method of antagonizing CD33 or EGFR and agonizing OX40 in a subject having a cancer expressing CD33 or EGFR, comprising administering an effective regime of the bispecific antibody of claim 1 to the subject having cancer.

12. The monoclonal antibody of claim 8, wherein the heavy chain variable region and the light chain variable region are in the form of an scFv.

13. A monoclonal antibody specifically binding to OX40, the monoclonal antibody comprising the amino acid sequence of SEQ ID NO:22 or 122.

14. The monoclonal antibody of claim 9 further comprising a second heavy chain variable region comprising residues 20-135 of SEQ ID NO:2 and a second light chain variable region comprising residues 21-131 of SEQ ID NO:7, whereby the monoclonal antibody also specifically binds to CD33.

15. The monoclonal antibody of claim 12, further comprising a second heavy chain variable region comprising residues 20-135 of SEQ ID NO:2 and a second light chain variable region comprising residues 21-131 of SEQ ID NO:7, whereby the monoclonal antibody also specifically binds to CD33.

16. The monoclonal antibody of claim 13 further comprising a second heavy chain variable region comprising residues 20-135 of SEQ ID NO:2 and a second light chain variable region comprising residues 21-131 of SEQ ID NO:7, whereby the monoclonal antibody also specifically binds to CD33.

17. The bispecific antibody of claim 1, wherein the first and second binding sites are humanized or veneered and the heavy and light chain constant regions are human.

18. The bispecific antibody of claim 1, wherein the isotype of the heavy chain constant region is human IgG1 and the light chain constant region is kappa.

19. The bispecific antibody of claim 1, wherein the heavy chain constant region has at least one mutation reducing FcγR binding.

20. The bispecific antibody of claim 1, wherein the heavy chain constant region has at least one mutation increasing binding to FcRn.

* * * * *